US009107907B2

(12) United States Patent
Goetsch

(10) Patent No.: US 9,107,907 B2
(45) Date of Patent: Aug. 18, 2015

(54) ANTIBODIES INHIBITING C-MET DIMERIZATION, AND USES THEREOF

(71) Applicant: Liliane Goetsch, Ayze (FR)

(72) Inventor: Liliane Goetsch, Ayze (FR)

(73) Assignee: Pierre Fabre Medicament, Boulogne-Billancourt (FR)

( * ) Notice: Subject to any disclaimer, the term of this patent is extended or adjusted under 35 U.S.C. 154(b) by 106 days.

(21) Appl. No.: 13/673,752

(22) Filed: Nov. 9, 2012

(65) Prior Publication Data

US 2013/0272957 A1    Oct. 17, 2013

Related U.S. Application Data

(62) Division of application No. 12/440,571, filed as application No. PCT/EP2008/059026 on Jul. 10, 2008, now Pat. No. 8,329,173.

(60) Provisional application No. 60/929,789, filed on Jul. 12, 2007, provisional application No. 61/020,639, filed on Jan. 11, 2008.

(30) Foreign Application Priority Data

Jul. 12, 2007    (EP) ..................... 07301231

(51) Int. Cl.
    *A61K 39/395*    (2006.01)
(52) U.S. Cl.
    CPC ............................... *A61K 39/39541* (2013.01)
(58) Field of Classification Search
    None
    See application file for complete search history.

(56) References Cited

U.S. PATENT DOCUMENTS

| 4,424,200 | A  | 1/1984  | Crockford et al. |
| 4,479,930 | A  | 10/1984 | Hnatowich |
| 4,816,567 | A  | 3/1989  | Cabilly et al. |
| 4,831,175 | A  | 5/1989  | Gansow et al. |
| 5,530,101 | A  | 6/1996  | Queen et al. |
| 5,585,089 | A  | 12/1996 | Queen et al. |
| 5,639,641 | A  | 6/1997  | Pedersen et al. |
| 5,693,761 | A  | 12/1997 | Queen et al. |
| 5,877,293 | A  | 3/1999  | Adair et al. |
| 5,886,152 | A  | 3/1999  | Nakatani et al. |
| 6,054,297 | A  | 4/2000  | Carter et al. |
| 6,180,370 | B1 | 1/2001  | Queen et al. |
| 6,207,152 | B1 | 3/2001  | Schwall et al. |
| 6,214,344 | B1 | 4/2001  | Schwall et al. |
| 2004/0175385 | A1 | 9/2004 | Marks et al. |
| 2005/0233960 | A1 | 10/2005 | Kong-Beltran et al. |
| 2006/0094059 | A1 | 5/2006 | Westwick et al. |

FOREIGN PATENT DOCUMENTS

| EP | 0 451216 | 10/1991 |
| EP | 0 566 647 | 10/1993 |
| EP | 0 682 040 | 11/1995 |
| EP | 0 939127 | 9/1999 |
| GB | 2 404 660 A | 2/2005 |
| WO | WO 96/38557 | 12/1996 |
| WO | WO 03/072036 A2 | 9/2003 |
| WO | WO 2005/000901 A2 | 1/2005 |
| WO | WO 2005/016382 | 2/2005 |
| WO | WO 2005/058965 A1 | 6/2005 |
| WO | WO 2006/015371 | 2/2006 |
| WO | WO 2006/020266 A2 | 2/2006 |
| WO | WO 2006/086586 A2 | 8/2006 |
| WO | WO 2006/116260 | 11/2006 |
| WO | WO 2007/011941 | 1/2007 |
| WO | WO 2007/016285 | 2/2007 |
| WO | WO 2007/090807 A1 | 8/2007 |
| WO | WO 2007/126799 A2 | 11/2007 |
| WO | WO 2010/064089 A1 | 6/2010 |
| WO | WO 2010/069765 A1 | 6/2010 |

OTHER PUBLICATIONS

White et al. (2001, Ann. Rev. Med., 2001, 52:125-145).*
Meibohm (Pharmacokinetics and Pharmacodynamics of Biotech Drugs, Wiley-VHC, 2006, chapter 3, p. 45-91).*
Aapro, M. S., et al., "Developments in cytotoxic chemotherapy: advances in treatment utilising vinorelbine," *Crit. Rev. Oncol. Hematol.*, 40:251-263 (2001).
Angers, S., et al., "Detection of $\beta_2$-adrenergic receptor dimerization in living cells using bioluminescence resonance energy transfer (BRET)," *Proc. Natl. Acad. Sci. USA*,97:3684-3689 (2000).
Bebbington, C. R., et al., "High-level expression of a recombinant antibody from myeloma cells using a glutamine synthetase gene as an amplifiable selectable marker," *Bio/Technology*, 10:169-175 (1992).
Bes, C., et al., "Efficient CD4 binding and immunosuppressive properties of the 13B8.2 monoclonal antibody are displayed by its CDR-HI-derived peptide CB1," *FEBS letters*, 508:67-74 (2001).
Bes, C., et al., "PIN-bodies: A new class of antibody-like proteins with CD4 specificity derived from the protein inhibitor of neuronal nitric oxide synthase," *BBRC*, 343:334-344 (2006).
Birchmeier, C., et al., "Met, metastasis, motility, and more," *Nat. Rev. Mol. Cell Biol.*, 4:915-925 (2003).
Bladt, F., et al., "Essential role for the c-met receptor in the migration of myogenic precursor cells into the limb bud," *Nature*, 376:768-771 (1995).
Bottaro, D. P., et al., "Identification of the Hepatocyte Growth Factor Receptor as the c-met Proto-Oncogene Product," *Science*, 251:802-804 (1991).
Brechbiel, M. W., et al., "Backbone-substituted DTPA ligands for 90Y radioimm.," *Bioconjug Che*, 2(3):187-194 (1991).

(Continued)

*Primary Examiner* — Laura B Goddard
*Assistant Examiner* — Meera Natarajan
(74) *Attorney, Agent, or Firm* — Finnegan, Henderson, Farabow, Garrett & Dunner, L.L.P.

(57) ABSTRACT

The present inventions relates to a process for the selection of anti c-Met antibodies capable to inhibit both ligand-dependent and ligand-independent activation of c-Met. More particularly, said process is based on the inhibition of the c-Met dimerization. In another aspect, the present invention concerns such antibodies and compositions comprising such antibodies for the preparation of a medicament to treat cancer. Diagnosis process and kits are also part of the invention.

30 Claims, 72 Drawing Sheets

(56) References Cited

OTHER PUBLICATIONS

Figure 1:
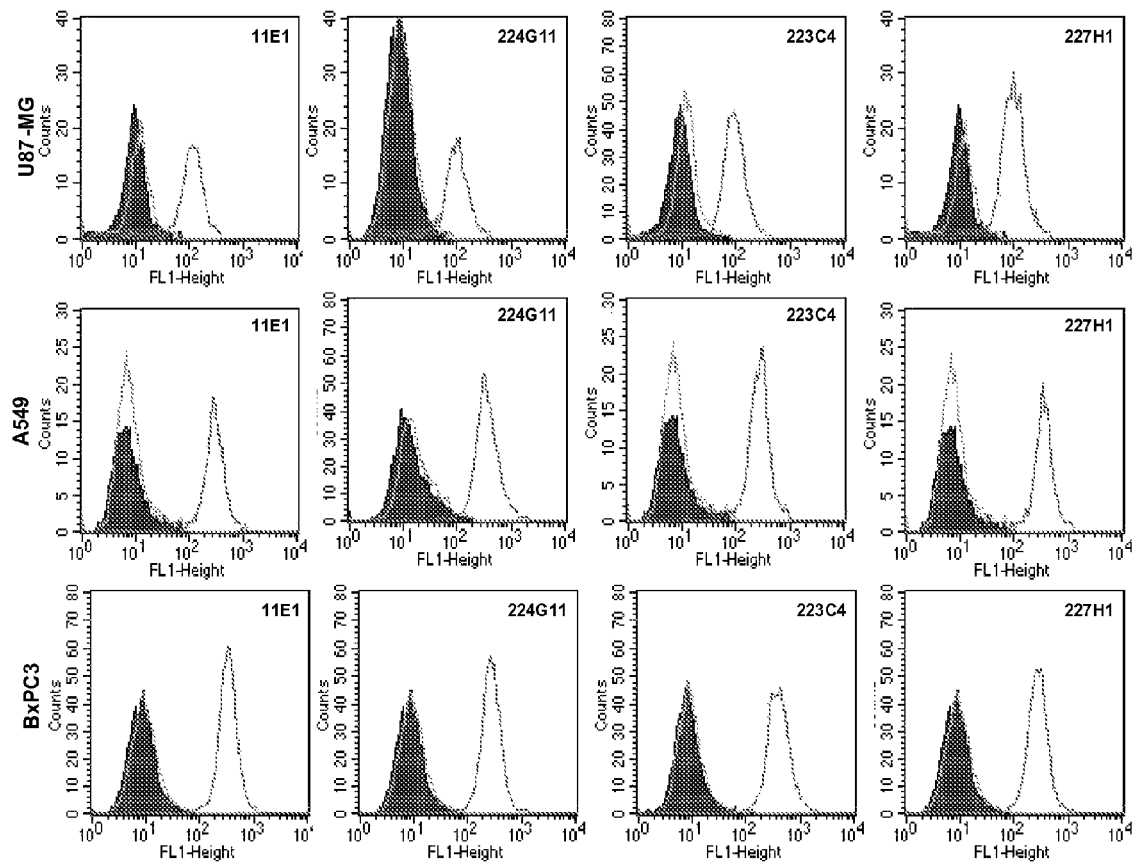

Burgess, T., et al., "Fully human monoclonal antibodies to hepatocyte growth factor with therapeutic potential against hepatocyte growth factor/c-Met-dependent human tumors," *Cancer Res*, 66(3):1721-1729 (2006).
Bussolino, F., et al., "Hepatocyte Growth Factor Is a Potent Angiogenic Factor Which Stimulates Endothelial Cell Motility and Growth," *J. Cell Biol.*, 119:629-641 (1992).
Cao, B., et al., "Neutralizing monoclonal antibodies to hepatocyte growth factor/scatter factor (HGF/SF) display antitumor activity in animal models," *Proc Natl Acad Sci U S A*, 98(13):7443-8 (2001).
Christensen, J. G., et al., "A Selective Small Molecule Inhibitor of c-Met Kinase Inhibits c-Met-Dependent Phenotypes in Vitro and Exhibits Cytoreductive Antitumor Activity in Vivo," *Cancer Res.*, 63:7345-55 (2003).
Christensen, J. G., et al., "c-Met as a target for human cancer and characterization of inhibitors for therapeutic intervention," *Cancer Letters*, 226:1-26 (2005).
Conrotto, P., et al., "Interplay between scatter factor receptors and B plexins controls invasive growth," *Oncogene*, 23:5131-7 (2004).
Conrotto, P., et al., "Sema4D induces angiogenesis through Met recruitment by Plexin B1," *Blood*, 105(11):4321-9 (2005).
Curran, M. P., et al., "Vinorelbine: A Review of its Use in Elderly Patients with Advanced Non-Small Cell Lung Cancer," *Drugs Aging*, 19:695-697 (2002).
Di Renzo, M. F., et al., "Expression of the Met/HGF receptor in normal neoplastic human tissues," *Oncogene*, 6:1997-2003 (1991).
Engelman, J. A., et al., "*MET* Amplification Leads to Gefitinib Resistance in Lung Cancer by Activating ERBB3 Signaljng," *Science*, 316:1039-43 (2007).
Fan, S., et al., "The cytokine hepatocyte growth factor/scatter factor inhibits apoptosis and enhances DNA repair by a common mechanism involving signaling through phosphatidyl inositol 3' kinase," *Oncogene*, 19(18):2212-23 (2000).
Furge, K. A., et al., "Met receptor tyrosine kinase: enhanced signaling through adapter proteins," *Oncogene*, 19(49):5582-9 (2000).
Gansow, O. A., et al., "Chelates and antibodies: current methods and new directions.," *Cancer Treat Res.*, 51:153-171 (1990).
Gansow, O. A., et al., "Newer Approaches to the Radiolabeling of Monoclonal Antibodies by Use of Metal Chelates," *Int J Rad Appl Instr B Nucl Med Biol*, 18(4):369-381 (1991).
Gao, C. F., et al., "HGF/SF-Met signaling in tumor progression," *Cell Res.*, 15(I):49-51 (2005).
Giordano, S., et al., "The Semaphorin 4D receptor controls invasive growth by coupling with Met," *Nat Cell Biol.*, 4(9):720-4 (2002).
Green, L. L., et al., "Antigen-specific human monoclonal antibodies from mice engineered with human Ig heavy and light chain YACs," *Nature Genetics*, 7:13-21 (1994).
Green, L., et al., "Regulation of B Cell Development by Variable Gene Complexity in Mice Reconstituted with Human Immunoglobulin Yeast Artificial Chromosomes," *J. Exp. Med.*, 188:483-495 (1998).
Gu, H., et al., "The 'Gab' in signal transduction," *Trends Cell Biol.*, 13(3):122-30 (2003).
Harlow, E., et al., "Antibodies: A Laboratory Manual, Cold Spring Harbor Laboratory," *Cold Spring Harbor Laboratory*, pp. 726-727 (1988).
Hays, J. L., et al., "Watowich S.J., Oligomerization-Dependent Changes in the Thermodynamic Properties of the TPR-MET Receptor Tyrosine Kinase," *Biochemistry*, 43:10570-8 (2004).
Hunter, W. M., et al., "Preparation of iodine-131 labelled human growth hormone of high specific activity," *Nature*, 194:495 (1962).
Jones, P. T., et al., "Replacing the complementarity-determining regions in a human antibody with those from a mouse," *Nature*, 321:522-525 (1986).
Kaas, Q., et al., "IMGT Colliers de Perles: Standardized Sequence-Structure Representations of the IgSF and MhcSF Superfamily Domains," *Current Bioinformatics*, 2:21-30 (2007).
Kaas, Q., et al., "IMGT/3Dstructure-DB and IMGT/StructuralQuery, a database and a tool for immunoglobulin, T cell receptor and MHC structural data," *Nucl. Acids. Res.*, 32:D208-D210 (2004).
Kohl, A., et al., "Designed to be stable: Crystal structure of a consensus ankyrin repeat protein," *PNAS*, 100:1700-1705 (2003).
Kohler, G., et al., "Continuous cultures of fused cells secreting antibody of predefined specificity," *Nature*, 256:495-497 (1975).
Kraus-Berthier, L., et al., "Histology and Sensitivity to Anticancer Drugs of Two Human Non-Small Cell Lung Carcinomas Implanted in the Pleural Cavity of Nude Mice," *Clin. Cancer Res.*, 6:297-304 (2000).
Krejcarek, G. E., et al., "Covalent Attachment of Chelating Groups to Macromolecules," BBRC, 77(2):581-585 (1977).
Kuba, K., et al., "HGF/NK4, a Four-Kringle Antagonist of Hepatocyte Growth Factor, Is an Angiogenesis Inhibitor that Suppresses Tumor Growth and Metastasis in Mice," *Cancer Res.*, 60:6737-43 (2000).
Lefranc, M.-P., "The IMGT Unique Numbering for Immunoglobulins, T-Cell Receptors, and Ig-Like Domains," *The Immunologist*, 7:132-136 (1999).
Lefranc, M.-P., "Unique database numbering system for immunogenetic analysis," *Immunology Today*, 18:509 (1997).
Lefranc, M.-P., et al., "IMGT unique numbering for immunoglobulin and T cell receptor variable domains and Ig superfamily V-like domains," *Dev. Comp. Immunol.*, 27:55-77 (2003).
Maroun, C. R., et al., "The Gab1 PH Domain Is Required for Localization of Gab1 at Sites of Cell-Cell Contact and Epithelial Morphogenesis Downstream from the Met Receptor Tyrosine Kinase," *Mol. Cell. Biol.*, 19:1784-1799 (1999).
Martens, T., et al., "A Novel One-Armed Anti-c-Met Antibody Inhibits Glioblastoma Growth In vivo," *Clin Cancer Res.*, 12(20):6144-52 (2006).
Meares, C. F., et al., "Conjugation of Antibodies with Bifunctional Chelating Agents: Isothiocyanate and Bromoacetamide Reagents, Methods of Analysis, and Subsequent Addition of Metal Ions," *Anal-Biochem*, 142(1):68-78 (1984).
Morrison, S. L., et al., "Chimeric human antibody molecules: Mouse antigen-binding domains with human constant region domains," *Proc. Natl. Acad. Sci. USA*, 82:6851-6855 (1984).
Mountain, A., et al., "Engineering Antibodies for Therapy," *Biotechnol. Genet. Eng. Rev.*, 10:1-142 (1992).
Nagayama, T., et al., "Post-ischemic delayed expression of hepatocyte growth factor and c-Met in mouse brain following focal cerebral ischemia," *Brain Res.*, 5;999(2):155-66 (2004).
Nakamura, Y., et al., "Expression of Local Hepatocyte Growth Factor System in Vascular Tissues," *Biochem. Biophys. Res. Commun.*, 215:483-488 (1995).
Naldini, L., et al., "Scatter factor and hepatocyte growth factor are indistinguishable ligands for the MET Receptor," *Eur. Mol. Biol. Org. J.*, 10:2867-2878 (1991).
Needleman, S. B., et al., "A General Method Applicable to the Search for Similarities in the Amino Acid Sequence of Two Proteins," *J. Mol. Biol.*, 48:443 (1970).
Nicaise, M., et al., "Affinity transfer by CDR grafting on a nonimmunoglobulin scaffold," *Protein Sci.*, 13(7):1882-91 (2004).
Pearson, W. R., et al., "Improved tools for biological sequence comparison," *Proc. Natl. Acad. Sci. USA*, 85:2444 (1988).
Riechmann, L., et al., "Reshaping human antibodies for therapy," *Nature*, 332:323-327 (1988).
Rosen, E. M., et al., "Scatter factor stimulates migration of vascular endothelium and capillary-like tube formation," *Cell Motility Factors, Experientia Supplementum*, 59:76-88 (1991).
Ruiz, M., et al., "IMGT gene identification and Colliers de Perles of human immunoglobins with known 3D structures," *Immunogenetics*, 53, 857-883 (2002).
Schmidt, C., et al., "Scatter factor/hepatocyte growth factor is essential for liver development," *Nature*, 373:699-702 (1995).
Singer, I. I., et al., "Optimal Humanization of 1 84, an Anti-C018 Murine Monoclonal Antibody, Is Achieved by Correct Choice of Human V-Region Framework Sequences," *J. Immun.*, 150:2844-2857 (1993).

(56) References Cited

OTHER PUBLICATIONS

Skerra, A., "'Anticalins': a new class of engineered ligand-binding proteins with antibody-like properties," *Reviews in Molecular Biotechnology*, 74(4):257-75 (2001).
Skerra, A., "Engineered protein scaffolds for molecular recognition," *J. Mol. Recogn.*, 13:167-187 (2000).
Smith, T. F., et al., "Comparison of Biosequences," *Ad. App. Math.*, 2:482 (1981).
Smolen, G. A., et al., "Amplification of MET may identify a subset of cancers with extreme sensitivity to the selective tyrosine kinase inhibitor PHA-665752," *Proc. Natl. Acad. Sci. USA*, 103(7):2316-2321 (2006).
Sonnenberg, E., et al., "Scatter Factor/Hepatocyte Growth Factor and Its Receptor, the c-met Tyrosine Kinase, Can Mediate a Signal Exchange between Mesenchyme and Epithelia during Mouse Development," *J. Cell. Biol.*, 123:223-235 (1993).
Tahara, Y., et al., "Hepatocyte Growth Factor Facilitates Colonic Mucosal Repair in Experimental Ulcerative Colitis in Rats," *J Pharmacol Exp Ther.*, 307(1):146-51 (2003).
Tatusova, T. A., et al., "Blast 2 sequences—a new tool for comparing protein and nucleotide sequences", *FEMS Microbiol Lett.*, 174:247-250 (1999).
Trusolino, L., et al., "A Signaling Adapter Function for α6β4 Integrin in the Control of HGF-Dependent Invasive Growth," *Cell*, 107:643-54 (2001).
Trusolino, L., et al., "Scatter-factor and semaphorin receptors: cell signaling for invasive growth," *Nat Rev. Cancer*, 2(4):289-300 (2002).
Tsarfaty, I., et al., "The Met Proto-Oncogene Mesenchymal to Epithelial Cell Conversion," *Science*, 263:98-101 (1994).
Van der Voort, R., et al., "Heparan Sulfate-modified CD44 Promotes Hepatocyte Growth Factor/Scatter Factor-induced Signal Transduction through the Receptor Tyrosine Kinase c-Met," *J Biol Chem.*, 274(10):6499-506 (1999).
Verhoeyen, M., et al., "Engineering of Antibodies," *BioEssays*, 8:74 (1988).
Verhoeyen, M., et al., "Reshaping Human Antibodies: Grafting an Antilysozyme Activity," *Science* 239:1534-1536 (1988).
Zou, H. Y., et al., "An Orally Available Small-Molecule Inhibitor of c-Met, PF-2341 066, Exhibits Cytoreductive Antitumor Efficacy through Antiproliferative and Antiangiogenic Mechanisms," *Cancer Res.*, 67:4408-4417 (2007).
International Search Report for PCT/EP2008/059026, mailed Feb. 17, 2009.
International Search Report for PCT/EP2009/066201, mailed Mar. 4, 2010.
International Search Report for PCT/IB2008/055663, mailed Aug. 19, 2009.
Huang, S. et al., "Dual-Agent Molecular Targeting of the Epidermal Growth Factor Receptor (EGFR): Combining Anti-EGFR Antibody with Tyrosine Kinase Inhibitor," *Can. Res.* 64:5355-5562 (2004).
Knudsen, B.S., et al., "Showering c-MET-Dependent Cancers With Drugs," *Curr. Opin. Gen.& Devl.* 18:87-96 (2008).
Liu, X. et al., "Targeting the c-MET Signaling Pathway for Cancer Therapy," *Expert Opin. Investig. Drugs*, 17:997-1011 (2008).
Matar, P. et al., "Combined Epidermal Growth Factor Receptor Targeting with the Tyrosine Kinase Inhibitor Gefitinib (ZD1839) and Monoclonal Antibody Cetuximab (IMC-C225): Superiority Over Single-Agent Receptor Targeting," *Clin. Can. Res.* 10:6487-6501 (2004).
Pozner-Moulis, S. et al., "Antibody Validation by Quantitative Analysis of Protein Expression Using Expression of Met in Breast Cancer as a Model," *Lab. Investig* 87:251-260 (2007).
Prat, M. et al., "C-Terminal Truncated Forms of Met, the Hepatocyte Growth Factor Receptor," *Mol. & Cel. Bio.* 11:5954-5962 (1991).
Co-pending U.S. Appl. No. 12/791,681, filed Jun. 1, 2010.
Beck, A. et al., "6th Annual European Antibody Congress 2010," *mAbs*, 3:111-132, (2011).
Davies, J. et al., "Affinity Improvement of Single Antibody VH Domains: Residues in All Three Hypervariable Regions Affect Antigen Binding," *Imm.*, 2:169-179, (1996).
Goetsch, L. et al., "Abstract B127: Single or Combined In Vivo Therapies of Cancer With h224G11, A Humanized Antibody Targeting the c-Met Receptor," *Mol. Can. Thera.*, 8 (12); Supplement 1 (2009).
Holt, L.J., et al., "Domain Antibodies: Proteins for Therapy," *Trends in Biotech.*, 21:484-490, (2003).
Maynard, J. et al., "Antibody Engineering," *Annu. Rev. Biomed. Eng.*, 2:339-376, (2000).
Pini, A. et al., "Design and Use of a Phage Display Library," *Am. Soc. Biochem & Mol. Bio., Inc.*, 274:21769-21776, (1988).
U.S. Appl. No. 13/673,726, filed Nov. 9, 2012.
U.S. Appl. No. 13/673,716, filed Nov. 9, 2012.
U.S. Appl. No. 13/673,690, filed Nov. 9, 2012.
U.S. Appl. No. 12/440,571, filed Mar. 9, 2009.
Beck, A. et al., "5th Annual European Antibody Congress 2009," *mAbs*, 2:108-128, (2010).

\* cited by examiner

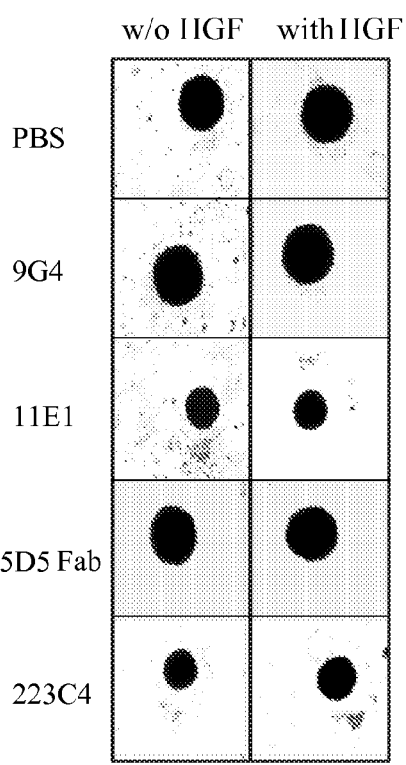
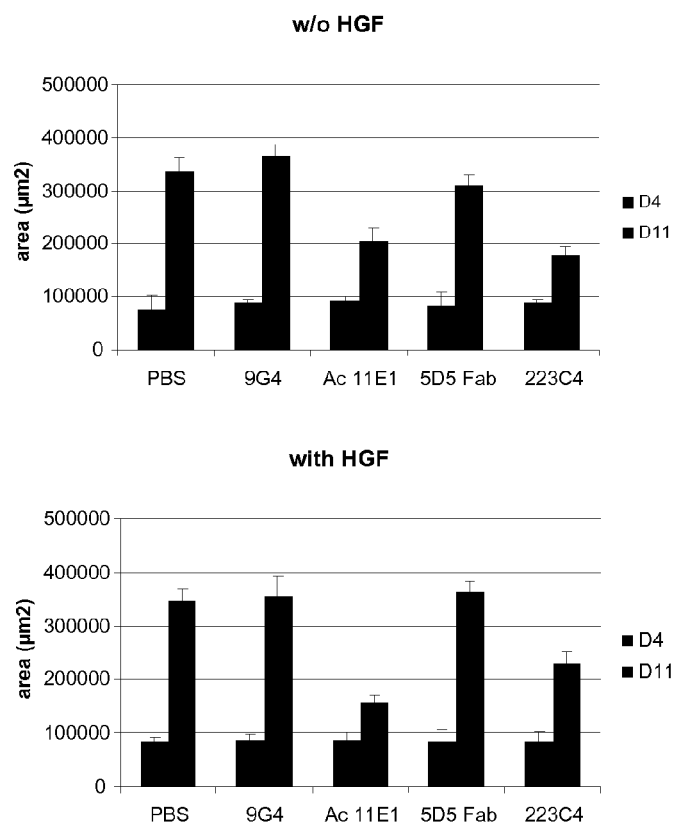
FIGURE 12A
FIGURE 12B

```
                          <------------------------------------------- FR1 - IMGT
                          1            5                   10                  15
                          D   I   V   L   T   Q   S   P   A   S   L   A   V   S   L
224G11 VL                 gac att gtg ctg acc caa tct cca gct tct ttg gct gtg tct cta K02161 IGKV3-5*01         --- --- --- --- --- --- --- --- --- --- --- --- --- --- ---

------------------------------------------->
                                           20                  25                  30
                          G   Q   R   A   T   I   S   C   R   A   S   E   S   V   D
224G11 VL                 ggg cag agg gcc acc ata tcc tgc aga gcc agt gaa agt gtt gat K02161 IGKV3-5*01         --- --- --- --- --- --- --- --- --- --- --- --- --- --- ---

__   CDR1 - IMGT                      <--------------------------
                                           35                  40                  45
                          S   Y   A   N   S   F               M   H   W   Y   Q   Q   K
224G11 VL                 agt tat gcc aat agt ttt ... ... atg cac tgg tac cag cag aaa
                                      G
K02161 IGKV3-5*01         --- --- -g- --- --- --- ... ... --- --- --- --- --- --- ---

FR2 - IMGT   ------------------------->                   CDR2
                                           50                  55                  60
                          P   G   Q   P   P   K   L   L   I   Y   R   A   S
224G11 VL                 cca gga cag cca ccc aaa ctc ctc atc tat cgt gca tcc ... ...

K02161 IGKV3-5*01         --- --- --- --- --- --- --- --- --- --- --- --- --- ... ...

- IMGT          <------------------------------------------
                                           65                  70                  75
                                          N   L   E   S   G   I   P       A   R
224G11 VL                 ... ... ... ... ... aac cta gaa tct ggg atc cct ... gcc agg K02161 IGKV3-5*01         ... ... ... ... ... --- --- --- --- --- --- --- ... --- ---

------------------------------  FR3 - IMGT  ---------------
                                           80                  85                  90
                          F   S   G   S   G           S   R   T   D   F   T   L   T
224G11 VL                 ttc agt ggc agt ggg ... ... tct agg aca gac ttc acc ctc acc K02161 IGKV3-5*01         --- --- --- --- --- ... ... --- --- --- --- --- --- --- ---

------------------------------------------------------->  ____
                                           95                  100                 105
                          I   N   P   V   E   A   D   D   V   A   T   Y   Y   C   Q
224G11 VL                 att aat cct gtc gag gct gat gat gtt gca acc tat tac tgt cag K02161 IGKV3-5*01         --- --- --- --- --- --- --- --- --- --- --- --- --- --- ---

_____   CDR3 - IMGT _____  <-------------  FR4 - IMGT
                                           110                 115                 120
                          Q   S   K   E   D   P   L   T   F   G   S   G   T   K   L
224G11 VL                 caa agt aag gac gat cct ctc acg ttc ggc tcg ggg aca aaa ttg
                                  N
K02161 IGKV3-5*01         --- --- --t --- --- --- -c- --- --- --- --- --- --- --- ---

---------->
                                           123
                          E   M   K
224G11 VL                 gaa atg aaa
```

FIGURE 17A

```
                 _____ CDR3 - IMGT _____    <------------- FR4 - IMGT
                                     110                         115                    120
                 Q   S   K   E   D   P   L   T   F   G   S   G   T   K   L
224G11 VL        caa agt aag gag gat cct ctc acg ttc ggc tcg ggg aca aaa ttg V00777 IGKJ4*01                                  --  --- --- --- --- --- --- --g ---

---------->
                         123
                 E   M   K
224G11 VL        gaa atg aaa
                     ⊥
V00777 IGKJ4*01  --- --a --- c
```

FIGURE 17B

```
                          <------------------------------------ FR1 - IMGT
                          1             5             10            15
                          D   I   V   L   T   Q   S   P   A   S   L   A   V   S   L
224G11 VL                 gac att ctg ctg acc caa tct cca gct tct ttg gct gtg tct cta
                                              E               T       S   L       P
X01668 IGKV3-11*01        --a --- --- t-- --a --g --- --- --c a-c c-- t-- t-- --- -c-
Z00023 IGKV4-1*01                     M               D --------------------------------------------->   _____
                                      20            25            30
                          G   Q   R   A   T   I   S   C   R   A   S   E   S   V   D
224G11 VL                 ggg cag agg gcc acc ata tcc tgc aga gcc agt gaa agt gtt gat
                              E               L                       Q           S
X01668 IGKV3-11*01        --- g-a --a --- --- c-c --- --- --g --- --- c-g --- --- agc
Z00023 IGKV4-1*01             E               N       K               Q           L ____ CDR1 - IMGT _____        <--------------------------
                                      35            40            45
                          S   Y   A   N   S   F   .   .   M   H   W   Y   Q   Q   K
224G11 VL                 agt tat gcc aat agt ttt ... ... atg cac tgg tac cag cag aaa
                                          .   .   .       L   A
X01668 IGKV3-11*01        --c --c ... ... ... ... ... ... t-a gc- --- --- --a --- ---
Z00023 IGKV4-1*01                 N               N   Y   L   A FR2 - IMGT ------------------------->   _____ CDR2
                                      50            55            60
                          P   G   Q   P   P   K   L   L   T   Y   R   A   S
224G11 VL                 cca gga cag cca ccc aaa ctc ctc atc tat cgt gca tcc ... ...
                                              A       R               D
X01668 IGKV3-11*01        --- --c --- g-t --- -gg --- --- --- --- ga- --- --- ... ...
Z00023 IGKV4-1*01                                                     W

- IMGT _____   <--------------------------------------
                                      65            70            75
                                              N   L   E   S   G   I   P       A   R
224G11 VL                 ... ... ... ... ... aac cta gaa tct ggg atc cct ... gcc agg
                                              R   A   T
X01668 IGKV3-11*01        ... ... ... ... ... --- agg -cc a-- --c --a ... --- ---
Z00023 IGKV4-1*01                             T   R           V               D ------------------------------- FR3 - IMGT ---------------
                                      80            85            90
                          F   S   G   S   G           S   R   T   D   F   T   L   T
224G11 VL                 ttc agt ggc agt ggg ... ... tct agg aca gac ttc acc ctc acc
                                                          G
X01668 IGKV3-11*01        --- --- --- --- --- ... ... --- g-- --- --- --t --- ---
Z00023 IGKV4-1*01                                         G --------------------------------------------------------->
                                      95            100           105
                          I   N   P   V   E   A   D   D   V   A   T   Y   Y   C   Q
224G11 VL                 atc aat cct gtg gag gct gat gat gtt gca acc tat tac tgt cag
                              S   S   L       P   E       F       V
X01668 IGKV3-11*01        --c -gc agc c-a --- c-- --a --- t-- --- gtt --- --- --- ---
Z00023 IGKV4-1*01             S   S   L       Q   E           V _____ CDR3 - IMGT _____   <----- FR4 - IMGT --------
                                      110           115           120
                          Q   S   K   E   D   P   L   T   F   G   S   G   T   K   L
224G11 VL                 caa agt aag gag gat cct ctc acg ttc ggc tcg ggg aca aaa ttg
                              R   S   N   W
X01668 IGKV3-11*01        --g c-- -gc a-c tgg --- -c
Z00023 IGKV4-1*01             Y   Y   S   T   P ---------->
                                      123
                          E   M   K
224G11 VL                 gaa atg aaa
```

FIGURE 18A

```
                    _____  CDR3 - IMGT  _____   <-----  FR4 - IMGT  --------
                                          110                   115                    120
                     Q    S    K    E    D    P    L    T    F    G    S    G    T    K    L
224G11 VL            caa  agt  aag  gag  gat  cct  ctc  acg  ttc  ggc  tcg  ggg  aca  aaa  ttg
                                                                       G                        V
AF103571 IGKJ4*02    --   ---  ---  ---  gga  ---  --c  --g  g--

---------->
                             123
                     E    M    K
224G11 VL            gaa  atg  aaa
                          I
AF103571 IGKJ4*02    --g  --c  ---  c
```

FIGURE 18B

```
                     FR1-IMGT             CDR1-IMGT        FR2-IMGT         CDR2-IMGT
                     (1-26)               (27-38)          (39-55)          (56-65)

1        10        20         30          40        50         60
               ....|....|....|....|....  ...|........  .|....|....|.....  ....|.....
224G11 VL      DIVLTQSPASLAVSLGQRATISCRAS ESVDSYANSF..  MHWYQQKPGQPPKLLIY  RAS.......
               3        3 33 2 3    3                  11        2 3
Human FR       E--------T-SL-P-E---L-----      ......  LA--------A-R----
224G11 HZ1VL   EIVLTQSPATLSLSPGERATLSCRAS ESVDSYANSF..  MHWYQQKPGQAPRLLIY  RAS.......

FR3-IMGT                     CDR3-IMGT       FR4-IMGT
                          (66-104)                     (105-113)       (114-123)

70        80        90       100         110            120
               ....|.........|.........|.........|....   .....|...     ......|.....
224G11 VL      NLESGIP.ARFSGSG..SRTDFTLTINPVEADDVATYYC    QQSKEDPLT     FGSGTKLEMK
rank            223            1         323 33 2 3                      3    3 3
Human FR       -RAT---.--------..-G-------SSL-PE-F-V---                 --G---V-I-
224G11 HZ1VL   NRATGIP.ARFSGSG..SRTDFTLTISSLEPEDFAVYYC    QQSKEDPLT     FGGGTKVEIK
```

FIGURE 19A

```
                     FR1-IMGT             CDR1-IMGT        FR2-IMGT         CDR2-IMGT
                     (1-26)               (27-38)          (39-55)          (56-65)

1        10        20         30          40        50         60
               ....|....|....|....|....  ...|........  .|....|....|.....  ....|.....
224G11 VL      DIVLTQSPASLAVSLGQRATISCRAS ESVDSYANSF..  MHWYQQKPGQPPKLLIY  RAS.......
               1        3        3  3 32                11
Human FR       DIVMTQSPDSLAVSLGERATINCKSS                LAWYQQKPGQPPKLLIY
224G11 HZ2VL   DIVLTQSPDSLAVSLGERATINCKSS ESVDSYANSF..   MHWYQQKPGQPPKLLIY  RAS.......

FR3-IMGT                     CDR3-IMGT       FR4-IMGT
                          (66-104)                     (105-113)       (114-123)

70        80        90       100         110            120
               ....|.........|.........|.........|....   .....|...     ......|.....
224G11 VL      NLESGIP.ARFSGSG..SRTDFTLTINPVEADDVATYYC    QQSKEDPLT     FGSGTKLEMK
                22  3 3         1         3233 3   3                     3    3 3
Human FR       TRESGVP.DRFSGSG..SGTDFTLTISSLQAEDVAVYYC                  FGGGTKVEIK
224G11 HZ2VL   TRESGVP.DRFSGSG..SRTDFTLTISSLQAEDVAVYYC    QQSKEDPLT     FGGGTKVEIK
```

FIGURE 19B

```
                    <----------------------------------------- FR1 - IMGT
                    1           5              10                15
                    E  V  Q  L  Q  Q  S  G  P     E  L  V  K  P
224G11 VH           gag gtc cag ctg caa cag tct gga cct ... gag ctg gtg aag cct

AC090843 IGHV1-18*01 --- --- --- --- --- --- --- --- --- ... --- --- --- --- ---

------------------------------------------>
                              20              25                30
                    G  A  S  V  K  I  S  C  K  T  S  G  Y  I  F
224G11 VH           ggg gct tca gtg aag ata tcc tgc aag act tct gga tac ata ttc
                                         P       A              T
AC090843 IGHV1-18*01 --- --- --- --- --- --- c-- --- --- g-- --- --- --- -c- ---

__ CDR1 - IMGT           <-------------------------
                              35                  40                45
                    T  A  Y  T              M  H  W  V  R  Q  S
224G11 VH           act gca tac acc ... ... ... ... atg cac tgg gtg agg cag agc
                       D  N                       D              K
AC090843 IGHV1-18*01 --- -ac --- -a- ... ... ... --- g-- --- --- -a- --- ---

FR2 - IMGT ------------------------------>      CDR2
                              50              55                60
                    L  G  E  S  L  D  W  I  G  G  I  K  P  N  N
224G11 VH           ctt gga gag agc ctt gac tgg att gga ggt att aaa cca aac aat
                    H     K        E           D           N
AC090843 IGHV1-18*01 -a- --- a-- --- --- -g- --- --- -a- --- --t --t --- ---

- IMGT                   <-----------------------------
                              65              70                75
                    G  L  A        N  Y  N  Q  K  F  K     G  K
224G11 VH           ggt ctt gct ... ... aac tac aac cag aag ttc aag ... ggc aag
                       G  T              T
AC090843 IGHV1-18*01 --- gg- a-- ... ... -t- --- --- --- --- --- --- ... --- ---

------------------------------ FR3 - IMGT ---------------
                              80              85                90
                    A  T  L  T  V  D  K  S  S  S  T  A  Y  M  D
224G11 VH           gcc aca ttg act gta gac aag tcc tcc agc aca gcc tac atg gac
                                                                        E
AC090843 IGHV1-18*01 --- --- --- --- --- --- --- --- --- --- --- --- --- --g ------------------------------------------------------>
                              95              100               105
                    L  R  S  L  T  S  E  D  S  A  V  Y  Y  C  A
224G11 VH           ctc cgc agc ctg aca tct gag gat tct gca gtc tat tac tgt gca
                                                  T
AC090843 IGHV1-18*01 --- --- --- --- --- --- --- --c a-- --- --- --- --- --- ---

CDR3 - IMGT           <-------------------
                              110               115               120
                    R  S  E  I  T  T  E  F  D  Y  W  G  Q  G  T
224G11 VH           aga tct gag att acg acg gaa ttt gac tac tgg ggc caa ggc acc

AC090843 IGHV1-18*01 ---

FR4 - IMGT -------->
                                126
                    A  L  T  V  S  S
224G11 VH           gct ctc aca gtc tcc tca
```

FIGURE 20A

```
                         _____ CDR3 -  IMGT _____
                    105                110                  115
                     A   R   S   E   I   T   T   E   F   D   Y
224G11 VH           gca aga tct gag att acg acg gaa ttt gac tac
J00431 IGHD2-4*01           a-- at- --- --- --
```

FIGURE 20B

```
                     _____ CDR3 -  IMGT _____        <------------------
                              110                  115                  120
                     R   S   E   I   T   T   E   F   D   Y   W   G   Q   G   T
224G11 VH           aga tct gag att acg acg gaa ttt gac tac tgg ggc caa ggc acc
                                                 Y
V00770 IGHJ2*01     ... ... ... ... ... .ac t-c --- --- --- --- --- --- ---

FR4 - IMGT -------->
                                      126
                     A   L   T   V   S   S
224G11 VH           gct ctc aca gtc tcc tca
                     T
V00770 IGHJ2*01     a-- --- --- --- --- --- g
```

FIGURE 20C

```
                          <---------------------------------------- FR1 - IMGT
                          1               5                   10                  15
                          E   V   Q   L   Q   Q   S   G   P       E   L   V   K   P
224G11 VH                 gag gtc cag ctg caa cag tct gga cct ... gag ctg gtg aag cct
                          Q               V               A               V   K
X62106 IGHV1-2*02         c-- --g --- --- gtg --- --- --g g-- ... --- g-- aa- --- ---

----------------------------------------->
                                          20                  25                  30
                          G   A   S   V   K   I   S   C   K   T   S   G   Y   I   F
224G11 VH                 ggg gct tca gtg aag ata tcc tgc aag act tct gga tac ata ttc
                                          V                   A                   T
X62106 IGHV1-2*02         --- --c --- --- --- g-c --- --- --- c-- --- --- --- -cc ---

___ CDR1 - IMGT _____ <--------------------------
                                          35                  40                  45
                          T   A   Y   T                       M   H   W   V   R   Q   S
224G11 VH                 act gca tac acc ... ... ... ... atg cac tgg gtg agg cag agc
                                  G   Y                                           A
X62106 IGHV1-2*02         --c -gc --- tat ... ... ... ... --- --- --- --- c-a --- gc- FR2 - IMGT ------------------------->                     CDR2
                                          50                  55                  60
                          L   G   E   S   L   D   W   I   G   G   I   K   P   N   N
224G11 VH                 ctt gga gag agc ctt gac tgg att gga ggt att aaa cca aac aat
                                  P   Q   G           E           M           W   S
X62106 IGHV1-2*02         -c- --- c-a g-g --- --g --- --g --- t-g --c --c --t --- -g-

- IMGT _____ <----------------------------------------
                                          65                  70                  75
                          G   L   A           N   Y   N   Q   K   F   K       G   K
224G11 VH                 ggt ctt gct ... ... aac tac aac cag aag ttc aag ... ggc aag
                                  C   T                       A                   Q   R
X62106 IGHV1-2*02         --- ggc a-a ... ... --- --t gca --- --- --t c-- ... --- -g-

------------------------------- FR3 - IMGT ----------------
                                          80                  85                  90
                          A   T   L   T   V   D   K   S   S   S   T   A   Y   M   D
224G11 VH                 gcc aca ttg act gta gac aag tcc tcc agc aca gcc tac atg gac
                                  V   M       R           T       I                   E
X62106 IGHV1-2*02         -t- --c a-- --c agg --- -c- --- at- --- --- --- --- --- --g ----------------------------------------->
                                          95                  100                 105
                          L   R   S   L   T   S   E   D   S   A   V   Y   Y   C   A
224G11 VH                 ctc cgc agc ctg aca tct gag gat tct gca gtc tat tac tgt gca
                                  S           R           R           D           T
X62106 IGHV1-2*02         --g a-- --g --- -g- --- --c --c a-g --c --g --- --- --- --g _____ CDR3 - IMGT _____ <----- FR4 - IMGT
                                          110                 115                 120
                          R   S   E   I   T   T   E   F   D   Y   W   G   Q   G   T
224G11 VH                 aga tct gag att acg acg gaa ttt gac tac tgg ggc caa ggc acc X62106 IGHV1-2*02         --- ga ---------------------->
                                          126
                          A   L   T   V   S   S
224G11 VH                 gct ctc aca gtc tcc tca
```

FIGURE 21A

```
                        _____ CDR3 - IMGT _____  <----- FR4 - IMGT
                                     110                115                  120
                        R   S   E   I   T   T   E   F   D   Y   W   G   Q   G   T
224G11 VH               aga tct gag att acg acg gaa ttt gac tac tgg ggc caa ggc acc
                                                        Y
J00256 IGHJ4*01         ... ... ... ... .ac t-c --- --- --- --- --- --- --a ---

---------------------->
                                         126
                        A   L   T   V   S   S
224G11 VH               gct ctc aca gtc tcc tca
                        L   V
J00256 IGHJ4*01         ctg g-- --c --- --- --- g
```

FIGURE 21B

```
                        FR1-IMGT              CDR1-IMGT          FR2-IMGT            CDR2-IMGT
                         (1-26)                (27-38)           (39-55)              (56-65)

1         10        20           30            40         50              60
              ....|.........|......     ...|........    .|.........|.....     ....|.....
224G11 VH     EVQLQQSGP.ELVKPGASVKISCKTS GYIFTAYT....    MHWVRQSLGESLDWIGG     IKPNNGLA..
rank          3    3   3 33        3   2                         33 22 1 2 1
Human FR      Q---V---A.-VK-------V---A-                 ------AP-QG-E-M-W
224G11 HZVH   QVQLVQSGA.EVKKPGASVKVSCKAS GYIFTAYT....    MHWVRQAPGQGLDWMGG     IKPNNGLA..

FR3-IMGT                      CDR3-IMGT        FR4-IMGT
                              (66-104)                      (105-115)        (116-126)

70        80        90       100              110              120
              ....|.........|.........|.........|....    .....|......     ....|......
224G11 VH     NYNQKFK.GKATLTVDKSSSTAYMDLRSLTSEDSAVYYC     ARSEITTEFDY      WGQGTALTVSS
rank            3   3   32 2 1 1 3   2 33 3 3 3                             33
Human FR      --A---Q.-RV-M-R-T-I-----E-SR-R-D-T-----                      -----LV----
224G11 HZVH   NYAQKFQ.GRVTMTVDKSISTAYMELSRLRSDDTAVYYC     ARSEITTEFDY      WGQGTLVTVSS
```

FIGURE 22

```
                    <------------------------------------------ FR1 - IMGT
                    1                   5                  10                  15
                    G    I    V    L    T    Q    S    P    A    S    L    A    V    S    L
227E1 VL            ggc  att  gtg  ttg  acc  caa  tct  cca  gct  tct  ttg  gct  gtg  tct  cta
                                                                                            D
K02161 IGKV3-5*01   -a-  ---  ---  c--  ---  ---  ---  ---  ---  ---  ---  ---  ---  ---  ---

--------------------------------------------->
                                   20                  25                  30
                    G    Q    R    A    T    I    S    C    R    V    S    E    S    I    D
227E1 VL            gga  cag  agg  gcc  acc  ata  tcc  tgc  aga  gtc  agt  gaa  agt  att  gat
                                                            A                   V
K02161 IGKV3-5*01   --g  ---  ---  ---  ---  ---  ---  ---  ---  -c-  ---  ---  ---  g--  ---

CDR1 - IMGT                       <--------------------------
                                       35                  40                  45
                    T    Y    G    N    S    F              I    H    W    Y    Q    Q    K
227E1 VL            act  tat  ggc  aat  agt  ttt  ...  ...  ata  cac  tgg  tac  cag  cag  aaa
                    S                                   M
K02161 IGKV3-5*01   -g-  ---  ---  ---  ---  ---  ...  ...  --g  ---  ---  ---  ---  ---  ---

FR2 - IMGT --------------------------->                         CDR2
                                   50                  55                  60
                    P    G    Q    P    P    K    L    L    I    Y    R    A    S
227E1 VL            cca  gga  cag  cca  ccc  aaa  ctc  ctc  atc  tat  cgt  gca  tcc  ...  ...
K02161 IGKV3-5*01   ---  ---  ---  ---  ---  ---  ---  ---  ---  ---  ---  ---  ---  ...  ...

- IMGT            <-----------------------------------------
                                   65                  70                  75
                                        N    L    E    S    G    I    P         A    R
227E1 VL            ...  ...  ...  ...  ...  aac  cta  gaa  tct  ggg  atc  cct  ...  gcc  agg
K02161 IGKV3-5*01   ...  ...  ...  ...  ...  ---  ---  ---  ---  ---  ---  ---  ...  ---  ---

------------------------------ FR3 - IMGT ---------------
                                   80                  85                  90
                    F    S    G    S    G              S    R    T    D    F    T    L    T
227E1 VL            ttc  agt  ggc  agt  ggg  ...  ...  tct  agg  aca  gac  ttc  acc  ctc  acc
K02161 IGKV3-5*01   ---  ---  ---  ---  ---  ...  ...  ---  ---  ---  ---  ---  ---  ---  ---

--------------------------------------------------------->
                                   95                 100                 105
                    I    N    P    V    E    A    D    D    S    A    T    Y    Y    C    Q
227E1 VL            att  aat  cct  gtg  gag  gct  gat  gat  tct  gca  acc  tat  tac  tgt  cag
                                                       V
K02161 IGKV3-5*01   ---  ---  ---  ---  ---  ---  ---  gt-  ---  ---  ---  ---  ---  ---  ---

CDR3 - IMGT               <-------------- FR4 - IMGT
                                       110                 115                 120
                    Q    S    N    E    D    P    F    T    F    G    S    G    T    K    L
227E1 VL            caa  agt  aat  gag  gat  cca  ttc  acg  ttc  ggc  tcg  ggg  aca  aag  ttg
K02161 IGKV3-5*01   ---  ---  ---  ---  ---  --t  cc ---------->
                              123
                    E    M    K
227E1 VL            gaa  atg  aaa
```

FIGURE 23A

```
              _____ CDR3 - IMGT _____   <------------- FR4 - IMGT
                            110                     115                120
                  Q   S   N   E   D   P   F   T   F   G   S   G   T   K   L
227H1 VL        caa agt aat gag gat cca ttc acg ttc ggc tcg ggg aca aag ttg V00777 IGKJ4*01                                 - --- --- --- --- --- --- --- --- ---

---------->
                       123
                  E   M   K
227H1 VL        gaa atg aaa
                       I
V00777 IGKJ4*01 --- --a --- c
```

FIGURE 23B

```
                         <------------------------------------------ FR1 - IMGT
                         1               5                   10                  15
                         G   I   V   L   T   Q   S   P   A   S   L   A   V   S   L
227H1 VL                 ggc att gtg ttg acc caa tct cca gct tct ttg gct gtg tct cta
                                                             T           S       P
X01668 IGKV3-11*01       -aa --- --- --- --a --g --- --- --c a-c c-- t-- t-- --- -c-
Z00023 IGKV4-1*01        D           M                   D ------------------------------------------>
                                         20                  25                  30
                         G   Q   R   A   T   I   S   C   R   V   S   E   S   I   D
227H1 VL                 gga cag agg gcc acc ata tcc tgc aga gtc agt gaa agt att gat
                             E           L               A       Q       V       S
X01668 IGKV3-11*01       --g g-a --a --- c-c --- --- --g -c- --- c-g --- g-- agc
Z00023 IGKV4-1*01            E           N       K   S       Q       V ___ CDR1 - IMGT _____  <--------------------------
                                         35                  40                  45
                         T   Y   G   N   S   F               I   H   W   Y   Q   Q   K
227H1 VL                 act tat ggc aat agt ttt ... ... ata cac tgg tac cag cag aaa
                         S                                   L   A
X01668 IGKV3-11*01       -gc --c ... ... ... ... ... ... t-- gc- --- --- --a --- ---
Z00023 IGKV4-1*01        Y   S   S       N   K   N   Y   L   A FR2 - IMGT -------------------------->         CDR2
                                         50                  55                  60
                         P   G   Q   P   P   K   L   L   I   Y   R   A   S
227H1 VL                 cca gga cag cca ccc aaa ctc ctc atc tat cgt gca tcc ... ...
                                         A               R               D
X01668 IGKV3-11*01       --t --c --- g-t --- -gg --- --- --- ga- --- --- ... ...
Z00023 IGKV4-1*01                                                            W

- IMGT _____  <----------------------------------------
                                         65                  70                  75
                                             N   L   E   S   G   T   P       A   R
227H1 VL                 ... ... ... ... ... aac cta gaa tct ggg atc cct ... gcc agg
                                             R   A   T
X01668 IGKV3-11*01       ... ... ... ... ... --- agg -cc a-- --c --- --a ... --- ---
Z00023 IGKV4-1*01                            T   R           V               D ------------------------------- FR3 - IMGT ---------------
                                         80                  85                  90
                         F   S   G   S   G               S   R   T   D   F   T   L   T
227H1 VL                 ttc agt ggc agt ggg ... ... tct agg aca gac ttc acc ctc acc
                                                         G
X01668 IGKV3-11*01       --- --- --- --- --- ... ... --- g-- --- --- --- --t --- ---
Z00023 IGKV4-1*01                                        G ------------------------------------------------------->  ___
                                         95                  100                 105
                         I   N   P   V   E   A   D   D   S   A   T   Y   Y   C   Q
227H1 VL                 att aat cct gtg gag gct gat gat tct gca acc tat tac tgt cag
                         S   S   L           P   E       F       V
X01668 IGKV3-11*01       --c -gc agc c-a --- c-- --a --- -t- --- gtt --- --- --- ---
Z00023 IGKV4-1*01        S   S   L       Q       E       V       V _____ CDR3 - IMGT _____   <-------------- FR4 - IMGT
                                         110                 115                 120
                         Q   S   N   Q   D   P   F   T   F   G   S   G   T   K   L
227H1 VL                 caa agt aat cag gat cca ttc acg ttc ggc tcg ggg aca aag ttg
                             R   S   N   W
X01668 IGKV3-11*01       --g c-- -gc a-c tgg --t cc
Z00023 IGKV4-1*01

---------->
                                         123
                         E   M   K
227H1 VL                 gaa atg aaa
```

FIGURE 24A

```
                    _____ CDR3 - IMGT _____  <------------- FR4 - IMGT
                                       110                115              120
                     Q   S   N   E   D   P   F   T   F   G   S   G   T   K   L
227H1 VL             caa agt aat gag gat cca ttc acg ttc ggc tcg ggg aca aag ttg
                                                     L               G           V
AF103571 IGKJ4*02                            g c-- --- --- --- gga --- --c --- g--

---------->
                            123
                     E   M   K
227H1 VL             gaa atg aaa
                         I
AF103571 IGKJ4*02    --g --c --- c
```

FIGURE 24B

```
                        FR1-IMGT           CDR1-IMGT       FR2-IMGT         CDR2-IMGT
                         (1-26)             (27-38)         (39-55)          (56-65)

1         10        20           30          40      50          60
                  .........|.........|......    ...|.......  .|........|.....   ....|.....
227H1 VL          GIVLTQSPASLAVSLGQRATISCRVS    ESIDTYGNSF.. IHWYQQKPGQPPKLLIY  RAS.......
                  3        3 33 2 3   3    2                 11         2 3
Human FR          E--------T-SL-P-E---L---A-    ......       LA--------A-R----  .......
227H1 HZ1VL       EIVLTQSPATLSLSPGERATLSCRAS    ESIDTYGNSF.. IHWYQQKPGQAPRLLIY  RAS.......

FR3-IMGT                      CDR3-IMGT    FR4-IMGT
                                (66-104)                      (105-113)    (114-123)

70        80        90        100           110          120
                  ....|.........|.........|.........|....      ....|...    ......|.....
227H1 VL          NLESGIP.ARFSGSG..SRTDFTLTINPVEADDSATYYC       QQSNEDPFT   FGSGTKLEMK
                  223           1        323 33 2 3                        3    3 3
Human FR          -RAT---.--------..-G-------SSL-PE-F-V---                  --G---V-I-
227H1 HZ1VL       NRATGIP.ARFSGSG..SRTDFTLTISSLEPEDFAVYYC       QQSNEDPFT   FGGGTKVEIK
```

FIGURE 25 A

```
                        FR1-IMGT           CDR1-IMGT       FR2-IMGT         CDR2-IMGT
                         (1-26)             (27-38)         (39-55)          (56-65)

1         10        20           30          40      50          60
                  .........|.........|......    ...|.......  .|........|.....   ....|.....
227H1 VL          GIVLTQSPASLAVSLGQRATISCRVS    ESIDTYGNSF.. IHWYQQKPGQPPKLLIY  RAS.......
                  3 1      3        3    3 32                11
Human FR          DIVMTQSPDSLAVSLGERATINCKSS                 LAWYQQKPGQPPKLLIY  .......
227H1 HZ2VL       DIVLTQSPDSLAVSLGERATINCKSS    ESIDTYGNSF.. IHWYQQKPGQPPKLLIY  RAS.......

FR3-IMGT                      CDR3-IMGT    FR4-IMGT
                                (66-104)                      (105-113)    (114-123)

70        80        90        100           110          120
                  ....|.........|.........|.........|....      ....|...    ......|.....
227H1 VL          NLESGIP.ARFSGSG..SRTDFTLTINPVEADDSATYYC       QQSNEDPFT   FGSGTKLEMK
                  22   3   3              1        3233 3 3 3              3    3 3
Human FR          TRESGVP.DRFSGSG..SGTDFTLTISSLQAEDVAVYYC                   FGGGTKVEIK
227H1 HZ2VL       TRESGVP.DRFSGSG..SRTDFTLTISSLQAEDVAVYYC       QQSNEDPFT   FGGGTKVEIK
```

FIGURE 25 B

```
                         <----------------------------------- FR1 - IMGT
                         1             5                  10                  15
                         E   V   Q   L   Q   Q   S   G   P       E   L   V   K   P
227H1 VH                 gag gtc cag ctg caa cag tct gga cct ... gaa ctg gtg aag cct AC090843 IGHV1-18*01     --- --- --- --- --- --- --- --- --- ... --g --- --- --- ---

------------------------------------------>
                                         20                  25                  30
                         G   A   S   M   K   I   S   C   K   A   S   G   Y   S   F
227H1 VH                 gga gct tca atg aag att tcc tgc aag gct tct ggt tat tca ttc
                                     V           P                           T
AC090843 IGHV1-18*01     --g --- --- g-- --- --a c-- --- --- --- --- --a --c a-- ---

CDR1 - IMGT
                                         35                      40                  45
                         T   D   Y   T                   L   N   W   V   K   Q   S
227H1 VH                 act gac tac acc ... ... ... ... ctg aac tgg gtg aag cag agc
                                     N                   M   D
AC090843 IGHV1-18*01     --- --- --- -a- ... ... ... ... a-- g-- --- --- --- --- ---

FR2 - IMGT ------------------------->                 CDR2
                                         50                  55                  60
                         H   G   K   T   L   E   W   I   G   L   I   N   P   Y   N
227H1 VH                 cat gga aag acc ctt gag tgg att gga ctt att aat cct tac aat
                                     S                   D               N
AC090843 IGHV1-18*01     --- --- --- -g- --- --- --- --- ga- --- --- --- a-- ---

- IMGT         <------------------------------------
                                        65                  70                  75
                         G   G   T               T   Y   N   Q   K   F   K       K
227H1 VH                 ggt ggt act ... ... acc tac aac cag aag ttc aag ... cgc aag
                                                 I
AC090843 IGHV1-18*01     --- --- --- ... ... -t- --- --- --- --- --- --- ... --- ---

----------------------------- FR3 - IMGT ---------------
                                         80                  85                  90
                         A   T   L   T   V   D   K   S   S   S   T   A   Y   M   E
227H1 VH                 gcc aca tta act gta gac aag tca tcc agc aca gcc tac atg gag AC090843 IGHV1-18*01     --- --- --g --- --- --- --- --c --- --- --- --- --- --- ---

--------------------------------------------------------->
                                         95                  100                 105
                         L   L   S   L   T   S   E   D   S   A   V   Y   Y   C   A
227H1 VH                 ctc ctc agt ctg aca tct gag gac tct gca gtc tat tac tgt gca
                                     R                   T
AC090843 IGHV1-18*01     --- -g- --c --- --- --- --- --- a-- --- --- --- --- --- ---

CDR3 - IMGT                 <-------------------
                                         110                 115                 120
                         R   E   E   I   T   K   D   F   D   F   W   G   Q   G   T
227H1 VH                 aga gag gaa att acg aag gac ttt gat ttc tgg ggc caa ggc acc

AC090843 IGHV1-18*01     ---

FR4 - IMGT -------->
                                         126
                         T   L   T   V   S   S
227H1 VH                 act ctc aca gtc tcc tca
```

FIGURE 26A

```
                          _____ CDR3 - IMGT _____
                         105                110                     115
                          A   R   E   E   I   T   K   D   F   D   F
227H1 VH                 gca aga gag gaa att acg aag gac ttt gat ttc
IGHD1-1*02                   -t- -t-     gc- --
```

FIGURE 26B

```
                            _____ CDR3 - IMGT _____  <------------------
                                        110                115                     120
                             R   E   E   I   T   K   D   F   D   F   W   G   Q   G   T
227H1 VH                    aga gag gaa att acg aag gac ttt gat ttc tgg ggc caa ggc acc
                                                         Y           Y
V00770 IGHJ2*01             ... ... ... ... .-c t-- --- --c -a- --- --- --- --- ---

FR4 - IMGT -------->
                                              126
                             T   L   T   V   S   S
227H1 VH                    act ctc aca gtc tcc tca V00770 IGHJ2*01             --- --- --- --- --- --- g
```

FIGURE 26C

```
                         <----------------------------------- FR1 - IMGT
                         1            5                  10                15
                         E   V   Q   L   Q   Q   S   G   P       E   L   V   K   P
227H1 VH                 gag gtc cag ctg caa cag tct gga cct ... caa ctg gtg aag cct
                             Q               V       A           Q       V   K
X62106 IGHV1-2*02        c-- --g --- --- gtg --- --- -g- g-- ... -g  g-- aa- --- ---

---------------------------------------->
                                     20                  25                30
                         G   A   S   M   K   I   S   C   K   A   S   G   Y   S   F
227H1 VH                 gga gct tca atg aag att tcc tgc aag gct tct ggt tat tca ttc
                                         V           V                       T
X62106 IGHV1-2*02        --g --c --- g-- --- g-c --- --- --- --- --- --- --a --a a-c ---

___ CDR1 - IMGT _____   <--------------------------
                                             35                40                45
                         T   D   Y   T                   L   N   W   V   K   Q   S
227H1 VH                 act gac tac acc ... ... ... ... ctg aac tgg gtg aag cag agc
                                 G   Y                   M   H           R       A
X62106 IGHV1-2*02        --c -g- --- tat ... ... ... ... a-- c-- --- --- cga --- gc- FR2 - IMGT ------------------------->          CDR2
                                             50                 55                 60
                         H   G   K   T   L   E   W   I   G   L   I   N   P   Y   N
227H1 VH                 cat gga aag acc ctt gag tgg att gga ctt att aat cct tac aat
                         P       Q   G                       M       W           N
X62106 IGHV1-2*02        -c- --- c-a ggg --- --- --- --g --- tgg --c --c --- a-- -g-

- IMGT _____                <----------------------------
                                         65                  70                  75
                         G   G   T                   T   Y   N   Q   K   F   K       G   K
227H1 VH                 ggt ggt act ... ... acc tac aac cag aag ttc aag ... ggc aag
                                                 N   A                   Q               R
X62106 IGHV1-2*02        --- --c --a ... ... -a- --t gca --- --- --t c-- ... --- -g-

------------------------------                 FR3 - IMGT ---------------
                                             80                 85                  90
                         A   T   L   T   V   D   K   S   S   S   T   A   Y   M   E
227H1 VH                 gcc aca tta act gta gac aag tca tcc agc aca gcc tac atg gag
                         V       M           R       T               I
X62106 IGHV1-2*02        -t- --- a-g --c agg --- -c- --c at- --- --- --- --- --- ---

-------------------------------------------------------> ___
                                             95                100                105
                         L   L   S   L   T   S   E   D   S   A   V   Y   Y   C   A
227H1 VH                 ctc ctc agt ctg aca tct gag gac tct gca gtc tat tac tgt gca
                                 S       R                   T
X62106 IGHV1-2*02        --g ag- --g --- -g- --- --c --- a-g --c --g --- --- --- --g CDR3 - IMGT _____           <--------------------
                                             110                115                120
                         R   E   E   I   T   K   D   F   D   F   W   G   Q   G   T
227H1 VH                 aga gag gaa att acg aag gac ttt gat ttc tgg ggc caa ggc acc
X62106 IGHV1-2*02        --- --

FR4 - IMGT -------->
                                             126
                         T   L   T   V   S   S
227H1 VH                 act ctc aca gtc tcc tca
```

FIGURE 27A

```
                        CDR3 - IMGT                       <------------------
                              110                115                     120
                     R   E   E   I   T   K   D   F   D   F   W   G   Q   G   T
227H1 VH             aga gag gaa att acg aag gac ttt ga. ttc tgg ggc caa ggc acc
                                                     Y           Y
J00256 IGHJ4*01      ... ... ... ... ... .-c t-- --- --c -a- --- --- --- --a ---

FR4 - IMGT  -------->
                                       126
                     T   L   T   V   S   S
227H1 VH             act ctc aca gtc tcc tca
                     L       V
J00256 IGHJ4*01      ctg g-- --c --- --- --- g
```

FIGURE 27B

```
                      FR1-IMGT           CDR1-IMGT          FR2-IMGT           CDR2-IMGT
                       (1-26)             (27-38)            (39-55)            (56-65)

1         10        20            30              40        50            60
                ....|....|....|....|......    ....|........      .|....|....|....      ....|.....
227H1  VH       EVQLQQSGP.ELVKPGASMKISCKAS    GYSFTDYT....       LNWVKQSHGKTLEWIGL     INPYNGGT..
rank            3         3  3  33    3 3                        11  3 33 22   2 1
Human FR        Q---V---A.-VK-----V-V-----                       MH--R-AP-QG---M-W
227H1  HZVH     QVQLVQSGA.EVKKPGASVKVSCKAS    GYSFTDYT....       LNWVRQAPGQGLEWMGL     INPYNGGT..

FR3-IMGT                               CDR3-IMGT          FR4-IMGT
                      (66-104)                               (105-115)          (116-126)

70        80        90       100              110                 120
                ....|........|.........|.........|....           ....|......         ....|......
227H1  VH       TYNQKFK.GKATLTVDKSSSTAYMELLSLTSEDSAVYYC           AREEITKDFDF         WGQGTTLTVSS
rank            1 3     3  32 2 1 1 3           33 3 3 3                                     3 3
Human FR        N-A---Q.-RV-M-R-T-I-------SR-R-D-T-----                              -----LV----
227H1  HZVH     TYAQKFQ.GRVTMTVDKSISTAYMELSRLRSDDTAVYYC           AREEITKDFDF         WGQGTLVTVSS
```

FIGURE 28

```
                    <------------------------------------------ FR1 - IMGT
                    1              5              10             15
                    D  I  Q  M  T  Q  S  P  A  S  L  S  V  S  V
VL 223C4            gac atc cag atg act cag tct cca gcc tcc cta tct gta tct gtg AJ235956 IGKV12-46*01  --- --- --- --- --- --- --- --- --- --- --- --- --- --- ---

------------------------------------------>
                                   20             25             30
                    G  E  T  V  T  I  T  C  R  A  S  E  N  I  Y
VL 223C4            gga gaa act gtc acc atc aca tgt cga gca agt gag aat att tac AJ235956 IGKV12-46*01  --- --- --- --- --- --- --- --- --- --- --- --- --- --- ---

CDR1 - IMGT              <-------------------------
                                   35                    40             45
                    S  N                    L  A  W  Y  Q  Q  K
VL 223C4            agt aat ... ... ... ... ... tta gca tgg tat cag cag aaa

AJ235956 IGKV12-46*01  --- --- ... ... ... ... ... --- --- --- --- --- --- ---

FR2 - IMGT ------------------------->              CDR2
                                   50             55             60
                    Q  G  K  S  P  Q  L  L  V  Y  A  A  T
VL 223C4            cag gga aaa tct cct cag ctc ctg gtc tat gct gca aca ... ...

AJ235956 IGKV12-46*01  --- --- --- --- --- --- --- --- --- --- --- --- --- ... ...

- IMGT              <------------------------------
                                   65             70             75
                                         N  L  V  D  G  V  P     S  R
VL 223C4            ... ... ... ... aac tta gta gat ggt gtg cca ... tca agg
                                                  A
AJ235956 IGKV12-46*01  ... ... ... ... --- --- -c- --- --- --- --- ... --- ---

-------------------------------- FR3 - IMGT ---------------
                                   80             85             90
                    F  S  G  S  G              S  G  T  Q  Y  S  L  K
VL 223C4            ttc agt ggc agt gga ... ... tca ggc aca cag tat tcc ctc aag AJ235956 IGKV12-46*01  --- --- --- --- --- ... ... --- --- --- --- --- --- --- ---

------------------------------------------------------>
                                   95             100            105
                    I  N  S  L  Q  S  E  D  F  G  S  Y  Y  C  Q
VL 223C4            atc aac agc ctg cag tct gaa gat ttt ggg agt tat tac tgt caa AJ235956 IGKV12-46*01  --- --- --- --- --- --- --- --- --- --- --- --- --- --- ---

CDR3 - IMGT            <--------------- FR4 - IMGT
                                   110            115            120
                    H  F  W  G  P  P  Y  T  F  G  G  G  T  K  L
VL 223C4            cat ttt tgg ggt cct ccg tac acg ttc gga ggg ggg acc aag ctg
                                            T
AJ235956 IGKV12-46*01  --- --- --- --- a-- --t cc
```

FIGURE 29A

```
                    CDR3 - IMGT           <--------------- FR4 - IMGT -------->
                           110                   115            120           123
                    G  P  P  Y  T  F  G  G  G  T  K  L  E  I  K
VL 223C4            ggt cct ccg tac acg ttc gga gcg ggg acc aag ctg gag ata aag V00777 IGKJ2*01        - --- --- --- --- --- --- --- --- --- --a --- --a
```

FIGURE 29B

```
                      <------------------------------------------- FR1 - IMGT
                      1               5               10              15
                      D   I   Q   M   T   Q   S   P   A   S   L   S   V   S   V
VL 223C4              gac atc cag atg act cag tct cca gcc tcc cta tct gta tct gtg
                                                  S               A
Y14865 IGKV1-NL1*01   --- --- --- --- --c --- --- --- t-- --- --g --- -c- --- --a ------------------------------------------->
                                      20              25              30
                      G   E   T   V   T   I   T   C   R   A   S   E   N   I   Y
VL 223C4              gga gaa act gtc acc atc aca tgt cga gca agt gag aat att tac
                          D       R                           Q           G   S
Y14865 IGKV1-NL1*01   --- --c -ga --- --- --- --t --c --g --g --- c-- --- ggc --- ag- __    CDR1 - IMGT _____    <-------------------------
                                      35              40              45
                                      S   N           L   A   W   Y   Q   Q   K
VL 223C4              agt aat ... ... ... ... ... ... tta gca tgg tat cag cag aaa
                                      N   S
Y14865 IGKV1-NL1*01   -a- tc- ... ... ... ... ... ... --- --c --- --- --- --- ---

FR2 - IMGT  ----------------------->  _____ CDR2
                                      50              55              60
                      Q   G   K   S   P   Q   L   L   V   Y   A   A   T
VL 223C4              cag gga aaa tct cct cag ctc ctg gtc tat gct gca aca ... ...
                                      P       A   K           L           S
Y14865 IGKV1-NL1*01   -ca --g --- g-c --- a-- --- --- c-- --- --- --- t-c ... ...

- IMGT            <--------------------------------------
                                      65              70              75
                                          N   L   V   D   G   V   P       S   R
VL 223C4              ... ... ... ... ... aac tta gta gat ggt gtg cca ... tca agg
                                          R           E       S
Y14865 IGKV1-NL1*01   ... ... ... ... ... -ga --g -a- ag- --g --c --- ... --c ---

------------------------------- FR3 - IMGT ---------------
                                      80              85              90
                      F   S   G   S   G           S   G   T   Q   Y   S   L   K
VL 223C4              ttc agt ggc agt gga ... ... tca ggc aca cag tat tcc ctc aag
                                                              D   T
Y14865 IGKV1-NL1*01   --- --- --- --- --- ... ... --t --g g-t --c a-t --- -cc ------------------------------------------->  ____
                                      95              100             104
                      I   N   S   L   Q   S   E   D   F   G   S   Y   Y   C   Q
VL 223C4              atc aac agc ctg cag tct gaa gat ttt ggg agt tat tac tgt caa
                                      S               P               A   T
Y14865 IGKV1-NL1*01   --- -g- --- --- --- c-- --- --- --- --- -ca -c- --- --- ---

_____   CDR3 - IMGT  _____  <-------- FR4 - IMGT -----
                                      110             115             120
                      H   F   W   G   P   P   Y   T   F   G   G   T   K   L
VL 223C4              cat ttt tgg ggt cct ccg tac acg ttc gga ggg ggg acc aag ctg
                      Q   Y   Y   S   T
Y14865 IGKV1-NL1*01   --g -a- -at a-- a-c --t cc
```

FIGURE 30A

```
                      CDR3 - IMGT  _____  <--------------- FR4 - IMGT -------->
                              110             115             120             123
                              G   P   P   Y   T   F   G   G   T   K   L   E   I   K
VL 223C4                      ggt cct ccg tac acg ttc gga ggg gcg acc aag ctg gag ata aag
                                                                              Q
J00242 IGKJ2*01               - --- --t --t --c ca- --- --- --- --- --- --c --a
```

FIGURE 30B

```
                  <----------------------------------------- FR1 - IMGT
                  1             5               10              15
                   E   V   L   L   Q   Q   S   G   P       E   L   V   K   P
VH 223C4          gag gtc ctg ctg caa cag tct gga cct ... gag ctg gtg aag cct
                                   Q
AC090843 IGHV1-18*01  --- --- -a- --- --- --- --- --- --- ... --- --- --- --- ---

----------------------------------------->
                                 20              25              30
                   G   A   S   V   K   I   P   C   K   A   S   G   Y   T   F
VH 223C4          ggg gct tca gtg aag ata ccc tgc aag gct tct gga tac aca ttc AC090843 IGHV1-18*01  --- --- --- --- --- --- --- --- --- --- --- --- --- --- ---

__ CDR1 - IMGT _____        <-------------------------
                                 35              40              45
                   T   D   Y   N                   M   D   W   V   K   Q   S
VH 223C4          act gac tac aac ... ... ... ... atg gac tgg gtg aag cag agc AC090843 IGHV1-18*01  --- --- --- --- ... ... ... ... --- --- --- --- --- --- ---

FR2 - IMGT ------------------------>  _____   CDR2
                                 50              55              60
                   H   G   M   S   L   E   W   I   G   D   I   N   P   N   N
VH 223C4          cat gga atg agc ctt gag tgg att gga gat att aat cct aac aat
                                 K
AC090843 IGHV1-18*01  --- --- -a- --- --- --- --- --- --- --- --- --- --- --- ---

- IMGT _____     <-----------------------------------
                                 65              70              75
                   G   G   T               I   F   N   Q   K   F   K       K
VH 223C4          ggt ggt act ... ... ... atc ttc aac cag aag ttc aag ... ggc aag
                                                       Y
AC090843 IGHV1-18*01  --- --- --- ... ... ... --- -a- --- --- --- --- --- ... --- ---

------------------------------ FR3 - IMGT ---------------
                                 80              85              90
                   A   T   L   T   V   D   K   S   S   S   T   A   Y   M   E
VH 223C4          gcc aca ttg act gta gac aag tcc tcc agc aca gcc tac atg gag AC090843 IGHV1-18*01  --- --- --- --- --- --- --- --- --- --- --- --- --- --- ---

----------------------------------------->   ___
                                 95              100             105
                   L   R   S   L   T   S   E   D   T   A   V   Y   Y   C   A
VH 223C4          ctc cgc agc ctg aca tct gag gac act gca gtc tat tac tgt gca AC090843 IGHV1-18*01  --- --- --- --- --- --- --- --- --- --- --- --- --- --- ---
```

FIGURE 32A

```
                           CDR3 - IMGT
                              110              115
                   R   G   R   Y   V   G   Y   Y   Y   A   M   D   Y
VH 223C4          aga ggg agg tat gtt ggt tac tac tat gct atg gac tac
                                       D
D13199 IGHD6-3*01          ... .tc --- -a- --- --- --- ---
```

FIGURE 32B

```
                 ___ CDR3 - IMGT _____  <------------- FR4 - IMGT ------------->
                                  115                120               125              129
                   G   Y   Y   Y   A   M   D   Y   W   G   Q   G   T   S   V   T   V   S   S
VH 223C4         ggt tac tac tat gct atg gac tac tgg ggt caa gga acc tca gtc acc gtc tcc tca V00770 IGHJ4*01  -t- --- --- --- --- --- --- --- --- --- --- --- --- --- --- --- --- --- ---
```

FIGURE 32C

```
                 <---------------------------------------------- FR1 - IMGT
                 1               5                   10                  15
                   E   V   L   L   Q   Q   S   G   P   E   L   V   K   P
VH 223C4         gag gtc ctg ctg caa cag tct gga cct ... gag ctg gtg aag cct
                   Q       Q   V               A           V   K
X62106 IGHV1-2*02 c-- --g -a- --- gtg --- --- -g g-- ... --- g-- aa- --- ---

-------------------------------------------->
                                 20                  25                  30
                   G   A   S   V   K   I   P   C   K   A   S   G   Y   T   F
VH 223C4         ggg gct tca gtg aag ata ccc tgc aag gct tct gga tac aca ttc
                                         V   S
X62106 IGHV1-2*02 --- --c --- --- --- g-c t-- --- --- --- --- --- --- --c ---

___ CDR1 - IMGT _____  <--------------------------
                                  35                  40                  45
                   T   D   Y   N                   M   D   W   V   K   Q   S
VH 223C4         act gac tac aac ... ... ... ... atg gac tgg gtg aag cag agc
                       G   Y                       H       R           R   A
X62106 IGHV1-2*02 --c -g- --- t-t ... ... ... ... --- c-- --- --- cga --- gc- FR2 - IMGT ------------------------->  _____  CDR2
                                 50                  55                  60
                   H   G   M   S   L   E   W   I   G   D   I   N   P   N   N
VH 223C4         cat gga atg agc ctt gag tgg att gga gat att aat cct aac aat
                   P   Q   G                   M   W                       S
X62106 IGHV1-2*02 -c- --- caa g-g --- --- --- --g --- tgg --c --c --- --- -g-

- IMGT _____  <--------------------------------------------
                             65                  70                  75
                   G   G   T           I   F   N   Q   K   F   K           G   K
VH 223C4         ggt ggt act ... ... atc ttc aac cag aag ttc aag ... gcc aag
                                       N   Y   A               Q               R
X62106 IGHV1-2*02 --- --c --a ... ... -a- -at gca --- --- --t c-- ... --- -g-

------------------------------  FR3 - IMGT ---------------
                                 80                  85                  90
                   A   T   L   T   V   D   K   S   S   S   T   A   Y   M   E
VH 223C4         gcc aca ttg act gta gac aag tcc tcc agc aca gcc tac atg gag
                   V       M       R           T       I
X62106 IGHV1-2*02 -t- --c a-- --c agg --- -c- --- at- --- --- --- --- --- ---

-------------------------------------------->
                                 95                  100                 105
                   L   R   S   L   T   S   E   D   T   A   V   Y   Y   C   A
VH 223C4         ctc cgc agc ctg aca tct gag gac act gca gtc tat tac tgt gca
                       S       R               D
X62106 IGHV1-2*02 --g a-- --g --- -g- --- --c --- -g- --c --g --- --- --- --g
```

FIGURE 33A

```
                              _____ CDR3 - IMGT _____
                                          110                115
                              R   G   R   Y   V   G   Y   Y   Y   A   M   D   Y
VH 223C4                      aga ggg agg tat gtt ggt tac tac tat gct atg gac tac X97051 IGHD1-26*01             -t  --- --c --c tac
```

FIGURE 33B

```
                              _____ CDR3 - IMGT _____  <-------------- FR4 - IMGT
                                          110                115                  120                125
                              R   Y   V   G   Y   Y   Y   A   M   D   Y   W   G   Q   G   T   S   V
VH 223C4                      agg tat gtt ggt tac tac tat gct atg gac tac tgg gct caa gga acc tca gtc
                                      Y   Y               G           V                           T
J00256 IGHJ6*01                -- tac tac --- --- --c -g- --- --- gt- --- --g --- --g --- a-g ---

------------->
                                          129
                              T   V   S   S
VH 223C4                      acc gtc tcc tca

J00256 IGHJ6*01               --- --- --- ---
```

FIGURE 33C

```
                           <----------------------------------------  FR1 - IMGT
                           1         5                   10                  15
Hz VH 223C4                Q  V  Q  L  V  Q  S  G  A     E  V  K  K  P
Back-mutation              E     L        Q        P        V
                           2     2        2        3        3

----------------------------------------->
                                          20                  25                  30
Hz VH 223C4                G  A  S  V  K  V  S  C  K  A  S  G  Y  T  F
Back-mutation                                   P
                                                3

__  CDR1 - IMGT  _____  <-------------------------
                                             35                  40                  45
Hz VH 223C4                T  D  Y  N              M  H  W  V  R  Q  A
Back-mutation                                         D              S
                                                      1              1

FR2 - IMGT ------------------------->  _____  CDR2
                                          50                  55                  60
Hz VH 223C4                P  G  Q  G  L  E  W  M  G  W  I  N  P  N  N
Back-mutation              H     M                    D
                           3     2                    1

-  IMGT  _____  <-----------------------------------
                                          65                  70                  75
Hz VH 223C4                G  G  T        N  Y  A  Q  K  F  Q     G  R
Back-mutation                             I  F
                                          1  1

------------------------------  FR3 - IMGT  ---------------
                                          80                  85                  90
Hz VH 223C4                V  T  M  T  R  D  T  S  I  S  T  A  Y  M  E
Back-mutation                          V
                                       2

------------------------------------------------------->
                                          95                  100                 105
Hz VH 223C4                L  S  R  L  R  S  D  D  T  A  V  Y  Y  C  A

_____  CDR3 - IMGT  _____  <-------
                                          110                 115                 120
Hz VH 223C4                R  G  R  Y  V  G  Y  Y  Y  A  M  D  Y  W  G

--------  FR4 - IMGT  ------------>
                                          125           129
Hz VH 223C4                Q  G  T  T  V  T  V  S  S
```

FIGURE 34

```
                        <-------------------------------- FR1 - IMGT
                        1           5              10             15
                         Q  I  V  L  T  Q  S  P  A  I  M  S  A  S  P
11E1 VL                 caa att gtt ctc acc cag tct cca gca atc atg tct gca tct cct AJ231214 IGKV4-79*01    --- --- --- --- --- --- --- --- --- --- --- --- --- --- ---

-------------------------------------->
                                       20             25             30
                         G  E  K  V  T  L  T  C  S  A  S  S  S  V  S
11E1 VL                 ggg gag aag gtc acc ttg acc tgc agt gcc agc tca agt gta agt AJ231214 IGKV4-79*01    --- --- --- --- --- --- --- --- --- --- --- --- --- --- ---

CDR1 - IMGT                <--------------------------
                                        35             40             45
                         S  T  Y                    L  Y  W  Y  Q  Q  K
11E1 VL                 tcc acc tac ... ... ... ... ... ttg tac tgg tac cag cag aag
                                  S
AJ231214 IGKV4-79*01    --- -g- --- ... ... ... ... ... --- --- --- --- --- --- ---

FR2 - IMGT  ------------------------->            CDR2
                                       50             55             60
                         P  G  S  S  P  K  L  W  I  Y  T  T  S
11E1 VL                 cca gga tcc tcc ccc aaa ctc tgg att tat aca aca tcc ... ...
                                                                     S
AJ231214 IGKV4-79*01    --- --- --- --- --- --- --- --- --- -g- --- --- ... ...

- IMGT            <---------------------------------------
                                        65             70             75
                                          I  L  A  S  G  V  P     A  R
11E1 VL                 ... ... ... ... ... atc ctg gct tct gga gtc cct ... gct cgc
                                             N
AJ231214 IGKV4-79*01    ... ... ... ... ... -a- --- --- --- --- --- --- ... --- ---

----------------------------- FR3 - IMGT ---------------
                                       80             85             90
                         F  S  G  S  G        S  G  T  S  Y  S  L  T
11E1 VL                 ttc agt ggc agt ggg ... ... tct ggg acc tct tac tct ctc aca AJ231214 IGKV4-79*01    --- --- --- --- --- ... ... --- --- --- --- --- --- --- ---

-------------------------------------------------------->
                                       95             100            105
                         I  S  S  M  E  T  E  D  A  A  S  Y  F  C  H
11E1 VL                 atc agc agc atg gag act gaa gat gct gcc tct tat ttc tgc cat
                                       A
AJ231214 IGKV4-79*01    --- --- --- --- --- g-- --- --- --- --- --- --- --- --- ---

CDR3 - IMGT             <------------- FR4 - IMGT
                                       110            115            120
                         Q  W  S  S  Y  P  F  T  F  G  S  G  T  K  L
11E1 VL                 cag tgg agt agt tac cca ttc acg ttc ggc tcg ggg aca aag ttg
                                                P
AJ231214 IGKV4-79*01    --- --- --- --- --- --- cc- c ---------->
                                      123
                         D  I  K
11E1 VL                 gac ata aaa
```

FIGURE 38A

```
                         _____  CDR3 - IMGT  _____   <------------- FR4 - IMGT
                                            110                  115                 120
                          Q   W   S   S   Y   P   F   T   F   G   S   G   T   K   L
11E1 VL                  cag tgg agt agt tac cca ttc acg ttc ggc tcg ggg aca aag ttg V00777 IGKJ4*01                                          --- --- --- --- --- --- --- --- ---

---------->
                                  123
                          D   I   K
11E1 VL                  gac ata aaa
                          E
V00777 IGKJ4*01          --a --- --- c
```

FIGURE 38B

```
                        <------------------------------------------ FR1 - IMGT
                        1               5               10              15
                        Q   I   V   L   T   Q   S   P   A   I   M   S   A   S   P
11E1 VL                 caa att gtt ctc acc cag tct cca gca atc atg tct gca tct cct
                        E               M                       T   L       L
X72820 IGKV3D-7*01      g-- --- --a a-g --a --- --- --- --c -c- c-- --- ttg --- --a ------------------------------------------>
                                        20              25              30
                        G   E   K   V   T   L   T   C   S   A   S   S   S   V   S
11E1 VL                 ggg gag aag gtc acc ttg acc tgc agt gcc agc tca agt gta agt
                                R   A           S       R               Q
X72820 IGKV3D-7*01      --- --a -ga -c- --- c-c t-- --- --g --- --t cag --- --t --c CDR1 - IMGT                     <-------------------------
                                        35                      40              45
                        S   T   Y                           L   Y   W   Y   Q   Q   K
11E1 VL                 tcc acc tac ... ... ... ... ... ... ttg tac tgg tac cag cag aag
                            S                                   S
X72820 IGKV3D-7*01      ag- -g- --- ... ... ... ... ... ... --a -c- --- --- --- --- --a FR2 - IMGT -------------------------->             CDR2
                                    50              55              60
                        P   G   S   S   P   K   L   W   I   Y   T   T   S
11E1 VL                 cca gga tcc tcc ccc aaa ctc tgg att tat acc aca tcc ... ...
                                Q   A       R   L               G   A
X72820 IGKV3D-7*01      --t --g cag g-t --- -gg --- ctc --c --- cgt g-- --- ... ...

- IMGT              <------------------------------------------
                                        65              70              75
                                        I   L   A   S   G   V   P       A   R
11E1 VL                 ... ... ... ... atc ctg gct tct gga gtc cct ... gct cgc
                                        T   R       T       I
X72820 IGKV3D-7*01      ... ... ... ... -c- ag- --c a-- --c a-- --a ... --c a-g ------------------------------ FR3 - IMGT ---------------
                                        80              85              90
                        F   S   G   S   G               S   G   T   S   Y   S   L   T
11E1 VL                 ttc agt ggc agt ggg ... ... tct ggg acc tct tac tct ctc aca
                                                                    D   F       T
X72820 IGKV3D-7*01      --- --- --- --- --- ... ... --- --- --a gac -t- a-- --- --c ------------------------------------------------------------>
                                        95              100             105
                        I   S   S   M   E   T   E   D   A   A   S   Y   F   C   H
11E1 VL                 atc agc agc atg gag act gaa gat gct gcc tct tat ttc tgc cat
                                        L   Q   P       F   V       Y       Q
X72820 IGKV3D-7*01      --- --- --- c-- g-- c-- --- --- tt- --a gt- --- -a- --t --g CDR3 - IMGT                 <----- FR4 - IMGT --------
                                        110             115             120
                        Q   W   S   S   Y   P   F   T   F   G   S   G   T   K   L
11E1 VL                 cag tgg agt agt tac cca ttc acg ttc ggc tcg ggg aca aag ttg
                                D   Y   N   L
X72820 IGKV3D-7*01      --- gat ta- -ac -ta --t cc ---------->
                                123
                        D   I   K
11E1 VL                 gac ata aaa
```

FIGURE 39A

```
                CDR3 -  TMGT      <------------ FR4 - TMGT ----------->
                  110               115              120            123
                   Y   P   F   T   F   G   S   G   T   K   L   D   I   K
11E1 VL          tac cca ttc acg ttc ggc tcg ggg aca aag ttg gac ata aaa
                                             G                 V   E
AF103571 IGKJ4*02 ......g c-- --- --- --- gga --- --c --- g-- -g- -c- ---
```

FIGURE 39B

```
                    FR1-IMGT              CDR1-IMGT         FR2-IMGT           CDR2-IMGT
                    (1-26)                (27-38)           (39-55)            (56-65)

1        10         20          30         40        50            60
              ..........|..........|......  ...|........ .|........|.....   ....|......
11E1 VL       QIVLTQSPAIMSASPGEKVTLTCSAS    SSVSSTY.....  LYWYQQKPGSSPKLWIY   TTS.......
rank          3 1     33 3      33  3 2                  1       33 3 2
Human FR      E--M-----TL-L----RA--S-R--                 -S-------QA-R-L--
11E1 HZVL     EIVLTQSPATLSLSPGERATLSCRAS    SSVSSTY.....  LYWYQQKPGQAPRLLIY   TTS.......

FR3-IMGT                          CDR3-IMGT          FR4-IMGT
                         (66-104)                          (105-113)          (114-123)

70        80        90        100          110               120
              ....|.........|.........|.........|....    .....|...        ......|...
11E1 VL       ILASGVP.ARFSGSG..SGTSYSLTISSMETEDAASYFC     HQWSSYPFT        FGSGTKLDIK
rank          22 3 3               213    321  2 3 3                      3    32
Human FR      TR-T-I-.--------..---DFT-----LQP--F-V-Y-                    --G---VE--
11E1 HZVL     TRATGIP.ARFSGSG..SGTDYTLTISSLQTEDFAVYYC     HQWSSYPFT        FGGGTKVEIK
```

FIGURE 40

```
                    <------------------------------------------- FR1 - IMGT
                    1               5                   10                  15
                    Q   V   Q   L   Q   Q   S   G   A       E   L   A   K   P
11E1 VH             cag gtc cag ctt cag cag tct ggg gct ... gaa ctg gca aaa cct AC090843 IGHV1-7*01 --- --- --- --g --- --- --- --- --- ... --- --- --- --- ---

------------------------------------------>
                                    20                  25                  30
                    G   A   S   V   K   M   S   C   K   A   S   G   Y   T   F
11E1 VH             ggg gcc tca gtg aag atg tcc tgc aag gct tct ggc tac act ttt
                                            L
AC090843 IGHV1-7*01 --- --- --- --- --- c-- --- --- --- --- --- --- --- --c ---

CDR1 - IMGT
                                    35                  40                  45
                    T   S   Y   W                   M   N   W   V   K   Q   R
11E1 VH             act tcc tac tgg ... ... ... ... atg aac tgg gtg aaa cag agg
                                                        H
AC090843 IGHV1-7*01 --- ag- --- --- ... ... ... ... --- c-- --- --a --- --- ---

FR2 - IMGT --------------------------->       CDR2
                                    50                  55                  60
                    P   G   Q   G   L   E   W   I   G   Y   I   N   P   T   T
11E1 VH             cct gga cag ggt ctg gaa tgg att gga tac att aac cct acc act
                                                                    S   S
AC090843 IGHV1-7*01 --- --- --- --- --- --- --- --- --- --- --t --- -g- -g-

- IMGT                    <------------------------------
                                    65                  70                  75
                    G   S   T           D   Y   N   Q   K   L   K       D   K
11E1 VH             ggt tct act ... ... gac tac aat cag aag tta aag ... gac aag
                        Y               K                   F
AC090843 IGHV1-7*01 --- -a- --- ... ... a-g --- --- --- --- --c --- ... --- ---

------------------------------ FR3 - IMGT ---------------
                                    80                  85                  90
                    A   T   L   T   A   D   K   S   S   N   T   A   Y   M   Q
11E1 VH             gcc aca ttg act gca gac aaa tcc tcc aac aca gcc tac atg caa
                                                            S
AC090843 IGHV1-7*01 --- --- --- --- --- --- --- --- --- -g- --- --- --- --- --g ------------------------------------------>
                                    95                  100                 105
                    L   S   S   L   T   S   E   D   S   A   V   Y   Y   C   A
11E1 VH             ctg agc agc ctg aca tct gag gac tct gca gtc tat tac tgt gca
                                            V
AC090843 IGHV1-7*01 --- --- --- --- --- -a- --- --- --- --- --- --- --- --- ---

CDR3 - IMGT                         <-----------------
                                    110                 115                 120
                    I   G   G   Y   G   S   W   F   A   Y   W   G   Q   G   T
11E1 VH             ata gga gga tat ggg tcc tgg ttt gct tac tgg ggc caa ggg act
                    R
AC090843 IGHV1-7*01 -g-

FR4 - IMGT -------->
                                    126
                    L   V   T   V   S   A
11E1 VH             ctg gtc act gtc tct gca
```

FIGURE 41A

```
                          _____ CDR3 - IMGT _____
                          105              110                        115
                           A   I   G   G   Y   G   S   W   F   A   Y
11E1 VH                   gca ata gga gga tat ggg tcc tgg ttt gct tac
L32868 IGHD4-1*01             -g  --- c
```

FIGURE 41B

```
                          _____ CDR3 - IMGT _____ <-------------------
                                           110              115                        120
                           I   G   G   Y   G   S   W   F   A   Y   W   G   Q   G   T
11E1 VH                   ata gga gga tat ggg tcc tgg ttt gct tac tgg ggc caa ggg act V00770 IGHJ3*01           ..  ... ... ... ... .-- --- --- --- --- --- --- --- --- ---

FR4 - IMGT -------->
                                               126
                           L   V   T   V   S   A
11E1 VH                   ctg gtc act gtc tct gca V00770 IGHJ3*01           --- --- --- --- --- --- g
```

FIGURE 41C

```
                                    <---------------------------------------- FR1 - IMGT
                          1              5              10             15
                          Q  V  Q  L  Q  Q  S  G  A     E  L  A  K  P
11E1 VH                   cag gtc cag ctt cag cag tct ggg gct ... gaa ctg gca aaa cct
                                                V
                                                                     V  K
X62106 IGHV1-2*C2         --- --g --- --g gt- --- --- --- ... --g g-- aag --g ---
IGHV1-46*01 (amino acid)         V                  ...              V  K -------------------------------------------------------->
                                  20             25             30
                          G  A  S  V  K  M  S  C  K  A  S  G  Y  T  F
11E1 VH                   ggg gcc tca gtg aag atg tcc tgc aag gct tct ggc tac act ttt
                                          V
X62106 IGHV1-2*C2         --- --- --- --- --- g-c --- --- --- --- --a --- --c --c
IGHV1-46*01 (amino acid)                  V ___ CDR1 - IMGT _____  <--------------------------
                                  35             40             45
                          T  S  Y  W              M  N  W  V  K  Q  R
11E1 VH                   act tcc tac tgg ... ... ... ... atg aac tgg gtg aaa cag agg
                                 G  Y                       H           R     A
X62106 IGHV1-2*C2         --c gg- --- -at ... ... ... ... c-- --- --- cg- --- gcc
IGHV1-46*01 (amino acid)         Y  ... ... ... ...         H           R     A FR2 - IMGT ------------------------>     ___ CDR2
                                  50             55             60
                          P  G  Q  G  L  E  W  I  G  Y  I  N  P  T  T
11E1 VH                   cct gga cag ggt ctg gaa tgg att gga tac att aac cct acc act
                                                            M  W                 N  S
X62106 IGHV1-2*C2         --- --- --a --g --t --g --- --g --- -gg --c --- --- -a- -g-
IGHV1-46*01 (amino acid)                                    M  I                 S  G

- IMGT _____  <----------------------------------
                                  65             70             75
                          G  S  T        D  Y  N  Q  K  L  K  D  K
11E1 VH                   ggt tct act ... ... gac tac aat cag aag tta aag ... gac aag
                             G           N        A              F  Q        G  R
X62106 IGHV1-2*C2         --- ggc --a ... ... a-- --t gca --- --- --t c-- ... -g- -g-
IGHV1-46*01 (amino acid)                 ... ... S     A              F  Q  ... G  R -------------------------------- FR3 - IMGT ---------------
                                  80             85             90
                          A  T  L  T  A  D  K  S  S  N  T  A  Y  M  Q
11E1 VH                   gcc aca ttg act gca gac aaa tcc tcc aac aca gcc tac atg caa
                          V     M     R        T           I  S                 E
X62106 IGHV1-2*C2         -t- --c a-- --c agg --- -cg --- at- -g- --- --- --- g-g
IGHV1-46*01 (amino acid)  V     M     R        T           T  S        V        E --------------------------------------------------->
                                  95             100            105
                          L  S  S  L  T  S  E  D  S  A  V  Y  Y  C  A
11E1 VH                   ctg agc agc ctg aca tct gag gac tct gca gtc tat tac tgt gca
                             R                 D  T
X62106 IGHV1-2*C2         --- --- --g --- -g- --c --- a-g --c --g --- --- --- --g
IGHV1-46*01 (amino acid)     R                 T _____ CDR3 - IMGT _____  <----- FR4 - IMGT
                                     110            115
                          I  G  G  Y  G  S  W  F  A  Y  W  G  Q  G  T
11E1 VH                   ata gga gga tat ggg tcc tgg ttt gct tac tgg ggc caa ggg act
                          R
X62106 IGHV1-2*C2         -g- -a
IGHV1-46*01 (amino acid)

---------------------->
                                        126
                          L  V  T  V  S  A
11E1 VH                   ctg gtc act gtc tct gca
```

FIGURE 42A

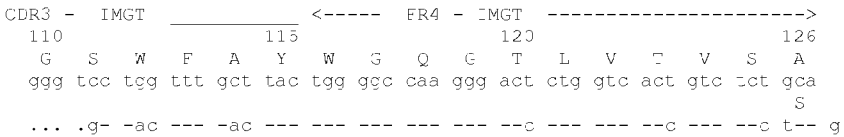

FIGURE 42B

```
                        FR1-IMGT              CDR1-IMGT         FR2-IMGT             CDR2-IMGT
                         (1-26)                (27-38)          (39-55)               (56-65)

1         10        20          30             40        50           60
              ....|.........|........     ...|.........   .|.........|.....    ....|.....
11E1 VH       QVQLQQSGA.ELAKPGASVKMSCKAS   GYTFTSYW....    MNWVKQRPGQGLEWIGY    INPTTGST..
rank              3       33       3                        1  3 3      2 1
Human FR      ----V-----.-VK-------V-----                  -H--R-A-------M-I
11E1 HZVH     QVQLVQSGA.EVKKPGASVKVSCKAS   GYTFTSYW....    MNWVRQAPGQGLEWMGY    INPTTGST..

FR3-IMGT                          CDR3-IMGT       FR4-IMGT
                         (66-104)                         (105-115)       (116-126)

70        80        90       100            110            120
              ....|.........|.........|.........|....    .....|......   ....|......
11E1 VH       DYNQKLK.DKATLTADKSSNTAYMQLSSLTSEDSAVYYC     AIGGYGSWFAY    WGQGTLVTVSA
rank          1    23 332 2 1 1 33 2  3     3   3                                  3
Human FR      S-A--FQ.GRV-M-R-T-TS-V--E----R---T-----                    ----------S
11E1 HZVH     DYAQKFQ.GRVTMTADKSTSTVYMELSSLRSEDTAVYYC     AIGGYGSWFAY    WGQGTLVTVSS
```

FIGURE 43

```
                     FR1-IMGT         CDR1-IMGT        FR2-IMGT         CDR2-IMGT
                      (1-26)           (27-38)         (39-55)           (56-65)

1         10        20        30        40        50        60
                 ....|....|....|....|....|....|....|....|....|....|....|....|....
227H1 VH         EVQLQQSGP.ELVKPGASMKISCKAS GYSFTDYT.... LNWVKQSHGKTLEWIGL INPYNGGT..
Human FR         Q---V---A.-VK-----V-V-----                MH--R-AP-QG---M-W
Changed in       *   *   2 *2         3 *                  11 * 33 22   2 1
227H1 HZ3VH      QVQLVQSGP.EVVKPGASMKVSCKAS GYSFTDYT.... LNWVRQSHGKTLEWIGL INPYNGGT..
227H1 HZ2VH      QVQLVQSG.EVKKPGASVKVSCKAS  GYSFTDYT.... LNWVRQAPGKTLEWIGL INPYNGGT..
227H1 HZ1VH      QVQLVQSGA.EVKKPGASVKVSCKAS GYSFTDYT.... LNWVRQAPGQGLEWMGL INPYNGGT..

FR3-IMGT                       CDR3-IMGT        FR4-IMGT
                              (66-104)                       (105-115)        (116-126)

70        80        90       100               110               120
                 ....|....|....|....|....|....|....|....      ....|.....       ....|......
227H1 VH         TYNQKFK.GKATLTVDKSSSTAYMELLSLTSEDSAVYYC       AREEITKDFDF      WGQGTTLTVSS
Human FR         N-A---Q.-RV-M-R-T-I-------SR-R-D-T-----                        -----LV----
Changed in       1 *   3 *2 2 1 1 3        ** 3 3 *                                  22
227H1 HZ3VH      TYAQKFK.GRATLTVDKSSSTAYMELSRLTSEDTAVYYC       AREEITKDFDF      WGQGTTLTVSS
227H1 HZ2VH      TYAQKFQ.GRATLTVDKSISTAYMELSRLRSDDTAVYYC       AREEITKDFDF      WGQGTTLTVSS
227H1 HZ1VH      TYAQKFQ.GRVTMTVDKSISTAYMELSRLRSDDTAVYYC       AREEITKDFDF      WGQGTLVTVSS
```

FIGURE 55

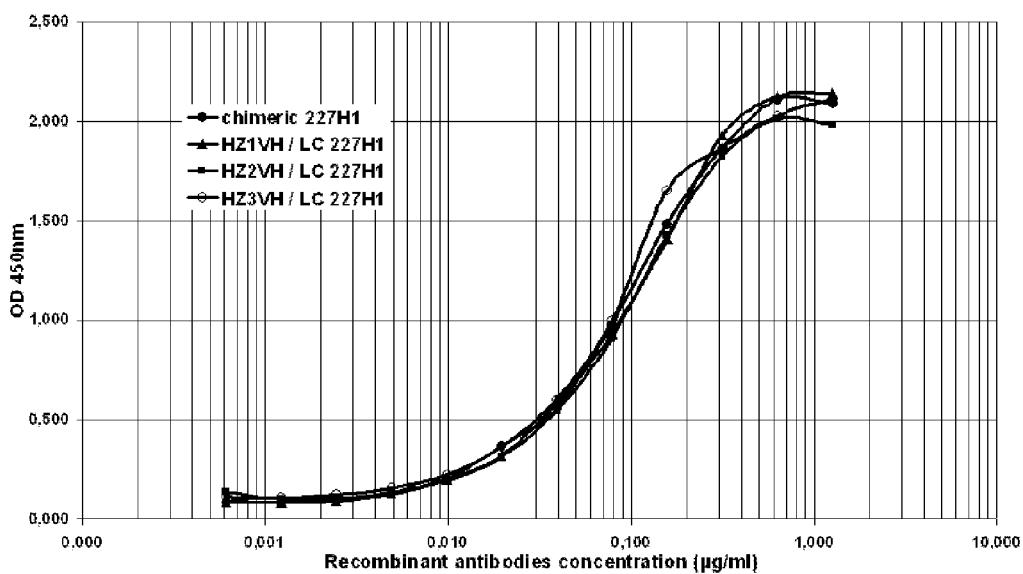

FIGURE 56

```
                          FR1-IMGT              CDR1-IMGT        FR2-IMGT          CDR2-IMGT
                           (1-26)                (27-38)         (39-55)            (56-65)

1        10        20          30            40        50          60
                  ..........|..........|......   ...|..........  .|..........|......  ....|......
227H1-HZ VH       QVQLVQSGA.EVKKPGASVKVSCKAS     GYSFTDYT....    MHWVRQAPGQGLEWMGW    INPYNGGT..
humanization      *    *   ! *!     ! *                          §§  *  !! !!   ! §

FR3-IMGT                              CDR3-IMGT        FR4-IMGT
                          (66-104)                              (105-115)        (116-126)

70        80        90       100          110             120
                  ....|..........|..........|..........|....   .....|......    ....|......
227H1-HZ VH       NYAQKFQ.GRVTMTRDTSISTAYMELSRLRSDDTAVYYC       AREEITKDFDF     WGQGTLVTVSS
humanization      § *   !  *! ! § § !         ** ! ! *                          !!
```

FIGURE 59

```
                          FR1-IMGT              CDR1-IMGT        FR2-IMGT          CDR2-IMGT
                           (1-26)                (27-38)         (39-55)            (56-65)

1        10        20          30            40        50          60
                  ..........|..........|......   ...|..........  .|..........|......  ....|......
11E1 VH           QVQLQQSGA.ELAKPGASVKMSCKAS     GYTFTSYW....    MNWVKQRPGQGLEWIGY    INPTTGST..
Human FR          ----V----.-VK-------V-----                     -H--R-A-------M-I
Changed in            *     **            3                      1  * *        2 1
11E1 HZ VH3       QVQLVQSGA.EVKKPGASVKMSCKAS     GYTFTSYW....    MNWVRQAPGQGLEWIGY    INPTTGST..
11E1 HZ VH2       QVQLVQSGA.EVKKPGASVKVSCKAS     GYTFTSYW....    MNWVRQAPGQGLEWIGY    INPTTGST..
11E1 HZ VH1       QVQLVQSGA.EVKKPGASVKVSCKAS     GYTFTSYW....    MNWVRQAPGQGLEWMGY    INPTTGST..

FR3-IMGT                              CDR3-IMGT        FR4-IMGT
                          (66-104)                              (105-115)        (116-126)

70        80        90       100          110             120
                  ....|..........|..........|..........|....   .....|......    ....|......
11E1 VH           DYNQKLK.DKATLTADKSSNTAYMQLSSLTSEDSAVYYC       AIGGYGSWFAY     WGQGTLVTVSA
Human FR          S-A--FQ.GRV-M-R-T-TS-V--E----R---T-----                       ---------S
Changed in        1 3   23 3 2 2 1 1 33 2         3   *                                 *
11E1 HZ VH3       DYNQKLK.DRATLTADKSSNTAYMELSSLTSEDTAVYYC       AIGGYGSWFAY     WGQGTLVTVSS
11E1 HZ VH2       DYAQKLQ.GRATLTADKSTSTAYMELSSLRSEDTAVYYC       AIGGYGSWFAY     WGQGTLVTVSS
11E1 HZ VH1       DYAQKFQ.GRVTMTADKSTSTVYMELSSLRSEDTAVYYC       AIGGYGSWFAY     WGQGTLVTVSS
```

FIGURE 60

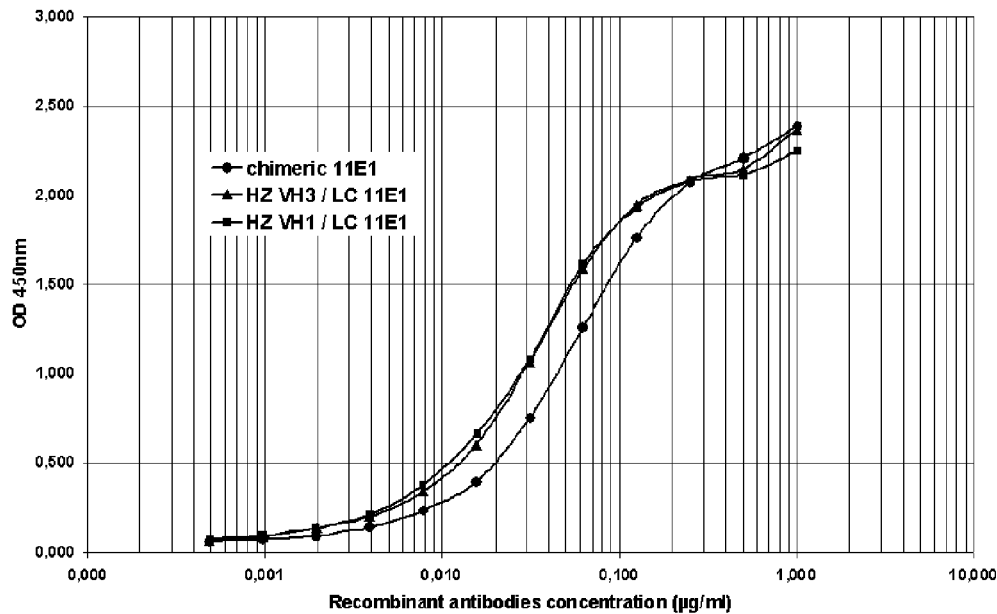

FIGURE 61

```
                    FR1-IMGT              CDR1-IMGT        FR2-IMGT           CDR2-IMGT
                     (1-26)                (27-38)          (39-55)            (56-65)

1         10        20         30              40       50          60
              ....|.........|........|.    ...|.......    .|.........|.....  ....|.....
11E1 VL       QIVLTQSPAIMSASPGEKVTLTCSAS   SSVSSTY.....   LYWYQQKPGSSPKLWIY  TTS.......
Human FR      E--M-----TL-L----RA--S-R--                  -S-------QA-R-L--
Changed in    *  1     *3 *     ** * 2                    1        33 * 2
11E1 HZ VL3   EIVLTQSPATMSLSPGERATLSCSAS   SSVSSTY.....   LYWYQQKPGSSPRLWIY  TTS.......
11E1 HZ VL2   EIVLTQSPATLSLSPGERATLSCSAS   SSVSSTY.....   LYWYQQKPGQAPRLWIY  TTS.......
11E1 HZ VL1   EIVLTQSPATLSLSPGERATLSCRAS   SSVSSTY.....   LYWYQQKPGQAPRLLIY  TTS.......

FR3-IMGT                              CDR3-IMGT          FR4-IMGT
                     (66-104)                             (105-113)          (114-123)

70        80        90        100              110              120
              ....|.........|........|........|....         .....|...        ......|...
11E1 VL       ILASGVP.ARFSGSG..SGTSYSLTISSMETEDAASYFC        HQWSSYPFT        FGSGTKLDIK
Human FR      TR-T-I-.-------..---DFT-----LQP--F-V-Y-                         --G---VE--
Changed in    22 * *          213          321  2 3 3                         3   *2
11E1 HZ VL3   ILATGIP.ARFSGSG..SGTSYSLTISSMETEDAASYFC        HQWSSYPFT        FGSGTKVDIK
11E1 HZ VL2   ILATGIP.ARFSGSG..SGTSYTLTISSLETEDAAVYYC        HQWSSYPFT        FGGGTKVDIK
11E1 HZ VL1   TRATGIP.ARFSGSG..SGTDYTLTISSLQTEDFAVYYC        HQWSSYPFT        FGGGTKVEIK
```

FIGURE 62

```
                       FR1-IMGT            CDR1-IMGT          FR2-IMGT              CDR2-IMGT
                        (1-26)              (27-38)           (39-55)                (56-65)

1         10        20             30           40        50             60
              ....|....|....|....|....     ....|....      .|....|....|....     ....|....
224G11 VH     EVQLQQSGP.ELVKPGASVKISCKTS    GYIFTAYT....   MHWVRQSLGESLDWIGG    IKPNNGLA..
227H1 VH      EVQLQQSGP.ELVKPGASMKISCKAS    GYSFTDYT....   LNWVKQSHGKTLEWIGL    INPYNGGT..
Human FR      Q---V---A.-VK-------V---A-                   ------AP-QG-E-M-W
224G11 HZ VH0 QVQLVQSGA.EVKKPGASVKVSCKAS    GYIFTAYT....   MHWVRQAPGQGLEWMGW    IKPNNGLA..

FR3-IMGT                            CDR3-IMGT        FR4-IMGT
                              (66-104)                            (105-115)        (116-126)

70        80        90        100                    110             120
              ....|....|....|....|....|....|....|....             ....|.....      ....|.....
224G11 VH     NYNQKFK.GKATLTVDKSSSTAYMDLRSLTSEDSAVYYC              ARSEITTEFDY     WGQGTALTVSS
227H1 VH      TYNQKFK.GKATLTVDKSSSTAYMELLSLTSEDSAVYYC              AREEITKDFDF     WGQGTTLTVSS
Human FR      --A---Q.-RV-M-R-T-I-----E-SR-R-D-T-----                              -----LV----
224G11 HZ VH0 NYAQKFQ.GRVTMTRDTSISTAYMELSRLRSDDTAVYYC              ARSEITTEFDY     WGQGTLVTVSS
```

FIGURE 65

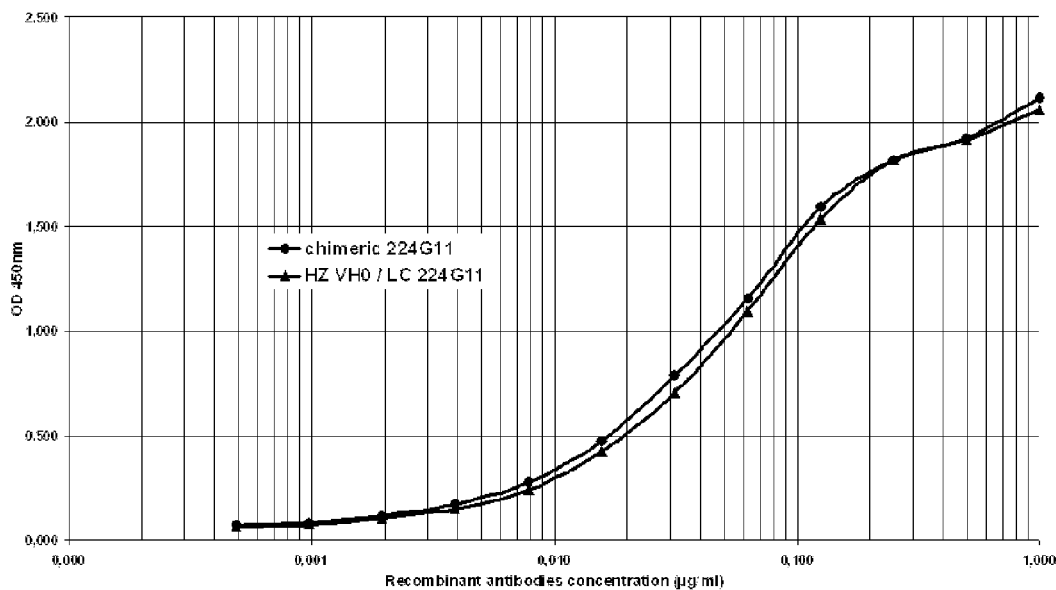

FIGURE 66

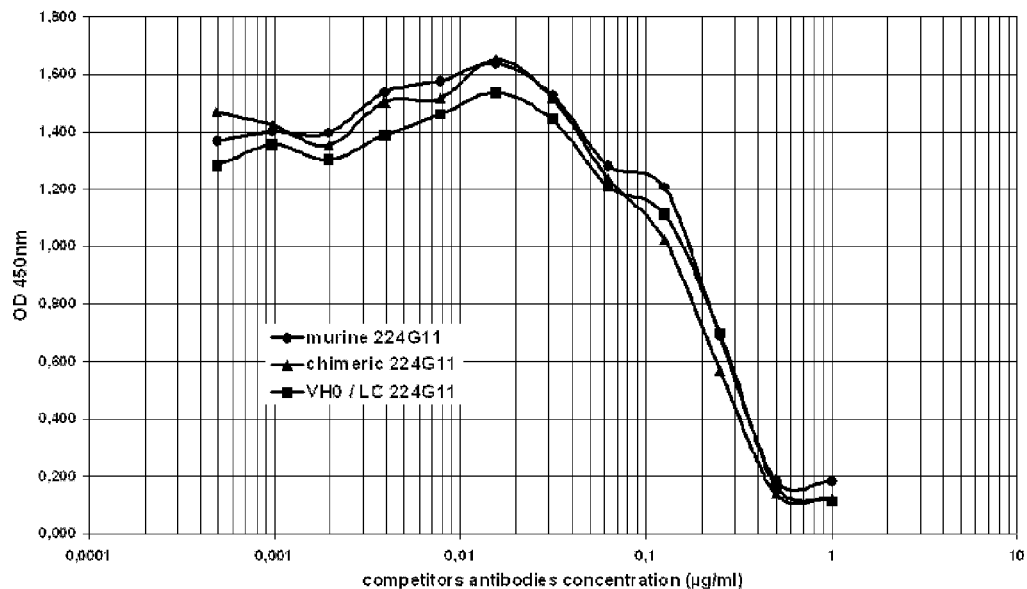

FIGURE 67

```
                        FR1-IMGT            CDR1-IMGT        FR2-IMGT           CDR2-IMGT
                         (1-26)              (27-38)          (39-55)            (56-65)

1        10       20           30            40       50           60
                 .........|........|......   ...|........   .|........|.....   ....|.....
224G11 VL        DIVLTQSPASLAVSLGQRATISCRAS   ESVDSYANSF..   MHWYQQKPGQPPKLLIY   RAS.......

Shorter Hu-FR    E--------T-SL-P-E---L-----                  LA--------A-R----
Rank             *         * 3* 2 3   *                      11         2 3
224G11 HZ VL3    EIVLTQSPATLALSLGQRATLSCRAS   ESVDSYANSF..   MHWYQQKPGQPPKLLIY   RAS.......

Longer Hu-FR     ---M----D-------E----N-KS-                  LA---------------
Rank              1    *         3   * 32                    11
224G11 HZ VL6    DIVLTQSPDSLAVSLGQRATINCRAS   ESVDSYANSF..   MHWYQQKPGQPPKLLIY   RAS.......

FR3-IMGT                       CDR3-IMGT   FR4-IMGT
                              (66-104)                       (105-113)   (114-123)

70        80        90       100             110          120
                 ....|.........|.........|.........|....     .....|...   ......|....
224G11 VL        NLESGIP.ARFSGSG..SRTDFTLTINPVEADDVATYYC      QQSKEDPLT   FGSGTKLEMK

Shorter Hu-FR    -RAT---.--------..-G-------SSL-PE-F-V---                 --G---V-I-
Rank             22*               1        32* 33 2 3                    3   * *
224G11 HZ VL3    NLETGIP.ARFSGSG..SRTDFTLTINPLEADDVATYYC      QQSKEDPLT   FGSGTKVEIK Longer Hu-FR     TR---V-.D-------..-G-------SSLQ-E---V---                 --G---V-I-
                 22   *  *         1        32*3 3   3                    3   * *
224G11 HZ VL6    NLESGVP.DRFSGSG..SRTDFTLTINPLEADDVATYYC      QQSKEDPLT   FGSGTKVEIK
```

FIGURE 68

ANTIBODIES INHIBITING C-MET DIMERIZATION, AND USES THEREOF

CROSS-REFERENCE TO PRIORITY APPLICATIONS

This application is a divisional of U.S. application Ser. No. 12/440,571, filed Mar. 9, 2009, now issued as U.S. Pat. No. 8,329,173, which claims priority under 35 U.S.C. §119 of EP 07301231.2, filed Jul. 12, 2007, U.S. Provisional Application No. 60/929,789, filed Jul. 12, 2007, U.S. Provisional Application No. 61/020,639, filed Jan. 11, 2008, and is a national phase of PCT/EP2008/059026, filed Jul. 10, 2008, and designating the United States (published in the English language on Jan. 15, 2009, as WO 2009/007427 A2; the title and abstract were also published in English), each hereby expressly incorporated by reference in its entirety and each assigned to the assignee hereof.

TECHNICAL FIELD

The present invention relates to novel antibodies capable of binding specifically to the human c-Met receptor and/or capable of specifically inhibiting the tyrosine kinase activity of said receptor, especially monoclonal antibodies of murine, chimeric and humanized origin, as well as the amino acid and nucleic acid sequences coding for these antibodies. More particularly, antibodies according to the invention are capable of inhibiting the c-Met dimerization. The invention likewise comprises the use of these antibodies as a medicament for the prophylactic and/or therapeutic treatment of cancers or any pathology connected with the overexpression of said receptor as well as in processes or kits for diagnosis of illnesses connected with the overexpression of c-Met. The invention finally comprises products and/or compositions comprising such antibodies in combination with other antibodies and/or chemical compounds directed against other growth factors involved in tumor progression or metastasis and/or compounds and/or anti-cancer agents or agents conjugated with toxins and their use for the prevention and/or the treatment of certain cancers.

BACKGROUND OF THE INVENTION

Receptor tyrosine kinase (RTK) targeted agents such as trastuzumab, cetuximab, bevacizumab, imatinib and gefitinib inhibitors have illustrated the interest of targeting this protein class for treatment of selected cancers.

c-Met, is the prototypic member of a sub-family of RTKs which also includes RON and SEA. The c-Met RTK family is structurally different from other RTK families and is the only known high-affinity receptor for hepatocyte growth factor (HGF), also called scater factor (SF) [D. P. Bottaro et al., Science 1991, 251: 802-804; L. Naldini et al., Eur. Mol. Biol. Org. J. 1991, 10:2867-2878]. c-Met and HGF are widely expressed in a variety of tissue and their expression is normally restricted to cells of epithelial and mesenchymal origin respectively [M. F. Di Renzo et al., Oncogene 1991, 6:1997-2003; E. Sonnenberg et al., J. Cell. Biol. 1993, 123:223-235]. They are both required for normal mammalian development and have been shown to be particularly important in cell migration, morphogenic differentiation, and organization of the three-dimensional tubular structures as well as growth and angiogenesis [F. Baldt et al., Nature 1995, 376:768-771; C. Schmidt et al., Nature. 1995:373:699-702; Tsarfaty et al., Science 1994, 263:98-101]. While the controlled regulation of c-Met and HGF have been shown to be important in mammalian development, tissue maintenance and repair [Nagayama T, Nagayama M, Kohara S, Kamiguchi H, Shibuya M, Katoh Y, Itoh J, Shinohara Y., Brain Res. 2004, 5; 999(2):155-66; Tahara Y, Ido A, Yamamoto S, Miyata Y, Uto H, Hori T, Hayashi K, Tsubouchi H., J Pharmacol Exp Ther. 2003, 307(1):146-51], their dysregulation is implicated in the progression of cancers.

Aberrant signalling driven by inappropriate activation of c-Met is one of the most frequent alteration observed in human cancers and plays a crucial role in tumorigenesis and metastasis [Birchmeier et al., Nat. Rev. Mol. Cell. Biol. 2003, 4:915-925; L. Trusolino and Comoglio P. M., Nat. Rev. Cancer. 2002, 2(4):289-300].

Inappropriate c-Met activation can arise by ligand-dependent and independent mechanisms, which include overexpression of c-Met, and/or paracrine or autocrine activation, or through gain in function mutation [J. G. Christensen, Burrows J. and Salgia R., Cancer Latters. 2005, 226:1-26]. However an oligomerization of c-Met receptor, in presence or in absence of the ligand, is required to regulate the binding affinity and binding kinetics of the kinase toward ATP and tyrosine-containing peptide substrates [Hays J L, Watowich S J, Biochemistry, 2004 Aug. 17, 43:10570-8]. Activated c-Met recruits signalling effectors to its multidocking site located in the cytoplasm domain, resulting in the activation of several key signalling pathways, including Ras-MAPK, PI3K, Src and Stat3 [Gao C F, Vande Woude G F, Cell Res. 2005, 15(1):49-51; Furge K A, Zhang Y W, Vande Woude G F, Oncogene. 2000, 19(49):5582-9]. These pathways are essential for tumour cell proliferation, invasion and angiogenesis and for evading apoptosis [Furge K A, Zhang Y W, Vande Woude G F, Oncogene, 2000, 19(49):5582-9; Gu H, Neel B G, Trends Cell Biol. 2003 March, 13(3):122-30; Fan S, Ma Y X, Wang J A, Yuan R Q, Meng Q, Cao Y, Laterra J J, Goldberg I D, Rosen E M, Oncogene. 2000 Apr. 27, 19(18):2212-23]. In addition, a unique facet of the c-Met signalling relative to other RTK is its reported interaction with focal adhesion complexes and non kinase binding partners such as a6134 integrins [Trusolino L, Bertotti A, Comoglio P M, Cell. 2001, 107:643-54], CD44v6 [Van der Voort R, Taher T E, Wielenga V J, Spaargaren M, Prevo R, Smit L, David G, Hartmann G, Gherardi E, Pals S T, J Biol. Chem. 1999, 274(10):6499-506], Plexin B1 or semaphorins [Giordano S, Corso S, Conrotto P, Artigiani S, Gilestro G, Barberis D, Tamagnone L, Comoglio P M, Nat Cell Biol. 2002, 4(9):720-4; Conrotto P, Valdembri D, Corso S, Serini G, Tamagnone L, Comoglio P M, Bussolino F, Giordano S, Blood. 2005, 105(11):4321-9; Conrotto P, Corso S, Gamberini S, Comoglio P M, Giordano S, Oncogene. 2004, 23:5131-7] which may further add to the complexity of regulation of cell function by this receptor. Finally recent data demonstrate that c-Met could be involved in tumor resistance to gefitinib or erlotinib suggesting that combination of compound targeting both EGFR and c-Met might be of significant interest [Engelman JA at al., Science, 2007, 316: 1039-43].

In the past few years, many different strategies have been developed to attenuate c-Met signalling in cancer cell lines. These strategies include i) neutralizing antibodies against c-Met or HGF/SF [Cao B, Su Y, Oskarsson M, Zhao P, Kort E J, Fisher R J, Wang L M, Vande Woude G F, Proc Natl Acad Sci USA. 2001, 98(13):7443-8; Martens T, Schmidt N O, Eckerich C, Fillbrandt R, Merchant M, Schwall R, Westphal M, Lamszus K, Clin Cancer Res. 2006, 12(20):6144-52] or the use of HGF/SF antagonist NK4 to prevent ligand binding to c-Met [Kuba K, Matsumoto K, Date K, Shimura H, Tanaka M, Nakamura T, Cancer Res., 2000, 60:6737-43], ii) small ATP binding site inhibitors to c-Met that block kinase activity

[Christensen J G, Schreck R, Burrows J, Kuruganti P, Chan E, Le P, Chen J, Wang X, Ruslim L, Blake R, Lipson K E, Ramphal J, Do S, Cui J J, Chemington J M, Mendel D B, Cancer Res. 2003, 63:7345-55], iii) engineered SH2 domain polypeptide that interferes with access to the multidocking site and RNAi or ribozyme that reduce receptor or ligand expression. Most of these approaches display a selective inhibition of c-Met resulting in tumor inhibition and showing that c-Met could be of interest for therapeutic intervention in cancer.

Within the molecules generated for c-Met targeting, some are antibodies.

The most extensively described is the anti-c-Met 5D5 antibody generated by Genentech [WO96/38557] which behaves as a potent agonist when added alone in various models and as an antagonist when used as a Fab fragment. A monovalent engineered form of this antibody described as one armed 5D5 (OA5D5) and produced as a recombinant protein in E. Coli is also the subject of a patent application [WO2006/015371] by Genentech. However, this molecule that could not be considered as an antibody because of its particular scarfold, displays also mutations that could be immunogenic in humans. In terms of activity, this unglycosylated molecule is devoided of effector functions and finally, no clear data demonstrate that OA5D5 inhibits dimerization of c-Met. Moreover, when tested in the G55 in vivo model, a glioblastoma cell line that expresses c-Met but not HGF mRNA and protein and that grows independently of the ligand, the one armed anti-c-Met had no significant effect on G55 tumor growth suggesting that OA5D5 acts primarily by blocking HGF binding and is not able to target tumors activated independently of HGF [Martens T. et al, Clin. Cancer Res., 2006, 12(20):6144-6152].

Another antibody targeting c-Met is described by Pfizer as an antibody acting "predominantly as c-Met antagonist, and in some instance as a c-Met agonist" [WO 2005/016382]. No data showing any effect of Pfizer antibodies on c-Met dimerization is described in this application.

One of the innovant aspects of the present invention is to generate mouse monoclonal antibodies without intrinsic agonist activity and inhibiting c-Met dimerization. In addition of targeting ligand-dependent tumors, this approach will also impair ligand-independent activations of c-Met due to its overexpression or mutations of the intra cellular domains which remained dependent to oligomerization for signalling. Another aspect of the activity of such antibodies could be a steric hindrance for c-Met interaction with its partners that will result in impairment of c-Met functions. These antibodies will be humanized and engineered preferentially, but not limited, as human IgG1 to get effector functions such as ADCC and CDC in addition to functions linked to the specific blockade of the c-Met receptor.

DISCLOSURE OF THE INVENTION

Surprisingly, for the first time, inventors have managed to generate an antibody capable of binding to c-Met but also capable of inhibiting the c-Met dimerization. If it is true that, in the prior art, it is sometimes suggested that an antibody capable of inhibiting the dimerization of c-Met with its partners could be an interesting one, it has never been disclosed, or clearly suggested, an antibody capable of doing so. Moreover, regarding antibody specificity, it was not evident at all to succeed in the generation of such an active antibody.

In a first aspect, a subject of the present invention is a process for the generation and the selection of antibodies according to the invention.

More particularly, the invention concerns a process for the selection of an anti c-Met antibody, or one of its functional fragments or derivatives, capable to inhibit both ligand-dependent and ligand-independent activation of c-Met, said process comprising the following steps:

i) screening the generated antibodies and selecting antibodies capable to bind specifically to c-Met;

ii) evaluating in vitro the selected antibodies of step i) and selecting antibodies capable to inhibit at least 50%, preferably at least 60%, 70% or 80% of tumoral cell proliferation for at least one tumor type; and then iii) testing the selected antibodies of step ii) and selecting antibodies capable to inhibit the c-Met dimerization.

As it was explained before, the inhibition of the c-Met dimerization is a capital aspect of the invention as such antibodies will present a real interest for a larger population of patients. Not only ligand-dependent activated c-Met cancer, as it was the case until the present invention, but also ligand-independent activated c-Met cancer could be treated with antibodies generated by the process of the present invention.

The generation of the antibody can be realized by any method known by the man skilled in the art, such as for example, fusion of a myeloma cell with spleen cells from immunized mice or other species compatible with the selected myeloma cells [Kohler & Milstein, 1975, Nature, 256:495-497]. The immunized animals could include transgenic mice with human immunoglobulin loci which then directly produce human antibodies. Another possible embodiment could consist in using phage display technologies to screen libraries.

The screening step i) can be realized by any method or process known by the man skilled in the art. As non limitative examples, can be mentioned ELISA, BIAcore, immunohistochemistry, FACS analysis and functional screens. A preferred process consists in a screen by ELISA on the c-Met recombinant protein and then by FACS analysis on at least a tumoral cell line to be sure that the produced antibodies will be able to also recognize the native receptor on tumor cells. This process will be described more precisely in the following examples.

In the same way, the step ii) can also be realized classically by known method or process such as, for example, using 3H-thymidine or any other DNA staining agent, MTT, ATP evaluation, etc. A preferred tumor cell model in the present invention can consist in the BxPC3 model.

By inhibiting c-Met dimerization, it must be understood preferably the c-Met homodimerization.

In a preferred embodiment of the step iii) of selection of the process of the invention, said step iii) consists in evaluating antibodies by BRET analysis on cells expressing both c-Met-RLuc/c-Met-YFP and selecting antibodies capable to inhibit at least 30%, preferably 35%, 40%, 45%, 50%, 55% and most preferably 60% of the BRET signal.

The technology BRET is a technology known as being representative of the protein dimerization [Angers et al., PNAS, 2000, 97:3684-89].

The technology BRET, used in the step iii) of the process, is well known by the man skill in the art and will be detailed in the following examples. More particularly, BRET (Bioluminescence Resonance Energy Transfer) is a non-radiative energy transfer occurring between a bioluminescent donor (Renilla Luciferase (Rluc)) and a fluorescent acceptor, a mutant of GFP (Green Fluorescent Protein) or YFP (Yellow fluorescent protein). In the present case EYFP (Enhanced Yellow Fluorescent Protein) was used. The efficacy of transfer depends on the orientation and the distance between the donor and the acceptor. Then, the energy transfer can occur only if the two molecules are in close proximity (1-10 nm). This property is used to generate protein-protein interaction assays. Indeed, in order to study the interaction between two partners, the first one is genetically fused to the Renilla Luciferase and the second one to the yellow mutant of the GFP. Fusion proteins are generally, but not obligatory, expressed in mammalian cells. In presence of its membrane permeable substrate (coelenterazine), Rluc emits blue light. If the GFP mutant is closer than 10 nm from the Rluc, an energy transfer can occur and an additional yellow signal can be detected. The BRET signal is measured as the ratio between the light emitted by the acceptor and the light emitted by the donor. So the BRET signal will increase as the two fusion proteins are brought into proximity or if a conformational change bring Rluc and GFP mutant closer.

If the BRET analysis consists in a preferred embodiment, any method known by the man skilled in the art can be used to measure c-Met dimerization. Without limitation, the following technologies can be mentioned: FRET (Fluorescence Resonance Energy Transfer), HTRF (Homogenous Time resolved Fluorescence), FLIM (Fluorescence Lifetime Imaging Microscopy) or SW-FCCS single wavelength fluorescence cross-correlation spectroscopy).

Other classical technologies could also be used, such as Co-immunoprecipitation, Alpha screen, Chemical cross-linking, Double-Hybrid, Affinity Chromatography, ELISA or Far western blot.

In a second aspect, a subject of the invention is an isolated antibody, or one of its functional fragments or derivatives, being obtained by said process. Said antibody or one of its said fragments or derivatives, is capable of binding specifically to the human c-Met and, if necessary, preferably moreover capable of inhibiting the natural attachment of its ligand HGF and/or capable of specifically inhibiting the tyrosine kinase activity of said c-Met, said antibody being also capable to inhib c-Met dimerization. More particularly, said antibodies will be capable of inhibiting both ligand-dependent and ligand-independent activation of c-Met.

The expressions "functional fragments and derivatives" will be defined in details later in the present specification.

It must be understood here that the invention does not relate to the antibodies in natural form, that is to say they are not in their natural environment but that they have been able to be isolated or obtained by purification from natural sources, or else obtained by genetic recombination, or by chemical synthesis, and that they can then contain unnatural amino acids as will be described further on.

More particularly, according to another aspect of the invention, it is claimed an antibody, or one of its functional fragments or derivatives, said antibody being characterized in that it comprises at least one complementary determining region CDR chosen from CDRs comprising the amino acid sequence SEQ ID Nos. 1 to 17 and 56 to 61.

Any antibody, or fragments or derivatives, having at least one CDR whose sequence has at least 80% identity, preferably 85%, 90%, 95% and 98% identity, after optimum alignment with the sequences SEQ ID Nos. 1 to 17 and 56 to 61 must be understood as a equivalent and, as a consequence, as being part of the invention.

By CDR regions or CDR(s), it is intended to indicate the hypervariable regions of the heavy and light chains of the immunoglobulins as defined by IMGT.

The IMGT unique numbering has been defined to compare the variable domains whatever the antigen receptor, the chain type, or the species [Lefranc M.-P., Immunology Today 18, 509 (1997)/Lefranc M.-P., The Immunologist, 7, 132-136 (1999)/Lefranc, M.-P., Pommie, C., Ruiz, M., Giudicelli, V., Foulquier, E., Truong, L., Thouvenin-Contet, V. and Lefranc, Dev. Comp. Immunol., 27, 55-77 (2003)]. In the IMGT unique numbering, the conserved amino acids always have the same position, for instance cysteine 23 (1st-CYS), tryptophan 41 (CONSERVED-TRP), hydrophobic amino acid 89, cysteine 104 (2nd-CYS), phenylalanine or tryptophan 118 (J-PHE or J-TRP). The IMGT unique numbering provides a standardized delimitation of the framework regions (FR1-IMGT: positions 1 to 26, FR2-IMGT: 39 to 55, FR3-IMGT: 66 to 104 and FR4-IMGT: 118 to 128) and of the complementarity determining regions: CDR1-IMGT: 27 to 38, CDR2-IMGT: 56 to 65 and CDR3-IMGT: 105 to 117. As gaps represent unoccupied positions, the CDR-IMGT lengths (shown between brackets and separated by dots, e.g. [8.8.13]) become crucial information. The IMGT unique numbering is used in 2D graphical representations, designated as IMGT Colliers de Perles [Ruiz, M. and Lefranc, M.-P., Immunogenetics, 53, 857-883 (2002)/Kaas, Q. and Lefranc, M.-P., Current Bioinformatics, 2, 21-30 (2007)], and in 3D structures in IMGT/3Dstructure-DB [Kaas, Q., Ruiz, M. and Lefranc, M.-P., T cell receptor and MHC structural data. Nucl. Acids. Res., 32, D208-D210 (2004)].

Three heavy chain CDRs and 3 light chain CDRs exist. The term CDR or CDRs is used here in order to indicate, according to the case, one of these regions or several, or even the whole, of these regions which contain the majority of the amino acid residues responsible for the binding by affinity of the antibody for the antigen or the epitope which it recognizes.

By "percentage of identity" between two nucleic acid or amino acid sequences in the sense of the present invention, it is intended to indicate a percentage of nucleotides or of identical amino acid residues between the two sequences to be compared, obtained after the best alignment (optimum alignment), this percentage being purely statistical and the differences between the two sequences being distributed randomly and over their entire length. The comparisons of sequences between two nucleic acid or amino acid sequences are traditionally carried out by comparing these sequences after having aligned them in an optimum manner, said comparison being able to be carried out by segment or by "comparison window". The optimum alignment of the sequences for the comparison can be carried out, in addition to manually, by means of the local homology algorithm of Smith and Waterman (1981) [Ad. App. Math. 2:482], by means of the local homology algorithm of Neddleman and Wunsch (1970) [J. Mol. Biol. 48: 443], by means of the similarity search method of Pearson and Lipman (1988) [Proc. Natl. Acad. Sci. USA 85:2444), by means of computer software using these algorithms (GAP, BESTFIT, FASTA and TFASTA in the Wisconsin Genetics Software Package, Genetics Computer Group, 575 Science Dr., Madison, Wis., or else by BLAST N or BLAST P comparison software).

The percentage of identity between two nucleic acid or amino acid sequences is determined by comparing these two sequences aligned in an optimum manner and in which the nucleic acid or amino acid sequence to be compared can comprise additions or deletions with respect to the reference sequence for an optimum alignment between these two sequences. The percentage of identity is calculated by determining the number of identical positions for which the nucleotide or the amino acid residue is identical between the two sequences, by dividing this number of identical positions by the total number of positions in the comparison window and by multiplying the result obtained by 100 in order to obtain the percentage of identity between these two sequences.

For example, it is possible to use the BLAST program, "BLAST 2 sequences" (Tatusova et al., "Blast 2 sequences—a new tool for comparing protein and nucleotide sequences", FEMS Microbiol Lett. 174:247-250) available on the site www.ncbi.nlm.nih.gov/gorf/b12.html, the parameters used being those given by default (in particular for the parameters "open gap penalty": 5, and "extension gap penalty": 2; the matrix chosen being, for example, the matrix "BLOSUM 62" proposed by the program), the percentage of identity between the two sequences to be compared being calculated directly by the program.

By amino acid sequence having at least 80%, preferably 85%, 90%, 95% and 98% identity with a reference amino acid sequence, those having, with respect to the reference sequence, certain modifications, in particular a deletion, addition or substitution of at least one amino acid, a truncation or an elongation are preferred. In the case of a substitution of one or more consecutive or nonconsecutive amino acid(s), the substitutions are preferred in which the substituted amino acids are replaced by "equivalent" amino acids. The expression "equivalent amino acids" is aimed here at indicating any amino acid capable of being substituted with one of the amino acids of the base structure without, however, essentially modifying the biological activities of the corresponding antibodies and such as will be defined later, especially in the examples. These equivalent amino acids can be determined either by relying on their structural homology with the amino acids which they replace, or on results of comparative trials of biological activity between the different antibodies capable of being carried out.

By way of example, mention is made of the possibilities of substitution capable of being carried out without resulting in a profound modification of the biological activity of the corresponding modified antibody.

As non limitative example, the following table 1 is giving substitution possibilities conceivable with a conservation of the biological activity of the modified antibody. The reverse substitutions are also, of course, possible in the same conditions.

TABLE 1

| Original residu | Substitution(s) |
|---|---|
| Ala (A) | Val, Gly, Pro |
| Arg (R) | Lys, His |
| Asn (N) | Gln |
| Asp (D) | Glu |
| Cys (C) | Ser |
| Gln (Q) | Asn |
| Glu (G) | Asp |
| Gly (G) | Ala |
| His (H) | Arg |
| Ile (I) | Leu |
| Leu (L) | Ile, Val, Met |
| Lys (K) | Arg |
| Met (M) | Leu |
| Phe (F) | Tyr |
| Pro (P) | Ala |
| Ser (S) | Thr, Cys |
| Thr (T) | Ser |
| Trp (W) | Tyr |
| Tyr (Y) | Phe, Trp |
| Val (V) | Leu, Ala |

It must be understood here that the invention does not relate to the antibodies in natural form, that is to say they are not in their natural environment but that they have been able to be isolated or obtained by purification from natural sources, or else obtained by genetic recombination, or by chemical synthesis, and that they can then contain unnatural amino acids as will be described further on.

According a first approach, the antibody will be defined by its heavy chain sequence. More particularly, the antibody of the invention, or one of its functional fragments or derivatives, is characterized in that it comprises a heavy chain comprising at least one CDR chosen from CDRs comprising the amino acid sequences SEQ ID Nos. 1 to 9 and 56 to 58.

The mentioned sequences are the following ones:

```
SEQ ID No. 1:
GYIFTAYT

SEQ ID No. 2:
IKPNNGLA

SEQ ID No. 3:
ARSEITTEFDY

SEQ ID No. 4:
GYSFTDYT

SEQ ID No. 5:
INPYNGGT

SEQ ID No. 6:
AREEITKDFDF

SEQ ID No. 7:
GYTFTDYN

SEQ ID No. 8:
INPNNGGT

SEQ ID No. 9:
ARGRYVGYYYAMDY

SEQ ID No. 56:
GYTFTSYW

SEQ ID No. 57:
INPTTGST

SEQ ID No. 58:
AIGGYGSWFAY
```

The CDRs of the heavy chain could be chosen randomly in the previous sequences, i.e. SEQ ID Nos. 1 to 9 and 56 to 58.

According to a preferred aspect, the antibody of the invention, or one of its functional fragments or derivatives, comprises a heavy chain comprising at least one CDR chosen from CDR-H1, CDR-H2 and CDR-H3, wherein:

CDR-H1 comprises the amino acid sequence SEQ ID No. 1, 4, 7 or 56,

CDR-H2 comprises the amino acid sequence SEQ ID No. 2, 5, 8 or 57, and

CDR-H3 comprises the amino acid sequence SEQ ID No. 3, 6, 9 or 58.

According to a first embodiment of said aspect, the antibody of the invention, or one of its functional fragments or derivatives, comprises a heavy chain comprising CDR-H1, CDR-H2 and CDR-H3, wherein CDR-H1 comprises the amino acid sequence SEQ ID No. 1, CDR-H2 comprises the amino acid sequence SEQ ID No. 2 and CDR-H3 comprises the amino acid sequence SEQ ID No. 3.

More particularly, said antibody, or one of its functional fragments or derivatives, according to this first embodiment comprises a heavy chain of sequence comprising the amino acid sequence SEQ ID No. 18.

```
SEQ ID No. 18:
EVQLQQSGPELVKPGASVKISCKTSGYIFTAYTMHWVRQSLGESLDWIG

GIKPNNGLANYNQKFKGKATLTVDKSSSTAYMDLRSLTSEDSAVYYCAR

SEITTEFDYWGQGTALTVSS
```

According to a second embodiment of said aspect, the antibody of the invention, or one of its functional fragments or derivatives, comprises a heavy chain comprising CDR-H1, CDR-H2 and CDR-H3, wherein CDR-H1 comprises the amino acid sequence SEQ ID No. 4, CDR-H2 comprises the amino acid sequence SEQ ID No. 5 and CDR-H3 comprises the amino acid sequence SEQ ID No. 6.

The antibody, or one of its functional fragments or derivatives, according to said second embodiment will preferably comprise a heavy chain of sequence comprising the amino acid sequence SEQ ID No. 19.

```
SEQ ID No. 19:
EVQLQQSGPELVKPGASMKISCKASGYSFTDYTLNWVKQSHGKTLEWIG

LINPYNGGTTYNQKFKGKATLTVDKSSSTAYMELLSLTSEDSAVYYCAR

EEITKDFDFWGQGTTLTVSS
```

According to a third embodiment of said aspect, the antibody of the invention, or one of its functional fragments or derivatives, comprises a heavy chain comprising CDR-H1, CDR-H2 and CDR-H3, wherein CDR-H1 comprises the amino acid sequence SEQ ID No. 7, CDR-H2 comprises the amino acid sequence SEQ ID No. 8 and CDR-H3 comprises the amino acid sequence SEQ ID No. 9.

The antibody, or one of its functional fragments or derivatives, according to said third embodiment will preferably comprise a heavy chain of sequence comprising the amino acid sequence SEQ ID No. 20.

```
SEQ ID No. 20:
EVLLQQSGPELVKPGASVKIPCKASGYTFTDYNMDWVKQSHGMSLEWIG

DINPNNGGTIFNQKFKGKATLTVDKSSSTAYMELRSLTSEDTAVYYCAR

GRYVGYYYAMDYWGQGTSVTVSS
```

According to a fourth embodiment of said aspect, the antibody of the invention, or one of its functional fragments or derivatives, comprises a heavy chain comprising CDR-H1, CDR-H2 and CDR-H3, wherein CDR-H1 comprises the amino acid sequence SEQ ID No. 56, CDR-H2 comprises the amino acid sequence SEQ ID No. 57 and CDR-H3 comprises the amino acid sequence SEQ ID No. 58.

The antibody, or one of its functional fragments or derivatives, according to said fourth embodiment will preferably comprise a heavy chain of sequence comprising the amino acid sequence SEQ ID No. 62.

```
SEQ ID No. 62:
QVQLQQSGAELAKPGASVKMSCKASGYTFTSYWMNWVKQRPGQGLEWIG

YINPTTGSTDYNQKLKDKATLTADKSSNTAYMQLSSLTSEDSAVYYCAI

GGYGSWFAYWGQGTLVTVSA
```

In a second approach, the antibody will be now define by its light chain sequence. More particularly, according to a second particular aspect of the invention, the antibody, or one of its functional fragments or derivatives, is characterized in that it comprises a light chain comprising at least one CDR chosen from CDRs comprising the amino acid sequence SEQ ID Nos. 10 to 17 and 59 to 61.

The mentioned sequences are the following ones:

```
SEQ ID No. 10:
ESVDSYANSF
```

```
SEQ ID No. 11:
RAS

SEQ ID No. 12:
QQSKEDPLT

SEQ ID No. 13:
ESIDTYGNSF

SEQ ID No. 14:
QQSNEDPFT

SEQ ID No. 15:
ENIYSN

SEQ ID No. 16:
AAT

SEQ ID No. 17:
QHFWGPPYT

SEQ ID No. 59:
SSVSSTY

SEQ ID No. 60:
TTS

SEQ ID No. 61:
HQWSSYPFT
```

The CDRs of the light chain could be chosen randomly in the previous sequences, i.e. SEQ ID Nos. 10 to 17 and 59 to 61.

According to another preferred aspect, the antibody of the invention, or one of its functional fragments or derivatives, comprises a light chain comprising at least one CDR chosen from CDR-L1, CDR-L2 and CDR-L3, wherein:
  CDR-L1 comprises the amino acid sequence SEQ ID No. 10, 13, 15 or 59,
  CDR-L2 comprises the amino acid sequence SEQ ID No. 11, 16 or 60, and
  CDR-L3 comprises the amino acid sequence SEQ ID No. 12, 14, 17 or 61.

According to a first embodiment of said another aspect, the antibody of the invention, or one of its functional fragments or derivatives, comprises a light chain comprising CDR-L1, CDR-L2 and CDR-L3, wherein CDR-L1 comprises the amino acid sequence SEQ ID No. 10, CDR-L2 comprises the amino acid sequence SEQ ID No. 11 and CDR-L3 comprises the amino acid sequence SEQ ID No. 12.

More particularly, said antibody, or one of its functional fragments or derivatives, according to this first embodiment comprises a light chain of sequence comprising the amino acid sequence SEQ ID No. 21.

```
SEQ ID No. 21:
DIVLTQSPASLAVSLGQRATISCRASESVDSYANSFMHWYQQKPGQPPK

LLIYRASNLESGIPARFSGSGSRTDFTLTINPVEADDVATYYCQQSKED

PLTFGSGTKLEMK
```

According to a second embodiment of said another aspect, the antibody of the invention, or one of its functional fragments or derivatives, comprises a light chain comprising CDR-L1, CDR-L2 and CDR-L3, wherein CDR-L1 comprises the amino acid sequence SEQ ID No. 13, CDR-L2 comprises the amino acid sequence SEQ ID No. 11 and CDR-L3 comprises the amino acid sequence SEQ ID No. 14.

The antibody, or one of its functional fragments or derivatives, according to said second embodiment will preferably comprise a light chain of sequence comprising the amino acid sequence SEQ ID No. 22.

SEQ ID No. 22:
GIVLTQSPASLAVSLGQRATISCRVSESIDTYGNSFIHWYQQKPGQPPK

LLIYRASNLESGIPARFSGSGSRTDFTLTINPVEADDSATYYCQQSNED

PFTFGSGTKLEMK

According to a third embodiment of said another aspect, the antibody of the invention, or one of its functional fragments or derivatives, comprises a light chain comprising CDR-L1, CDR-L2 and CDR-L3, wherein CDR-L1 comprises the amino acid sequence SEQ ID No. 15, CDR-L2 comprises the amino acid sequence SEQ ID No. 16 and CDR-L3 comprises the amino acid sequence SEQ ID No. 17.

The antibody, or one of its functional fragments or derivatives, according to said third embodiment will preferably comprise a light chain of sequence comprising the amino acid sequence SEQ ID No. 23.

SEQ ID No. 23:
DIQMTQSPASLSVSVGETVTITCRASENIYSNLAWYQQKQGKSPQLLVY

AATNLVDGVPSRFSGSGSGTQYSLKINSLQSEDFGSYYCQHFWGPPYTF

GGGTKLEIK

According to a fourth embodiment of said another aspect, the antibody of the invention, or one of its functional fragments or derivatives, comprises a light chain comprising CDR-L1, CDR-L2 and CDR-L3, wherein CDR-L1 comprises the amino acid sequence SEQ ID No. 59, CDR-L2 comprises the amino acid sequence SEQ ID No. 60 and CDR-L3 comprises the amino acid sequence SEQ ID No. 61.

The antibody, or one of its functional fragments or derivatives, according to said third embodiment will preferably comprise a light chain of sequence comprising the amino acid sequence SEQ ID No. 63.

SEQ ID No. 63:
QIVLTQSPAIMSASPGEKVTLTCSASSSVSSTYLYWYQQKPGSSPKLWI

YTTSILASGVPARFSGSGSGTSYSLTISSMETEDAASYFCHQWSSYPFT

FGSGTKLDIK

According a third approach, the antibody will be now defined both by its light chain sequence and its heavy chain sequence. The antibody of the invention, or one of its functional fragments or derivatives, is characterized in that it comprises a heavy chain comprising the amino acid sequence SEQ ID No. 18, 19, 20 or 62 and a light chain comprising the amino acid sequence SEQ ID No. 21, 22, 23 or 63.

More particularly, a preferred antibody, or one of its functional fragments or derivatives, according to the invention, named 224G11, comprises a heavy chain comprising CDR-H1, CDR-H2 and CDR-H3 comprising respectively the amino acid sequence SEQ ID Nos. 1, 2 and 3; and a light chain comprising CDR-L1, CDR-L2 and CDR-L3 comprising respectively the amino acid sequence SEQ ID Nos. 10, 11 and 12.

In another aspect, the antibody 224G11 comprises a heavy chain comprising the amino acid sequence SEQ ID No. 18 and a light chain comprising the amino acid sequence SEQ ID No. 21.

Another preferred antibody, or one of its functional fragments or derivatives, according to the invention, named 227H1, comprises a heavy chain comprising CDR-H1, CDR-H2 and CDR-H3 comprising respectively the amino acid sequence SEQ ID Nos. 4, 5 and 6; and a light chain comprising CDR-L1, CDR-L2 and CDR-L3 comprising respectively the amino acid sequence SEQ ID Nos. 13, 11 and 14.

In another aspect, the antibody 227H1 comprises a heavy chain comprising the amino acid sequence SEQ ID No. 19 and a light chain comprising the amino acid sequence SEQ ID No. 22.

Still another preferred antibody, or one of its functional fragments or derivatives, named 223C4, comprises a heavy chain comprising CDR-H1, CDR-H2 and CDR-H3 comprising respectively the amino acid sequence SEQ ID Nos. 7, 8 and 9; and a light chain comprising CDR-L1, CDR-L2 and CDR-L3 comprising respectively the amino acid sequence SEQ ID Nos. 15, 16 and 17.

In another aspect, the antibody 223C4 comprises a heavy chain comprising the amino acid sequence SEQ ID No. 20 and a light chain comprising the amino acid sequence SEQ ID No. 23.

Still another preferred antibody, or one of its functional fragments or derivatives, named 11E1, comprises a heavy chain comprising CDR-H1, CDR-H2 and CDR-H3 comprising respectively the amino acid sequence SEQ ID Nos. 56, 57 and 58; and a light chain comprising CDR-L1, CDR-L2 and CDR-L3 comprising respectively the amino acid sequence SEQ ID Nos. 59, 60 and 61.

In another aspect, the antibody 11E1 comprises a heavy chain comprising the amino acid sequence SEQ ID No. 62 and a light chain comprising the amino acid sequence SEQ ID No. 63.

According to another aspect, the invention relates to murine hybridoma capable of secreting monoclonal antibodies according to the present invention, especially hybridoma of murine origin such as deposited at the Collection Nationale de Cultures de Microorganismes (CNCM, National Collection of Microorganism Cultures) (Institut Pasteur, Paris, France).

The monoclonal antibodies according to the invention, or one of their functional fragments or derivatives, are characterized in that said antibodies are secreted by the hybridoma deposited at the CNCM on Mar. 14, 2007 under the numbers CNCM I-3724 (corresponding to 11E1), I-3731 (corresponding to 224G11), I-3732 (corresponding to 227H1) and on Jul. 6, 2007 under the number I-3786 (corresponding to 223C4). These hybridoma consist in murine hybridoma resulting in the cellular fusion of immunized mouse splenocytes with a myeloma cell line (Sp20 Ag14).

The following table 2 regroups elements concerning the preferred antibodies.

TABLE 2

| | 224G11 I-3731 | | 227H1 I-3732 | | 223C4 I-3786 | | 11E1 I-3724 | |
|---|---|---|---|---|---|---|---|---|
| | Prot. SEQ ID | Nucl. SEQ ID | Prot; SEQ ID | Nucl. SEQ ID | Prot. SEQ ID | Nucl. SEQ ID | Prot. SEQ ID | Nucl. SEQ ID |
| CDR-H1 | 1 | 24 | 4 | 27 | 7 | 30 | 56 | 64 |
| CDR-H2 | 2 | 25 | 5 | 28 | 8 | 31 | 57 | 65 |
| CDR-H3 | 3 | 26 | 6 | 29 | 9 | 32 | 58 | 66 |
| H. chain | 18 | 41 | 19 | 42 | 20 | 43 | 62 | 70 |

TABLE 2-continued

| | 224G11 I-3731 | | 227H1 I-3732 | | 223C4 I-3786 | | 11E1 I-3724 | |
|---|---|---|---|---|---|---|---|---|
| | Prot. SEQ ID | Nucl. SEQ ID | Prot; SEQ ID | Nucl. SEQ ID | Prot. SEQ ID | Nucl. SEQ ID | Prot. SEQ ID | Nucl. SEQ ID |
| CDR-L1 | 10 | 33 | 13 | 36 | 15 | 38 | 59 | 67 |
| CDR-L2 | 11 | 34 | 11 | 34 | 16 | 39 | 60 | 68 |
| CDR-L3 | 12 | 35 | 14 | 37 | 17 | 40 | 61 | 69 |
| L. chain | 21 | 44 | 22 | 45 | 23 | 46 | 63 | 71 |

From table 2, it clearly appears that CDR-L2 of the antibodies 227H1 and 224G11 is similar. This example clearly supports the claims of the present application covering antibodies comprising at least one CDR randomly chosen through described CDR sequences.

According to a preferred embodiment, the invention relates to monoclonal antibodies.

The term <<Monoclonal Antibody>> or is used in accordance with its ordinary meaning to denote an antibody obtained from a population of substantially homogeneous antibodies, i.e. the individual antibodies comprising the population are identical except for possible naturally occurring mutations that may be present in minor amounts. In other words, a monoclonal antibody consists in a homogenous antibody resulting from the proliferation of a single clone of cells (e.g., hybridoma cells, eukaryotic host cells transfected with DNA encoding the homogenous antibody, prokaryotic host cells transformed with DNA encoding the homogenous antibody, etc.), and which is generally characterized by heavy chains of a single class and subclass, and light chains of a single type. Monoclonal antibodies are highly specific, being directed against a single antigen. Furthermore, in contrast to polyclonal antibodies preparations that typically include different antibodies directed against different determinants, or epitope, each monoclonal antibody is directed against a single determinant on the antigen.

In the present description, the terms polypeptides, polypeptide sequences, amino acid sequences, peptides and proteins attached to antibody compounds or to their sequence are interchangeable.

According to a likewise particular aspect, the present invention relates to a chimeric antibody, or one of its functional fragments, according to the invention, characterized in that said antibody moreover comprises the light chain and heavy chain constant regions derived from an antibody of a species heterologous to the mouse, especially man, and in a preferred manner in that the light chain and heavy chain constant regions derived from a human antibody are respectively the kappa and gamma-1, gamma-2 or gamma-4 region.

In the present application, IgG1 are preferred to get effector functions, and most preferably ADCC and CDC.

The skilled artisan will recognize that effector functions include, for example, C1q binding; complement dependent cytotoxicity (CDC); Fc receptor binding; antibody-dependent cell-mediated cytotoxicity (ADCC); phagocytosis; and down regulation of cell surface receptors (e.g. B cell receptor; BCR).

The antibodies according to the present invention, are preferably specific monoclonal antibodies, especially of murine, chimeric or humanized origin, which can be obtained according to the standard methods well known to the person skilled in the art.

In general, for the preparation of monoclonal antibodies or their functional fragments or derivatives, especially of murine origin, it is possible to refer to techniques which are described in particular in the manual "Antibodies" (Harlow and Lane, Antibodies: A Laboratory Manual, Cold Spring Harbor Laboratory, Cold Spring Harbor N.Y., pp. 726, 1988) or to the technique of preparation from hybridomas described by Kohler and Milstein (Nature, 256:495-497, 1975).

The monoclonal antibodies according to the invention can be obtained, for example, from an animal cell immunized against the c-Met, or one of its fragments containing the epitope specifically recognized by said monoclonal antibodies according to the invention. Said c-Met, or one of its said fragments, can especially be produced according to the usual working methods, by genetic recombination starting with a nucleic acid sequence contained in the cDNA sequence coding for the c-Met or by peptide synthesis starting from a sequence of amino acids comprised in the peptide sequence of the c-Met.

The monoclonal antibodies according to the invention can, for example, be purified on an affinity column on which the c-Met or one of its fragments containing the epitope specifically recognized by said monoclonal antibodies according to the invention has previously been immobilized. More particularly, said monoclonal antibodies can be purified by chromatography on protein A and/or G, followed or not followed by ion-exchange chromatography aimed at eliminating the residual protein contaminants as well as the DNA and the LPS, in itself followed or not followed by exclusion chromatography on Sepharose™ gel in order to eliminate the potential aggregates due to the presence of dimers or of other multimers. In an even more preferred manner, the whole of these techniques can be used simultaneously or successively.

Chimeric or humanized antibodies are likewise included in antibodies according to the present invention.

By chimeric antibody, it is intended to indicate an antibody which contains a natural variable (light chain and heavy chain) region derived from an antibody of a given species in combination with the light chain and heavy chain constant regions of an antibody of a species heterologous to said given species (e.g. mouse, horse, rabbit, dog, cow, chicken, etc.).

The antibodies or their fragments of chimeric type according to the invention can be prepared by using the techniques of genetic recombination. For example, the chimeric antibody can be produced by cloning a recombinant DNA containing a promoter and a sequence coding for the variable region of a non-human, especially murine, monoclonal antibody according to the invention and a sequence coding for the constant region of human antibody. A chimeric antibody of the invention encoded by such a recombinant gene will be, for example, a mouse-man chimera, the specificity of this antibody being determined by the variable region derived from the murine DNA and its isotype determined by the constant region derived from the human DNA. For the methods of preparation of chimeric antibodies, it is possible, for example, to refer to the documents Verhoeyn et al. (BioEssays, 8:74, 1988), Morrison et al. (Proc. Natl. Acad. Sci. USA 82:6851-6855, 1984) ou le brevet U.S. Pat. No. 4,816,567.

By humanized antibody, it is intended to indicate an antibody which contains CDR regions derived from an antibody of nonhuman origin, the other parts of the antibody molecule being derived from one (or from several) human antibodies. Moreover, some of the residues of the segments of the skeleton (called FR) can be modified in order to conserve the affinity of the binding (Jones et al., Nature, 321:522-525, 1986; Verhoeyen et al., Science, 239:1534-1536, 1988; Riechmann et al., Nature, 332:323-327, 1988).

The humanized antibodies according to the invention or their fragments can be prepared by techniques known to the person skilled in the art (such as, for example, those described in the documents Singer et al., J. Immun. 150:2844-2857, 1992; Mountain et al., Biotechnol. Genet. Eng. Rev., 10:1-142, 1992; or Bebbington et al., Bio/Technology, 10:169-175, 1992).

Other humanization method are known by the man skill in the art as, for example, the "CDR Grafting" method described by Protein Design Lab (PDL) in the patent applications EP 0 451216, EP 0 682 040, EP 0 939127, EP 0 566 647 or U.S. Pat. No. 5,530,101, U.S. Pat. No. 6,180,370, U.S. Pat. No. 5,585,089 and U.S. Pat. No. 5,693,761. The following patent applications can also be mentioned: U.S. Pat. No. 5,639,641; U.S. Pat. No. 6,054,297; U.S. Pat. No. 5,886,152 and U.S. Pat. No. 5,877,293.

By "functional fragment" of an antibody according to the invention, it is intended to indicate in particular an antibody fragment, such as Fv, scFv (sc for single chain), Fab, F(ab')$_2$, Fab', scFv-Fc fragments or diabodies, or any fragment of which the half-life time would have been increased by chemical modification, such as the addition of poly(alkylene) glycol such as poly(ethylene) glycol ("PEGylation") (pegylated fragments called Fv-PEG, scFv-PEG, Fab-PEG, F(ab')$_2$-PEG or Fab'-PEG) ("PEG" for Poly(Ethylene) Glycol), or by incorporation in a liposome, said fragments having at least one of the characteristic CDRs of sequence SEQ ID Nos. 1 to 17 and 56 to 61 according to the invention, and, especially, in that it is capable of exerting in a general manner an even partial activity of the antibody from which it is descended, such as in particular the capacity to recognize and to bind to the c-Met, and, if necessary, to inhibit the activity of the c-Met.

Preferably, said functional fragments will be constituted or will comprise a partial sequence of the heavy or light variable chain of the antibody from which they are derived, said partial sequence being sufficient to retain the same specificity of binding as the antibody from which it is descended and a sufficient affinity, preferably at least equal to 1/100, in a more preferred manner to at least 1/10, of that of the antibody from which it is descended, with respect to the c-Met. Such a functional fragment will contain at the minimum 5 amino acids, preferably 6, 7, 8, 9, 10, 12, 15, 25, 50 and 100 consecutive amino acids of the sequence of the antibody from which it is descended.

Preferably, these functional fragments will be fragments of Fv, scFv, Fab, F(ab')$_2$, F(ab'), scFv-Fc type or diabodies, which generally have the same specificity of binding as the antibody from which they are descended. In a more preferred embodiment of the invention, these fragments are selected among divalent fragments such as F(ab')$_2$ fragments. According to the present invention, antibody fragments of the invention can be obtained starting from antibodies such as described above by methods such as digestion by enzymes, such as pepsin or papain and/or by cleavage of the disulfide bridges by chemical reduction. In another manner, the antibody fragments comprised in the present invention can be obtained by techniques of genetic recombination likewise well known to the person skilled in the art or else by peptide synthesis by means of, for example, automatic peptide synthesizers such as those supplied by the company Applied Biosystems, etc.

By "divalent fragment", it must be understood any antibody fragments comprising two arms and, more particularly, F(ab')$_2$ fragments.

More particularly, the invention comprises the antibodies, or their functional fragments, according to the present invention, especially chimeric or humanized antibodies, obtained by genetic recombination or by chemical synthesis.

By <<derivatives>> of an antibody according to the invention, it is meant a binding protein comprising a protein scaffold and at least on of the CDRs selected from the original antibody in order to maintain the binding capacity. Such compounds are well known by the man skilled in the art and will be described in more details in the following specification.

More particularly, the antibody, or one of its functional fragments or derivatives, according to the invention is characterized in that sand derivative consists in a binding protein comprising a scaffold on which at least one CDR has been grafted for the conservation of the original antibody paratopic recognizing properties.

One or several sequences through the 6 CDR sequences described in the invention can be presented on a protein scaffold. In this case, the protein scaffold reproduces the protein backbone with appropriate folding of the grafted CDR(s), thus allowing it (or them) to maintain their antigen paratopic recognizing properties.

The man skilled in the art knows how to select the protein scaffold on which at least one CDR selected from the original antibody could be grafted. More particularly, it is known that, to be selected, such scaffold should display several features as follow (Skerra A., J. Mol. Recogn., 13, 2000, 167-187):
  phylogenetically good conservation,
  robust architecture with a well known three-dimensional molecular organization (such as, for example, crystallography or NMR),
  small size,
  no or only low degree of post-translational modifications,
  easy to produce, express and purify.

Such protein scaffold can be, but without limitation, structure selected from the group consisting in fibronectin and preferentially the tenth fibronectin type III domain (FNfn10), lipocalin, anticalin (Skerra A., J. Biotechnol., 2001, 74(4): 257-75), the protein Z derivative from the domain B of staphylococcal protein A, thioredoxin A or any protein with repeated domain such as "ankyrin repeat" (Kohl et al., PNAS, 2003, vol. 100, No. 4, 1700-1705), "armadillo repeat", "leucin-rich repeat" or "tetratricopeptide repeat".

It could also be mentioned scaffold derivative from toxins (such as, for example, scorpion, insect, plant or mollusc toxins) or protein inhibitors of neuronal nitric oxide synthase (PIN).

As non limitative example of such hybrid constructions, it can be mentioned the insertion of the CDR-H1 (heavy chain) of an anti-CD4 antibody, i.e. the 13B8.2 antibody, into one of the exposed loop of the PIN. The binding properties of the obtained binding protein remain similar to the original antibody (Bes et al., BBRC 343, 2006, 334-344). It can also be mentioned the grafting of the CDR-H3 (heavy chain) of an anti-lyzozyme VHH antibody on a loop of neocarzinostatine (Nicaise et al., 2004).

In the case of the present invention, an interesting CDR to conserve could be, without limitation, the CDR-L2 as it is conserved in two identified antibodies of the invention, i.e. 227H1 and 224G11.

As above mentioned, such protein scaffold can comprise from 1 to 6 CDR(s) from the original antibody. In a preferred embodiment, but without any limitation, the man skilled in the art would select at least a CDR from the heavy chain, said heavy chain being known to be particularly implicated in the antibody specificity. The selection of the CDR(s) of interest will be evident for the man of the art with known method (BES et al., FEBS letters 508, 2001, 67-74).

As an evidence, these examples are not limitative and any other scaffold known or described must be included in the present specification.

According to a novel aspect, the present invention relates to an isolated nucleic acid, characterized in that it is chosen from the following nucleic acids:

a) a nucleic acid, DNA or RNA, coding for an antibody, or one of its functional fragments or derivatives, according to the invention;

b) a nucleic acid comprising a DNA sequence selecting from the group of sequences consisting of:
  a nucleic sequence comprising the sequences SEQ ID No. 24, SEQ ID No. 25, SEQ ID No. 26 and the sequences SEQ ID No. 33, SEQ ID No. 34 and SEQ ID No. 35;
  a nucleic sequence comprising the sequences SEQ ID No. 27, SEQ ID No. 28, SEQ ID No. 29 and the sequences SEQ ID No. 36, SEQ ID No. 34 and SEQ ID No. 37;
  a nucleic sequence comprising the sequences SEQ ID No. 30, SEQ ID No. 31, SEQ ID No. 32 and the sequences SEQ ID No. 38, SEQ ID No. 39 and SEQ ID No. 40; and
  a nucleic sequence comprising the sequences SEQ ID No. 64, SEQ ID No. 65, SEQ ID No. 66 and the sequences SEQ ID No. 67, SEQ ID No. 68 and SEQ ID No. 69;

c) a nucleic acid comprising a DNA sequence selecting from the group of sequences consisting of:
  a nucleic sequence comprising the sequences SEQ ID No. 41 and SEQ ID No. 44;
  a nucleic sequence comprising the sequences SEQ ID No. 42 and SEQ ID No. 45;
  a nucleic sequence comprising the sequences SEQ ID No. 43 and SEQ ID No. 46, and
  a nucleic sequence comprising the sequences SEQ ID No. 70 and SEQ ID No. 71;

d) the corresponding RNA nucleic acids of the nucleic acids as defined in b) or c);

e) the complementary nucleic acids of the nucleic acids as defined in a), b) and c); and f) a nucleic acid of at least 18 nucleotides capable of hybridizing under conditions of height stringency with at least one of the CDRs of sequence SEQ ID Nos. 24 to 40 and 64 to 69.

By nucleic acid, nucleic or nucleic acid sequence, polynucleotide, oligonucleotide, polynucleotide sequence, nucleotide sequence, terms which will be employed indifferently in the present invention, it is intended to indicate a precise linkage of nucleotides, which are modified or unmodified, allowing a fragment or a region of a nucleic acid to be defined, containing or not containing unnatural nucleotides, and being able to correspond just as well to a double-stranded DNA, a single-stranded DNA as to the transcription products of said DNAs.

It must also be understood here that the present invention does not concern the nucleotide sequences in their natural chromosomal environment, that is to say in the natural state. It concerns sequences which have been isolated and/or purified, that is to say that they have been selected directly or indirectly, for example by copy, their environment having been at least partially modified. It is thus likewise intended to indicate here the isolated nucleic acids obtained by genetic recombination by means, for example, of host cells or obtained by chemical synthesis.

An hybridization under conditions of high stringency signifies that the temperature conditions and ionic strength conditions are chosen in such a way that they allow the maintenance of the hybridization between two fragments of complementary DNA. By way of illustration, conditions of high stringency of the hybridization step for the purposes of defining the polynucleotide fragments described above are advantageously the following.

The DNA-DNA or DNA-RNA hybridization is carried out in two steps: (1) prehybridization at 42° C. for 3 hours in phosphate buffer (20 mM, pH 7.5) containing 5×SSC (1×SSC corresponds to a 0.15 M NaCl+0.015 M sodium citrate solution), 50% of formamide, 7% of sodium dodecyl sulfate (SDS), 10×Denhardt's, 5% of dextran sulfate and 1% of salmon sperm DNA; (2) actual hybridization for 20 hours at a temperature dependent on the size of the probe (i.e.: 42° C., for a probe size >100 nucleotides) followed by 2 washes of 20 minutes at 20° C. in 2×SSC+2% of SDS, 1 wash of 20 minutes at 20° C. in 0.1×SSC+0.1% of SDS. The last wash is carried out in 0.1×SSC+0.1% of SDS for 30 minutes at 60° C. for a probe size >100 nucleotides. The hybridization conditions of high stringency described above for a polynucleotide of defined size can be adapted by the person skilled in the art for oligonucleotides of greater or smaller size, according to the teaching of Sambrook et al. (1989, Molecular cloning: a laboratory manual. 2nd Ed. Cold Spring Harbor).

The invention likewise relates to a vector comprising a nucleic acid according to the present invention.

The invention aims especially at cloning and/or expression vectors which contain a nucleotide sequence according to the invention.

The vectors according to the invention preferably contain elements which allow the expression and/or the secretion of the nucleotide sequences in a determined host cell. The vector must therefore contain a promoter, signals of initiation and termination of translation, as well as appropriate regions of regulation of transcription. It must be able to be maintained in a stable manner in the host cell and can optionally have particular signals which specify the secretion of the translated protein. These different elements are chosen and optimized by the person skilled in the art as a function of the host cell used. To this effect, the nucleotide sequences according to the invention can be inserted into autonomous replication vectors in the chosen host, or be integrative vectors of the chosen host.

Such vectors are prepared by methods currently used by the person skilled in the art, and the resulting clones can be introduced into an appropriate host by standard methods, such as lipofection, electroporation, thermal shock, or chemical methods.

The vectors according to the invention are, for example, vectors of plasmidic or viral origin. They are useful for transforming host cells in order to clone or to express the nucleotide sequences according to the invention.

The invention likewise comprises the host cells transformed by or comprising a vector according to the invention.

The host cell can be chosen from prokaryotic or eukaryotic systems, for example bacterial cells but likewise yeast cells or animal cells, in particular mammalian cells. It is likewise possible to use insect cells or plant cells.

The invention likewise concerns animals, except man, which comprise at least one cell transformed according to the invention.

According to another aspect, a subject of the invention is a process for production of an antibody, or one of its functional fragments according to the invention, characterized in that it comprises the following stages:

a) culture in a medium and appropriate culture conditions of a host cell according to the invention; and b) the recovery of said antibodies, or one of their functional fragments, thus produced starting from the culture medium or said cultured cells.

The cells transformed according to the invention can be used in processes for preparation of recombinant polypeptides according to the invention. The processes for preparation of a polypeptide according to the invention in recombinant form, characterized in that they employ a vector and/or a cell transformed by a vector according to the invention, are themselves comprised in the present invention. Preferably, a cell transformed by a vector according to the invention is cultured under conditions which allow the expression of said polypeptide and said recombinant peptide is recovered.

As has been said, the host cell can be chosen from prokaryotic or eukaryotic systems. In particular, it is possible to identify nucleotide sequences according to the invention, facilitating secretion in such a prokaryotic or eukaryotic system. A vector according to the invention carrying such a sequence can therefore advantageously be used for the production of recombinant proteins, intended to be secreted. In effect, the purification of these recombinant proteins of interest will be facilitated by the fact that they are present in the supernatant of the cell culture rather than in the interior of the host cells.

It is likewise possible to prepare the polypeptides according to the invention by chemical synthesis. Such a preparation process is likewise a subject of the invention. The person skilled in the art knows the processes of chemical synthesis, for example the techniques employing solid phases [Steward et al., 1984, Solid phase peptide synthesis, Pierce Chem. Company, Rockford, 111, 2nd ed., (1984)] or techniques using partial solid phases, by condensation of fragments or by a classical synthesis in solution. The polypeptides obtained by chemical synthesis and being able to contain corresponding unnatural amino acids are likewise comprised in the invention.

The antibodies, or one of their functional fragments or derivatives, capable of being obtained by a process according to the invention are likewise comprised in the present invention.

The invention also concerns the antibody of the invention as a medicament.

The invention likewise concerns a pharmaceutical composition comprising by way of active principle a compound consisting of an antibody, or one of its functional fragments according to the invention, preferably mixed with an excipient and/or a pharmaceutically acceptable vehicle.

Another complementary embodiment of the invention consists in a composition such as described above which comprises, moreover, as a combination product for simultaneous, separate or sequential use, an anti-tumoral antibody.

Most preferably, said second anti-tumoral antibody could be chosen through anti-IGF-IR, anti-EGFR, anti-HER2/neu, anti-VEGFR, anti-VEGF, etc., antibodies or any other anti-tumoral antibodies known by the man skilled in the art. It is evident that the use, as second antibody, of functional fragments or derivatives of above mentioned antibodies is part of the invention.

As a most preferred antibody, anti-EGFR antibodies are selected such as for example the antibody C225 (Erbitux).

"Simultaneous use" is understood as meaning the administration of the two compounds of the composition according to the invention in a single and identical pharmaceutical form.

"Separate use" is understood as meaning the administration, at the same time, of the two compounds of the composition according to the invention in distinct pharmaceutical forms.

"Sequential use" is understood as meaning the successive administration of the two compounds of the composition according to the invention, each in a distinct pharmaceutical form.

In a general fashion, the composition according to the invention considerably increases the efficacy of the treatment of cancer. In other words, the therapeutic effect of the anti-c-Met antibodies according to the invention is potentiated in an unexpected manner by the administration of a cytotoxic agent. Another major subsequent advantage produced by a composition according to the invention concerns the possibility of using lower efficacious doses of active principle, which allows the risks of appearance of secondary effects to be avoided or to be reduced, in particular the effects of the cytotoxic agent.

In addition, this composition according to the invention would allow the expected therapeutic effect to be attained more rapidly.

The composition of the invention can also be characterized in that it comprises, moreover, as a combination product for simultaneous, separate or sequential use, a cytotoxic/cytostatic agent.

By "anti-cancer therapeutic agents" or "cytotoxic/cytostatic agents", it is intended a substance which, when administered to a subject, treats or prevents the development of cancer in the subject's body. As non limitative example of such agents, it can be mentioned alkylating agents, anti-metabolites, anti-tumor antibiotics, mitotic inhibitors, chromatin function inhibitors, anti-angiogenesis agents, anti-estrogens, anti-androgens or immunomodulators.

Such agents are, for example, cited in the 2001 edition of VIDAL, on the page devoted to the compounds attached to the cancerology and hematology column "Cytotoxics", these cytotoxic compounds cited with reference to this document are cited here as preferred cytotoxic agents.

More particularly, the following agents are preferred according to the invention.

"Alkylating agent" refers to any substance which can cross-link or alkylate any molecule, preferably nucleic acid (e.g., DNA), within a cell. Examples of alkylating agents include nitrogen mustard such as mechlorethamine, chlorambucol, melphalen, chlorydrate, pipobromen, prednimustin, disodic-phosphate or estramustine; oxazophorins such as cyclophosphamide, altretamine, trofosfamide, sulfofosfamide or ifosfamide; aziridines or imine-ethylenes such as thiotepa, triethylenamine or altetramine; nitrosourea such as carmustine, streptozocin, fotemustin or lomustine; alkylesulfonates such as busulfan, treosulfan or improsulfan; triazenes such as dacarbazine; or platinum complexes such as cis-platinum, oxaliplatin and carboplatin.

"Anti-metabolites" refer to substances that block cell growth and/or metabolism by interfering with certain activities, usually DNA synthesis. Examples of anti-metabolites include methotrexate, 5-fluoruracil, floxuridine, 5-fluorodeoxyuridine, capecitabine, cytarabine, fludarabine, cytosine arabinoside, 6-mercaptopurine (6-MP), 6-thioguanine (6-TG), chlorodesoxyadenosine, 5-azacytidine, gemcitabine, cladribine, deoxycoformycin and pentostatin.

"Anti-tumor antibiotics" refer to compounds which may prevent or inhibit DNA, RNA and/or protein synthesis. Examples of anti-tumor antibiotics include doxorubicin, daunorubicin, idarubicin, valrubicin, mitoxantrone, dactinomycin, mithramycin, plicamycin, mitomycin C, bleomycin, and procarbazine.

"Mitotic inhibitors" prevent normal progression of the cell cycle and mitosis. In general, microtubule inhibitors or taxoides such as paclitaxel and docetaxel are capable of inhibiting mitosis. Vinca alkaloid such as vinblastine, vincristine, vindesine and vinorelbine are also capable of inhibiting mitosis.

"Chromatin function inhibitors" or "topoisomerase inhibitors" refer to substances which inhibit the normal function of chromatin modeling proteins such as topoisomerase I or topoisomerase II. Examples of chromatin function inhibitors include, for topoisomerase I, camptothecine and its derivatives such as topotecan or irinotecan, and, for topoisomerase II, etoposide, etoposide phosphate and teniposide.

"Anti-angiogenesis agent" refers to any drug, compound, substance or agent which inhibits growth of blood vessels. Exemplary anti-angiogenesis agents include, but are by no means limited to, razoxin, marimastat, batimastat, prinomastat, tanomastat, ilomastat, CGS-27023A, halofuginon, COL-3, neovastat, BMS-275291, thalidomide, CDC 501, DMXAA, L-651582, squalamine, endostatin, SU5416, SU6668, interferon-alpha,EMD121974, interleukin-12, IM862, angiostatin and vitaxin.

"Anti-estrogen" or "anti-estrogenic agent" refer to any substance which reduces, antagonizes or inhibits the action of estrogen. Examples of anti-estrogen agents are tamoxifen, toremifene, raloxifene, droloxifene, iodoxyfene, anastrozole, letrozole, and exemestane.

"Anti-androgens" or "anti-androgen agents" refer to any substance which reduces, antagonizes or inhibits the action of an androgen. Examples of anti-androgens are flutamide, nilutamide, bicalutamide, sprironolactone, cyproterone acetate, finasteride and cimitidine.

"Immunomodulators" are substances which stimulate the immune system.

Examples of immunomodulators include interferon, interleukin such as aldesleukine, OCT-43, denileukin diflitox and interleukin-2, tumoral necrose fators such as tasonermine or others immunomodulators such as lentinan, sizofiran, roquinimex, pidotimod, pegademase, thymopentine, poly I:C or levamisole in conjunction with 5-fluorouracil.

For more detail, the man skill in the art could refer to the manual edited by the "Association Française des Enseignants de Chimie Thérapeutique" and entitled "traité de chimie thérapeutique, vol. 6, Médicaments antitumoraux et perspectives dans le traitement des cancers, edition TEC & DOC, 2003".

Can also be mentioned as chemical agents or cytotoxic agents, all kinase inhibitors such as, for example, gefitinib or erlotinib.

In a particularly preferred embodiment, said composition as a combination product according to the invention is characterized in that said cytotoxic agent is coupled chemically to said antibody for simultaneous use.

In order to facilitate the coupling between said cytotoxic agent and said antibody according to the invention, it is especially possible to introduce spacer molecules between the two compounds to be coupled, such as poly(alkylene) glycols like polyethylene glycol, or else amino acids, or, in another embodiment, to use active derivatives of said cytotoxic agents into which would have been introduced functions capable of reacting with said antibody according to the invention. These coupling techniques are well known to the person skilled in the art and will not be expanded upon in the present description.

The invention relates, in another aspect, to a composition characterized in that one, at least, of said antibodies, or one of their functional fragments or derivatives, is conjugated with a cell toxin and/or a radioelement.

Preferably, said toxin or said radioelement is capable of inhibiting at least one cell activity of cells expressing the c-Met, in a more preferred manner capable of preventing the growth or the proliferation of said cell, especially of totally inactivating said cell.

Preferably also, said toxin is an enterobacterial toxin, especially *Pseudomonas* exotoxin A.

The radioelements (or radioisotopes) preferably conjugated to the antibodies employed for the therapy are radioisotopes which emit gamma rays and preferably iodine$^{131}$, yttrium$^{90}$, gold$^{199}$, palladium$^{100}$, copper$^{67}$, bismuth$^{217}$ and antimony$^{211}$. The radioisotopes which emit beta and alpha rays can likewise be used for the therapy.

By toxin or radioelement conjugated to at least one antibody, or one of its functional fragments, according to the invention, it is intended to indicate any means allowing said toxin or said radioelement to bind to said at least one antibody, especially by covalent coupling between the two compounds, with or without introduction of a linking molecule.

Among the agents allowing binding in a chemical (covalent), electrostatic or noncovalent manner of all or part of the components of the conjugate, mention may particularly be made of benzoquinone, carbodiimide and more particularly EDC (1-ethyl-3-[3-dimethyl-aminopropyl]-carbodiimide hydrochloride), dimaleimide, dithiobis-nitrobenzoic acid (DTNB), N-succinimidyl S-acetyl thio-acetate (SATA), the bridging agents having one or more phenylazide groups reacting with the ultraviolets (U.V.) and preferably N-[-4-(azidosalicylamino)butyl]-3'-(2'-pyridyldithio)-propionamide (APDP), N-succinimid-yl 3-(2-pyridyldithio)propionate (SPDP), 6-hydrazino-nicotinamide (HYNIC).

Another form of coupling, especially for the radioelements, can consist in the use of a bifunctional ion chelator.

Among these chelates, it is possible to mention the chelates derived from EDTA (ethylenediaminetetraacetic acid) or from DTPA (diethylenetriaminepentaacetic acid) which have been developed for binding metals, especially radioactive metals, and immunoglobulins. Thus, DTPA and its derivatives can be substituted by different groups on the carbon chain in order to increase the stability and the rigidity of the ligand-metal complex (Krejcarek et al. (1977); Brechbiel et al. (1991); Gansow (1991); U.S. Pat. No. 4,831,175).

For example diethylenetriaminepentaacetic acid (DTPA) and its derivatives, which have been widely used in medicine and in biology for a long time either in their free form, or in the form of a complex with a metallic ion, have the remarkable characteristic of forming stable chelates with metallic ions and of being coupled with proteins of therapeutic or diagnostic interest such as antibodies for the development of radioimmunoconjugates in cancer therapy (Meases et al., (1984); Gansow et al. (1990)).

Likewise preferably, said at least one antibody forming said conjugate according to the invention is chosen from its functional fragments, especially the fragments amputated of their Fc component such as the scFv fragments.

As already mentioned, in a preferred embodiment of the invention, said cytotoxic/cytostatic agent or said toxin and/or a radioelement is coupled chemically to at least one of the elements of said composition for simultaneous use.

The present invention comprises the described composition as a medicament.

The present invention moreover comprises the use of the composition according to the invention for the preparation of a medicament.

In another aspect, the invention deals with the use of an antibody, or one of its functional fragments or derivatives, and/or of a composition as above described for the preparation of a medicament intended to inhibit the growth and/or the proliferation of tumor cells.

Another aspect of the invention consists in the use of an antibody, or one of its functional fragments or derivatives and/or of a composition, as described above or the use above mentioned, for the preparation of a medicament intended for the prevention or for the treatment of cancer.

Is also comprises in the present invention a method intended to inhibit the growth and/or the proliferation of tumor cells in a patient comprising the administration to a patient in need thereof of an antibody, or one of its functional fragments or derivatives according to the invention, an antibody produced by an hybridoma according to the invention or a composition according to the invention.

The present invention further comprises a method for the prevention or the treatment of cancer in a patient in need thereof, comprising the administration to the patient of an antibody, or one of its functional fragments or derivatives according to the invention, an antibody produced by an hybridoma according to the invention or a composition according to the invention.

In a particular preferred aspect, said cancer is a cancer chosen from prostate cancer, osteosarcomas, lung cancer, breast cancer, endometrial cancer, glioblastoma or colon cancer.

As explained before, an advantage of the invention is to allow the treatment of HGF dependent and independent Met-activation related cancers.

The invention, in yet another aspect, encompasses a method of in vitro diagnosis of illnesses induced by an overexpression or an underexpression of the c-Met receptor starting from a biological sample in which the abnormal presence of c-Met receptor is suspected, said method being characterized in that it comprises a step wherein said biological sample is contacted with an antibody of the invention, it being possible for said antibody to be, if necessary, labeled.

Preferably, said illnesses connected with an abnormal presence of c-Met receptor in said diagnosis method will be cancers.

Said antibody, or one of its functional fragments, can be present in the form of an immunoconjugate or of a labeled antibody so as to obtain a detectable and/or quantifiable signal.

The antibodies labeled according to the invention or their functional fragments include, for example, antibodies called immunoconjugates which can be conjugated, for example, with enzymes such as peroxidase, alkaline phosphatase, beta-D-galactosidase, glucose oxydase, glucose amylase, carbonic anhydrase, acetylcholinesterase, lysozyme, malate dehydrogenase or glucose 6-phosphate dehydrogenase or by a molecule such as biotin, digoxygenin or 5-bromodeoxyuridine. Fluorescent labels can be likewise conjugated to the antibodies or to their functional fragments according to the invention and especially include fluorescein and its derivatives, fluorochrome, rhodamine and its derivatives, GFP (GFP for "Green Fluorescent Protein"), dansyl, umbelliferone etc. In such conjugates, the antibodies of the invention or their functional fragments can be prepared by methods known to the person skilled in the art. They can be coupled to the enzymes or to the fluorescent labels directly or by the intermediary of a spacer group or of a linking group such as a polyaldehyde, like glutaraldehyde, ethylenediaminetetraacetic acid (EDTA), diethylene-triaminepentaacetic acid (DPTA), or in the presence of coupling agents such as those mentioned above for the therapeutic conjugates. The conjugates containing labels of fluorescein type can be prepared by reaction with an isothiocyanate.

Other conjugates can likewise include chemoluminescent labels such as luminol and the dioxetanes, bio-luminescent labels such as luciferase and luciferin, or else radioactive labels such as iodine$^{123}$, iodine$^{125}$, iodine$^{126}$, iodine$^{133}$, bromine$^{77}$, technetium$^{99m}$, indiumm$^{111}$, indium$^{113m}$, gallium$^{67}$, gallium$^{68}$, ruthenium$^{95}$, ruthenium$^{97}$, ruthenium$^{103}$, ruthenium$^{105}$, mercury$^{107}$, mercury$^{203}$, rhenium$^{99m}$, rhenium$^{101}$, rhenium$^{105}$, scandium$^{47}$, tellurium$^{121m}$, tellurium$^{122m}$, tellurium$^{125m}$, thulium$^{165}$, thulium$^{167}$, thulium$^{168}$, fluorine$^{18}$, yttrium$^{199}$, iodine$^{131}$. The methods known to the person skilled in the art existing for coupling the therapeutic radio-isotopes to the antibodies either directly or via a chelating agent such as EDTA, DTPA mentioned above can be used for the radioelements which can be used in diagnosis. It is likewise possible to mention labeling with Na[I$^{125}$] by the chloramine T method [Hunter W. M. and Greenwood F. C. (1962) Nature 194:495] or else with technetium$^{99m}$ by the technique of Crockford et al. (U.S. Pat. No. 4,424,200) or attached via DTPA as described by Hnatowich (U.S. Pat. No. 4,479,930).

Thus, the antibodies, or their functional fragments, according to the invention can be employed in a process for the detection and/or the quantification of an overexpression or of an underexpression, preferably an overexpression, of the c-Met receptor in a biological sample, characterized in that it comprises the following steps:

a) the contacting of the biological sample with an antibody, or one of its functional fragments, according to the invention; and b) the demonstration of the c-Met/antibody complex possibly formed.

In a particular embodiment, the antibodies, or their functional fragments, according to the invention, can be employed in a process for the detection and/or the quantification of the c-Met receptor in a biological sample, for the monitoring of the efficacy of a prophylactic and/or therapeutic treatment of c-Met-dependent cancer.

More generally, the antibodies, or their functional fragments, according to the invention can be advantageously employed in any situation where the expression of the c-Met-receptor must be observed in a qualitative and/or quantitative manner.

Preferably, the biological sample is formed by a biological fluid, such as serum, whole blood, cells, a tissue sample or biopsies of human origin.

Any procedure or conventional test can be employed in order to carry out such a detection and/or dosage. Said test can be a competition or sandwich test, or any test known to the person skilled in the art dependent on the formation of an immune complex of antibody-antigen type. Following the applications according to the invention, the antibody or one of its functional fragments can be immobilized or labeled. This immobilization can be carried out on numerous supports known to the person skilled in the art. These supports can especially include glass, polystyrene, poly-propylene, poly-ethylene, dextran, nylon, or natural or modified cells. These supports can be either soluble or insoluble.

By way of example, a preferred method brings into play immunoenzymatic processes according to the ELISA technique, by immunofluorescence, or radio-immunoassay (RIA) technique or equivalent.

Thus, the present invention likewise comprises the kits or sets necessary for carrying out a method of diagnosis of illnesses induced by an overexpression or an underexpression of the c-Met receptor or for carrying out a process for the detection and/or the quantification of an overexpression or of an underexpression of the c-Met receptor in a biological sample, preferably an overexpression of said receptor, characterized in that said kit or set comprises the following elements:

a) an antibody, or one of its functional fragments, according to the invention;

b) optionally, the reagents for the formation of the medium favorable to the immunological reaction;

c) optionally, the reagents allowing the demonstration of c-Met/antibody complexes produced by the immunological reaction.

A subject of the invention is likewise the use of an antibody or a composition according to the invention for the preparation of a medicament intended for the specific targeting of a biologically active compound to cells expressing or overexpressing the c-Met receptor.

It is intended here by biologically active compound to indicate any compound capable of modulating, especially of inhibiting, cell activity, in particular their growth, their proliferation, transcription or gene translation.

A subject of the invention is also an in vivo diagnostic reagent comprising an antibody according to the invention, or one of its functional fragments, preferably labeled, especially radiolabeled, and its use in medical imaging, in particular for the detection of cancer connected with the expression or the overexpression by a cell of the c-Met receptor.

The invention likewise relates to a composition as a combination product or to an anti-c-Met/toxin conjugate or radioelement, according to the invention, as a medicament.

Preferably, said composition as a combination product or said conjugate according to the invention will be mixed with an excipient and/or a pharmaceutically acceptable vehicle.

In the present description, pharmaceutically acceptable vehicle is intended to indicate a compound or a combination of compounds entering into a pharmaceutical composition not provoking secondary reactions and which allows, for example, facilitation of the administration of the active compound(s), an increase in its lifespan and/or in its efficacy in the body, an increase in its solubility in solution or else an improvement in its conservation. These pharmaceutically acceptable vehicles are well known and will be adapted by the person skilled in the art as a function of the nature and of the mode of administration of the active compound(s) chosen.

Preferably, these compounds will be administered by the systemic route, in particular by the intravenous route, by the intramuscular, intradermal, intraperitoneal or subcutaneous route, or by the oral route. In a more preferred manner, the composition comprising the antibodies according to the invention will be administered several times, in a sequential manner.

Their modes of administration, dosages and optimum pharmaceutical forms can be determined according to the criteria generally taken into account in the establishment of a treatment adapted to a patient such as, for example, the age or the body weight of the patient, the seriousness of his/her general condition, the tolerance to the treatment and the secondary effects noted.

Figure 2A:
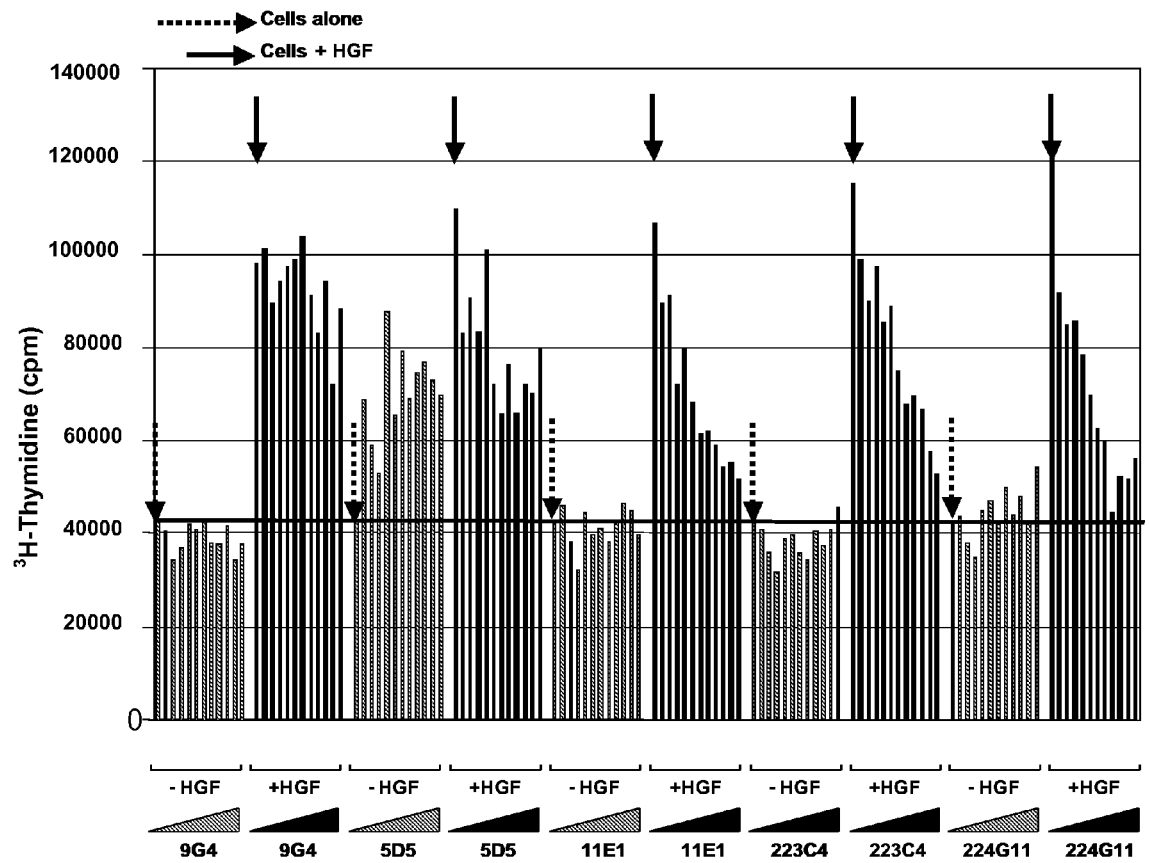
Figure 2B:
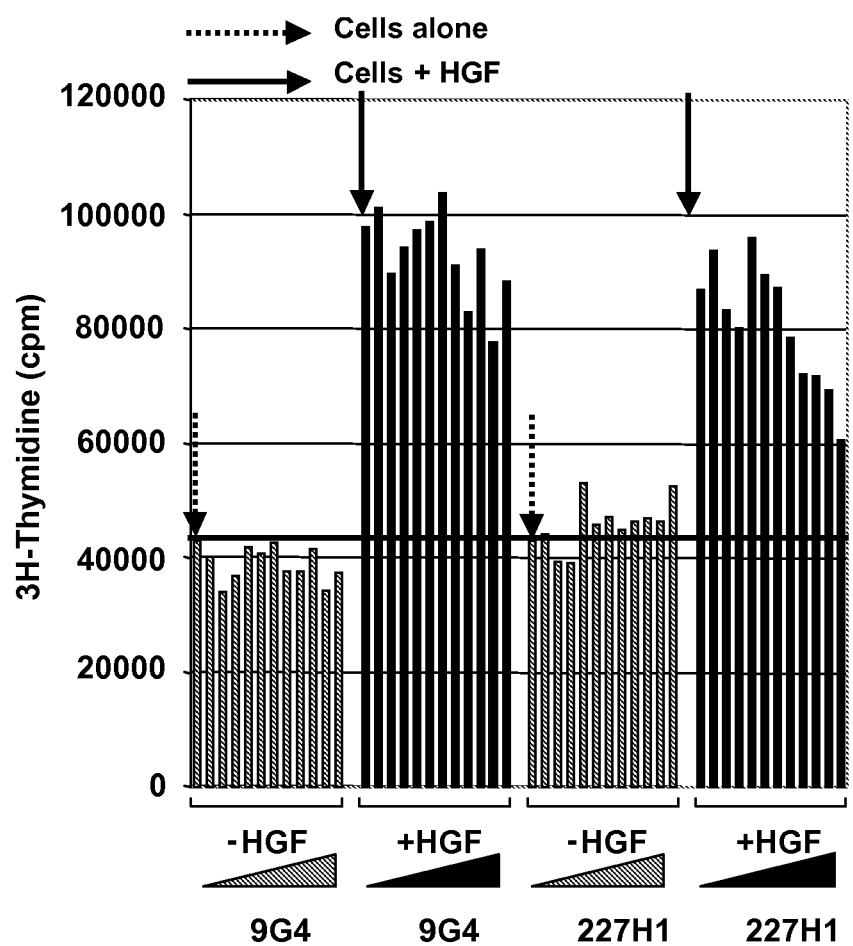
Figure 3:
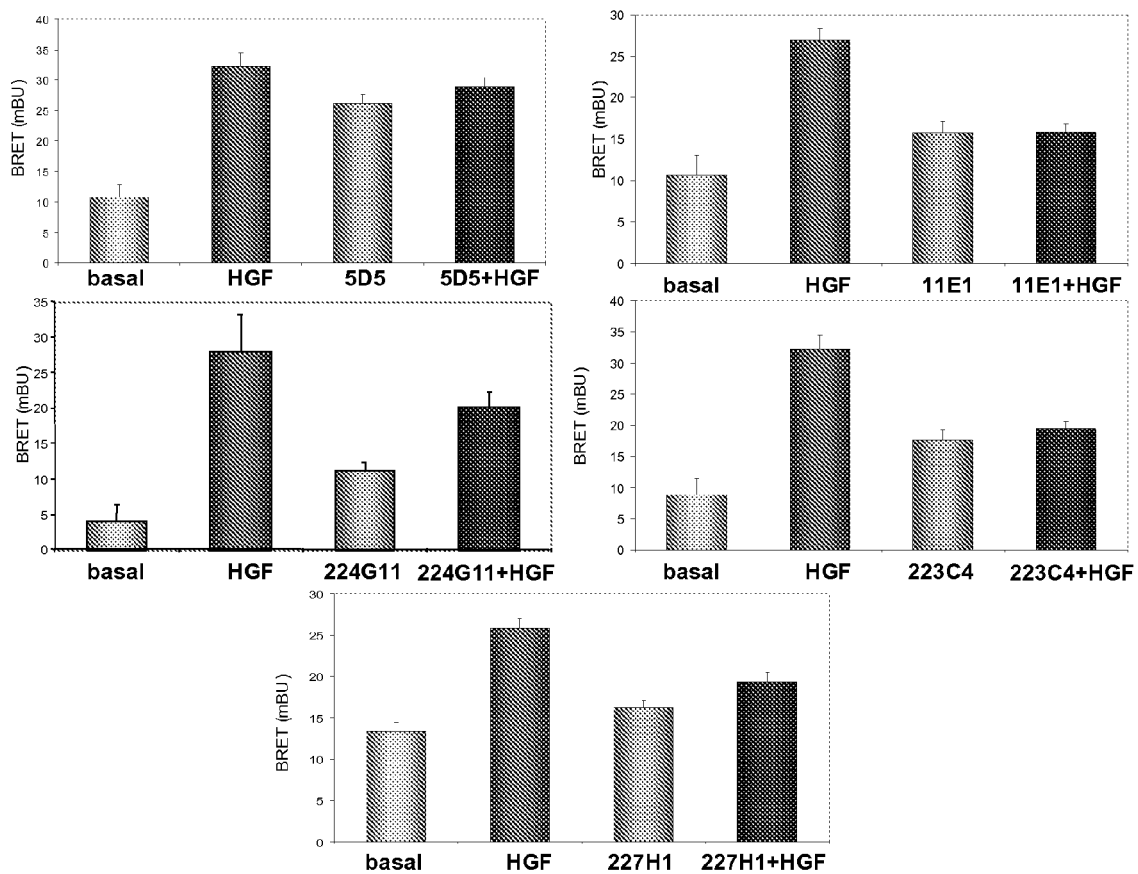
Figure 4:
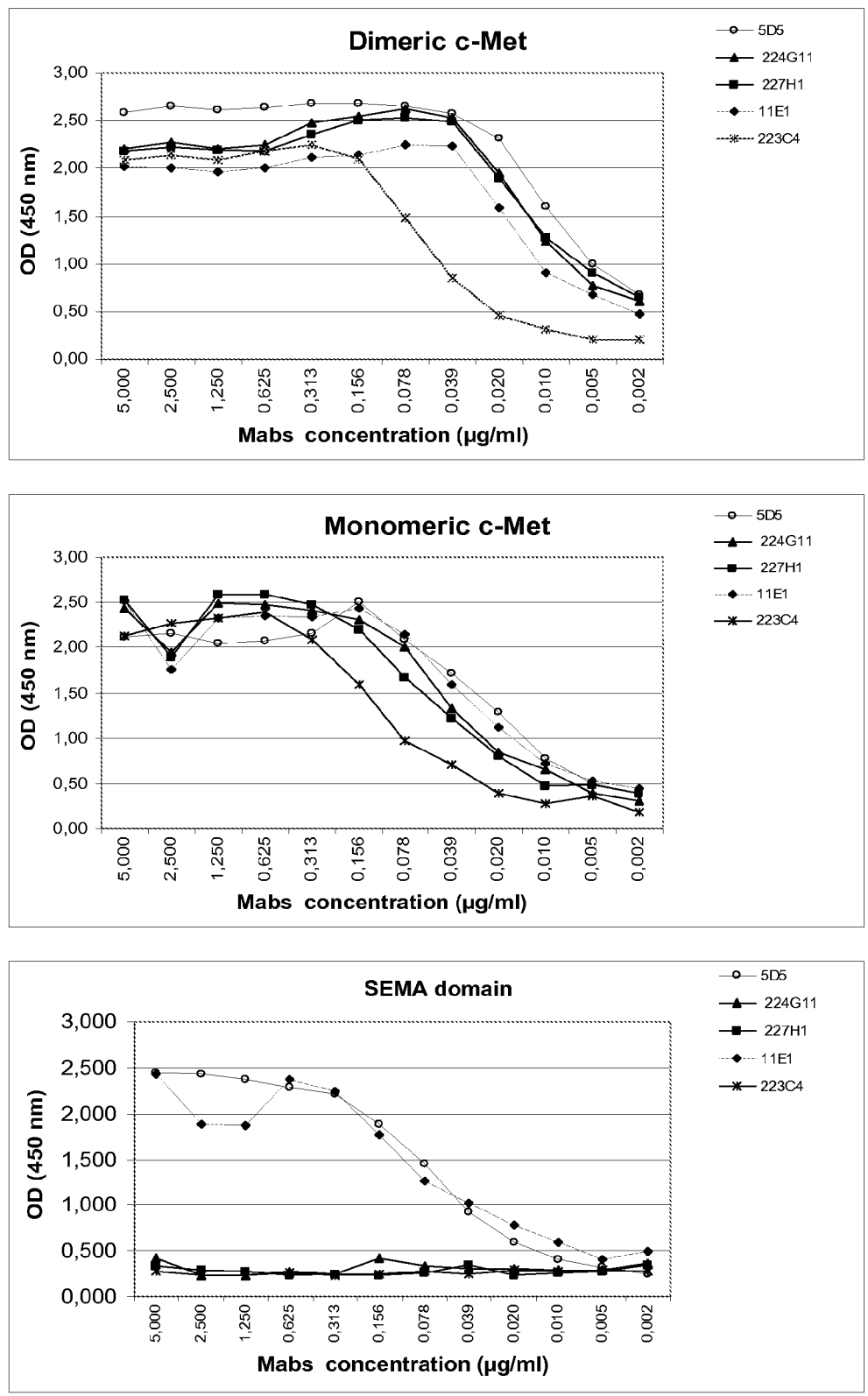
Figure 5A:
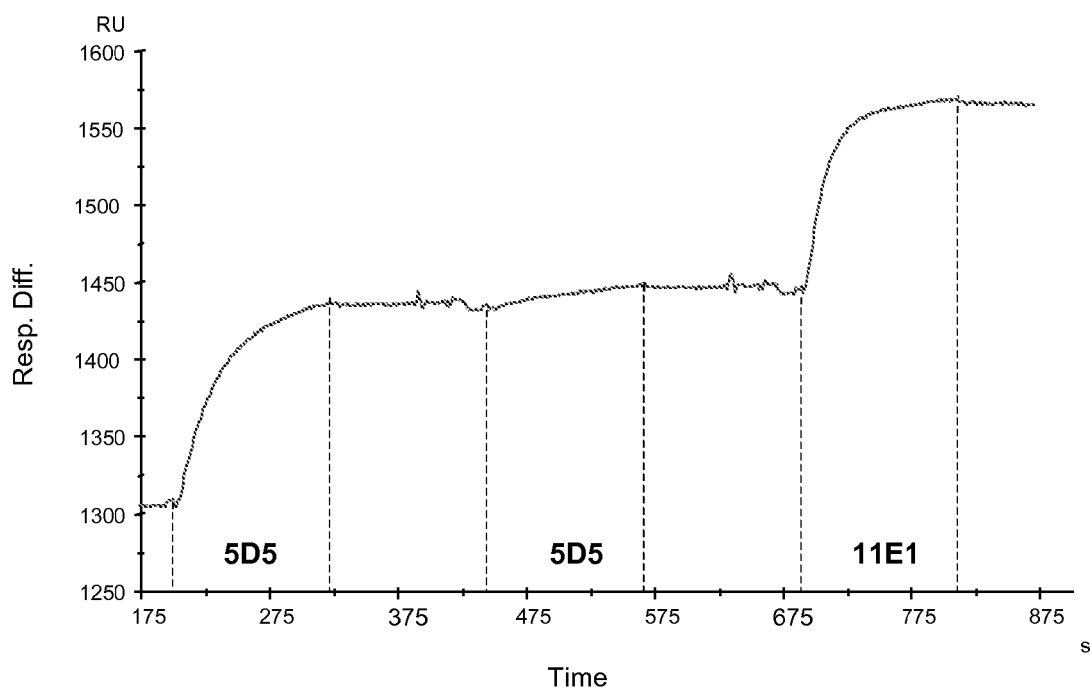
Figure 5B:
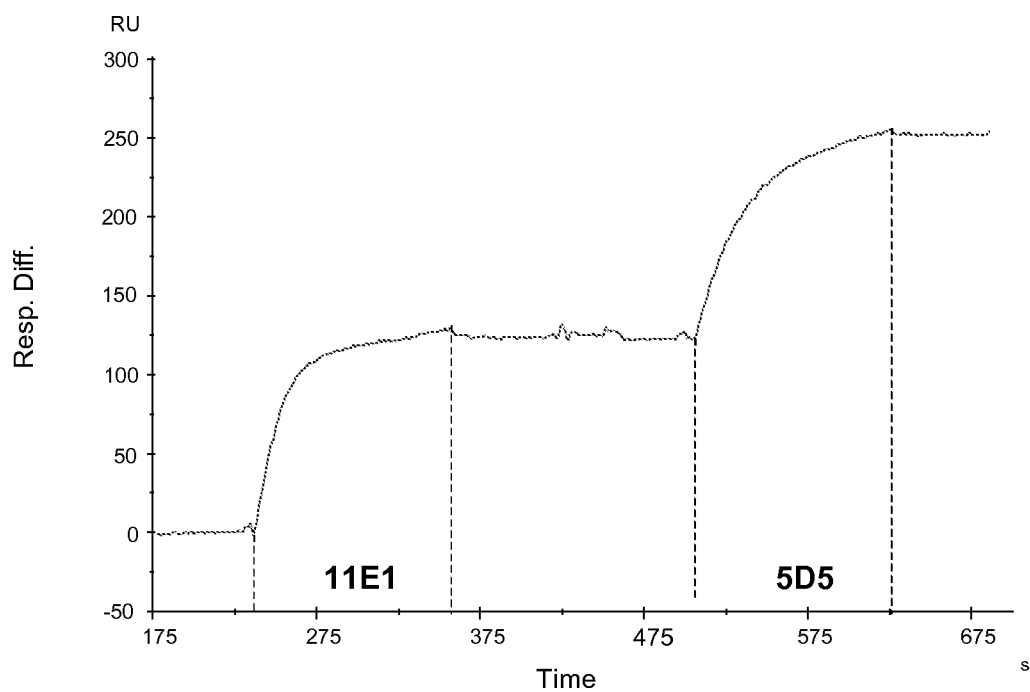
Figure 6A:
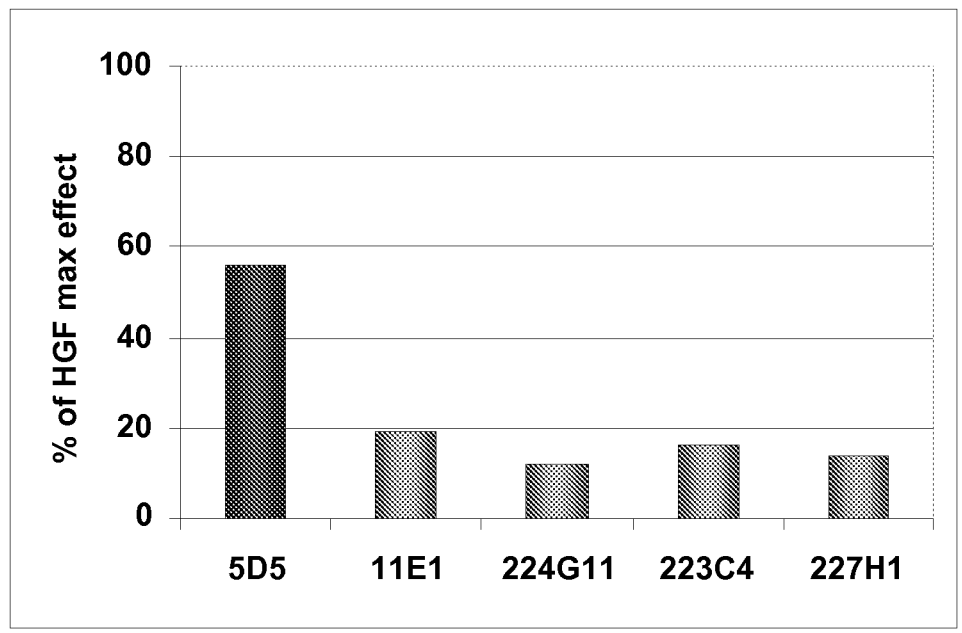
Figure 6B:
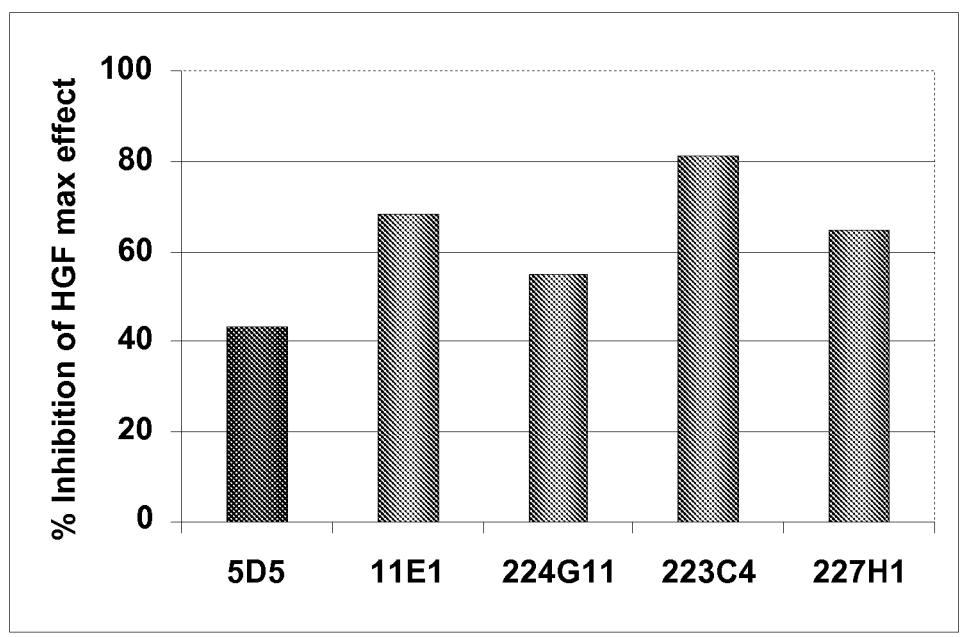
Figure 7A:
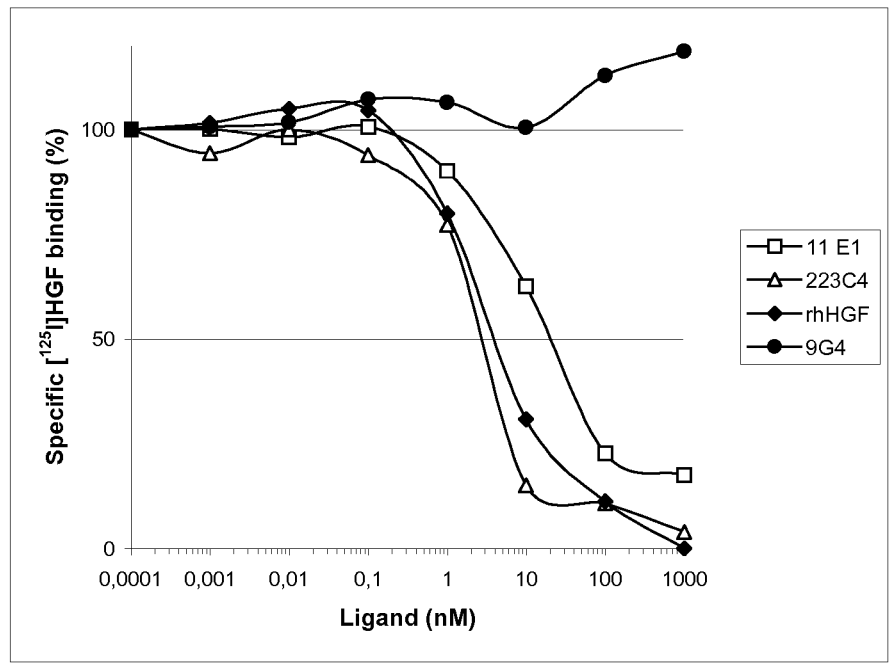
Figure 7B:
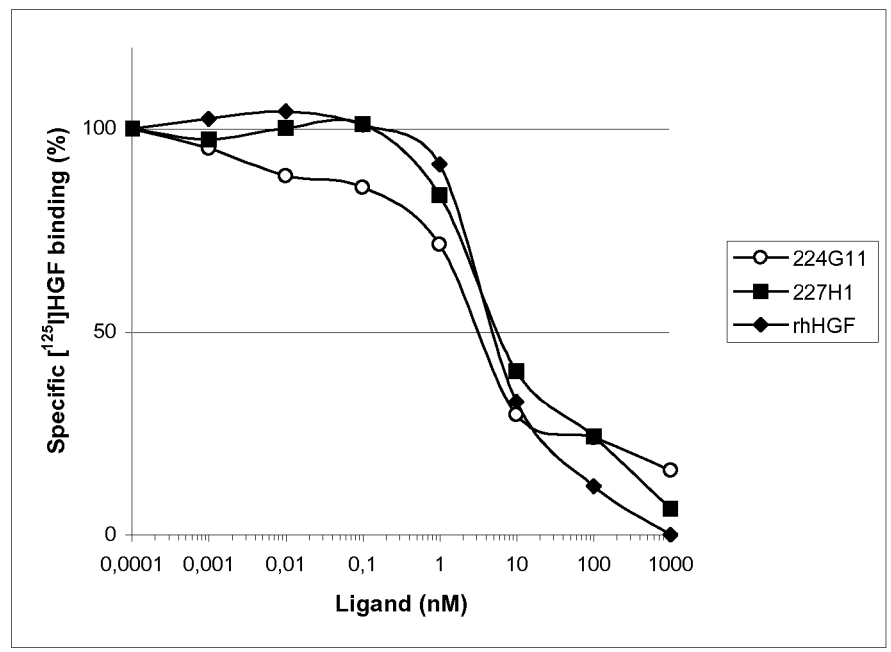
Figure 8:
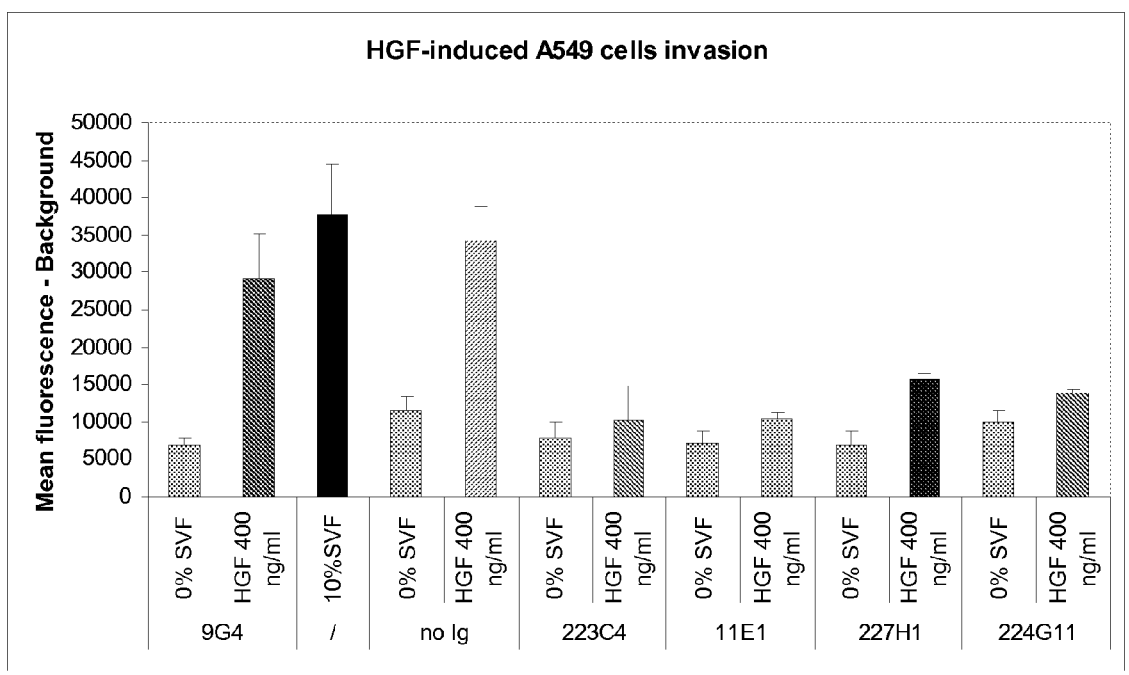
Figure 9:
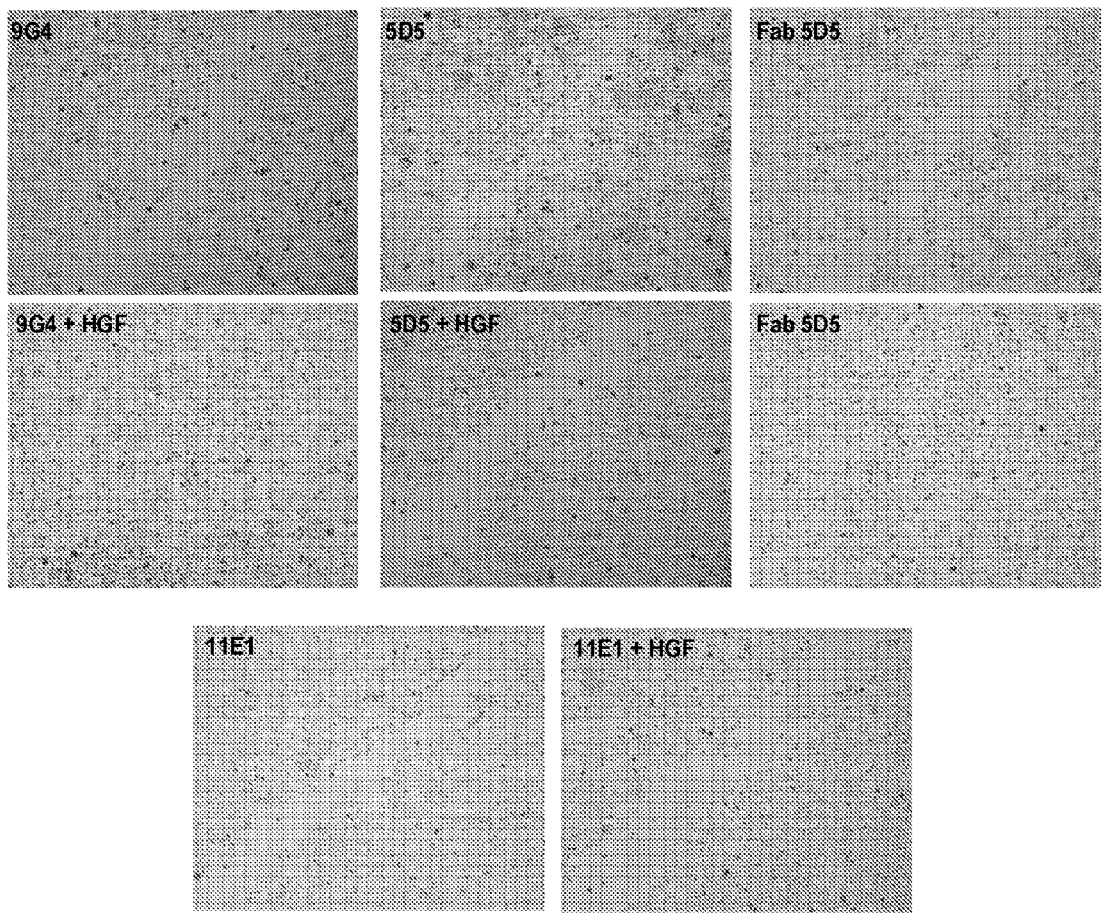
Figure 10A:
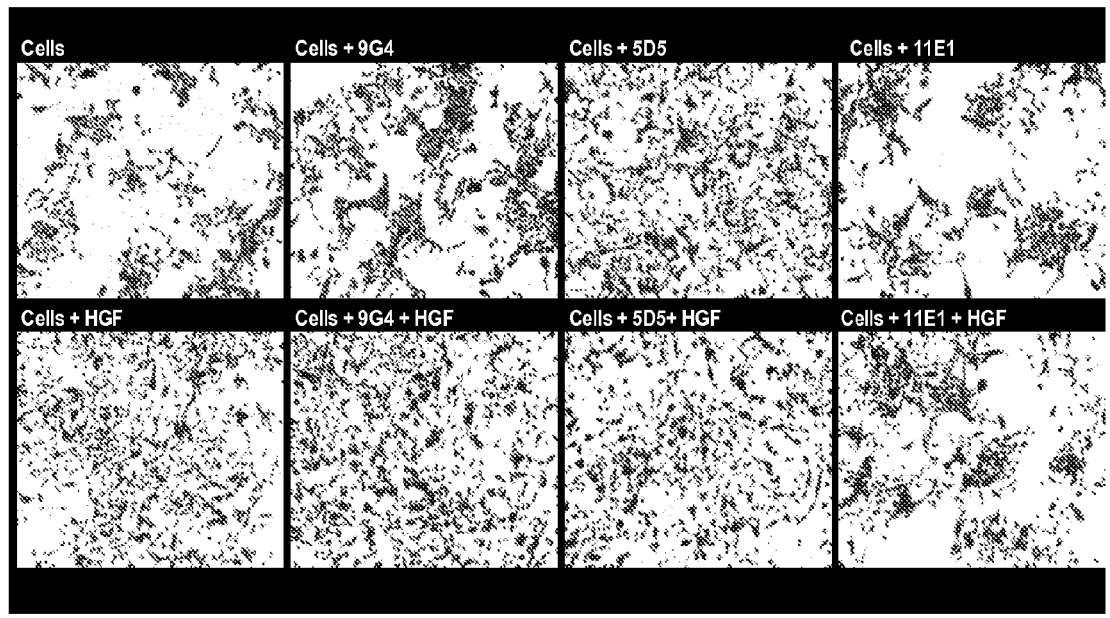
Figure 10B:
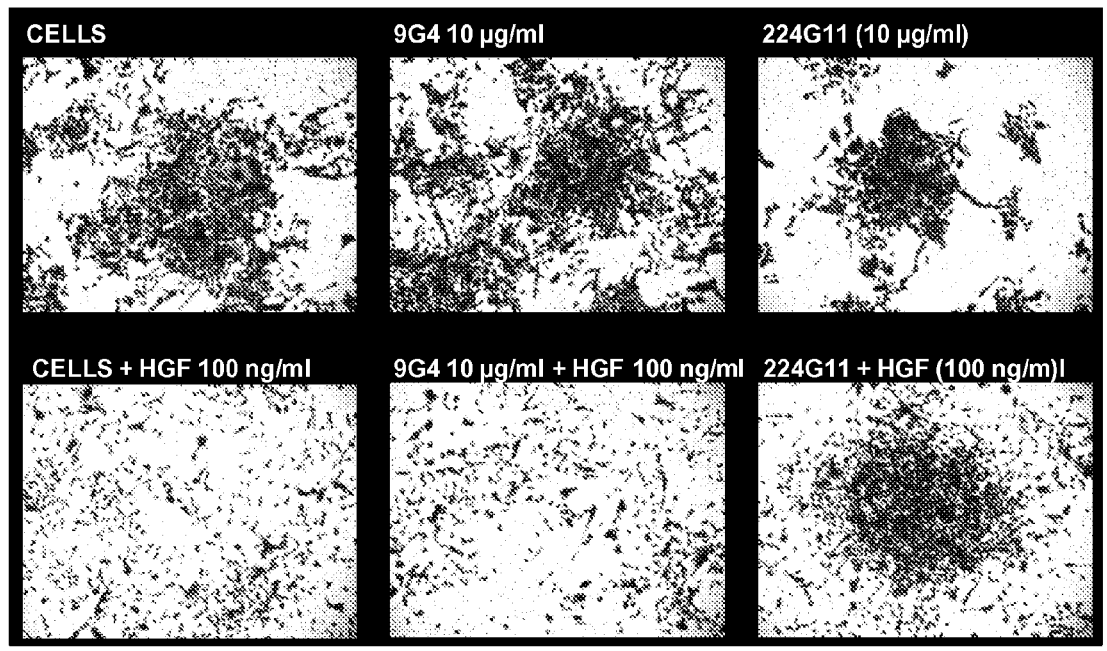
Figure 11:
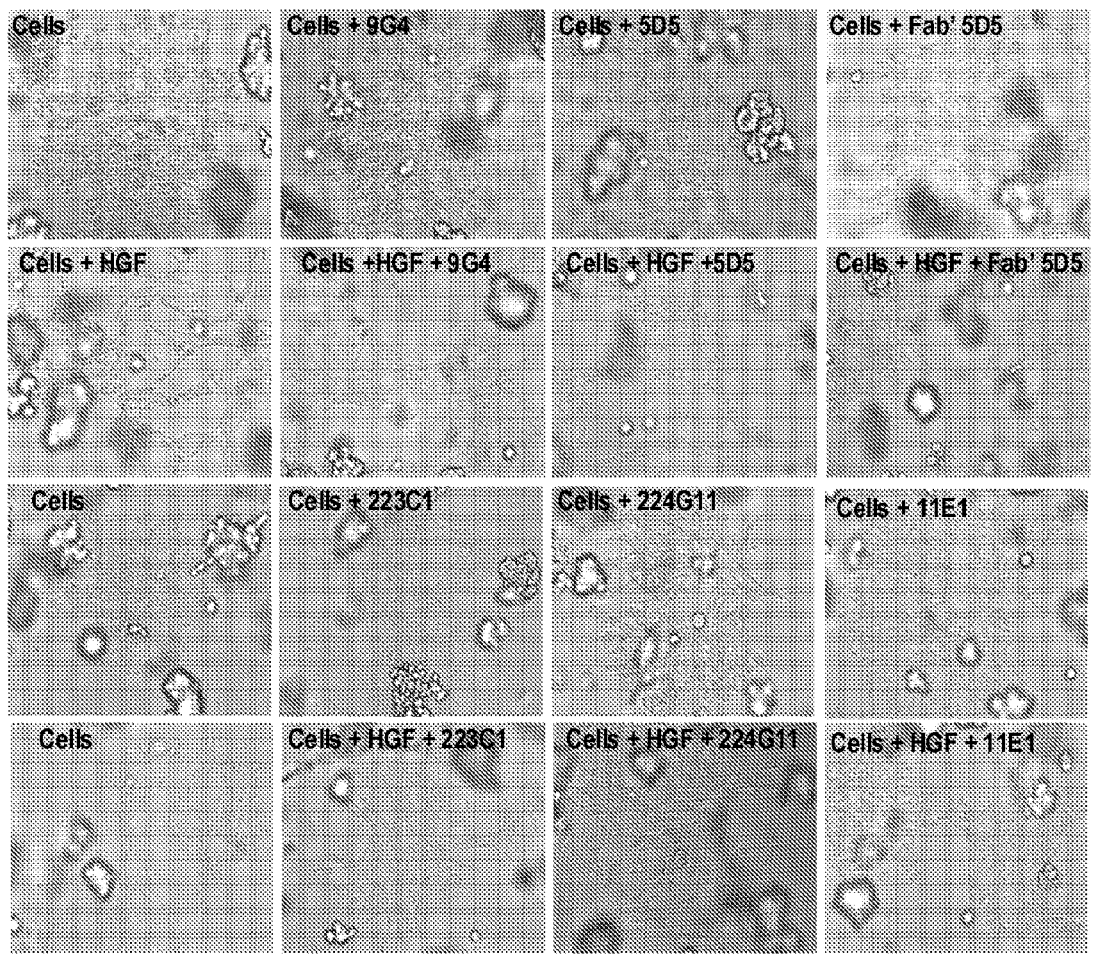
Figure 13:
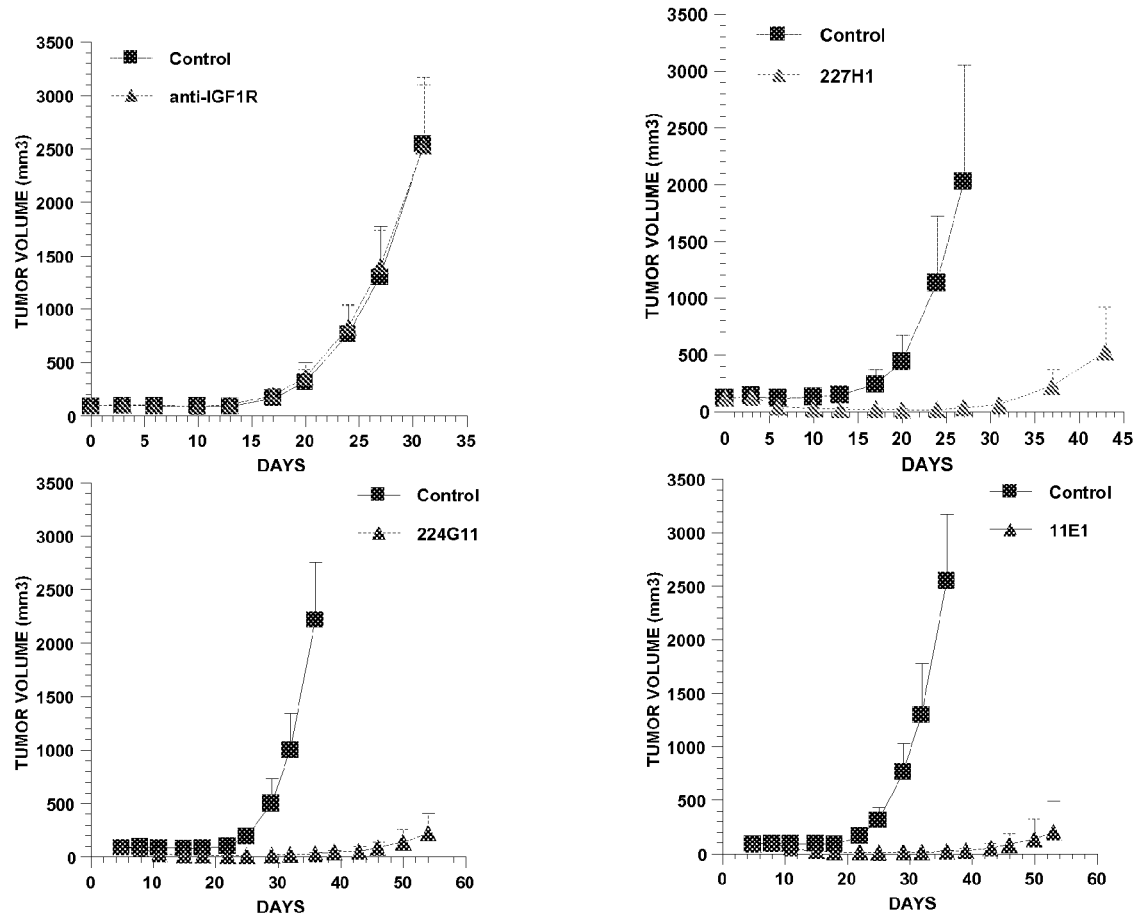
Figure 14:
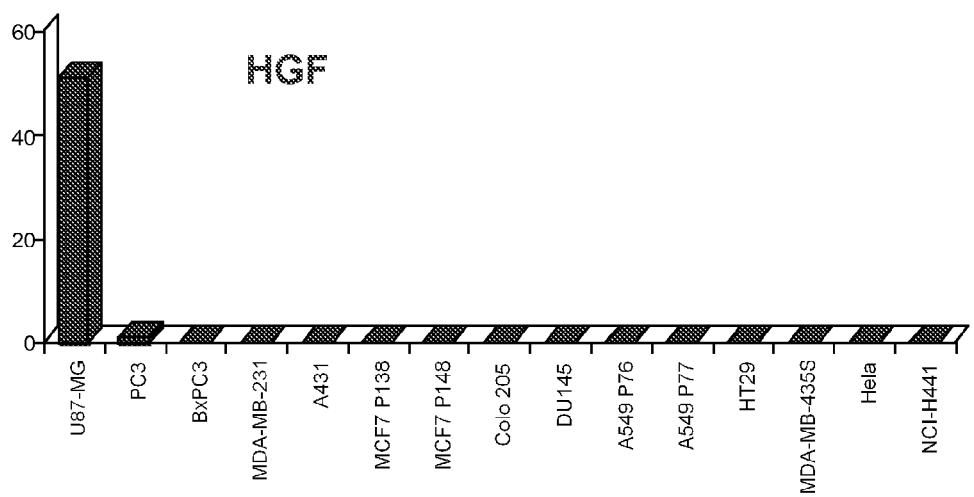
Figure 15A:
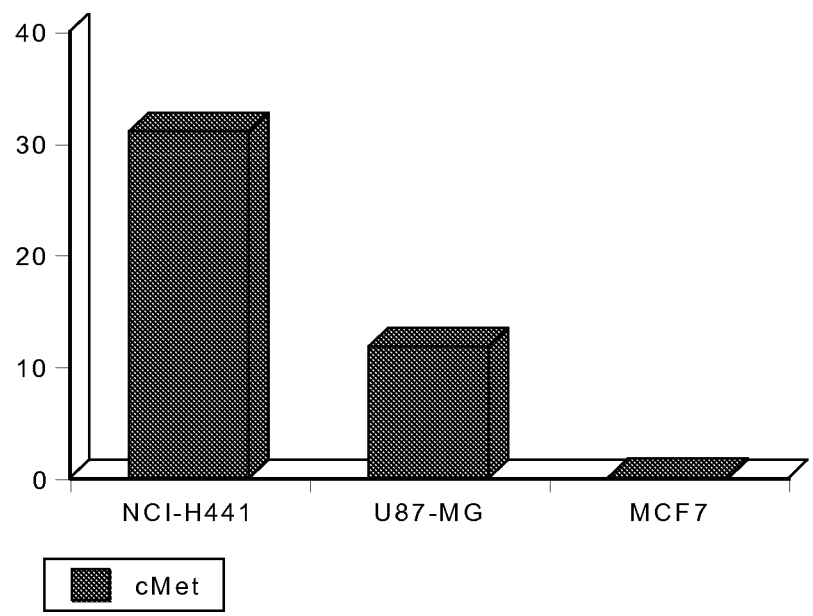
Figure 15B:
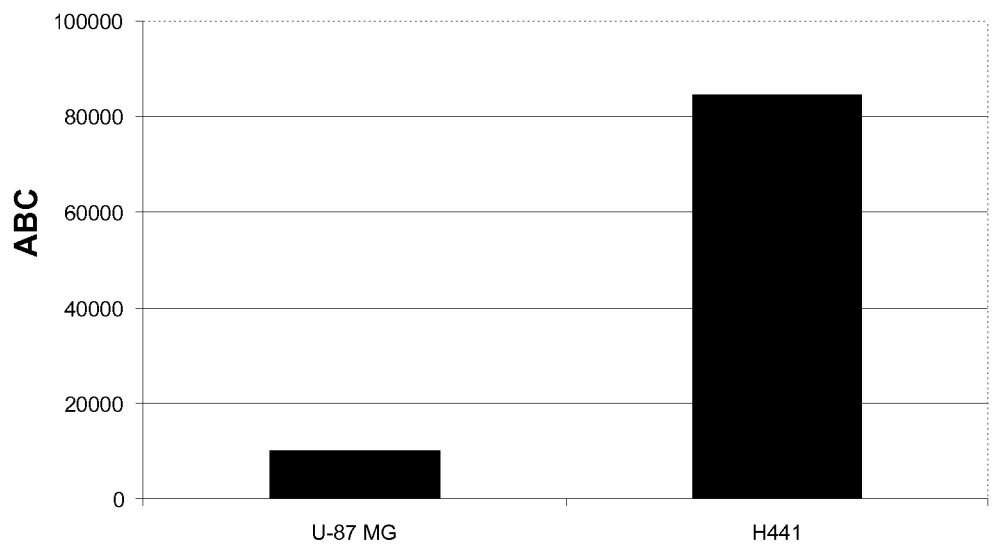
Figure 16:
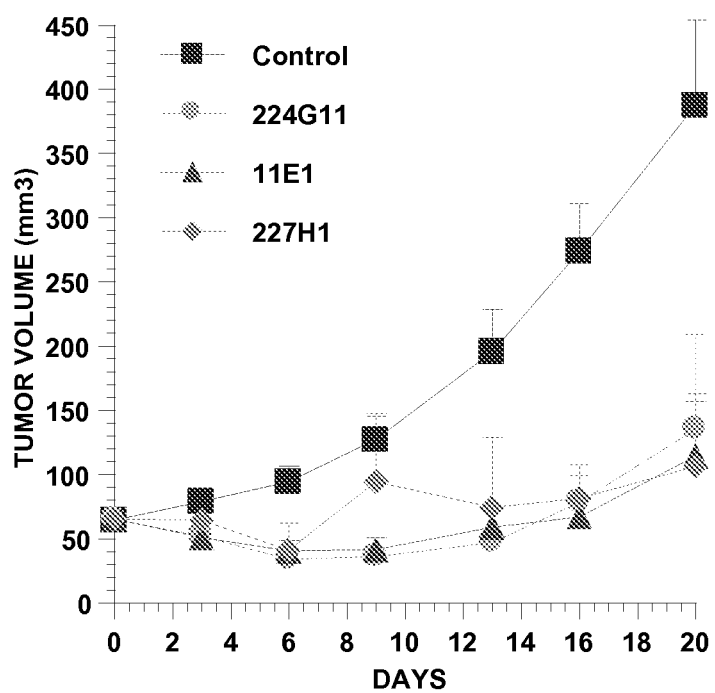
Figure 31:
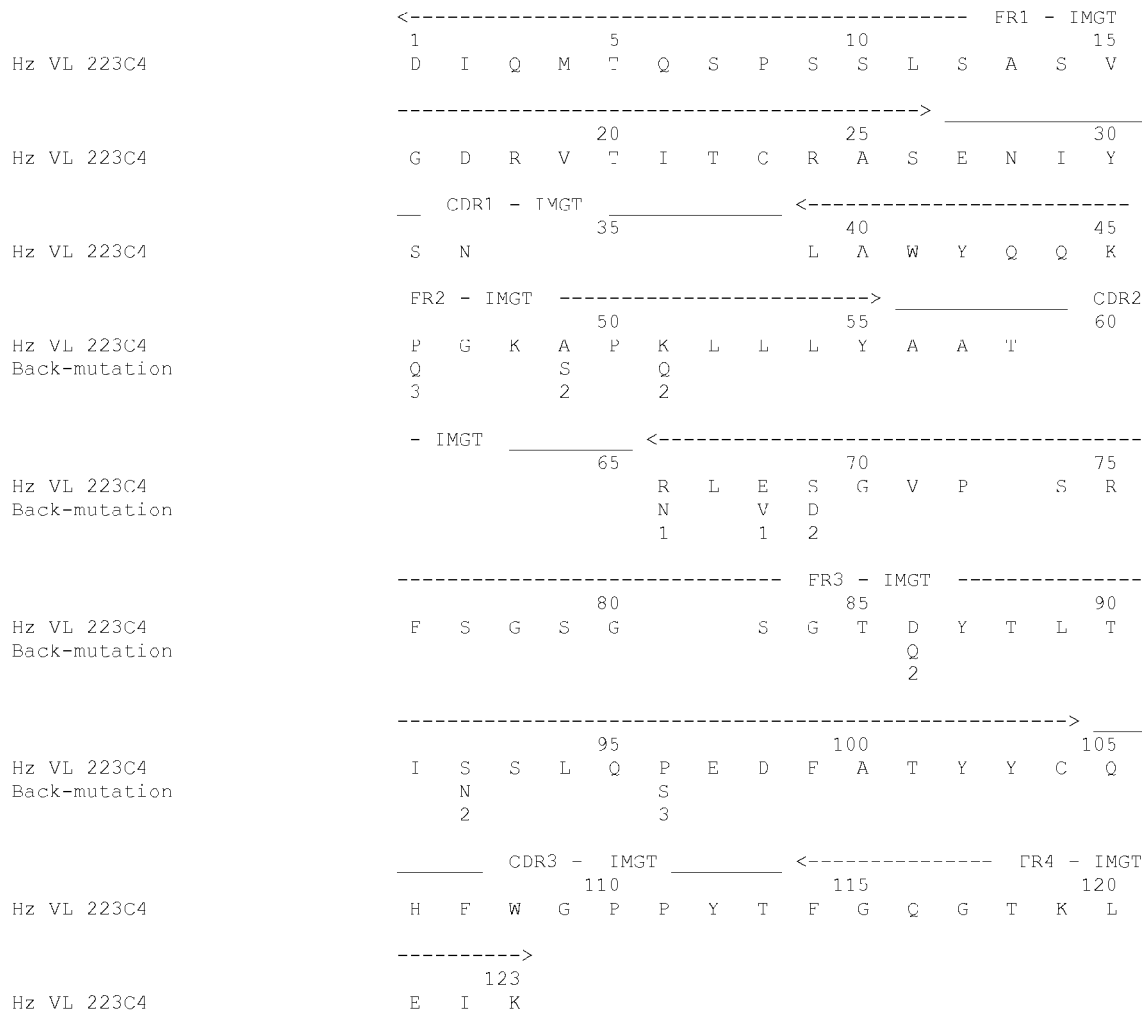

Other characteristics and advantages of the invention appear in the continuation of the description with the examples and the figures wherein:

FIG. 1: Examples of FACS profiles of the selected anti-c-Met antibodies;

FIGS. 2A and 2B: In vitro inhibition of BXPC3 proliferation by antibodies targeting c-Met;

FIG. 3: Inhibition of c-Met dimerization;

FIG. 4: Protein recognition by anti-c-Met antibodies;

FIGS. 5A and 5B: "Epitope mapping" of 11E1 and 5D5 by BIAcore analysis;

FIGS. 6A and 6B: Effect of MAbs on c-Met phosphorylation;

FIGS. 7A and 7B: Displacement of radio-labeled HGF by anti-c-Met antibodies;

FIG. 8: Inhibition of invasion by anti-c-Met antibodies [in this figure, SVF means Fetal Calf Serum (FCS)];

FIG. 9: Effect of anti c-Met antibodies on wound healing;

FIGS. 10A and 10B: Scatter assay;

FIG. 11: Three-dimensional tubulogenesis assay;

FIGS. 12A and 12B: Effect of antibodies on spheroid formation;

FIG. 13: In vivo activity of anti-c-Met Mabs in the U87MG xenograft model;

FIG. 14: HGF expression by a set of tumour cell lines;

FIGS. 15A and 15B: Characterization of the NCI-H441 cell line; with FIG. 15A corresponding to quantitative RT-PCR analysis and FIG. 15B corresponding to FACS analysis;

FIG. 16: In vivo activity of anti-c-Met antibodies on NCI-H441 xenograft model;

FIG. 17A: Alignment of 224G11 VL to murine IGKV3-5*01 germline gene;

FIG. 17B: Alignment of 224G11 VL to murine IGKJ4*01 germline gene;

FIG. 18A: Alignment of 224G11 VL to human IGKV3-11*01 and IGKV4-1*01 germline genes;

FIG. 18B: Alignment of 224G11 VL to human IGKJ4*02 germline gene;

FIG. 19A: IGKV3-11*01 based humanized version of 224G11 VL with mentioned mutations;

FIG. 19B: IGKV4-1*01 based humanized version of 224G11 VL with mentioned mutations;

FIG. 20A: Alignment of 224G11 VH to murine IGHV1-18*01 germline gene;

FIG. 20B: Alignment of 224G11 VH to murine IGHD2-4*01 germline gene;

FIG. 20C: Alignment of 224G11 VH to murine IGHJ2*01 germline gene;

FIG. 21A: Alignment of 224G11 VH to human IGHV1-2*02 germline gene;

FIG. 21B: Alignment of 224G11 VH to human IGHJ4*01 germline gene;

FIG. 22: Humanized 224G11 VH with mentioned mutations;

FIG. 23A: Alignment of 227H1 VL to murine IGKV3-5*01 germline gene;

FIG. 23B: Alignment of 227H1 VL to murine IGKJ4*01 germline gene;

FIG. 24A: Alignment of 227H1 VL to human IGKV3-11*01 and IGKV4-1*01 germline genes;

FIG. 24B: Alignment of 227H1 VL to human IGKJ4*02 germline gene;

FIG. 25A: IGKV3-11*01 based humanized version of 227H1 VL with mentioned mutations;

FIG. 25B: IGKV4-1*01 based humanized version of 227H1 VL with mentioned mutations;

FIG. 26A: Alignment of 227H1 VH to murine IGHV1-18*01 germline gene;

FIG. 26B: Alignment of 227H1 VH to murine IGHD1-1*02 germline gene;

FIG. 26C: Alignment of 227H1 VH to murine IGHJ2*01 germline gene;

FIG. 27A: Alignment of 227H1 VH to human IGHV1-2*02 germline gene;

FIG. 27B: Alignment of 227H1 VH to human IGHJ4*01 germline gene;

FIG. 28: Humanized 227H1 VH with mentioned mutations;

FIG. 29A: Alignment of 223C4 VL to murine IGKV12-46*01 germline gene;

FIG. 29B: Alignment of 223C4 VL to murine IGKJ2*01 germline gene;

FIG. 30A: Alignment of 223C4 VL to human IGKV1-NL1*01 germline gene;

FIG. 30B: Alignement of 223C4 VL to human IGKJ2*01 germline gene;

FIG. 31: Humanized 223C4 VL with mentioned mutations;

FIG. 32A: Alignment of 223C4 VH to murine IGHV1-18*01 germline gene;

FIG. 32B: Alignment of 223C4 VH to murine IGHD6-3*01 germline gene;

FIG. 32C: Alignment of 223C4 VH to murine IGHJ4*01 germline gene;

FIG. 33A: Alignment of 223C4 VH to human IGHV1-2*02 germline gene;

FIG. 33B: Alignment of 223C4 VH to human IGHD1-26*01 germline gene;

FIG. 33C: Alignment of 223C4 VH to human IGHJ6*01 germline gene; and

Figure 35:
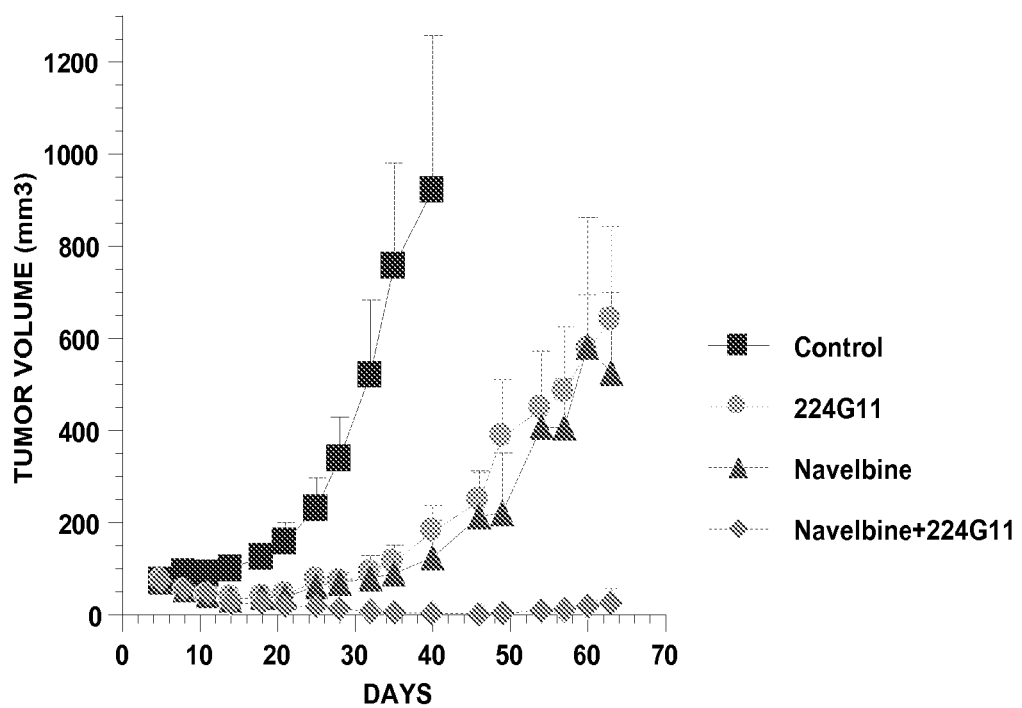
Figure 36:
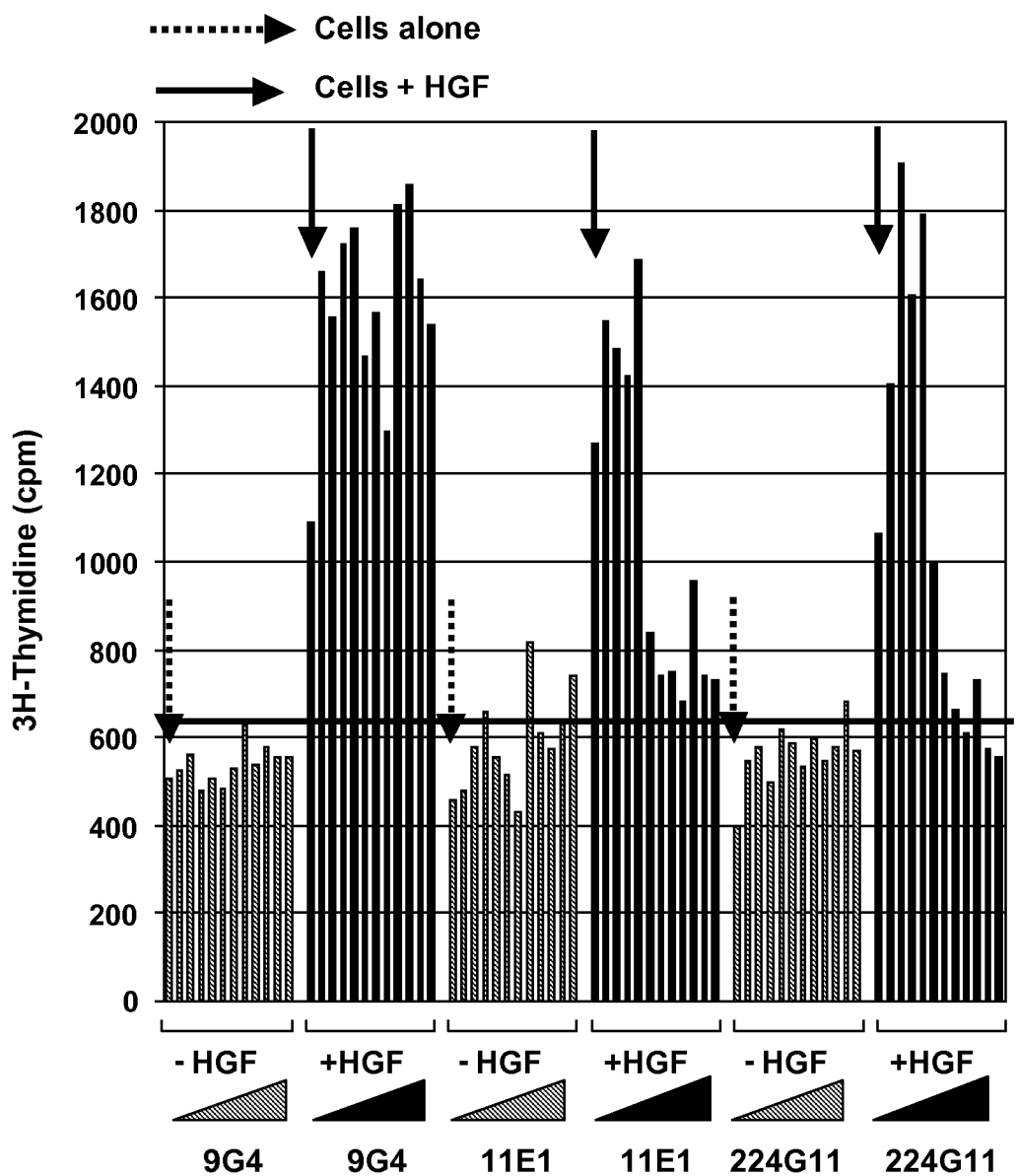
Figure 37:
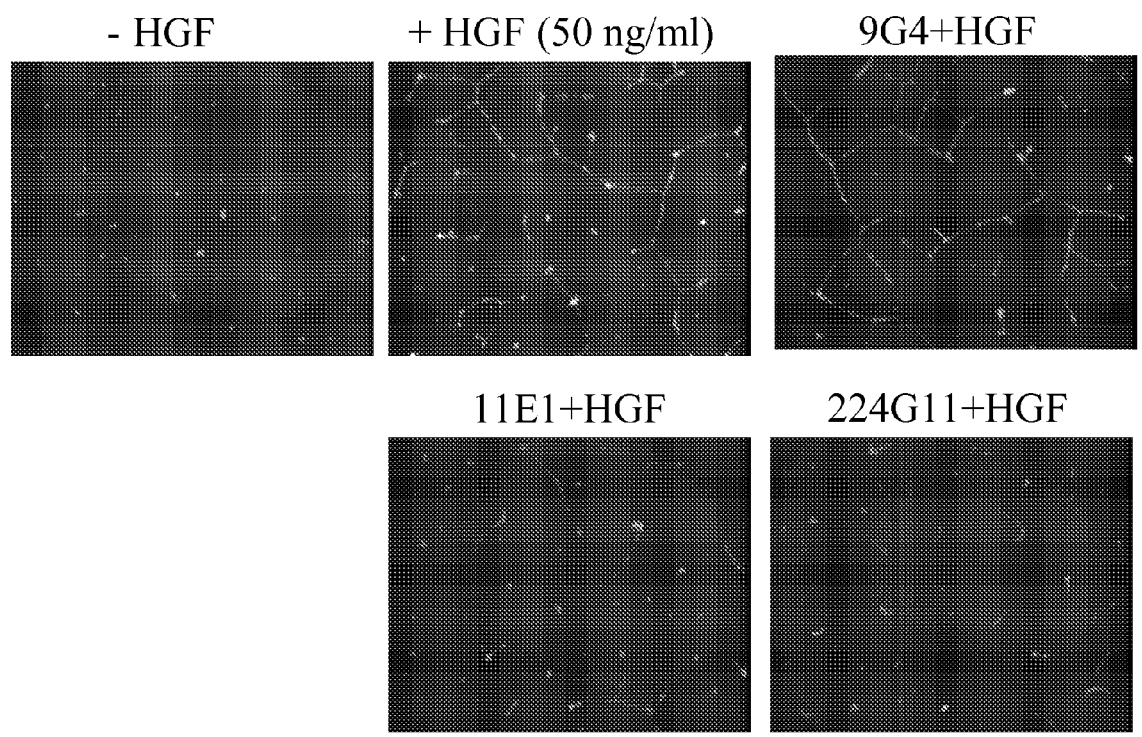
Figure 44A:
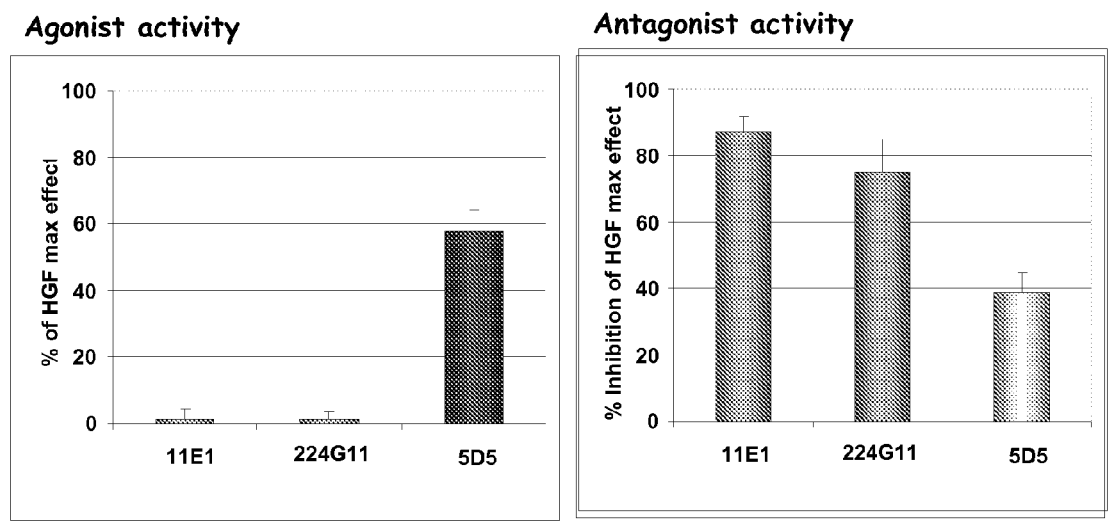
Figure 44B:
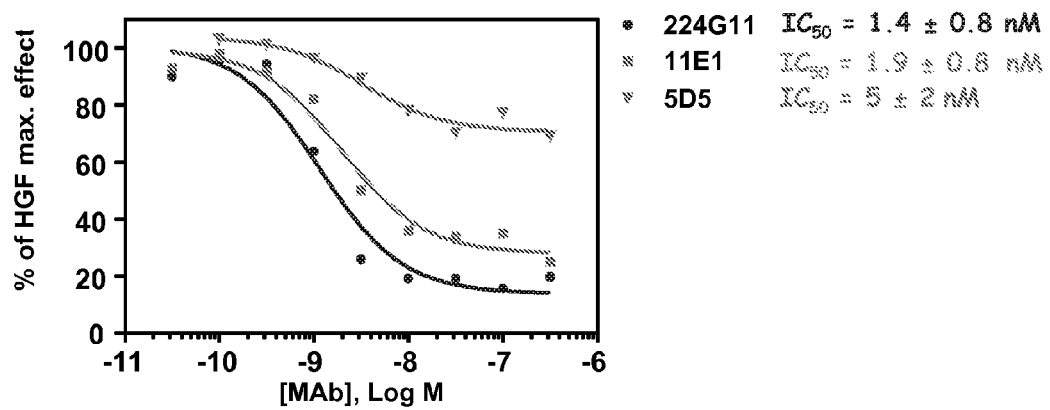
Figure 45:
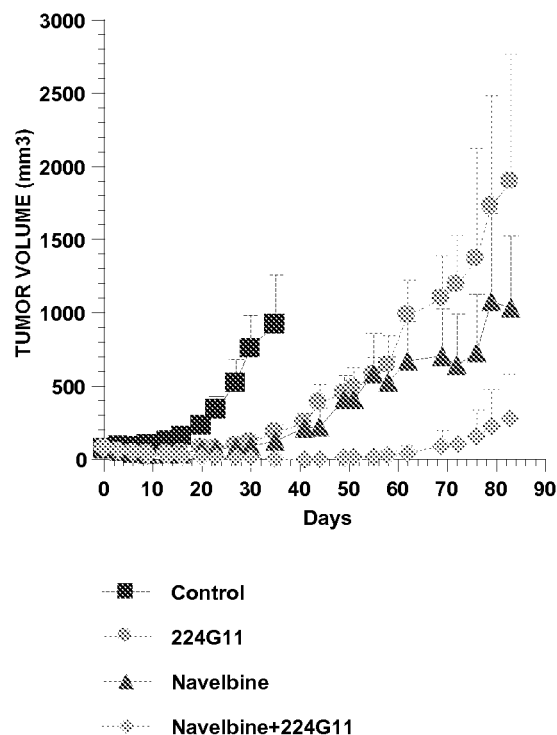
Figure 46:
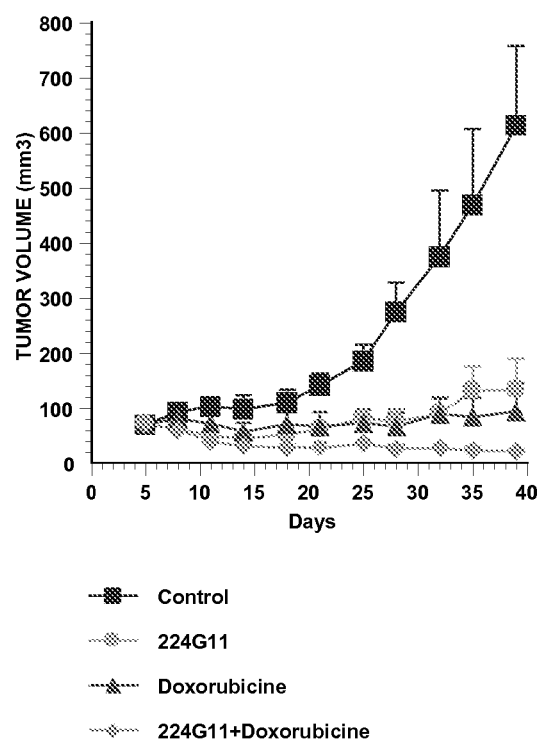
Figure 47:
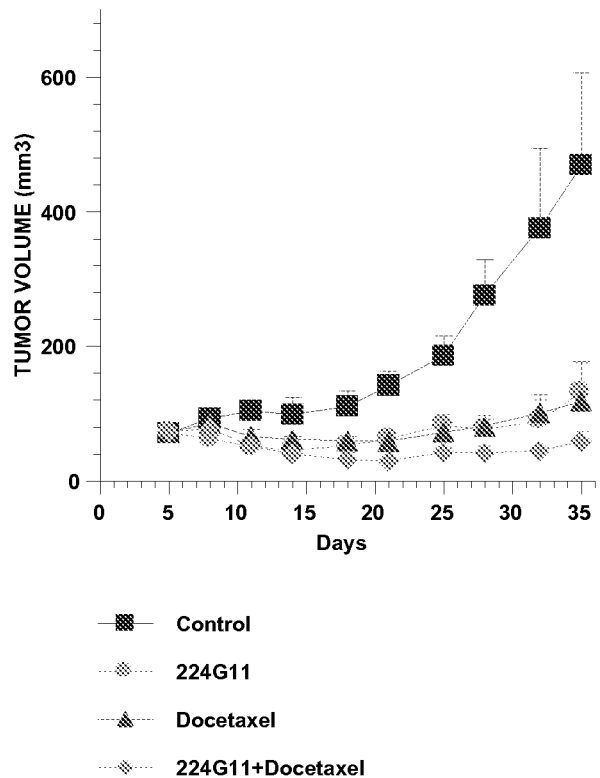
Figure 48:
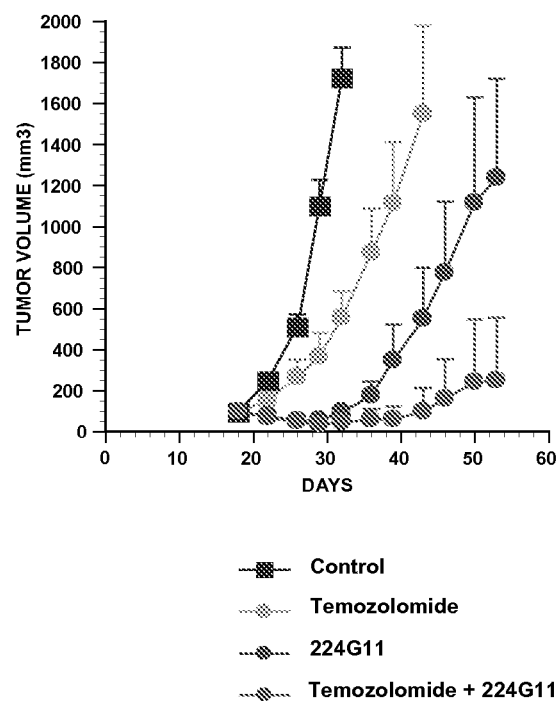
Figures 50A, 50B:
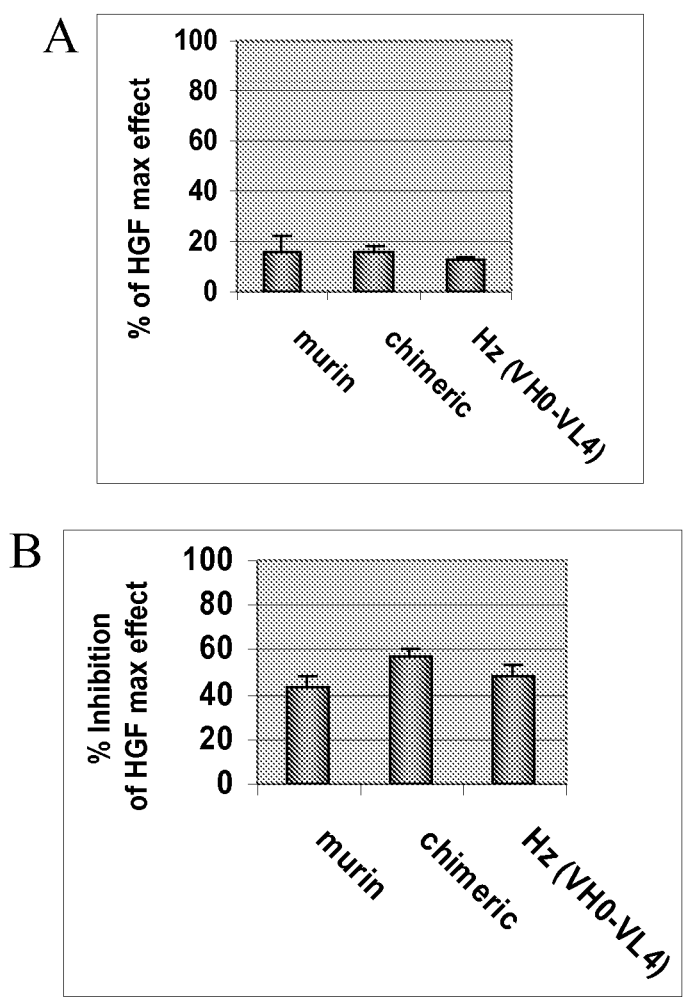
Figure 51:
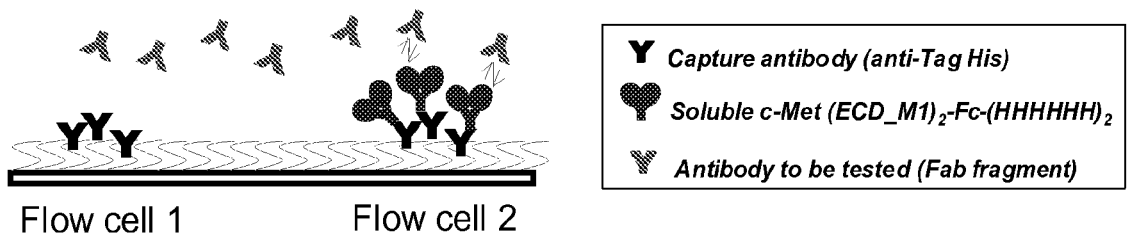
Figure 52:
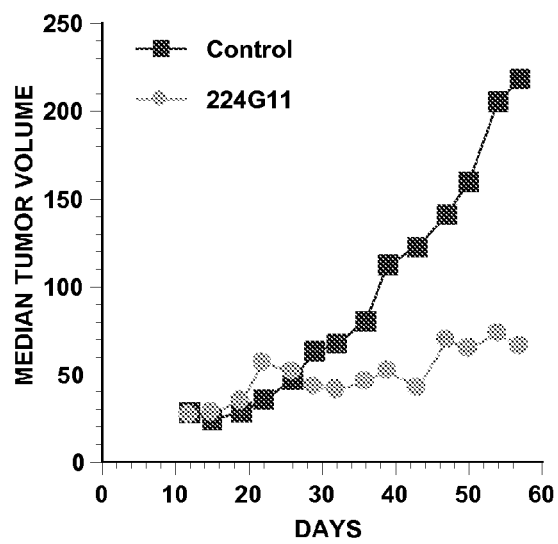
Figure 53:
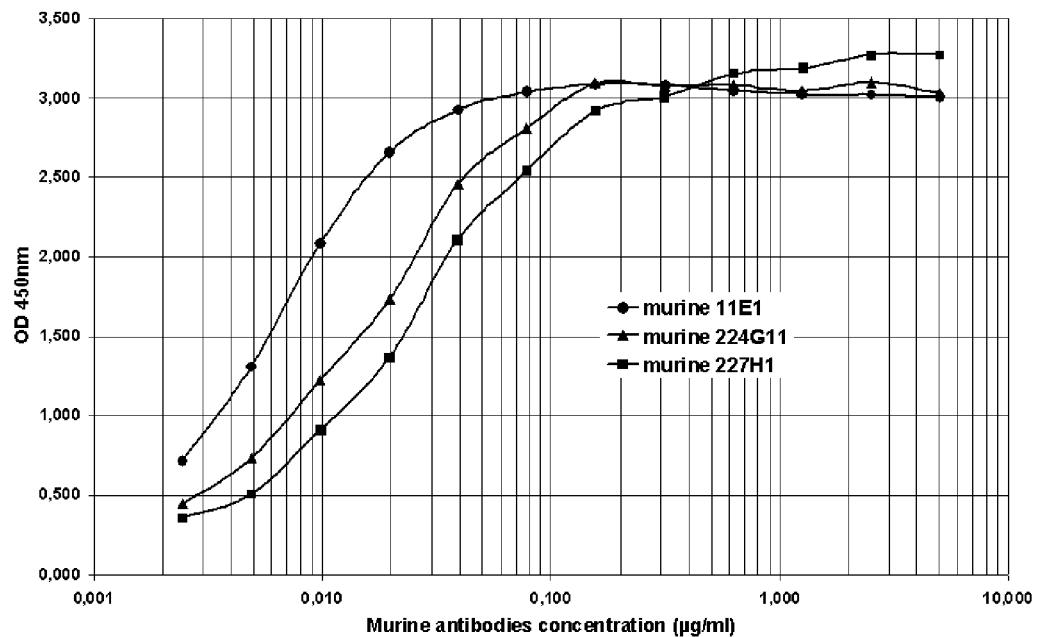
Figure 54:
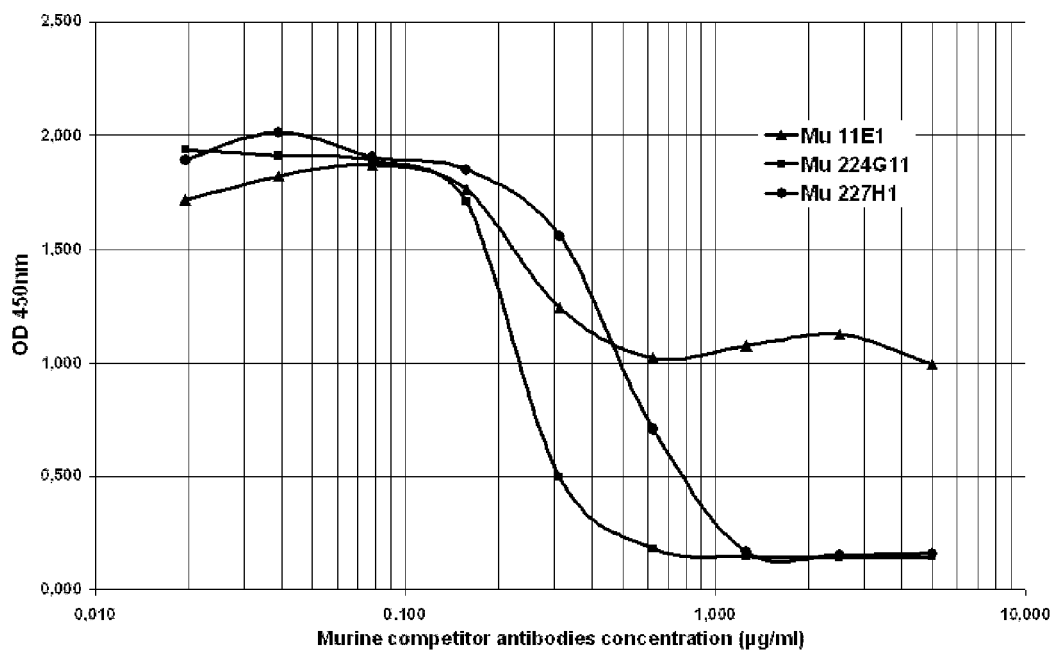
Figure 57:
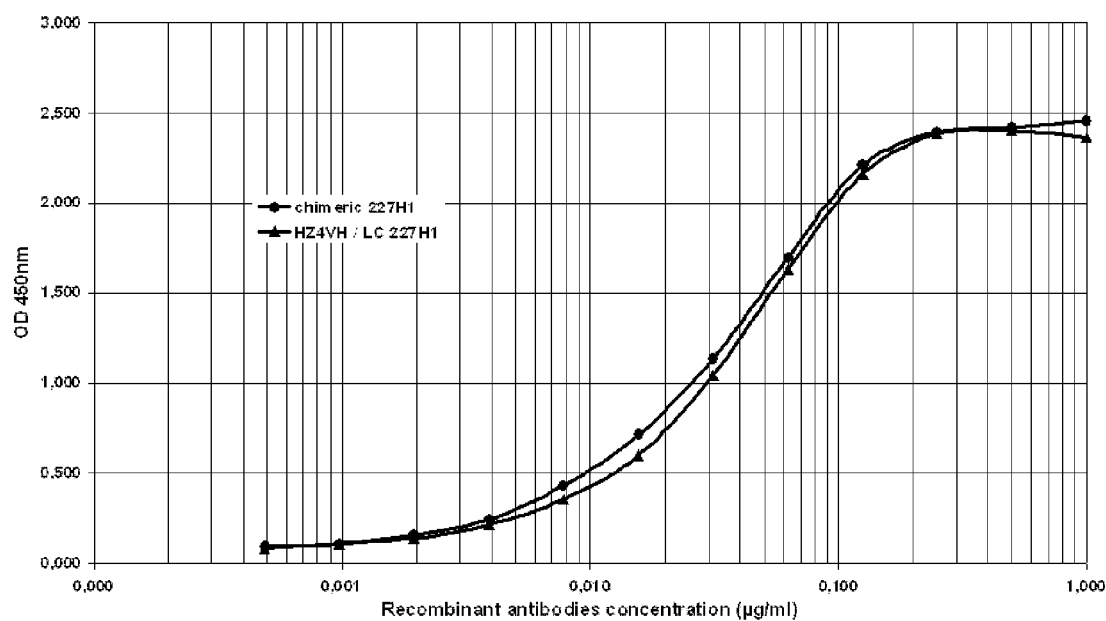
Figure 58:
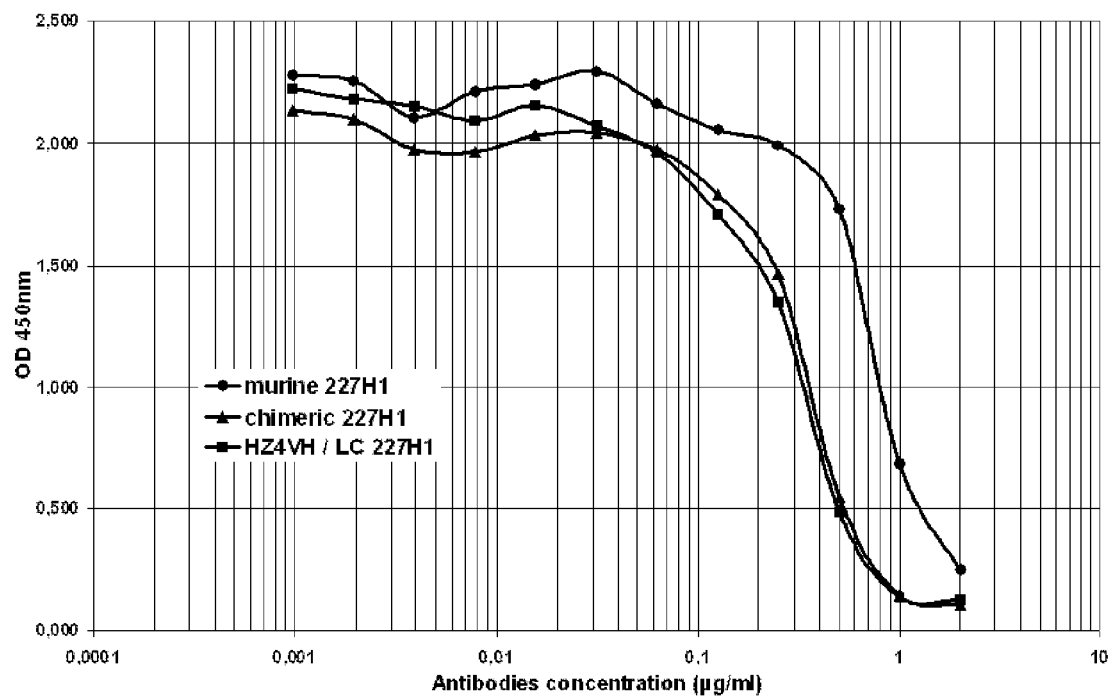
Figure 63:
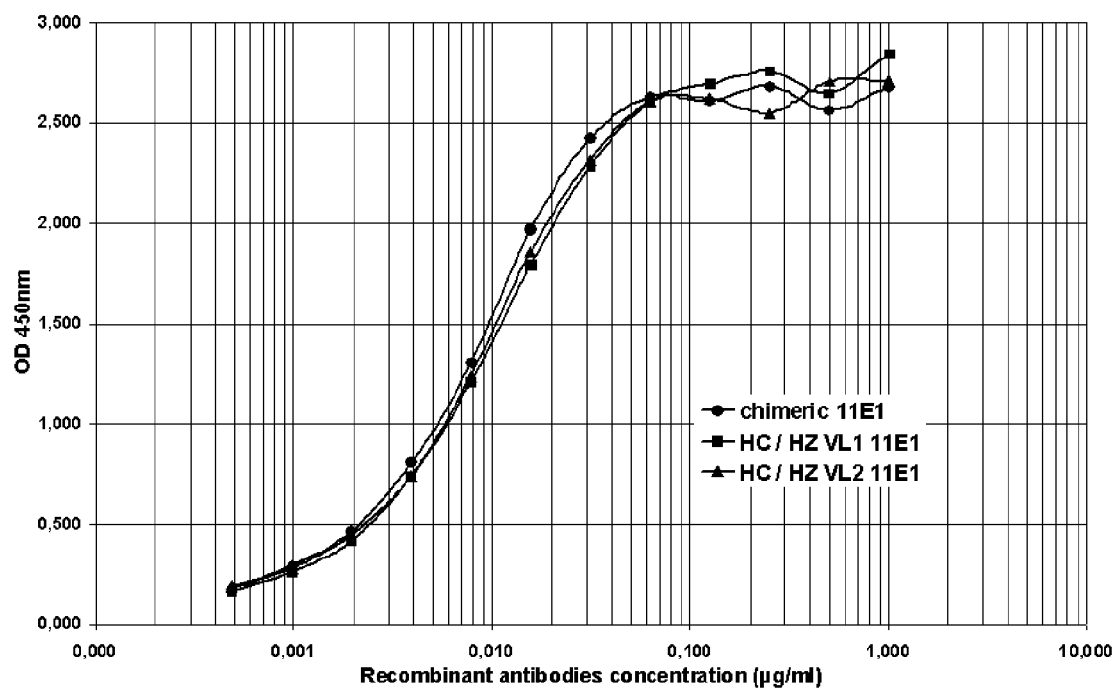
Figure 64:
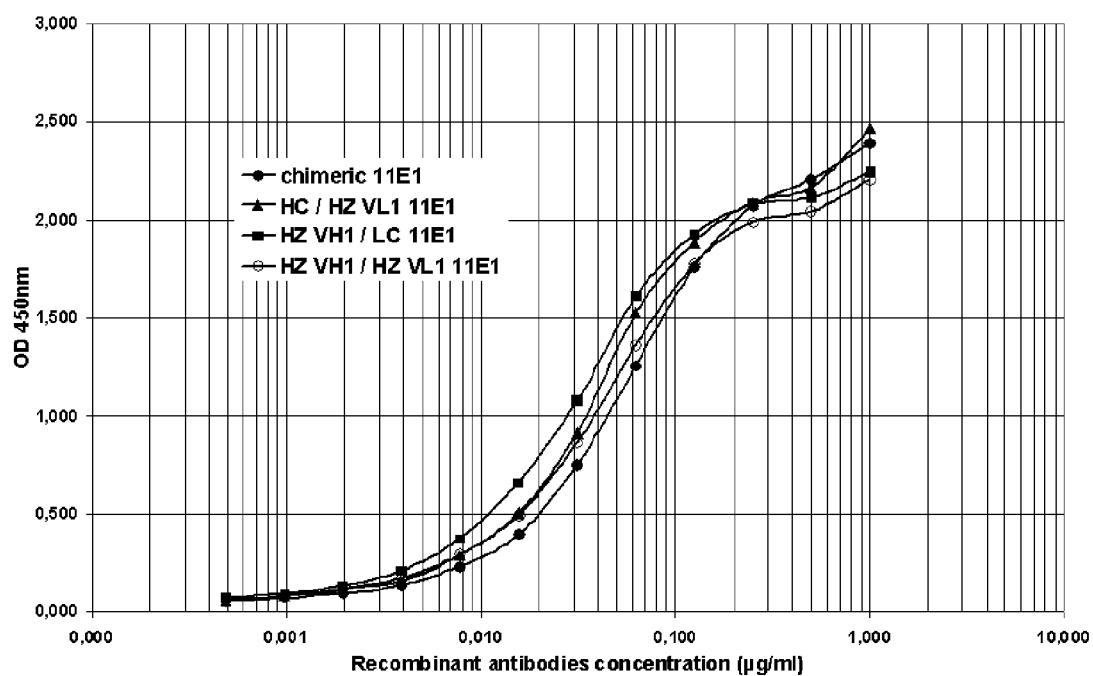
Figure 69:
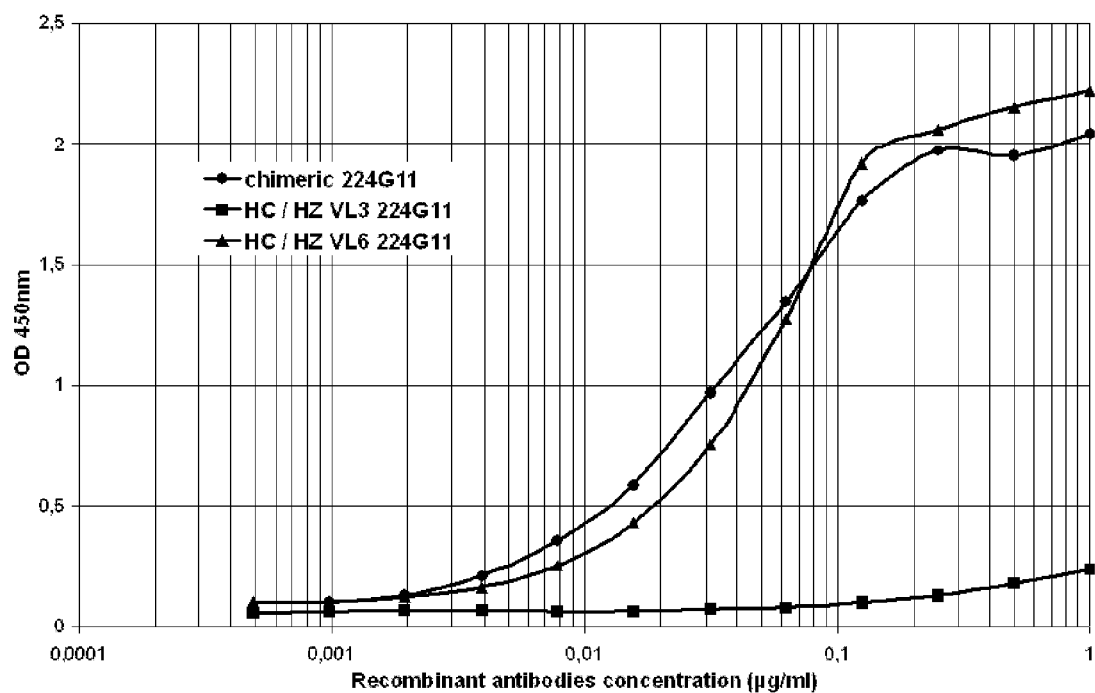
Figure 70:
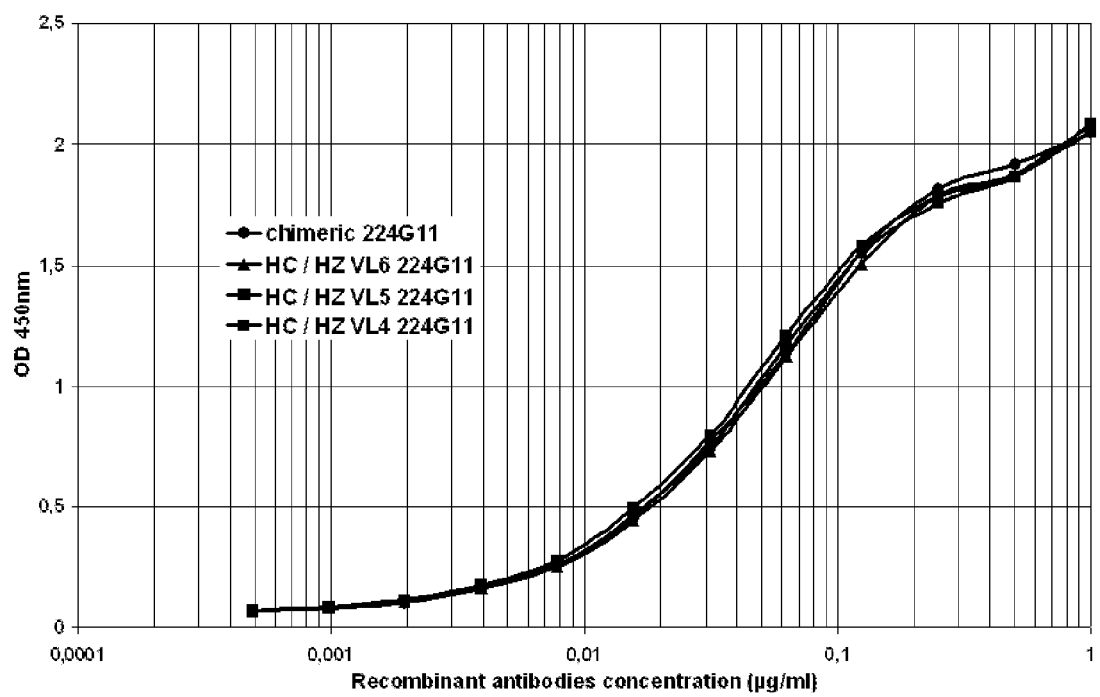
Figure 71:
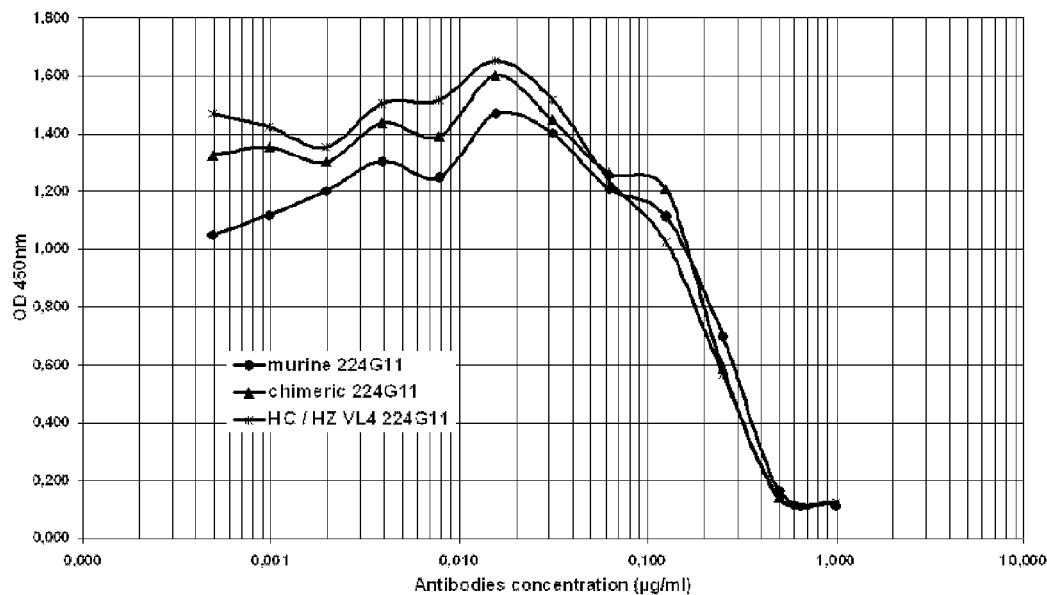
Figure 72:
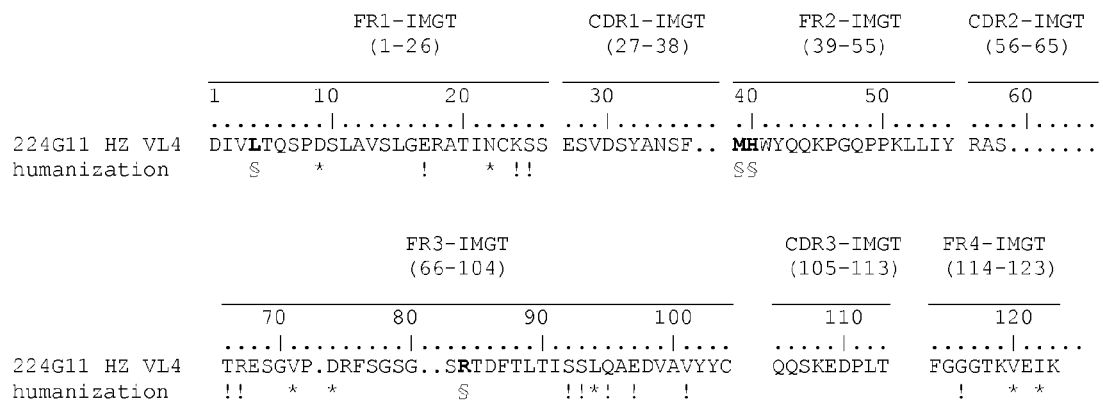
Figure 73:
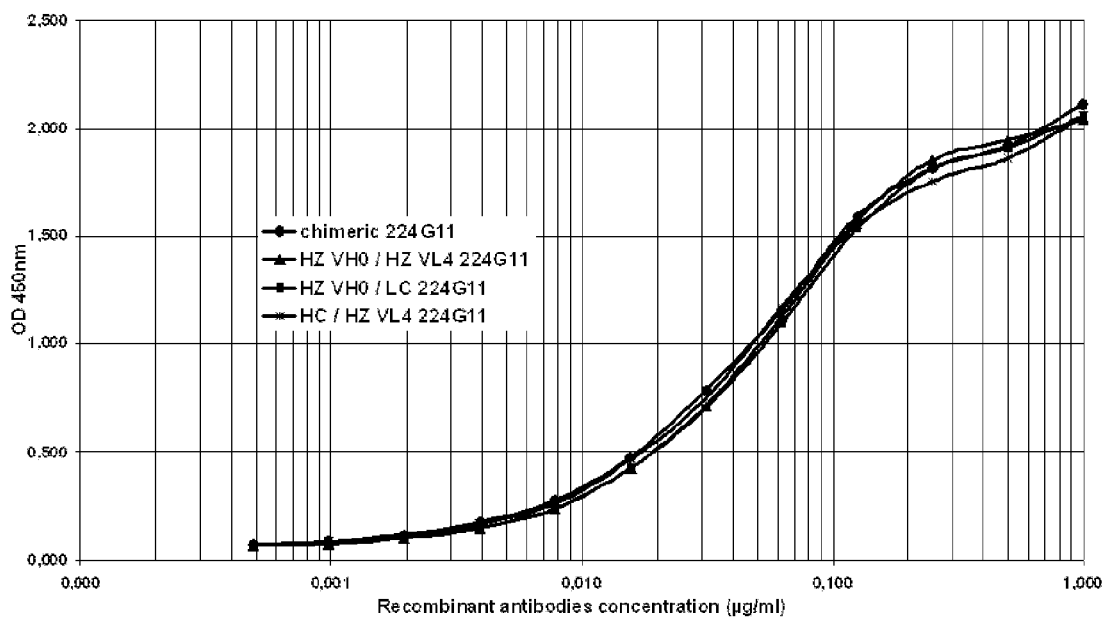
Figure 74:
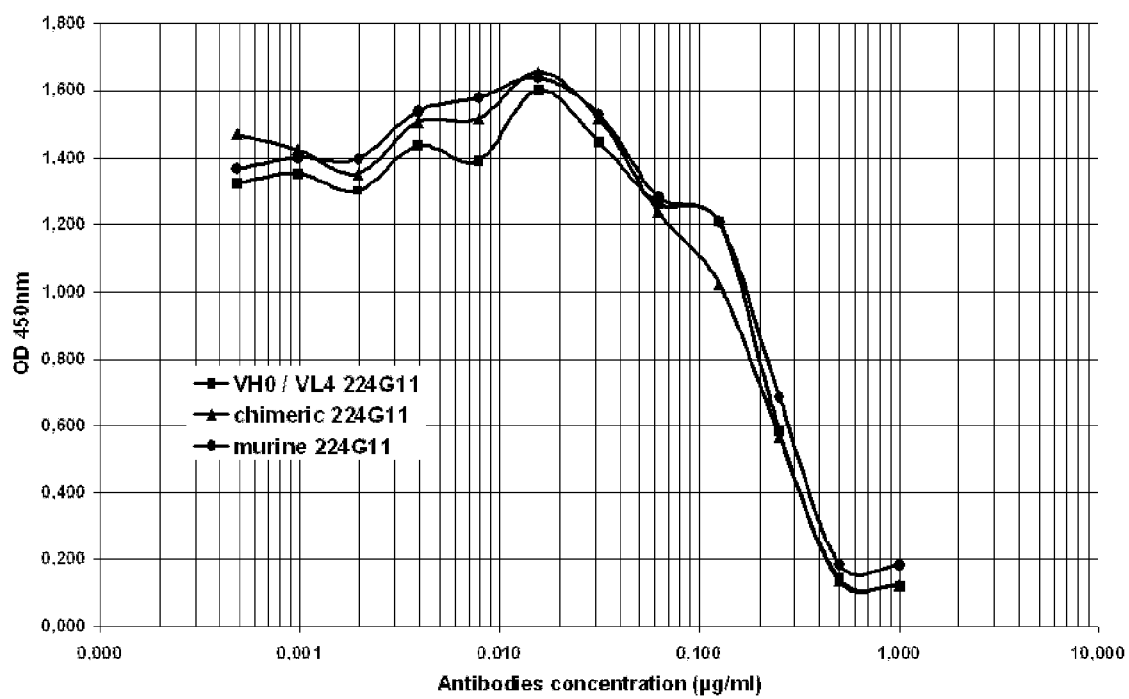
Figure 75:
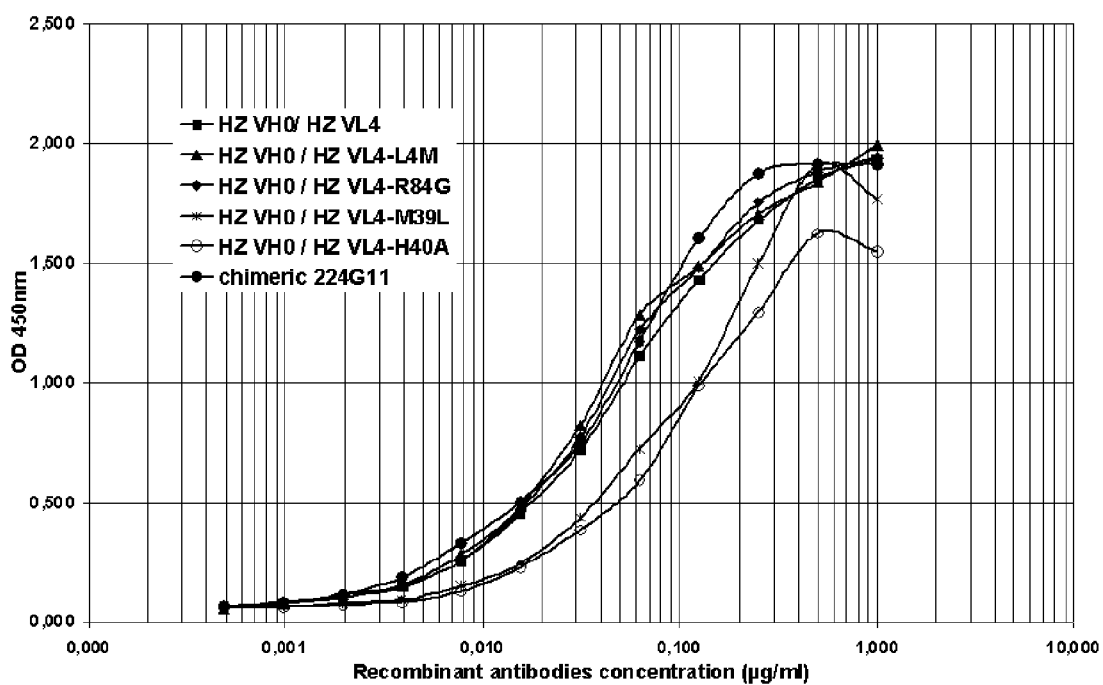
Figure 76:
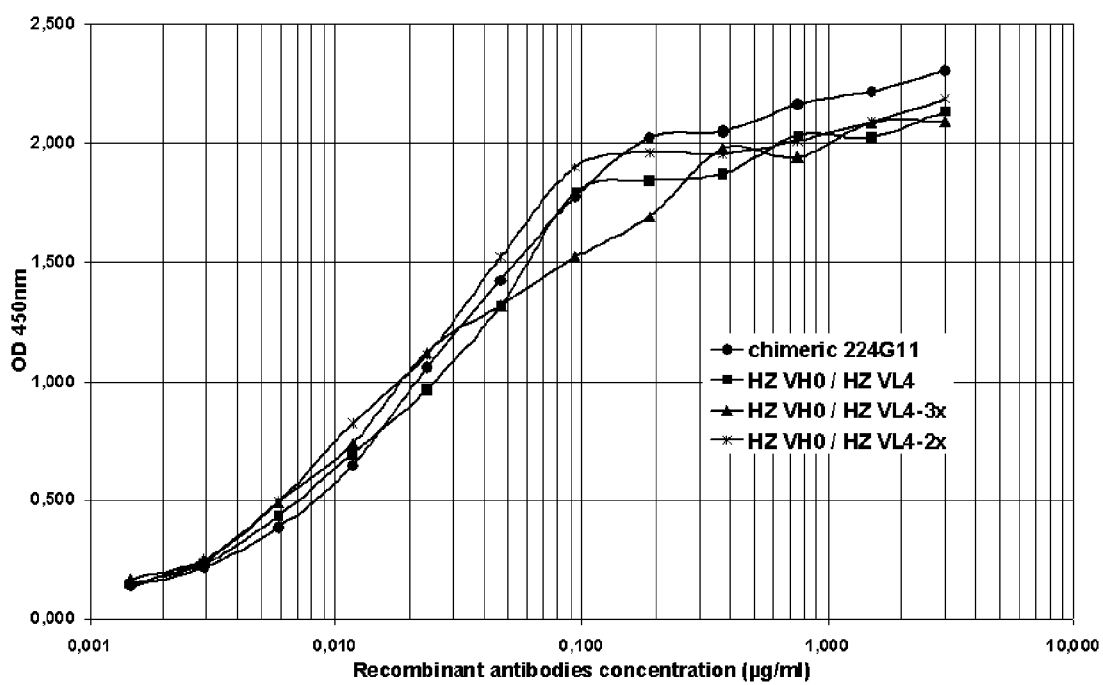
Figure 77:
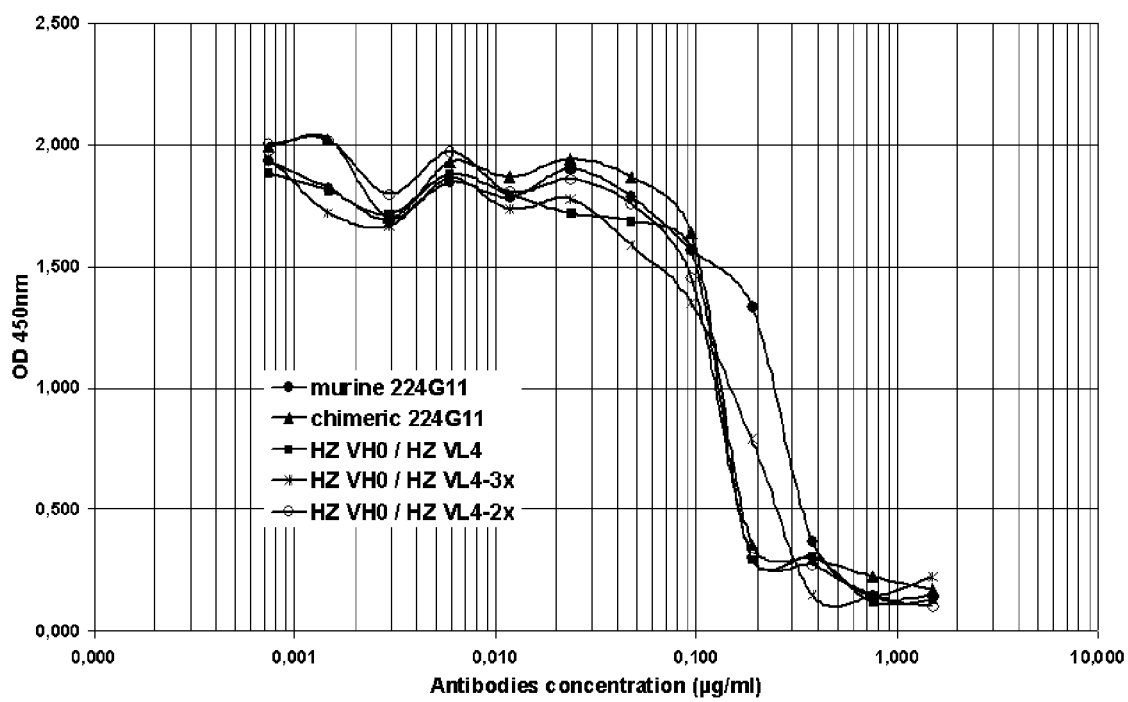

FIG. 34: Humanized 223C4 VH with mentioned mutations;

FIG. 35: Anti-tumor activity of the murine 224G11 Mab alone or combined with Navelbine® on the established xenograft NCI-H441 tumor model;

FIG. 36: Evaluation of anti-c-Met Mabs on HUVEC proliferation;

FIG. 37: Evaluation of anti-c-Met Mabs on HUVEC tube formation;

FIG. 38A: Alignment of 11E1 VL to murine IGKV4-79*01 germline gene;

FIG. 38B: Alignment of 11E1 VL to murine IGKJ4*01 germline gene;

FIG. 39A: Alignment of 11E1 VL to human IGKV3D-7*01 germline gene;

FIG. 39B: Alignment of 11E1 VL to human IGKJ4*02 germline gene;

FIG. 40: Humanized version of 11E1 VL with mentioned mutations;

FIG. 41A: Alignment of 11E1 VH to murine IGHV1-7*01 germline gene;

FIG. 41B: Alignment of 11E1 VH to murine IGHD4-1*01 germline gene;

FIG. 41C: Alignment of 11E1 VH to murine IGHJ3*01 germline gene;

FIG. 42A: Alignment of 11E1 VH to human IGHV1-2*02 and IGHV1-46*01 germline genes;

FIG. 42B: Alignment of 11E1 VH to human IGHJ4*03 germline gene;

FIG. 43: Humanized 11E1 VH with mentioned mutations;

FIGS. 44A and 44B: c-Met Phosphorylation assay on A549 cells. Evaluation of 11E1 and 224G11 purified Mabs, in absence or in presence of HGF, either at 30 μg/ml (FIG. 44A) or within a dose range from 0.0015 to 30 μg/ml in order to determine $EC_{50}$ values (FIG. 44B);

FIG. 45: In vivo combination of 224G11 Mab with Navelbine® in the NSCLC NCI-H441 xenograft model;

FIG. 46: In vivo combination of 224G11 Mab with Doxorubicin in the NSCLC NCI-H441 xenograft model;

FIG. 47: In vivo combination of 224G11 Mab with Docetaxel in the NSCLC NCI-H441 xenograft model;

FIG. 48: In vivo combination of 224G11 Mab with Temozolomide in the NSCLC NCI-H441 xenograft model;

FIGS. 49A, 49B, 49C and 49D: Effect of anti-c-Met Mabs on U87-MG spheroid growth;

FIGS. 50A and 50B: In vitro activity of chimeric and humanized forms of 224G11 in the phospho-c-Met assay;

FIG. 51: Settings of Biacore analysis;

FIG. 52: In vivo activity of 224G11 on MDA-MB-231 cells co-implanted with MRC5 cells as human HGF source on Athymic nude mice;

FIG. 53: ELISA based binding assay to Fc-cMet. Anti-Fc-c-Met binding activity was measured in an ELISA-based assay where anti-murine Fc conjugates was used to detect the purified murine monoclonal antibodies 11E1, 224G11 and 227H1. Dose-dependent binding activities onto plastic-coated recombinant Fc-cMet was measured at 450 nm;

FIG. 54: HGF-cMet competition assay. In this ELISA-based assay, recombinant Fc-cMET residual binding to plastic coated HGF in the presence of purified murine monoclonal antibodies 11E1, 224G11 and 227H1 was detected with anti-murine Fc conjugate and measured at 450 nm;

FIG. 55: Amino acid sequences alignment of 227H1-derived recombinant VH domains. The 227H1 VH amino acid sequence is aligned with the selected human receiving framework sequence, with only mentioned the amino acids that were found different from the murine 227H1 VH sequence. 227H1 HZ1, HZ2 and HZ3 VH sequences correspond to implemented humanized versions of the 227H1 murine VH domain, with remaining murine residues in bold. In HZ3, 10 residues (*) were automatically changed for their human counterparts. In HZ2, the seven residues from the third group (3) have been studied. In HZ1VH, the nine residues from the second group (2) have been mutated into their human counterparts, only the six residues from the first group (1) remain murine;

FIG. 56: ELISA based binding assay to Fc-cMet of recombinant 227H1 antibodies. Anti-Fc-cMet binding activity was measured in an ELISA-based assay where anti-human Fc conjugates was used to detect chimeric and humanized 227H1-derived recombinant antibodies. Dose-dependent binding activities onto plastic-coated recombinant Fc-cMet of humanized VH domains-derived 227H1 antibodies was measured at 450 nm and then compare to those of the parental/reference chimeric antibody;

FIG. 57: ELISA based binding assay to Fc-cMet of recombinant 227H1-derived antibodies. Anti-Fc-cMet binding activity was measured in an ELISA-based assay where anti-human Fc conjugates was used to detect chimeric and humanized 227H1-derived recombinant antibodies. Dose-dependent binding activity onto plastic-coated recombinant Fc-cMet of humanized HZ4VH-derived 227H1 antibody was measured at 450 nm and then compared to those of the parental/reference chimeric antibody;

FIG. 58: HGF-cMet competition assay of 227H1 murine and recombinant antibodies. In this ELISA-based assay, recombinant Fc-cMet residual binding to plastic coated HGF in the presence of the different forms of the 227H1 antibody was detected with a biotinylated unrelated anti-cMet antibody. Purified murine 227H1 monoclonal antibody, chimeric and HZ4VH-derived humanized 227H1-derived recombinant antibodies were tested and compared for their abilities to compete with HGF-cMet binding when measured at 450 nm;

FIG. 59: 227H1-HZ VH humanized variable domain sequence. *, corresponds to amino acids changed de facto to their human counterparts; !, corresponds to amino acids humanized during the HZ3 to HZ1 implementation; §, corresponds to amino acids humanized in the final 227H1-HZ VH sequence;

FIG. 60: Amino acid sequences alignment of 11E1-derived recombinant VH domains. The 11E1 VH amino acid sequence is aligned with the selected human receiving framework sequence, with only mentioned the amino acids that were found different from the murine 11E1 VH sequence. 11E1 HZ VH1, VH2 and VH3 sequences correspond to implemented humanized versions of the 11E1 murine VH domain, with remaining murine residues in bold. In HZ VH3, seven residues (*) were automatically changed for their human counterparts. In HZ VH2, the seven residues from the third group (3) have been studied. In HZ VH1, the five residues from the second group (2) have been mutated into their human counterparts, only the five residues from the first group (1) remain murine;

FIG. 61: ELISA based binding assay to Fc-cMet of recombinant 11E1 antibodies. Anti-Fc-cMet binding activity was measured in an ELISA-based assay where anti-human Fc conjugates was used to detect chimeric and humanized 11E1-derived recombinant antibodies. Dose-dependent binding activities onto plastic-coated recombinant Fc-cMet of humanized VH domains-derived 11E1 antibodies was measured at 450 nm and then compare to those of the parental/reference chimeric antibody;

FIG. 62: Amino acid sequences alignment of 11E1-derived recombinant VL domains. The 11E1 VL amino acid sequence is aligned with the selected human receiving framework sequence, with only mentioned the amino acids that were found different from the murine 11E1 VL sequence. 11E1 HZ VL1, VL2 and VL3 sequences correspond to implemented humanized versions of the 11E1 murine VL domain, with remaining murine residues in bold. In HZ VL3, ten residues (*) were automatically changed for their human counterparts. In HZ VL2, the eight residues from the third group (3) have been studied. In HZ VL1, the eight residues from the second group (2) have been mutated into their human counterparts, only the four residues from the first group (1) remain murine;

FIG. 63: ELISA based binding assay to Fc-cMet of recombinant 11E1 antibodies. Anti-Fc-cMet binding activity was measured in an ELISA-based assay where anti-human Fc conjugates was used to detect chimeric and humanized 11E1-derived recombinant antibodies. Dose-dependent binding activities onto plastic-coated recombinant Fc-cMet of humanized VL domains-derived 11E1 antibodies was measured at 450 nm and then compare to those of the parental/reference chimeric antibody;

FIG. 64: ELISA based binding assay to Fc-cMet of recombinant 11E1 antibodies. Anti-Fc-cMet binding activity was measured in an ELISA-based assay where anti-human Fc conjugates was used to detect chimeric and humanized 11E1-derived recombinant antibodies. Dose-dependent binding activities onto plastic-coated recombinant Fc-cMet of single or double humanized domains-derived 11E1 antibodies was measured at 450 nm and then compared to those of the parental/reference chimeric antibody;

FIG. 65: Amino acid sequences alignment of 224G11 VH domain sequence. The 224G11 VH amino acid sequence is aligned with the 227H1 VH sequence (underlined are non homologous residues) and with the selected human receiving framework sequence, with only mentioned the amino acids that were found different from the murine 224G11 VH sequence. 224G11 HZ VH0 sequence correspond to "227H1-based/full-IMGT" humanized version of the 224G11 murine VH domain. In this sequence no outside-IMGT-CDRs residues remain murine;

FIG. 66: ELISA based binding assay to Fc-cMet of recombinant 224G11 antibodies. Anti-Fc-cMet binding activity was measured in an ELISA-based assay where anti-human Fc conjugates was used to detect chimeric and HZVH0-derived humanized 224G11-derived recombinant antibodies. Dose-dependent binding activity onto plastic-coated recombinant Fc-cMet of the HZVH0 "full-IMGT" humanized VH domain-derived 224G11 antibody was measured at 450 nm and then compared to those of the parental/reference chimeric antibody;

FIG. 67: HGF-cMet competition assay of 224G11 murine and recombinant antibodies. In this ELISA-based assay, recombinant Fc-cMet residual binding to plastic coated HGF in the presence of the different forms of the 224G11 antibody was detected with a biotinylated unrelated anti-cMet antibody. Purified murine 224G11 monoclonal antibody, chimeric and HZVH0-derived humanized 224G11-derived recombinant antibodies were tested and compared for their abilities to compete with HGF-cMet binding when measured at 450 nm;

FIG. 68: Amino acid sequences alignment of 224G11 VL domain sequences. The 224G11 VL amino acid sequence is aligned with the two selected human receiving framework sequences, with only mentioned the amino acids that were found different from the murine 224G11 VL sequence. 224G11 HZ VL3 sequence correspond to "shorter-CDR1" humanized version of the 224G11 murine VH domain while HZ VL6 correspond to the "longer-CDR1" version, with the remaining murine residues in bold. For both basic humanized versions, the remaining murine residues are ranked for further humanization process where * corresponds to amino acids humanized in the basic versions, and 3, 2 and 1 correspond to the residues groups for the design of the implemented humanized versions;

FIG. 69: ELISA based binding assay to Fc-cMet of recombinant 224G11 antibodies. Anti-Fc-cMet binding activity was measured in an ELISA-based assay where anti-human Fc conjugates was used to detect chimeric and humanized 22G11-derived recombinant antibodies. Dose-dependent binding activities onto plastic-coated recombinant Fc-cMet of humanized VL3 and VL6 domains-derived 224G11 antibodies was measured at 450 nm and then compare to those of the parental/reference chimeric antibody;

FIG. 70: ELISA based binding assay to Fc-cMet of recombinant 224G11 antibodies. Anti-Fc-cMet binding activity was measured in an ELISA-based assay where anti-human Fc conjugates was used to detect chimeric and humanized 224G11-derived recombinant antibodies. Dose-dependent binding activities onto plastic-coated recombinant Fc-cMet of humanized VL domains-derived 224G11 antibodies was measured at 450 nm and then compare to those of the parental/reference chimeric antibody;

FIG. 71: HGF-cMet competition assay of 224G11 murine and recombinant antibodies. In this ELISA-based assay, recombinant Fc-cMet residual binding to plastic coated HGF in the presence of the different forms of the 224G11 antibody was detected with a biotinylated unrelated anti-cMet antibody. Purified murine 224G11 monoclonal antibody, chimeric and HZ VL4-derived humanized 224G11-derived recombinant antibodies were tested and compared for their abilities to compete with HGF-cMet binding when measured at 450 nm;

FIG. 72: Amino acid sequence of VL4 humanized 224G11 VL domain sequence. *, corresponds to amino acids changed de facto to their human counterparts in the basic HZ VL6 version; !, corresponds to amino acids humanized during the HZ VL6 to HZ VL4 implementation; §, corresponds to amino acids that remain murine in the 224G11-HZ VL4 sequence;

FIG. 73: ELISA based binding assay to Fc-cMet of recombinant 224G11 antibodies. Anti-Fc-cMet binding activity was measured in an ELISA-based assay where anti-human Fc conjugates was used to detect chimeric and humanized 22G11-derived recombinant antibodies. Dose-dependent binding activities onto plastic-coated recombinant Fc-cMet of single- or double-humanized domains-derived 224G11 antibodies was measured at 450 nm and then compare to those of the parental/reference chimeric antibody;

FIG. 74: HGF-cMet competition assay of 224G11 murine and recombinant antibodies. In this ELISA-based assay, recombinant Fc-cMet residual binding to plastic coated HGF in the presence of the different forms of the 224G11 antibody was detected with a biotinylated unrelated anti-cMet antibody. Purified murine 224G11 monoclonal antibody, chimeric and fully humanized 224G11-derived recombinant antibodies were tested and compared for their abilities to compete with HGF-cMet binding when measured at 450 nm;

FIG. 75: ELISA based binding assay to Fc-cMet of recombinant 224G11 antibodies. Anti-Fc-cMet binding activity was measured in an ELISA-based assay where anti-human Fc conjugates was used to detect chimeric and humanized 22G11-derived recombinant antibodies. Dose-dependent binding activities onto plastic-coated recombinant Fc-cMet of single mutants of the VL4-derived fully humanized 224G11 antibodies was measured at 450 nm and then compare to those of the parental/reference chimeric antibody;

FIG. 76: ELISA based binding assay to Fc-cMet of recombinant 224G11 antibodies. Anti-Fc-cMet binding activity was measured in an ELISA-based assay where anti-human Fc conjugates was used to detect chimeric and humanized 22G11-derived recombinant antibodies. Dose-dependent binding activities onto plastic-coated recombinant Fc-cMet of single and multiple mutants of the VL4-derived fully humanized 224G11 antibodies was measured at 450 nm and then compare to those of the parental/reference chimeric antibody; and FIG. 77: HGF-cMet competition assay of 224G11 murine and recombinant antibodies. In this ELISA-based assay, recombinant Fc-cMet residual binding to plastic coated HGF in the presence of the different forms of the 224G11 antibody was detected with a biotinylated unrelated anti-cMet antibody. Purified murine 224G11 monoclonal antibody, chimeric and single or multiple mutants of the VL4-derived fully humanized 224G11 recombinant antibodies were tested and compared for their abilities to compete with HGF-cMet binding when measured at 450 nm.

EXAMPLE 1

Generation of Antibodies Against c-Met

To generate anti-c-Met antibodies 8 weeks old BALB/c mice were immunized either 3 to 5 times subcutaneously with a CHO transfected cell line that express c-Met on its plasma membrane ($20 \times 10^6$ cells/dose/mouse) or 2 to 3 times with a c-Met extracellular domain fusion protein (10-15 ng/dose/mouse) (R&D Systems, Catalog #358MT) or fragments of this recombinant protein mixed with complete Freund adjuvant for the first immunization and incomplete Freund adjuvant for the following ones. Mixed protocols in which mice received both CHO-cMet cells and recombinant proteins were also performed. Three days before cell fusion, mice were boosted i.p. or i.v. with the recombinant protein or fragments. Then spleens of mice were collected and fused to SP2/0-Ag14 myeloma cells (ATCC) and subjected to HAT selection. Four fusions were performed. In general, for the preparation of monoclonal antibodies or their functional fragments, especially of murine origin, it is possible to refer to techniques which are described in particular in the manual "Antibodies" (Harlow and Lane, Antibodies: A Laboratory Manual, Cold Spring Harbor Laboratory, Cold Spring Harbor N.Y., pp. 726, 1988) or to the technique of preparation of hybridomas described by Kohler and Milstein (Nature, 256: 495-497, 1975).

Obtained hybridomas were initially screened by ELISA on the c-Met recombinant protein and then by FACS analysis on A549 NSCLC, BxPC3 pancreatic, and U87-MG glioblastoma cell lines (representative profiles were presented in FIG. 1) to be sure that the produced antibodies will be able to also recognize the native receptor on tumor cells. Positive reactors on these 2 tests were amplified, cloned and a set of hybridomas was recovered, purified and screened for its ability to inhibit in vitro cell proliferation in the BxPC3 model.

For that purpose 50 000 BxPC3 cells were plated in 96 well plates in RPMI medium, 2 mM L. Glutamine, without SVF. 24 hours after plating, antibodies to be tested were added at a final concentration ranging from 0.0097 to 40 ng/ml 60 min before addition of 100 ng/ml of hHGF. After 3 days, cells were pulsed with 0.5 nCi of [$^3$H]thymidine for 16 hours. The magnitude of [$^3$H]thymidine incorporated into trichloroacetic acid-insoluble DNA was quantified by liquid scintillation counting. Results were expressed as raw data to really evaluate the intrinsic agonistic effect of each Mab (FIGS. 2A and 2B).

Then antibodies inhibiting at least 50% cell proliferation were evaluated as supernatants by BRET analysis on c-Met transfected cells. For that purpose, CHO stable cell lines expressing C-Met-Rluc or C-Met-Rluc and C-Met-K1100A-YFP were generated. Cells were distributed in white 96 well microplates in DMEM-F12/FBS 5% culture medium one or two days before BRET experiments. Cells were first cultured at 37° C. with CO2 5% in order to allow cell attachment to the plate. Cells were then starved with 200 µl DMEM/well overnight Immediately prior to the experiment, DMEM was removed and cells quickly washed with PBS. Cells were incubated in PBS in the presence or absence of antibodies to be tested or reference compounds, 10 min at 37° C. prior to the addition of coelenterazine with or without HGF in a final volume of 50 µl. After incubation for further 10 minutes at 37° C., light-emission acquisition at 485 nm and 530 nm was initiated using the Mithras luminometer (Berthold) (1 s/wave length/well repeated 15 times).

BRET ratio has been defined previously [Angers et al., Proc. Natl. Acad. Sci. USA, 2000, 97:3684-3689] as: [(emission at 530 nm)−(emission at 485 nm)×Cf]/(emission at 485 nm), where Cf corresponds to (emission at 530 nm)/(emission at 485 nm) for cells expressing Rluc fusion protein alone in the same experimental conditions. Simplifying this equation shows that BRET ratio corresponds to the ratio 530/485 nm obtained when the two partners were present, corrected by the ratio 530/485 nm obtained under the same experimental conditions, when only the partner fused to R. reniformis luciferase was present in the assay. For the sake of readability, results are expressed in milliBRET units (mBU); mBU corresponds to the BRET ratio multiplied by 1000.

After this second in vitro test, 4 antibodies i) without intrinsic activity as a whole molecule in the functional test of proliferation, ii) inhibiting significantly BxPC3 proliferation (FIGS. 2A and 2B) and iii) inhibiting c-Met dimerization (FIG. 3) were selected. These 3 antibodies of IgG1 kappa isotype were described as 11E1, 224G11, 223C4 and 227H1. In the experiments, the 5D5 Mab, generated by Genentech, and available at the ATCC, was added as a control for the intrinsic agonistic activity.

FIGS. 2A and 2B demonstrates that 11E1, 224G11, 223C4 and 227H1 were without any agonist activity in contrast to 5D5 which induced a dose dependent stimulation of cell proliferation in absence of ligand. A significant inhibition of cell proliferation was observed with the 4 selected antibodies. 5D5 is without effect on HGF-induced cell proliferation in this test.

When evaluated for blockade of dimerization significant effects reaching 32, 55, 69 and 52% inhibition of dimerization for 224G11, 223C4, 11E1 and 227H1 respectively were observed. Compared to basal signals in the respective experiments, 5D5 antibody is without effect in this dimerization model.

EXAMPLE 2

Protein Recognition by Anti-c-Met Antibodies

To characterize the pattern of recognition of the 3 selected antibodies, 3 ELISA have been set up with the recombinant c-Met protein, its monomeric fragment (obtained by cleavage of the recombinant c-Met-Fc protein and the recombinant SEMA domain.

Results presented in FIG. 4 demonstrated that the 4 antibodies recognized both dimeric and monomeric proteins. To perform these ELISA the human dimeric c-Met protein (R&D sytems, cat#358MT) is coated at the concentration of 0.7 µg/ml in PBS overnight at 4° C. After saturation of the plates (Costar #3690) with a 0.5% gelatin solution 2 hours at 37° C., hybridoma supernatants are incubated 1 hour at 37° C. Once rinsed with PBS, the anti-mouse HRP-antibody (Jackson ImmunoResearch, catalog #115-035-164) is added to each well at a 1/5000 dilution in ELISA buffer (0.1% gelatin/ 0.05% Tween 20 in PBS) and the plates incubated for 1 hour at 37° C. After 3 washes in PBS, the activity of the peroxydase is revealed by the addition of 50 µl of TMB substrate (Uptima). The reaction is left to occur for 5 min at room temperature. The reaction is stopped by the addition of 50 µl/well of a 1 M $H_2SO_4$ solution and read on a plate reader at 450 nm. The same kind of protocol was performed on monomeric c-Met and SEMA domain but in that cases proteins were coated at 5 and 3 µg/ml respectively.

The 5D5 Mab introduced as a positive control recognized as expected the SEMA protein. 224G11, 227H1 and 223C4 did not bind the SEMA domain. 11E1 is able to bind the SEMA.

To determine whether 11E1 and 5D5, both recognizing the SEMA domain compete for overlapping epitopes, BIAcore analysis were performed. BIAcore system based on the Surface Plasmon Resonance phenomenon deliver data by monitoring binding events in real-time. It is then useful to group antibodies in a so called "epitope mapping" experiments. A couple of antibodies unable to bind at the same time on the antigen molecule are classified in the same group (identical or neighbouring binding sites). At the opposite when their respective binding sites are sufficiently distant to allow a simultaneous binding of both antibodies these later are classified into two different groups. In such experiments, the antigen is commonly used as the ligand (immobilized on the sensorchip) and the antibodies are used without any labelling as analytes (solution phase).

All the experiments described have been done on a BIAcore X instrument (GE Healthcare Europe GmbH). A CM5 sensorchip (BIAcore) activated by a mouse anti-Tag-6His Mab (R&D System ref MAB050) has been prepared following the manufacturer instructions by using the amine coupling kit (BIAcore). The running buffer (HBS-EP) and regeneration buffer (Glycine, HCl) are from BIAcore. A recombinant soluble version of the human HGF receptor produced as a chimeric molecule c-Met-Fc-Tag His was from R&D systems (ref 358-MT-CF). The experiments were done at 25° C., at a flow rate of 30 nl/min. A 10 ng/ml solution of c-Met in running buffer was injected during one minute on the flowcell2 (fc2) typically 270 RU of the soluble form of c-Met were captured. The flowcell1 (fc1) was used as a reference to check any non specific binding of the antibodies to the sensorchip matrix.

Sequential injections of antibodies to be tested were performed. An antibody was injected on both flowcells during 2 minutes. A second antibody (or the same) was then injected in the same conditions. If no significant binding was observed a third injection was done with another antibody. The sensorchip was then regenerated by a single 30 s injection of the regeneration buffer. Either antibodies and c-Met-Fc were discarded at this stage.

Analysis of the Results:

The ability of an antibody "A" to block the binding of an antibody "B" is calculated by the ratio BIA/C=(R2A/B/ R1B)×100: where R2A/B is the response corresponding to the binding of the MAb "B" when it was injected after Mab "A" and R1B is the response corresponding to the binding of the MAb "B" when it was injected first. A BIA/C below 20% means that A is able to block the binding of B so that A and B have neighbouring binding sites.

The epitope mapping has been performed with 2 Mabs, 11E1 and 5D5.

TABLE 3

| $2^{nd}$ Ab (B)<br>$1^{st}$ Ab (A) | 11E1 | 5D5 |
|---|---|---|
| 11E1 | *6.5%* | 84.2% |
| 5D5 | 98.4% | *11.0%* |

Visualisation of the binding on around 270RU of captured c-Met-Fc by the sequential 2 minutes injections of Mabs 5D5 (first), 5D5 (second) and 11E1 (third) at a concentration of 10 ng/ml each demonstrated that 5D5 and 11E1 bind clearly to two distant sites (FIG. 5A). This observation was confirmed by the reciprocal sequence of antibody (FIG. 5B).

Table 3 summarized the calculation ratio obtained with the different sequences of these 2 antibodies. Black values (over 75%) mean that Mab A does not block the binding of Mab B. Bold/italic values (below 20%) mean that the binding sites of both antibody (A and B) are identical or sufficiently close to unable a simultaneous binding.

EXAMPLE 3

Effect of Mabs on c-Met Phosphorylation

To determine the activity of anti-c-Met antibodies on c-Met phosphorylation a phospho c-Met ELISA assay was set-up.

Briefly 500 000 A549 cells were seeded in each well of 6-well plates in F12K medium+10% FCS. 16 hours before HGF addition (100 ng/ml), cells were starved and each antibody to be tested was added at a final concentration of 30 ng/ml 15 minutes before ligand stimulation. 15 minutes after HGF addition, cold lysis buffer was added, cells were scraped and cell lysates collected and centrifuged at 13 000 rpm for 10 min at 4° C. Supernatants were quantified with a BCA kit (Pierce) and stored at −20° C. For ELISA assay, a goat anti-c-Met antibody (R&D ref. AF276) was used as a capture antibody (coating overnight at 4° C.) and after a saturation step (1 h at RT) with a TBS-BSA 5% buffer, 25 ng of protein from the different cell lysates was added to each well of the 96-well plate. After a 90 minute-incubation time at RT, plates were washed four times and an anti-phospho-c-Met antibody (Rabbit anti-pY1230-1234-1235 c-Met) was added. After an additional 1 hour incubation time and 4 washes an anti-rabbit-HRP (Biosource) was added for 1 hour at RT and then Luminol substrate was added before evaluation the luminescence with a Mithras device. Results presented in FIG. 6B demonstrated that 11E1, 224G11, 223C4 and 227H1 inhibit c-Met phosphorylation by 68, 54, 80 and 65% respectively compared to the 5D5 Mab which displayed a weaker inhibition of c-Met phosphorylation (42%). In this test, a weak basal effect (less to 20%) was observed with the 4 candidate antibodies (FIG. 6A). As described in the various examples presented in this patent, this weak basal effect has no consequences on the activity of antibodies in other in vitro and in vivo tests. The 5D5 used as a control displayed, in this test a significant basal effect.

EXAMPLE 4

Displacement of Radio-Labelled HGF by Anti-c-Met Antibodies

To determine whether the anti-c-Met antibodies were able to displace HGF, binding experiments were set up. Briefly, protein A FlashPlate 96-well microplates (Perkin Elmer) were saturated with 0.5% gelatine in PBS (200 µl/well, 2 h at room temperature) before adding recombinant c-Met-Fc (R&D Systems) as a coating protein. Two thousand µl of a 1 µg/ml c-Met-Fc solution in PBS were added to each well. Plates were then incubated overnight at 4° C. Free residual Protein A sites were further saturated with a non relevant hIgG (0.5 µg/well in PBS) for 2 h at room temperature. Plates were washed with PBS after each step.

For competition assays, binding of $[^{125}I]$-HGF (specific activity ~2,000 Ci/mmol) at 200 pM to immobilized c-Met was measured in the presence of varying concentrations of the anti-c-Met monoclonal antibodies 11E1, 224G11, 223C4, 227H1 or HGF (R&D Systems) ranging from 0.1 pM to 1 µM in PBS pH 7.4. The plates were incubated at room temperature for 6 h, then counted on a Packard Top Count Microplate Scintillation Counter. Non specific binding was determined in the presence of 1 µM of HGF. The monoclonal antibody 9G4, which is not directed at c-Met but specifically recognizes an *E. coli* protein, was used as mouse IgG1 isotype control.

Percent of total specific $[^{125}I]$-HGF binding was plotted as a function of ligand concentration on semilog graphs. Concentrations of the various inhibitors required to inhibit the radioligand binding by 50% ($IC_{50}$) were determined graphically from the sigmoid competition curves obtained (FIGS. 7A and 7B).

As expected, non radiolabeled HGF was able to fully displace $[^{125}I]$-HGF binding to immobilized c-Met, whereas the control antibody 9G4 did not show any HGF blocking activity (FIGS. 7A and 7B). Monoclonal anti-c-Met antibodies 11E1, 224G11, 223C4 and 227H1 were able to inhibit $[^{125}I]$-HGF binding to immobilized c-Met, with $IC_{50}$ values of 20 nM, 3 nM, 2.7 nM and 5.8 nM, respectively. The $IC_{50}$ values determined for antibodies 224G11, 223C4 and 227H1 were comparable to the $IC_{50}$ value determined for non radiolabeled HGF, which was comprised between 3 and 5 nM, whereas antibody 11E1 exhibited a higher $IC_{50}$ value.

EXAMPLE 5

Inhibition of Invasion by Anti-c-Met Antibodies

To evaluate the inhibiting effect of the anti-c-Met antibodies on the invasion process, A549 cells were plated in the upper chamber of BD BioCoat™ Matrigel™ invasion chambers (6.5 mm diameter wells with 8-µm pre size polycarbonate membranes). A459 cells were starved 24 hours before performing the invasion assay. Then 500 000 A549 cells were plated in chemotaxis buffer (DMEM medium, 0.1% BSA, 12 mM Hepes) in the upper well of each chamber, upon the Matrigel coating either with or without the antibody to be tested (final Mab concentration 10 µg/ml). After 1 hour incubation of the plates at 37° C. with 5% $CO_2$, the lower chambers were filled with either growth medium containing 400 ng/ml of rhHGF or with growth medium alone. The chambers were incubated for 48 additional hours at 37° C. with 5% CO2. At the end of this incubation time, cells that remained on upper surface of the filter were gently removed with a cotton swab, cells that migrated to the lower surface of the filter were lysed, stained with CyQuant GR dye buffer (Invitrogen) and counted using a fluorescence reader Berthold Mithras LB940. All conditions were tested as triplicates.

As expected HGF induced a significant invasion of tumor cells comparable to the one observed with 10% FCS introduced as a positive control (FIG. 8). The murine IgG1 9G4 introduced as an isotype control is without significant effect on basal or HGF-induced invasion when compared to cells plated without IgG. No agonist effect was noticed with 11E1, 224G11, 223C4 and 227H1 when added alone and a significant and comparable inhibition of the HGF-induced invasion was observed with the 3 Mabs.

EXAMPLE 6

Inhibition of Wound Healing by Anti-c-Met Antibodies

HGF stimulates motility. To determine whether the anti-HGF antibodies were able to inhibit migration, NCI-H441 cells were grown to high density and a gap was introduced with a P200 pipette tip. Cells were then stimulate to migrate across the gap with HGF (100 ng/ml) in presence or in absence of 11E1. Wells with 11E1 alone were also evaluated. Each tested condition was evaluated as a sextuplicate and 3 independent experiments were performed. After an overnight incubation, cells were visualized with an Axio Vision Camera (objective ×4).

HGF induced a significant migration resulting in a complete closure of the gad within one night (FIG. 9). The 9G4 irrelevant IgG1 used as an isotype control is without any effect on cell migration. As expected an agonist effect was observed with the 5D5 when added alone but a significant inhibition of cell migration is observed with this antibody in presence of HGF in the portion of the gap remained open. The Fab fragment of 5D5 is without any agonist effect when added alone. However no activity of this fragment was observed in presence of HGF. As observed with the isotype control 9G4, the MAb 11E1 had no agonist effect when added alone and behave as a full antagonist in presence of HGF.

EXAMPLE 7

Scatter Assay

SK-HEP-1 cells were seeded at low density ($1.10^4$ cells/well) in a 24-well plate in DMEM with 10% FCS and grown for 24 hours before addition, at the same time, of HGF (100 ng/ml) and antibodies to be tested (10 µg/ml). After 72 hours incubation, colonies were fixed and stained with 0.2% crystal violet in methanol and assessed for scattering visually. Each tested condition was tested as a triplicate and 3 independent experiments were performed.

Addition of HGF to SK-HEP-1 cells induced a significant cell scattering (FIGS. 10A and 10B). The 9G4 antibody introduced as an isotype control is without effect neither alone or in presence of HGF. As expected the 5D5 antibody displayed a significant agonist effect alone and no inhibitory effect was observed when 5D5 was added with HGF (FIG. 10A). No agonistic effect was observed neither with 11E1 (FIG. 10A) nor with 224G11 (FIG. 10B) added alone. A very significant inhibitory effect of these antibodies was demonstrated in presence of HGF (FIGS. 10A and 10B).

EXAMPLE 8

Three-Dimensional Tubulogenesis Assay

SK-HEP-1 cells were seeded at $1.10^4$ cells/well in a 24-well plate in DMEM with 10% FCS/Matrigel (50/50) and incubated for 30 min before addition, at the same time, of HGF (100 ng/ml) and antibodies to be tested (10 ng/ml). After 7 days incubation, cells were assessed for tube formation visually. Each tested condition was tested as a triplicate and 3 independent experiments were performed.

Addition of HGF induced a significant SK-HEP-1 tube formation (FIG. 11). The antibody 9G4 introduced as an isotype control was without effect neither alone or in presence of HGF. As expected the 5D5 antibody displayed a significant agonist effect alone and no inhibitory effect was observed when 5D5 was added with HGF. No agonistic effect was observed with 11E1, 223C4 and 224G11 added alone and a full inhibitory effect was demonstrate with both 11E1 and 223C4 in presence of HGF. A partial but significant inhibition was observed with the 224G11Mab.

EXAMPLE 9

Spheroid Formation

To evaluate the ability of anti-c-Met antibodies to inhibit in vitro tumor growth, in a model closer to an in vivo situation, U-87MG, human glioblastoma cells (ATCC # HTB-14) spheroids were generated. Cells grown as a monolayer were detached with trypsine-EDTA and resuspended into complete cell culture media (DMEM) supplemented with 10% FBS. Spheroids were initiated by inoculating 625 cells into single wells of round bottom, 96 plates in DMEM-10% FCS. To prohibit cell adhesion to a substratum, the plates were pre-coated with polyHEMA in 95% ethanol and air dried at room temperature. The plates were incubated under standard cell culture conditions at 37° C., 5% $CO_2$ in humidified incubators. Purified monoclonal antibodies (10 µg/ml) were added after 3 and 7 days of spheroid culture. HGF (400 ng/ml) was added once after 4 days of culture. Spheroids were kept in culture for at least 10 days. Then, spheroid growth was monitored by measuring the area of spheroids using automeasure module of axiovision software. Area was expressed in $\mu m^2$. 8-16 spheroids were evaluated for each condition.

FIGS. 12A and 12B showed that in presence of 10% FCS no stimulation was observed when HGF was added to the complete medium. As expected the 9G4 isotype control is without effect on spheroid growth. 11E1 and 223C4 reduced significantly spheroid growth both in presence and in absence of HGF. No effect was observed with the 5D5 Fab fragment.

EXAMPLE 10

In Vivo Activity of Anti-c-Met Mabs in the U87MG Xenograft Model

Six to eight weeks old athymic mice were housed in sterilized filter-topped cages, maintained in sterile conditions and manipulated according to French and European guidelines. U87-MG, a glioblastoma cell line, expressing c-Met and autocrine for the ligand HGF, was selected for in vivo evaluations. Mice were injected subcutaneously with $5 \times 10^6$ cells. Then, six days after cell implantation, tumors were measurable (approximately 100 $mm^3$), animals were divided into groups of 6 mice with comparable tumor size and treated twice a week with 1 mg/dose of each antibody to be tested. The mice were followed for the observation of xenograft growth rate and body weight changes. Tumor volume was calculated by the formula: $\pi(Pi)/6 \times length \times width \times height$.

The results obtained were summarized in FIG. 13 and demonstrated that all tested antibodies inhibit significantly in vivo growth of U87-MG cells. The use of a neutralizing anti-IGF-1R antibody (IgG1) in panel A demonstrates that the observed in vivo inhibition is specifically related to a HGF-cMet axis modulation.

EXAMPLE 11

In Vivo Activity of Anti-c-Met Mabs in the NCI-H441 Xenograft Model

NCI-H441 is derived from papillary lung adenocarcinoma, expresses high levels of c-Met, and demonstrates constitutive phosphorylation of c-Met RTK.

To determine whether this cell line expresses high levels of c-Met and is able to produce HGF, both quantitative RT-PCRs and FACS or ELISA (Quantikine HGF; R&D systems) were performed. For quantitative RT-PCRs, total HGF or cMet transcript expression levels in cell lines were assessed by quantitative PCR using standard TaqMan™ technique. HGF or c-Met transcript levels were normalized to the housekeeping gene Ribosomal protein, large, P0 (RPL0) and results were expressed as normalized expression values (2-ddCT method).

The primer/probe sets for RPL0 were forward, 5'-gaaactct-gcattctcgcttcctg-3' (SEQ ID No. 47); reverse, 5'-aggactcgtttg-tacccgttga-3' (SEQ ID No. 48); and probe, 5'-(FAM)-tgcagat-tggctacccaactgttgca-(TAMRA)-3' (SEQ ID No. 49). The primer/probe sets for HGF were forward, 5'-aacaatgcctctggt-tcc-3' (SEQ ID No. 50); reverse, 5'-cttgtagagCgtccttac-3' (SEQ ID No. 51); and probe, 5'-(FAM)-ccttcaatagcatgt-caagtggagtga-(TAMRA)-3' (SEQ ID No. 52). The primer/probe sets for cMet were forward, 5'-cattaaaggagacctcaccat-agctaat-3' (SEQ ID No. 53); reverse, 5'-cctgatcgagaaaccacaacct-3' (SEQ ID No. 54); and probe, 5'-(FAM)-catgaagcgaccctctgatgtccca-(TAMRA)-3' (SEQ ID No. 55). The thermocycling protocol consisted of melting at 50° C. for 2 minutes and 95° C. for 10 minutes, followed by 40 cycles at 95° C. for 15 seconds and 62° C. for 1 minute.

No mRNA for HGF was found in NCI-H441 (FIG. 14) and HGF is not detectable by ELISA in NCI-H441 supernatants. In these experiments U87-MG, a glioblastoma cell line known as an autocrine cell line for HGF, was introduced as a positive control. The RT-PCR analysis showed a significant level of HGF mRNA in U87-MG and 1.9 ng HGF/million cells was detected in the supernatant of U87-MG cells. Both quantitative RT-PCRs and FACS analysis FIGS. 15A and 15B demonstrated that as expected NCI-H441 cells significantly overexpressed c-Met and that this expression was dramatically higher than the one observed for U87-MG cells. In this experiment the MCF-7 cell line was introduced as a negative control. Taken together NCI-H441 appears as a non autocrine constitutively activated cell line able to grow independently of HGF ligand in which a ligand-independent dimerization of c-met occurred as a consequence of the overexpression of the receptor.

The evaluation of anti-c-met antibodies on the in vivo activity of this non autocrine cell line could give some insights about their potency to impact on c-met dimerization.

FIG. 16 demonstrates that 224G11, 11E1 and 227H1 inhibited significantly in vivo growth of NCI-H441 suggesting that in addition to ligand dependent inhibition, these antibodies able to inhibit dimerization are also able to target a ligand-independent inhibition of c-met. As mentioned above in the specification, with that last property, 224G11, 11E1 and 227H1 are shown to be different from the 5D5 one armed (OA-5D5) anti-c-Met antibody.

EXAMPLE 12

Humanization Process by CDR-Grafting of the Antibody 224G11

I—Humanization of the Light Chain Variable Domain

Comparison of the Nucleotidic Sequence of the 224G11VL with Murine Germline Genes As a preliminary step, the nucleotidic sequence of the 224G11 VL was compared to the murine germline genes sequences part of the IMGT database (imgt.cines.fr).

Murine IGKV3-5*01 and IGKJ4*01 germline genes with a sequence identity of 99.31% for the V region and 94.28% for the J region, respectively, have been identified. Regarding the obtained identity, it has been decided to directly use the 224G11VL sequences to look for human homologies.

These alignments are represented in FIGS. 17A for the V gene and 17B for the J gene.

Comparison of the Nucleotidic Sequence of the 224G11VL with Human Germline Genes In order to identify the best human candidate for the CDR grafting, the human germline gene displaying the best identity with the 224G11VL has been searched. To this end, the nucleotidic sequence of 224G11VL has been aligned with the human germline genes sequences part of the IMGT database. For optimization of the selection, alignments between the proteic sequences were made to search for better homologies.

These two complementary methods led to the identification of two possible receiving human V sequences for the murine 224G11 VL CDRs. Nucleotidic alignment gives the human IGKV3-11*01 germline gene with a sequence identity of 75.99% whereas proteic alignment gives the human IGKV4-1*01 germline gene with a sequence identity of 67.30%. It worthnoting that in both cases, the two closest germline genes and the analysed sequences show different CDR1 amino acid lengths (10 amino acids in 224G11 VL; 6 amino acids in IGKV3-11*01; 12 amino acids in IGKV4-1*01).

For the J region, the best homology score was first obtained with human the human IGKJ3*01 showing a sequence identity of 80%. But a higher number of consecutive identical nucleotides and a better amino acid fitting has been found in the alignment with human IGKJ4*02 germline gene (sequence identity of 77.14%). Thus the IGKJ4*02 germline gene was selected as receiving human J region for the murine 11E1 VL CDRs.

Alignments are represented in FIGS. 18A for the V region and 18B for the J region.

Humanized Version of 224G11 VL

Given the possibility of two receiving human V regions for the murine 224G11 VL CDRs, two humanized versions of the 224G11 VL domain will be described. The first corresponds to an initial trial for a human framework with a shorter CDR1 length (IGKV3-11*01), the second with a longer CDR1 length (IGKV4-1*01).

a) IGKV3-11*01 Based Humanized Version of 224G11 VL

The following steps in the humanization process consist in linking the selected germline genes sequences IGKV3-11*01 and IGKJ4*02 and also the CDRs of the murine 224G11 VL to the frameworks of these germline genes sequences.

As depicted in FIG. 19A, the bolded residues in the 224G11 VL sequence correspond to the twenty-five amino acids that were found different between 224G11 VL domain and the selected human frameworks (Human FR, i.e. IGKV3-11*01 and IGKJ4*02).

Regarding to several criteriae such as their known participation in VH/VL interface, in antigen binding or in CDR structure, the amino acid class changes between murine and human residues, localization of the residue in the 3D structure of the variable domain, three out of the twenty-five different residues have been identified to be eventually mutated. These three most important defined residues and mutations into their human counterparts being murine M39 into human L, H40 into A and R84 into G. These ranked one residues are shown in FIG. 19A as bolded residues in the 224G11 HZ1VL sequence where they remained murine.

Of course, the above mentioned residues to be tested are not limited but must be considered as preferential mutations.

With the help of a molecular model, other mutations could be identified. Can be mentioned the following ranked two residues, i.e. residues 15 (L/P), 49 (P/A), 67 (L/R), 68 (E/A), 93 (P/S) and 99 (V/F) on which mutations could also be envisaged in another preferred embodiment.

Of course, the above mentioned residues to be eventually tested are not limited but must be considered as preferential mutations. In another preferred embodiment, all the sixteen others ranked three residues among the twenty-five different amino acids could be reconsidered.

All the above mentioned mutations will be tested individually or according various combinations.

FIG. 19A represents the implemented IGKV3-11*01 based humanized 224G11 VL with above mentioned mutations clearly identified. The number under each proposed mutation corresponds to the rank at which said mutation will be done.

b) IGKV4-1*01 Based Humanized Version of 224G11 VL

The following steps in the humanization process consist in linking the selected germline genes sequences IGKV4-1*01 and IGKJ4*02 and also the CDRs of the murine 224G11 VL to the frameworks of these germline genes sequences.

As depicted in FIG. 19B, the bolded residues in the 224G11 VL sequence corresponds to the twenty-two amino acids that were found different between 224G11 VL domain and the selected human frameworks (Human FR, i.e. IGKV4-1*01 and IGKJ4*02).

Regarding to several criteriae such as their known participation in VH/VL interface, in antigen binding or in CDR structure, the amino acid class changes between murine and human residues, localization of the residue in the 3D structure of the variable domain, four out of the twenty-two different residues have been identified to be eventually mutated. These four most important defined residues and mutations into their human counterparts being murine L4 into human M, M39 into L, H40 into A and R84 into G. These ranked one residues are shown in FIG. 19B as bolded residues in the 224G11 HZ2VL sequence where they remained murine.

Of course, the above mentioned residues to be tested are not limited but must be considered as preferential mutations.

With the help of a molecular model, other mutations could be identified. Can be mentioned the following ranked two residues, i.e. residues 25 (A/S), 66 (N/T), 67 (L/R), and 93 (P/S) on which mutations could also be envisaged in another preferred embodiment.

Of course, the above mentioned residues to be eventually tested are not limited but must be considered as preferential mutations. In another preferred embodiment, all the fourteen others ranked three residues among the twenty-two different amino acids could be reconsidered.

All the above mentioned mutations will be tested individually or according various combinations.

FIG. 19B represents the implemented IGKV4-1*01 based humanized 224G11 VL with above mentioned mutations clearly identified. The number under each proposed mutation corresponds to the rank at which said mutation will be done.

II—Humanization of the Heavy Chain Variable Domain

Comparison of the Nucleotidic Sequence of the 224G11 VH with Murine Germline Genes As a preliminary step, the nucleotidic sequence of the 224G11 VH was compared to the murine germline genes sequences part of the IMGT database (imgt.cines.fr).

Murine IGHV1-18*01, IGHD2-4*01 and IGHJ2*01 germline genes with a sequence identity of 92.70% for the V region, 75.00% for the D region and 89.36% for the J region, respectively, have been identified. Regarding the obtained identity, it has been decided to directly use the 224G11 VH sequences to look for human homologies.

These alignments are represented in FIGS. 20A for the V gene, 20B for the D gene and 20C for the J gene.

Comparison of the Nucleotidic Sequence of the 224G11 VH with Human Germline genes In order to identify the best human candidate for the CDR grafting, the human germline gene displaying the best identity with the 224G11 VH has been searched. To this end, the nucleotidic sequence of 224G11 VH has been aligned with the human germline genes sequences part of the IMGT database. For optimization of the selection, alignments between the proteic sequences were made to search for better homologies.

These two complementary methods led to the identification of the same receiving human IGHV1-2*02 V sequence for the murine 224G11 VH CDRs with a sequence identity of 75.00% at the nucleotidic level and 64.30% at the proteic level.

It is worthnoting that the D region strictly belongs to the CDR3 region in the VH domain. The humanization process is based on a <<CDR-grafting>> approach. Analysis of the closest human D-genes is not usefull in this strategy.

Looking for homologies for the J region led to the identification of the human IGHJ4*04 germline gene with a sequence identity of 78.72%.

Human IGHV1-2*02 V germline gene and human IGHJ4*01 J germline gene have thus been selected as receiving human sequences for the murine 224G11 VH CDRs.

Alignments are represented in FIG. 21A for the V region and 21B for the J region.

Humanized Version of 224G11 VH

The following steps in the humanization process consist in linking the selected germline genes sequences IGHV1-2*02 and IGHJ4*01 and also the CDRs of the murine 224G11 VH to the frameworks of these germline genes sequences.

As depicted in FIG. 22, the bolded residues in the 224G11 VH sequence correspond to the thirty amino acids that were found different between 224G11 VH domain and the selected human frameworks (Human FR, i.e. IGHV1-2*02 and IGHJ4*01).

Regarding to several criteriae such as their known participation in VH/VL interface, in antigen binding or in CDR structure, the amino acid class changes between murine and human residues, localization of the residue in the 3D structure of the variable domain, four out of the thirty different residues have been identified to be eventually mutated. These four most important defined residues and mutations into their human counterparts being murine D51 into human E, G55 into W, V80 into R and K82 into T. These ranked one residues are shown in FIG. 22 as bolded residues in the 224G11 HZVH sequence where they remained murine.

Of course, the above mentioned residues to be tested are not limited but must be considered as preferential mutations.

With the help of a molecular model, other mutations could be identified. Can be mentioned the following ranked two residues, i.e. residues 25 (T/A), 48 (E/Q), 49 (S/G), 53 (I/M), 76 (A/V), 78 (L/M) and 90 (D/E) on which mutations could also be envisaged in another preferred embodiment.

Of course, the above mentioned residues to be eventually tested are not limited but must be considered as preferential mutations. In another preferred embodiment, all the nineteen others ranked three residues among the thirty different amino acids could be reconsidered.

All the above mentioned mutations will be tested individually or according various combinations.

FIG. 22 represents the humanized 224G11 VH with above mentioned mutations clearly identified. The number under each proposed mutation corresponds to the rank at which said mutation will be done.

EXAMPLE 13

Humanization Process by CDR-Grafting of the Antibody 227H1

I—Humanization of the Light Chain Variable Domain

Comparison of the Nucleotidic Sequence of the 227H1 VL with Murine Germline Genes As a preliminary step, the nucleotidic sequence of the 224G11 VL was compared to the murine germline genes sequences part of the IMGT database (imqt.cines.fr).

Murine IGKV3-5*01 and IGKJ4*01 germline genes with a sequence identity of 96.90% for the V region and 97.29% for the J region, respectively, have been identified. Regarding the obtained identity, it has been decided to directly use the 227H1 VL sequences to look for human homologies.

These alignments are represented in FIGS. 23A for the V gene and 23B for the J gene.

Comparison of the Nucleotidic Sequence of the 227H1 VL with Human Germline Genes In order to identify the best human candidate for the CDR grafting, the human germline gene displaying the best identity with the 227H1 VL has been searched. To this end, the nucleotidic sequence of 227H1 VL has been aligned with the human germline genes sequences part of the IMGT database. For optimization of the selection, alignments between the proteic sequences were made to search for better homologies.

These two complementary methods led to the identification of two possible receiving human V sequences for the murine 227H1 VL CDRs. Nucleotidic alignment gives the human IGKV3-11*01 germline gene with a sequence identity of 7491% whereas proteic alignment gives the human IGKV4-1*01 germline gene with a sequence identity of 64.00%. It worthnoting that in both cases, the two closest germline genes and the analysed sequences show different CDR1 amino acid lengths (10 amino acids in 227H1 VL; 6 amino acids in IGKV3-11*01; 12 amino acids in IGKV4-1*01).

For the J region, the best homology score was first obtained with human the human IGKJ3*01 showing a sequence identity of 78.38%. But a higher number of consecutive identical nucleotides and a better amino acid fitting has been found in the alignment with human IGKJ4*02 germline gene (sequence identity of 75.68%). Thus the IGKJ4*02 germline gene was selected as receiving human J region for the murine 227H1 VL CDRs.

Alignments are represented in FIGS. 24A for the V region and 24B for the J region.

Humanized Version of 224G11 VL

Given the possibility of two receiving human V regions for the murine 227H1 VL CDRs, two humanized versions of the 227H1 VL domain will be described. The first corresponds to an initial trial for a human framework with a shorter CDR1 length (IGKV3-11*01), the second with a longer CDR1 length (IGKV4-1*01).

a) IGKV3-11*01 Based Humanized Version of 227H1 VL

The following steps in the humanization process consist in linking the selected germline genes sequences IGKV3-11*01 and IGKJ4*02 and also the CDRs of the murine 227H1 VL to the frameworks of these germline genes sequences.

As depicted in FIG. 25A, the bolded residues in the 227H1 VL sequence corresponds to the twenty-six amino acids that were found different between 227H1 VL domain and the selected human frameworks (Human FR, i.e. IGKV3-11*01 and IGKJ4*02).

Regarding to several criteriae such as their known participation in VH/VL interface, in antigen binding or in CDR structure, the amino acid class changes between murine and human residues, localization of the residue in the 3D structure of the variable domain, three out of the twenty-six different residues have been identified to be eventually mutated. These three most important defined residues and mutations into their human counterparts being murine 139 into human L, H40 into A and R84 into G. These ranked one residues are shown in FIG. 25A as bolded residues in the 227H1 HZ1VL sequence where they remained murine.

Of course, the above mentioned residues to be tested are not limited but must be considered as preferential mutations.

With the help of a molecular model, other mutations could be identified. Can be mentioned the following ranked two residues, i.e. residues 15 (L/P), 25 (V/A), 49 (P/A), 67 (L/R), 68 (E/A), 93 (P/S) and 99 (S/F) on which mutations could also be envisaged in another preferred embodiment.

Of course, the above mentioned residues to be eventually tested are not limited but must be considered as preferential mutations. In another preferred embodiment, all the sixteen others ranked three residues among the twenty-five different amino acids could be reconsidered.

All the above mentioned mutations will be tested individually or according various combinations.

FIG. 25A represents the implemented IGKV3-11*01 based humanized 227H1 VL with above mentioned mutations clearly identified. The number under each proposed mutation corresponds to the rank at which said mutation will be done.

b) IGKV4-1*01 Based Humanized Version of 227H1 VL

The following steps in the humanization process consist in linking the selected germline genes sequences IGKV4-1*01 and IGKJ4*02 and also the CDRs of the murine 227H1 VL to the frameworks of these germline genes sequences.

As depicted in FIG. 25B, the bolded residues in the 227H1 VL sequence corresponds to the twenty-four amino acids that were found different between 227H1 VL domain and the selected human frameworks (Human FR, i.e. IGKV4-1*01 and IGKJ4*02).

Regarding to several criteriae such as their known participation in VH/VL interface, in antigen binding or in CDR structure, the amino acid class changes between murine and human residues, localization of the residue in the 3D structure of the variable domain, four out of the twenty-four different residues have been identified to be eventually mutated. These four most important defined residues and mutations into their human counterparts being murine L4 into human M, 139 into L, H40 into A and R84 into G. These ranked one residues are shown in FIG. 25B as bolded residues in the 227H1 HZ2VL sequence where they remained murine.

Of course, the above mentioned residues to be tested are not limited but must be considered as preferential mutations.

With the help of a molecular model, other mutations could be identified. Can be mentioned the following ranked two residues, i.e. residues 25 (V/S), 66 (N/T), 67 (L/R), and 93 (P/S) on which mutations could also be envisaged in another preferred embodiment.

Of course, the above mentioned residues to be eventually tested are not limited but must be considered as preferential mutations. In another preferred embodiment, all the sixteen others ranked three residues among the twenty-two different amino acids could be reconsidered.

All the above mentioned mutations will be tested individually or according various combinations.

FIG. 25B represents the implemented IGKV4-1*01 based humanized 227H1 VL with above mentioned mutations clearly identified. The number under each proposed mutation corresponds to the rank at which said mutation will be done.

II—Humanization of the Heavy Chain Variable Domain

Comparison of the Nucleotidic Sequence of the 227H1 VH with Murine Germline genes As a preliminary step, the nucleotidic sequence of the 224G11 VH was compared to the murine germline genes sequences part of the IMGT database (imqt.cines.fr).

Murine IGHV1-18*01, IGHD1-1*02 and IGHJ2*01 germline genes with a sequence identity of 92.70% for the V region, 63.63% for the D region and 91.48% for the J region, respectively, have been identified. Regarding the obtained identity, it has been decided to directly use the 227H1 VH sequences to look for human homologies.

These alignments are represented in FIGS. 26A for the V gene, 26B for the D gene and 26C for the J gene.

Comparison of the Nucleotidic Sequence of the 227H1 VH with Human Germline Genes In order to identify the best human candidate for the CDR grafting, the human germline gene displaying the best identity with the 224G11 VH has been searched. To this end, the nucleotidic sequence of 227H1 VH has been aligned with the human germline genes sequences part of the IMGT database. The receiving human IGHV1-2*02 V sequence for the murine 224G11 VH CDRs with a sequence identity of 72.92% was thus identified.

It is worthnoting that the D region strictly belongs to the CDR3 region in the VH domain. The humanization process is based on a <<CDR-grafting>> approach. Analysis of the closest human D-genes is not usefull in this strategy.

Looking for homologies for the J region led to the identification of the human IGHJ4*01 germline gene with a sequence identity of 78.72%.

Human IGHV1-2*02 V germline gene and human IGHJ4*01 J germline gene have thus been selected as receiving human sequences for the murine 227H1 VH CDRs.

Alignments are represented in FIGS. 27A for the V region and 27B for the J region.

For optimisation of the selection, the man skilled in the art could also make alignments between the proteic sequences in order to help him in the choice.

Humanized Version of 227H1 VH

The following steps in the humanization process consist in linking the selected germline genes sequences IGHV1-2*02 and IGHJ4*01 and also the CDRs of the murine 227H1 VH to the frameworks of these germline genes sequences.

As depicted in FIG. 28, the bolded residues in the 227H1 VH sequence correspond to the thirty-two amino acids that were found different between 227H1 VH domain and the selected human frameworks (Human FR, i.e. IGHV1-2*02 and IGHJ4*01).

Regarding to several criteriae such as their known participation in VH/VL interface, in antigen binding or in CDR structure, the amino acid class changes between murine and human residues, localization of the residue in the 3D structure of the variable domain, six out of the thirty-two different residues have been identified to be eventually mutated. These six most important defined residues and mutations into their human counterparts being murine L39 into human M, N40 into H, L55 into W, T66 into N, V80 into R and K82 into T. These ranked one residues are shown in FIG. 28 as bolded residues in the 227H1 HZVH sequence where they remained murine.

Of course, the above mentioned residues to be tested are not limited but must be considered as preferential mutations.

With the help of a molecular model, other mutations could be identified. Can be mentioned the following ranked two residues, i.e. residues 48 (K/Q), 49 (T/G), 53 (I/M), 76 (A/V) and 78 (L/M) on which mutations could also be envisaged in another preferred embodiment.

Of course, the above mentioned residues to be eventually tested are not limited but must be considered as preferential mutations. In another preferred embodiment, all the twenty-one others ranked three residues among the thirty different amino acids could be reconsidered.

All the above mentioned mutations will be tested individually or according various combinations.

FIG. 28 represents the humanized 227H1 VH with above mentioned mutations clearly identified. The number under each proposed mutation corresponds to the rank at which said mutation will be done.

EXAMPLE 14

Humanization Process by CDR-Grafting of the Antibody 223C4

I—Humanization of the Light Chain Variable Domain

Comparison of the Nucleotidic Sequence of the 223C4 VL with Murine Germline Genes As a preliminary step, the nucleotidic sequence of the 224G11 VL was compared to the murine germline genes sequences part of the IMGT database (imqt.cines.fr).

Murine IGKV12-46*01 and IGKJ2*01germline genes with a sequence identity of 99.64% for the V region and 94.59% for the J region, respectively, have been identified.

Regarding the obtained identity, it has been decided to directly use the 223C4 VL sequences to look for human homologies.

These alignments are represented in FIGS. 29A for the V gene and 29B for the J gene.

Comparison of the Nucleotidic Sequence of the 223C4 VL with Human Germline Genes In order to identify the best human candidate for the CDR grafting, the human germline gene displaying the best identity with the 223C4 VL has been searched. To this end, the nucleotidic sequence of 223C4 VL has been aligned with the human germline genes sequences part of the IMGT database.

Human IGKV1-NL1*01 and IGKJ2*01 germline genes with a sequence identity of 78.49% for the V region and 81.08% for the J region, respectively, have been identified. The germline genes IGKV1-NL1*01 for the V region and IGKJ2*01 for the J region have thus been selected as receiving human sequences for the murine 223C4 VL CDRs.

Alignments are represented in FIGS. 30A for the V region and 30B for the J region.

For optimisation of the selection, the man skilled in the art could also make alignments between the proteic sequences in order to help him in the choice.

Humanized Version of 223C4 VL

The following steps in the humanization process consist in linking the selected germline genes sequences IGKV1-NL1*01 and IGKJ2*01 and also the CDRs of the murine 223C4 VL to the frameworks of these germline genes sequences.

At this stage of the process, a molecular model of the 223C4 murine Fv domains could be developed and useful in the choice of the murine residues to be conserved due to their roles in the maintenance of the three-dimensional structure of the molecule or in the antigen binding site and function. More particularly, 9 residues to be eventually mutated have been identified.

In a first step, residues involved in the CDR anchors or structure will be tested. Such residus are residu 66 (R/N) and residu 68 (EN).

In a second step, residus exposed to solvant, and as such that may involve immunogenicity, will also be tested. These are residues 49 (A/S), 51 (K/Q), 69 (S/D), 86 (D/Q) and 92 (S/N).

Then, in a third step, residus involved in structure/folding of variable domain could also be mutated. These residues are residu 46 (P/Q) and residu 96 (P/S).

Of course, the above mentioned residus to be tested are not limitated but must be considered as preferential mutations.

With the help of a molecular model, other mutations could be identified. Can be mentionned the following residues, i.e. residues 9 (S/A), 13 (A/V), 17 (D/E), 18 (R/T), 54 (LN), 88 (T/S), 90 (T/K), 100 (A/G) and 101 (T/S), on which mutations could also be envisaged in another preferred embodiment.

All the above mentioned mutations will be tested individually or according various combinations.

FIG. 31 represents the humanized 223C4 VL with above mentioned mutations clearly identified. The number under each proposed mutation corresponds to the rank at which said mutation will be done.

II—Humanization of the Heavy Chain Variable Domain

Comparison of the Nucleotidic Sequence of the 223C4 VH with Murine Germline Genes As a preliminary step, the nucleotidic sequence of the 224G11 VH was compared to the murine germline genes sequences part of the IMGT database (imqt.cines.fr).

Murine IGHV1-18*01, IGHD6-3*01 and IGHJ4*01 germline genes with a sequence identity of 98.95% for the V region, 72.72% for the D region and 98.11% for the J region, respectively, have been identified. Regarding the obtained identity, it has been decided to directly use the 223C4 VH sequences to look for human homologies.

These alignments are represented in FIGS. 32A for the V gene, 32B for the D gene and 32C for the J gene.

Comparison of the Nucleotidic Sequence of the 223C4 VH with Human Germline Genes In order to identify the best human candidate for the CDR grafting, the human germline gene displaying the best identity with the 223C4 VH has been searched. To this end, the nucleotidic sequence of 223C4 VH has been aligned with the human germline genes sequences part of the IMGT database.

Human IGHV1-2*02, IGHD1-26*01 and IGHJ6*01 germline genes with a sequence identity of 76.38% for the V region, 75.00% for the D region and 77.41% for the J region, respectively, have been identified. The germline genes IGHV1-2*02 for the V region and IGHJ6*01 for the J region have thus been selected as receiving human sequences for the murine 223C4 VH CDRs.

Alignments are represented in FIGS. 33A for the V region, 33B for the D region and 33C for the J region.

For optimisation of the selection, the man skilled in the art could also make alignments between the proteic sequences in order to help him in the choice.

Humanized Version of 223C4 VH

The following steps in the humanization process consist in linking the selected germline genes sequences IGHV1-2*02 and IGHJ6*01 and also the CDRs of the murine 223C4 VH to the frameworks of these germline genes sequences.

At this stage of the process, a molecular model of the 223C4 murine Fv domains could be developed and useful in the choice of the murine residues to be conserved due to their roles in the maintenance of the three-dimensional structure of the molecule or in the antigen binding site and function. More particularly, 14 residues to be eventually mutated have been identified.

In a first step, residues involved in the CDR anchors or structure will be tested. Such residues are residues 40 (H/D), 45 (A/S), 55 (W/D), 66 (N/I) and 67 (Y/F).

In a second step, residues exposed to solvant, and as such that may involve immunogenicity, will also be tested. These are residues 1 (Q/E), 3 (Q/L), 5 (V/Q), 48 (Q/M) and 80 (R/V).

Then, in a third step, residues involved in structure/folding of variable domain could also be mutated. These are residues 9 (A/P), 13 (K/V), 22 (S/P) and 46 (P/H).

Of course, the above mentioned residus to be tested are not limited but must be considered as preferential mutations.

With the help of a molecular model, other mutations could be identified. Can be mentionned the following residues, i.e. residues 12 (V/L), 21 (V/I), 43 (R/K), 49 (G/S), 53 (M/I), 68 (A/N), 72 (Q/K), 75 (R/K), 76 (V/A), 78 (M/L), 82 (T/K), 84 (I/S), 92 (S/R), 93 (R/S), 95 (R/T) and 97 (D/E), on which mutations could also be envisaged in another preferred embodiment.

All the above mentioned mutations will be tested individually or according various combinations.

FIG. 34 represents the humanized 223C4 VH with above mentioned mutations clearly identified. The number under each proposed mutation corresponds to the rank at which said mutation will be done.

EXAMPLE 15

Anti-Tumor Activity of the Murine 224G11 MAb Alone or Combined with the Chemotherapeutic Agent Navelbine® on the Established Xenograft NCI-H441 Tumor Model Successful chemotherapeutic approaches depend in part on the cellular response to apoptotic inducers and the balance between pro- and anti-apoptotic pathways within the cell. The protective effect of the activated c-Met on cell survival has been documented. It mainly results from an increase expression of the anti-apoptotic Bcl-xl and Bcl-2 protein as a consequence of PI3-K-mediated signaling which in turn inhibit mitochondrial-dependent apoptosis (caspase 9). Indeed, it is conceivable that the HGF/c-Met system with its marked regulatory effect on apoptotic process can also influence the chemosensitivity of cancer cells. This hypothesis as been tested with Navelbine®, a marketed chemotherapeutic agent used for lung cancer treatment (Aapro et al., Crit. Rev. Oncol. Hematol. 2001, 40:251-263; Curran et al., Drugs Aging. 2002, 19:695-697). The xenograft NCI-H441 NSCLC model was used as it has been previously described that this cell line is sensitive to both Navelbine (Kraus-Berthier et al., Clin. Cancer Res., 2000; 6:297-304) and therapy targeting c-Met (Zou H. T. et al., Cancer Res. 2007, 67: 4408-4417).

Briefly, NCI-H441 cells from ATCC were routinely cultured in RPMI 1640 medium, 10% FCS and 1% L-Glutamine. Cells were split two days before engraftment so that they were in exponential phase of growth. Ten million NCI-H441 cells were engrafted in PBS to 7 weeks old Swiss nude mice. Three days after implantation, tumors were measured and animals were divided into 4 groups of 6 mice with comparable tumor size. Mice were treated i.p. with a loading dose of 2 mg of 224G11/mouse and then twice a week, for 43 days, with 1 mg of antibody/mouse. The 9G4 MAb was used as an isotype control.

Navelbine® was given by i.p. injections at a dose of 8 mg/kg on days 5, 12, 19 post-cell injection. For combined therapy with both 224G11 and Navelbine®, the two compounds were administered separately. In this experience the 2 compounds were used at their optimal dosage. Tumor volume was measured twice a week and calculated by the formula: p/6×length×width×height.

FIG. 35 demonstrates that 224G11 is as efficient as Navelbine® when used alone as a single agent therapy. A significant benefit of combining both therapy was observed with complete tumor regressions observed for 3 out of 6 mice at day 63.

EXAMPLE 16

C-Met Inhibitors and Angiogenesis

In addition to its direct role in the regulation of a variety of tumor cell functions, activation of c-met has also been implicated in tumor angiogenesis. Endothelial cells expresse c-Met and HGF stimulates endothelial cell growth, invasion and motility (Nakamura Y. et al., Biochem. Biophys. Res., Commun 1995, 215:483-488; Bussolino F. et al., J. Cell Biol. 1992, 119:629-641). The coordinate regulation of growth, invasion and motility in vascular endothelial cells by HGF/c-Met has been demonstrated to results in the formation of 3D capillary endothelial tubes in vitro (Rosen E. M. et al., Supplementum to Experientia 1991, 59:76-88).

To determine a potential interference of anti-c-Met MAbs with HGF-induced angiogenesis, two sets of experiments were performed including i) the evaluation of MAbs on HUVEC proliferation and ii) the test of MAbs of HUVEC tube formation.

For proliferation experiments, 7500 HUVEC were plated in each well of a 96 well plate previously coated with laminin. Cells were grown 24 hours of EMB-2 assay medium supplemented with 0.5% FBS and heparin. Then, MAbs to be tested (0.15 to 40 µg/ml) were added for 1 h before addition of 20 ng/ml of HGF. After 24 additional hours, cells were pulsed with 0.5 µCi of [$^3$H] Thymidine. The magnitude of [$^3$H] Thymidine incorporated was quantified by liquid scintillation counting. In This experiment the 9G4 MAb is an irrelevant antibody used as an IgG1 isotype control.

Results expressed as raw data in FIG. 36 demonstrate that, as expected HGF is a potent inducer of HUVEC cell growth. Antibodies evaluated in absence of HGF did not display any agonist proliferative activity on HUVEC whatever the tested dose. In presence of HGF, a dramatic dose dependent inhibition was observed for both 11E1 and 224G11 MAbs.

For evaluation of HUVEC tube formation, 25000 cells incubated 30 min with antibodies to be tested were plated in 48-well plates coated with matrigel. Then HGF 50 ng/ml was added and plates were incubated at 37° C. Medium was then harvested and 5 µM CMFDA was added for 15 min before microscopic observation.

Results shown in FIG. 37 demonstrate that, as expected HGF induces a significant tube formation. The 9G4 antibody introduced as an IgG1 isotype control was without any effect on HGF-induced tube formation whereas both 11E1 and 224G11 inhibit dramatically tube formation.

EXAMPLE 17

Humanization Process by CDR-Grafting of the Antibody 11E1

I—Humanization of the Light Chain Variable Domain

Comparison of the Nucleotidic Sequence of the 11E1 VL with Murine Germline Genes As a preliminary step, the nucleotidic sequence of the 11 E1 VL was compared to the murine germline genes sequences part of the IMGT database (imqt.cines.fr).

Murine IGKV4-79*01 and IGKJ4*01 germline genes with a sequence identity of 98.58% for the V region and 97.22% for the J region, respectively, have been identified. Regarding the obtained identity, it has been decided to directly use the 11E1 VL sequences to look for human homologies.

These alignments are represented in FIGS. 38A for the V gene and 38B for the J gene.

Comparison of the Nucleotidic Sequence of the 11E1 VL with Human Germline Genes

In order to identify the best human candidate for the CDR grafting, the human germline gene displaying the best identity with the 11E1 VL has been searched. To this end, the nucleotidic sequence of 11E1 VL has been aligned with the human germline genes sequences part of the IMGT database.

Human IGKV3-7*02 and IGKV3D-7*01 with a sequence identity for both germline genes of 69.86% for the V region have been identified. IGKV3-7*02 human germline gene is known in the IMGT database as an "ORF" which mean that this sequence has been found in the human genome but may present some recombination problems leading to non functional IGKV3-7*02 derived natural antibodies. Thus the IGKV3D-7*01 germline gene was selected as receiving human V region for the murine 11E1 VL CDRs.

For the J region, the best homology score was first obtained with human, the human IGKJ3*01 showing a sequence identity of 78.38%. But a higher number of consecutive identical nucleotides and a better amino acid fitting has been found in the alignment with human IGKJ4*02 germline gene (sequence identity of 75.68%). Thus the IGKJ4*02 germline gene was selected as receiving human J region for the murine 11E1 VL CDRs.

Alignments are represented in FIGS. 39A for the V region and 39B for the J region.

For optimisation of the selection, the man skilled in the art could also make alignments between the proteic sequences in order to help him in the choice.

Humanized Version of 11E1 VL

The following steps in the humanization process consist in linking the selected germline genes sequences IGKV3D-7*01 and IGKJ4*02 and also the CDRs of the murine 11E1 VL to the frameworks of these germline genes sequences.

As depicted in FIG. 40, the bolded residues in the 11E1 VL sequence corresponds to the thirty amino acids that were found different between 11E1 VL domain and the selected human frameworks (Human FR, i.e. IGKV3D-7*01 and IGKJ4*02).

Regarding to several criteriae such as their known participation in VH/VL interface, in antigen binding or in CDR structure, the amino acid class changes between murine and human residues, localization of the residue in the 3D structure of the variable domain, four out of the thirty differents residues have been identified to be eventually mutated. These four most important defined residues and mutations into their human counterparts being murine L4 into human M, Y40 into S, Y87 into F and T96 into P. These ranked one residues are shown in FIG. 40 as bolded residues in the 11E1 HZVL sequence where they remained murine.

Of course, the above mentioned residues to be tested are not limited but must be considered as preferential mutations.

With the help of a molecular model, other mutations could be identified. Can be mentioned the following ranked two residues, i.e. residues 24 (S/R), 53 (W/L), 66 (I/T), 67 (L/R), 86 (S/D), 95 (Q/E), 99 (A/F) or 121 (E/D) on which mutations could also be envisaged in another preferred embodiment.

Of course, the above mentioned residues to be eventually tested are not limited but must be considered as preferential mutations. In another preferred embodiment, all the eighteen others ranked three residues among the thirty different amino acids could be reconsidered.

All the above mentioned mutations will be tested individually or according various combinations.

FIG. 40 represents the implemented humanized 11E1 VL with above mentioned mutations clearly identified. The number under each proposed mutation corresponds to the rank at which said mutation will be done.

II—Humanization of the Heavy Chain Variable Domain

Comparison of the Nucleotidic Sequence of the 11E1 VH with Murine Germline Genes As a preliminary step, the nucleotidic sequence of the 11E1 VH was compared to the murine germline genes sequences part of the IMGT database (imqt.cines.fr).

Murine IGHV1-7*01, IGHD4-1*01 and IGHJ3*01 germline genes with a sequence identity of 94.10% for the V region, 66.67% for the D region and 100% for the J region, respectively, have been identified. Regarding the obtained identity, it has been decided to directly use the 11E1 VH sequences to look for human homologies.

These alignments are represented in FIGS. 41A for the V gene, 41B for the D gene and 41C for the J gene.

Comparison of the Nucleotidic Sequence of the 11E1 VH with Human Germline Genes

In order to identify the best human candidate for the CDR grafting, the human germline gene displaying the best identity with the 11E1 VH has been searched. To this end, the nucleotidic sequence of 11E1 VH has been aligned with the human germline genes sequences part of the IMGT database. For optimization of the selection, alignments between the proteic sequences were made to search for better homologies.

These two complementary methods led to the identification of two possible receiving human V sequences for the murine 11E1 VH CDRs. Nucleotidic alignment gives the human IGHV1-2*02 germline gene with a sequence identity of 75.69% whereas proteic alignment gives the human IGHV1-46*01 germline gene with a sequence identity of 71.10%.

It is worthnoting that the D region strictly belongs to the CDR3 region in the VH domain. The humanization process is based on a <<CDR-grafting>> approach. Analysis of the closest human D-genes is not usefull in this strategy.

Looking for homologies for the J region led to the identification of the human IGHJ4*03 germline gene with a sequence identity of 80.85%.

Looking to the overall similarities and sequences alignments, human IGHV1-46*01 V germline gene and human IGHJ4*03 J germline gene have thus been selected as receiving human sequences for the murine 11E1 VH CDRs.

Alignments are represented in FIGS. 42A for the V region and 42B for the J region.

Humanized Version of 11E1 VH

The following steps in the humanization process consist in linking the selected germline genes sequences IGHV1-46*01 and IGHJ4*03 and also the CDRs of the murine 11E1 VH to the frameworks of these germline genes sequences.

As depicted in FIG. 43, the bolded residues in the 11E1 VH sequence corresponds to the twenty-six amino acids that were found different between 11E1 VH domain and the selected human frameworks (Human FR, i.e. IGHV1-46*01 and IGHJ4*03).

Regarding to several criteriae such as their known participation in VH/VL interface, in antigen binding or in CDR structure, the amino acid class changes between murine and human residues, localization of the residue in the 3D structure of the variable domain, five out of the twenty-six differents residues have been identified to be eventually mutated. These five most important defined residues and mutations into their human counterparts being murine N40 into human H, Y55 into I, D66 into S, A80 into R and K82 into T. These ranked one residues are shown in FIG. 43 as bolded residues in the 11E1 HZVH sequence where they remained murine.

Of course, the above mentioned residues to be tested are not limited but must be considered as preferential mutations.

With the help of a molecular model, other mutations could be identified. Can be mentioned the following ranked two residues, i.e. residues 53 (I/M), 71 (L/F), 76 (A/V), 78 (L/M) and 87 (A/V) on which mutations could also be envisaged in another preferred embodiment.

Of course, the above mentioned residues to be eventually tested are not limited but must be considered as preferential mutations. In another preferred embodiment, all the sixteen others ranked three residues among the twenty-six different amino acids could be reconsidered.

All the above mentioned mutations will be tested individually or according various combinations.

FIG. 43 represents the implemented humanized 11E1 VH with above mentioned mutations clearly identified. The number under each proposed mutation corresponds to the rank at which said mutation will be done.

EXAMPLE 18

Effect of Purified Mabs on c-Met Phosphorylation

In example 3, the effect of anti-c-Met Mabs on phosphorylation was assessed with dosed supernatants from each hybridoma to be evaluated. The test has been performed again with purified 11E1 and 224G11 Mabs that have been evaluated either at a final concentration of 30 μg/ml (200 nM) or at a dose range from 0.0015 to 30 μg/ml (0.01-200 nM) in order to determine the $IC_{50}$ of each antibody. The protocol used is the same as the one described in example 3.

Results of 3 independent experiments are presented in FIG. 44 and demonstrate that once purified 11E1 and 224G11 displayed no agonist effect when added alone to A549 cells and respectively 87 and 75% antagonist effect in presence of HGF. As expected 5D5 Mab introduced as an agonist positive control showed a significant (58%) agonist effect when added alone and only a moderate antagonist effect (39%) in presence of HGF. Regarding to $EC_{50}$ calculations, both 11E1 and 224G11 had nanomolar $IC_{50}$s.

EXAMPLE 19

In Vivo Combination of 224G11 and Navelbine® on NCI-H441 Xenograft Model

NCI-H441 cells from ATCC were routinely cultured in RPMI 1640 medium, 10% FCS, 1% L-Glutamine. Cells were split two days before engraftment being in exponential phase of growth. Ten million NCI-H441 cells were engrafted to Athymic nude mice. Five days after implantation, tumors were measurable and animals were divided into groups of 6 mice with comparable tumor size. Mice were treated i.p. either with a loading dose of 2 mg of 224G11 Mab/mouse and then twice a week with 1 mg of antibody/mouse until Day 38 or with 3 injections of Navelbine® (D5, D12, D19) at 8 mg/kg. A third group administered with the combine treatment was also included. Navelbine® was given by i.p. injections. Tumor volume was measured twice a week and calculated by the formula: π/6×length×width×height and animal weights were monitored every day over the period of Navelbine® treatment. Statistical analysis was performed at each measured time using either a t-test or a Mann-Whitney test. In this experiment, the average tumor volume of single modality treated groups is reduced by 72%, 76% and 99.8% for 224G11, Navelbine® and Navelbine®+224G11 respectively at day 41 post first injection. At day 41, the combined therapy improved significantly tumor growth compared to single therapy treatments (p≤0.041 compared to Navelbine® alone and p≤0.002 compared to 224G11 alone on day 41), 4 out of 6 mice being without tumors in the combined therapy group. Results are represented in FIG. 45.

These results were confirmed 50 days after the end of treatments (D88) where 66% of mice receiving the combined treatment remained free of tumors.

EXAMPLE 20

In Vivo Combination of 224G11 and Doxorubicine on NCI-H441 Xenograft Model

NCI-H441 cells from ATCC were routinely cultured in RPMI 1640 medium, 10% FCS, 1% L-Glutamine. Cells were split two days before engraftment being in exponential phase of growth. Ten million NCI-H441 cells were engrafted to Athymic nude mice. Five days after implantation, tumors were measurable and animals were divided into groups of 6 mice with comparable tumor size. Mice were treated i.p. either with a loading dose of 2 mg of 224G11 Mab/mouse and then twice a week with 1 mg of antibody/mouse or with 4 injections of Doxorubicin (D5, D12, D19, D26) at 5 mg/kg. A third group administered with the combine treatment was also included. Doxorubicin was given by i.v. injections. Tumor volume was measured twice a week and calculated by the formula: $\pi/6 \times length \times width \times height$ and animal weights were monitored every day over the period of Doxorubicin treatment. Statistical analysis was performed at each measured time using either a t-test or a Mann-Whitney test. Both single therapies and combined treatment displayed significant anti-tumor activity compared to the control group ($p \leq 0.002$ from D11 to D39). Results are represented in FIG. 46.

Combined treatment also demonstrates a significant anti-tumour growth activity compared to single modality treatment between D11 and D39 indicating that there is a benefit to combine Doxorubicin to an anti-c-Met treatment.

EXAMPLE 21

In Vivo Combination of 224G11 and Docetaxel on NCI-H441 Xenograft Model

NCI-H441 cells from ATCC were routinely cultured in RPMI 1640 medium, 10% FCS, 1% L-Glutamine. Cells were split two days before engraftment being in exponential phase of growth. Nine million NCI-H441 cells were engrafted to Athymic nude mice. Five days after implantation, tumors were measurable and animals were divided into groups of 6 mice with comparable tumor size. Mice were treated i.p. either with a loading dose of 2 mg of 224G11 Mab/mouse and then twice a week with 1 mg of antibody/mouse or with 4 injections of Docetaxel (D5, D12, D19, D26) at 7.5 mg/kg. A third group administered with the combine treatment was also included. Docetaxel was given by i.p. injections. Tumor volume was measured twice a week and calculated by the formula: $\pi/6 \times length \times width \times height$ and animal weights were monitored every day over the period of Docetaxel treatment. Statistical analysis was performed at each measured time using either a t-test or a Mann-Whitney test. Both single therapies and combined treatment displayed significant anti-tumor activity compared to the control group ($p \leq 0.002$ from D11 to D35). Results are represented in FIG. 47.

Combined treatment also demonstrated a significant anti-tumour growth activity compared to single modality treatment between D18 and D35 indicating that there is a benefit to combine Docetaxel to an anti-c-Met treatment.

EXAMPLE 22

In Vivo Combination of 224G11 and Temozolomide on U87MG Xenograft Model

U87-MG cells from ATCC were routinely cultured in DMEM medium, 10% FCS, 1% L-Glutamine. Cells were split two days before engraftment being in exponential phase of growth. Five million U87-MG cells were engrafted to Athymic nude mice. Nineteen days after implantation, tumors were measurable and animals were divided into groups of 6 mice with comparable tumor size. Mice were treated i.p. either with a loading dose of 2 mg of 224G11 Mab/mouse and then twice a week with 1 mg of antibody/ mouse or with 3 injections of Temozolomide (D19, D26, D33) at 5 mg/kg. A third group administered with the combine treatment was also included. Temozolomide was given by i.p. injections. Tumor volume was measured twice a week and calculated by the formula: $\pi/6 \times length \times width \times height$ and animal weights were monitored every day over the period of Temozolomide treatment. Statistical analysis was performed at each measured time using either a t-test or a Mann-Whitney test. Both single therapies and combined treatment displayed significant anti-tumor activity compared to the control group ($p \leq 0.002$ from D22 to D32 (where control mice were euthanized for ethical reasons)). Results are represented in FIG. 48.

Combined treatment also demonstrate a significant anti-tumour growth activity compared to single modality treatments ($P \leq 0.002$ from day 22 to day 43 (where control mice were euthanized for ethical reasons) for Temozolomide and from day 29 to day 53 (last day of treatment) for 224G11. Taken together, these data indicate that there is a benefit to combine Temozolomide to an anti-c-Met treatment.

EXAMPLE 23

Spheroid Formation

As already described in Example 9 for other Mabs, we evaluate the ability of 224G11 Mab to inhibit in vitro tumor growth in the U87-MG spheroid model. For that purpose, U87-MG cells grown as a monolayer were detached with trypsine-EDTA and resuspended into complete cell culture media. Spheroids were initiated by inoculating 625 cells into single wells of round bottom, 96 plates in DMEM-2.5% FCS. To prohibit cell adhesion to a substratum, the plates were pre-coated with polyHEMA in 95% ethanol and air dried at room temperature. The plates were incubated under standard cell culture conditions at 37° C., 5% $CO_2$ in humidified incubators. Purified monoclonal antibodies (10 µg/ml) were added after 4 and 10 days of spheroid culture. Spheroids were kept in culture for 17 days. Then, spheroid growth was monitored by measuring the area of spheroids using automeasure module of axiovision software. Area was expressed in $\mu m^2$. 8-16 spheroids were evaluated for each condition. Spheroid size was measured before addition of antibodies, after 10 days of culture and after 17 days of culture.

Figures 49A, 49B, 49C, 49D:
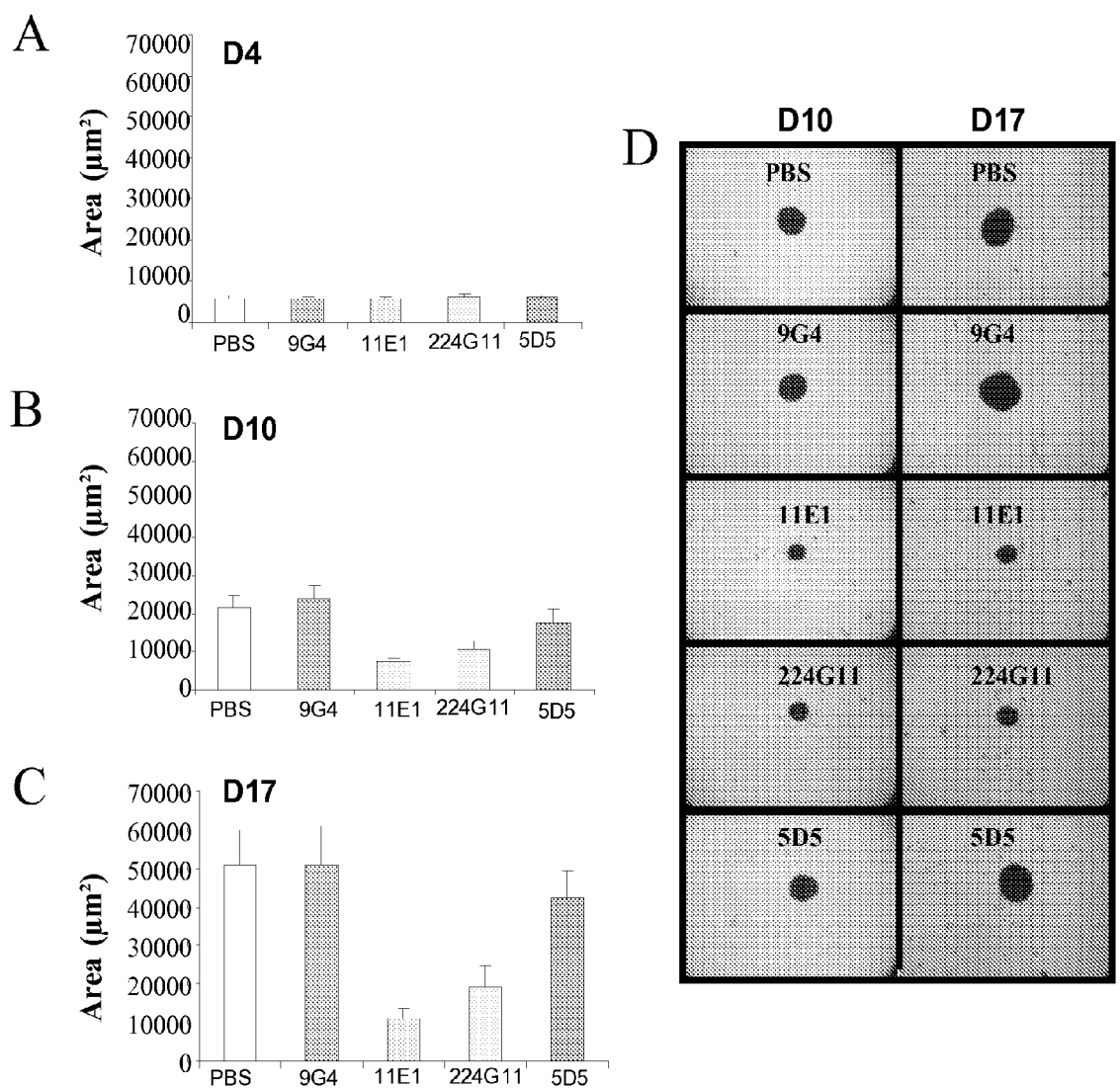

In those conditions, homogeneous spheroids were obtained and no statistical difference was observed before addition of antibodies (FIG. 49A).

As illustrated in FIGS. 49B-49D, isotype control, 9G4 did not affected growth of spheroids after 10 or 17 days of culture. While addition of 5D5 had no major effect on spheroid size, addition of either 224G11 and 11E1 markedly inhibited tumor growth.

EXAMPLE 24

In Vitro Activity of Chimeric and Humanized Forms of 224G11 in the Phospho-c-Met Assay In order to compare the in vitro efficacy of murine, chimeric and humanized forms in a functional assay, culture supernatants resulting from 224G11 hybridoma, and HEK293 transfected cells were dosed and tested as described in Example 3. Data summarized in FIG. 50 showed the expected results for the unpurified morin antibody as already described in FIG. 6B. Both chimeric and humanized unpurified antibodies displayed a comparable activity either when added alone (FIG. 50A) or when incubated in presence of HGF (FIG. 50B).

EXAMPLE 25

Determination of Affinity Constants (KD) of Anti-c-Met Antibodies by Biacore Analysis The binding affinity of purified 11E1 and 224G11 antibodies was investigated by BIAcore X using recombinant c-Met-Extra-Cellular Domain (ECD) fused to an human IgG1 Fc domain (R&D Systems) as antigen (MW=129 kDa). As both c-Met-Fc fusion proteins and antibodies are bivalent compounds, Fab fragments of mAbs 11E1 and 224G11 (MW=50 kDa) were generated by papain cleavage, purified and used in this assay to avoid interference with avidity parameter. For the assay, an anti-Tag histidine capture antibody was coated on CM5 sensorchips. The running buffer was HBS-EP, the flow rate was 30 µl/min and the test was performed at 25° C. Soluble c-Met (ECD_M1)2-Fc-(HHHHHH)$_2$ antigen was captured on the sensorchip (around 270 RU), and the antibodies to be tested were used in solution as analytes. The sensorship was regenerated using Glycine, HCl pH 1.5 buffer on both flowcells for half a minute.

FIG. 51 illustrates the principle of this analysis. The resulting kinetic parameters are summarized in the following table 4. They indicate that both 11E1 and 224G11 anti-c-Met antibodies bind the recombinant c-Met-Fc fusion protein with comparable affinities ranging about 40 pM.

TABLE 4

| | $K_{on1} \times 10^{-6}$ [1/M·s] | $K_{on1} \times 10^{-6}$ [1/M·s] | Half-Life [h] | K [pM] |
|---|---|---|---|---|
| 11E1 Fab | 1.13 ± 0.01 | 4.68 ± 0.001 | 4.1 | 41.4 ± 0.5 |
| 224G11 Fab | 2.04 ± 0.01 | 7.79 ± 0.40 | 2.5 | 34.8 ± 1.9 |

EXAMPLE 26

In Vivo Activity of 224G11 on MDA-MB-231 Cells Co-Implanted With MRC5 Cells as Human HGF Source on Athymic Nude Mice MDA-MB-213 and MRC5 cells from ATCC were both cultured in DMEM medium, 10% FCS, 1% L-Glutamine. Cells were split two days before engraftment being in exponential phase of growth. Five million MDA-MB-231 cells and 500 000 MRC5 cells were co-injected s.c. to Athymic nude mice. Twelve days after implantation, tumors were measurable and animals were divided into groups of 6 mice with comparable tumor size. Mice were treated i.p. either with a loading dose of 2 mg of 224G11 Mab/mouse and then twice a week with 1 mg of antibody/mouse. Tumor volume was measured twice a week and calculated by the formula: π/6× length×width×height.

Results described in FIG. 52 showed a significant difference in median tumors growth of mice treated with 224G11 compared to the one of the control group.

EXAMPLE 27

Complementary Elements on Humanization of Antibodies 227H1, 11E1 and 224G11

General Procedure

Humanization of the anti-cMet antibodies were performed independently for each chain and sequentially, regarding to the analysed amino acids in each variable domain. The humanization process was evaluated in a first attempt in an ELISA-based binding assay to recombinant Fc-cMet; binding activities the humanized antibodies being compared to the recombinant chimeric antibody. In a second attempt, anti-cMet humanized antibodies were evaluated for their abilities to displace the Fc-cMet binding onto plastic-coated recombinant HGF; this competition assay allowing the direct comparison of murine, chimeric and humanized versions of the anti-cMet antibodies.

In FIGS. 53 and 54 are exemplified the typical anti-cMet binding activities of 227H1, 11E1 and 224G11 murine monoclonal antibodies.

FIG. 53 shows anti-cMet direct binding activities of detected purified murine antibodies. In this assay, murine monoclonal anti-cMet antibodies display different but still dose-dependent anti-cMet binding activities.

FIG. 54 shows the HGF-cMet binding competition activities of purified murine antibodies. The competition assay reveals reliable differences between these anti-cMet monoclonal antibodies with a moderate, not full but reliable competitive activity for 11E1 monoclonal antibody whereas murine 224G11 and 227H1 display similar pattern of competitive activities with a 100% of maximum of HGF binding displacement at high antibody concentration. The 224G11 monoclonal antibody showing the best IC$_{50}$ value.

It is worthnoting that the direct binding activities of the murine antibodies do not reflect their intrinsic HGF-binding competitive properties.

These two assays were used to characterize the recombinant chimeric and humanized versions of the murine anti-cMet antibodies. To this end, briefly, anti-cMet variable domains, either murine or humanized, were cloned into LONZA's pCONplus expression vectors series and recombinant IgG$_1$/κ-derived antibodies were expressed in CHO cells. Expression culture supernatants were concentrated and extensively dialysed against PBS and then dosed for expressed antibodies concentrations and directly used to assess corresponding anti-cMet binding activities. Both direct binding and HGF-competition assays were assessed to better characterize recombinant chimeric or humanized versions.

EXAMPLE 27-1

Humanization of 227H1 Heavy Chain Variable Domain

In order to identify the best human candidate for the CDR grafting, the human germline gene displaying the best identity with the 227H1 VH murine sequence has been searched. With the help of the IMGT database, human IGHV1-2*02 V germline gene and human IGHJ4*01 J germline gene have thus been selected as receiving human sequences for the murine 227H1 VH CDRs.

FIG. 55 represents an amino acid alignment of the murine 227H1 VH domain with the selected human framework. In the human FR lane, only the amino acid that was found different from the 227H1 murine VH domain is depicted. HZ3VH, HZ2VH and HZ1VH lanes correspond to implemented humanized versions of the 227H1 VH domain with above ("changed in" lane) mentioned mutations clearly identified. The number under each proposed mutation corresponds to the rank at which said mutation will be done.

In a first series of experiments, we constructed and analysed the anti-cMet binding activities of the three first humanized versions of the 227H1 murine VH domain when expressed in combination with the 227H1 chimeric light chain. Results obtained from the anti-cMet direct binding assay are shown in FIG. 56. In this experiment, no differences in the binding capabilities of the tested 227H1-derived chimeric or partially humanized recombinant antibodies were observed. At this point, 26 out of the 32 amino acids that were found different between the murine 227H1 VH domain and the selected human framework have been analysed and found not relevant for anti-cMet binding activity of the 227H1 humanized VH domain, when combined with the chimeric light chain.

In conjonction with a site-directed mutagenesis analysis of the last six murine residues in the HZ1VH humanized version of the 227H1 VH domain, we constructed an original HZ4VH <<full-IMGT humanized>> version and tested its anti-cMet binding properties. Results are given in FIG. 57 for the direct binding assay and in FIG. 58 for the HGF binding competition assay. It is worthnoting that both the recombinant chimeric and humanized 227H1 versions display a better competitive activity than the parental murine antibody.

Nevertheless, given the experimental data obtained regarding the anti-cMet binding properties of the "full-IMGT" humanized 227H1 VH domain, the resulting amino acid sequence depicted in FIG. 59 was selected and a bioinformatic analysis was then performed to evaluate the <<humaness>> level of the so-called 227H1-HZ VH humanized variable domain.

To this end a simple comparison of the frameworks sequences to human database was performed using the IMGT tools. Given the humanization level that we reached during this process, out of the 89 analysed amino acids corresponding to the framework residues, 89 were found reliable with a human origin. Only residues from the CDRs can be found different, but if so there are different from the corresponding human germline gene, and are obviously at hypervariable positions. Based on the IMGT numbering system and homology analysis tools, we first totally humanized an antibody variable domain of murine origin.

EXAMPLE 27-2

11E1 Monoclonal Antibody Humanization

I—Humanization of 11E1 Heavy Chain Variable Domain

In order to identify the best human candidate for the CDR grafting, the human germline gene displaying the best identity with the 11E1 VH murine sequence has been searched. With the help of the IMGT database, human IGHV1-46*01 V germline gene and human IGHJ4*03 J germline gene have thus been selected as receiving human sequences for the murine 11E1 VH CDRs.

FIG. 60 represents an amino acid alignment of the murine 11E1 VH domain with the selected human framework. In the human FR lane, only the amino acid that was found different from the 11E1 murine VH domain is depicted. HZ VH3, HZ VH2 and HZ VH1 lanes correspond to implemented humanized versions of the 11E1 VH domain with above ("changed in" lane) mentioned mutations clearly identified. The number under each proposed mutation corresponds to the rank at which said mutation will be done.

In a first serie of experiments, we constructed and analysed the anti-cMet binding activities of the three first humanized versions of the 11E1 murine VH domain when expressed in combination with the 11E1 chimeric light chain. Results obtained from the anti-cMet direct binding assay are shown in FIG. 61. In this experiment, a similar binding capability of the tested 11E1-derived chimeric or partially humanized recombinant antibodies was observed. At this point, 19 out of the 24 amino acids that were found different between the murine 11E1 VH domain and the selected human framework have been analysed and found not relevant for anti-cMet binding activity of the 11E1 humanized VH domain, when combined with the chimeric light chain.

II—Humanization of 11E1 Light Chain Variable Domain

In order to identify the best human candidate for the CDR grafting, the human germline gene displaying the best identity with the 11E1 VL murine sequence has been searched. With the help of the IMGT database, human IGKV3D-7*01 V germline gene and human IGKJ4*01 J germline gene have thus been selected as receiving human sequences for the murine 11E1 VL CDRs.

FIG. 62 represents an amino acid alignment of the murine 11E1 VL domain with the selected human framework. In the human FR lane, only the amino acid that was found different from the 11E1 murine VL domain is depicted. HZ VL3, HZ VL2 and HZ VL1 lanes correspond to implemented humanized versions of the 11E1 VL domain with above ("changed in" lane) mentioned mutations clearly identified. The number under each proposed mutation corresponds to the rank at which said mutation will be done.

In a first serie of experiments, was constructed and the analysed the anti-cMet binding activities of the three first humanized versions of the 11E1 murine VL domain when expressed in combination with the 11E1 chimeric heavy chain. Results obtained from the anti-cMet direct binding assay are shown in FIG. 63. In this experiment, we observed similar binding capabilities of the tested 11E1-derived chimeric or partially humanized recombinant antibodies. At this point, 26 out of the 30 amino acids that were found different between the murine 11E1 VL domain and the selected human framework have been analysed and found not relevant for anti-cMet binding activity of the 11E1 humanized VL domain, when combined with the chimeric heavy chain.

III—Humanization of 11E1 Antibody

At this stage of the 11E1 monoclonal antibody humanization, the theoretical resulting humanized antibody sequence contains only five outside-CDRs residues coming from the parental murine VH domain and four outside-CDRs residues coming from the parental murine VL sequence (see FIG. 60, lane HZ VH1 and FIG. 62, lane HZ VL1). It has then be decided to immediately characterize the resulting combined heavy and light chain humanized version of the 11E1 antibody. Results are given in FIG. 64 for the anti-cMet direct binding assay.

In this experiment, it has been observed similar binding capabilities for the tested 11E1-derived chimeric or humanized recombinant antibodies. Analysis of the HGF-binding competitive properties and site-directed mutagenesis analysis of the contribution of the nine left murine residues remaining to be performed independently or in combination in this selected VH1/VL1 "pre-humanized" version of the 11E1 monoclonal antibody.

EXAMPLE 27-3

224G11 Monoclonal Antibody Humanization

I—Humanization of 224G11 Heavy Chain Variable Domain

In order to identify the best human candidate for the CDR grafting, the human germline gene displaying the best identity with the 224G11 VH murine sequence has been searched. Regarding the high sequence homology between the 224G11 and the 227H1 VH domains sequences, and as confirmed by the use of the IMGT database tools, the same human IGHV1-2*02 V germline gene and human IGHJ4*01

J germline gene have thus been selected as receiving human sequences for the murine 224G11 VH CDRs.

Based on this high homology, it has been decided to directly transfert the humanization informations gained from the 227H1 VH domain humanization (see Example 27) and we then designed a "full-IMGT" humanized version as depicted in FIG. 65 which represents an amino acid alignment of the murine 227H1 and 224G11 VH domains with the selected human framework. In the human FR lane, only the amino acid that was found different from the 224G11 murine VH domain is depicted. HZVH0 lane corresponds to <<full-IMGT>> humanized version of the 224G11 VH domain as obtained for the "full-IMGT" 227H1-HZVH domain.

The <<full-IMGT>> humanized version of the 224G11 murine VH domain has then been constructed and its anti-cMet binding activities were analysed, when expressed in combination with the 224G11 chimeric light chain. Results obtained from the anti-cMet direct binding assay are shown in FIG. 66 while FIG. 67 illustrates the HGF binding competition assay. Given the experimental data obtained regarding the anti-cMet binding properties of the "full-IMGT" humanized 224G11 VH domain, the resulting amino acid sequence as depicted in FIG. 65 was selected and a bioinformatic analysis was then performed to evaluate the <<humaness>> level of the so-called 224G11-HZ VH0 domain.

Given the humanization strategy applied here, it has to be referred to the Example 27 for the humaness analysis of the 224G11 HZ VH0 sequence. As described for the 227H1 VH domain humanization, we confirm the reliability of the IMGT numbering system and homology analysis tools, and also demonstrate the possibility of transferring the humanization strategy between antibodies under the limits of their intrinsec homology.

II—Humanization of 224G11 Light Chain Variable Domain

In order to identify the best human candidate for the CDR grafting, the human germline gene displaying the best identity with the 224G11 VL murine sequence has been searched. With the help of the IMGT database analysis tools, two possible receiving human V regions for the murine 224G11 VL CDRs were identified. Thus, two humanization strategies have been planed for the 224G11 VL domain. The first corresponds to an initial trial for a human framework with a shorter CDR1 length (IGKV3-11*01), the second with a longer CDR1 length (IGKV4-1*01).

FIG. 68 represents an amino acid alignment of the murine 224G11 VL domain with the two selected human frameworks. In the both shorter and longer Hu-FR FR lanes, only the amino acid that was found different from the 224G11 murine VL domain is depicted. HZ VL3 and HZ VL6 lanes correspond to basic humanized versions of the 224G11 VL domain with above ("rank" lane) mentioned mutations clearly identified. The number under each proposed mutation corresponds to the rank at which said mutation will be done whenever the basic "shorter" or "longer" CDR1-framework will be selected.

In a first set of experiments, the two basic humanized versions of the 224G11 murine VL domain were constructed and their anti-cMet binding activities were analysed, when expressed in combination with the 224G11 chimeric heavy chain. Results obtained from the anti-cMet direct binding assay are shown in FIG. 69. In this experiment, a similar anti-cMet binding activity was observed for the chimeric and HZ VL6 (<<longer-CDR1>>) version whereas almost no binding was detected for the HZ VL3 (<<shorter-CDR1) recombinant 224G11-derived antibody.

In a second set of experiments, we constructed and analysed the anti-cMet binding activities of the implemented humanized versions of the HZ VL6-derived 224G11 VH domain when expressed in combination with the 224G11 chimeric heavy chain. Two additional humanized form was analysed; in the HZ VL5 version the seven residues from the third group (rank 3) are humanized and in the HZ VL4 version the four left residues from the first group (rank 1 residues) only remained murine. Results obtained from the anti-cMet direct binding assay are shown in FIG. 70. In this experiment, no differences in the binding capabilities of the tested 224G11-derived chimeric or partially humanized recombinant antibodies were observed. At this point, 18 out of the 22 amino acids that were found different between the murine 224G11 VL domain and the selected <<longer-CDR1>> human framework have been analysed and found not relevant for anti-cMet binding activity of the 224G11 humanized VL domain, when combined with the chimeric heavy chain.

It has then be tested the HZ VL4 humanized version of the 224G11 VL domain in the HGF binding competition assay. As shown in FIG. 71, the results obtained demonstrate the similar competitive activity of murine and recombinant chimeric and HZ VL4 humanized 224G11-derived antibodies.

At this stage of the 224G11 VL domain humanization, the resulting sequence contains only four outside-CDRs residues coming from the murine parental sequence. As shown in FIG. 72, these four §-labelled residues are L4, M39, H40 and R84.

Based on the IMGT numbering system and homology analysis tools, we demonstrated that human framework displaying structural differences in term of CDR length may still be suitable in a humanization process. It has then been decided to characterize the resulting heavy and light chain humanized version of the 224G11 antibody. Site-directed mutagenesis analysis of the contribution of the remaining four murine residues being then performed when expressed in combination with the VH0 humanized version of the heavy chain.

III—Humanization of 224G11 Antibody

In a first serie of experiments, we constructed and analysed the anti-cMet binding activities of the fully humanized version of the 224G11 antibody. This recombinant version encompass both VH0 and VL4 humanized VH and VL domains respectively. Results obtained from the anti-cMet direct binding assay are shown in FIG. 73. In this experiment, the fully human 224G11 anti-cMet binding activity was found similar to that of <<single-chain>> humanized and chimeric recombinant 224G11 versions.

It has then been tested the fully humanized version of the 224G11 VL domain in the HGF binding competition assay. The results obtained as shown in FIG. 74 demonstrate the similar competitive activity of parental murine and recombinant chimeric and fully humanized 224G11-derived antibodies.

At this stage of the 224G11 antibody humanization, the resulting sequence contains only four outside-CDRs residues coming from the murine parental light chain variable domain sequence. We then analysed site-directed mutagenesis single variants of the VL4 humanized VL domain when expressed in combination with the VH0 humanized version of the heavy chain. As examplified in FIG. 75 for the direct binding assay we identified potential relevant residues among the four tested, being M39 and H40.

It has been decided to analyse multiple mutants of the HZ VL4 humanized 224G11 VL domain when expressed in combination with the HZ VH0 humanized 224G11 VH domain. As shown in FIG. 76 for the direct binding assay and in FIG. 77 for the HGF binding competition assay, multiple amino acids mutants of the VL4 domain were analysed to identify the best humanized combination. Based on the single mutants analysis, it has been focused on double and triple mutants that may exhibits the best anti-cMet activities. The VH0/VL4-2× mutant correspond to the HZ VH0 224G11 humanized VH domain expressed with the HZ VL4 224G11 humanized VL domain with the double mutation L4M/R84G. The VH0/VL4-3× mutant correspond to the HZ VH0 224G11 humanized VH domain expressed with the HZ VL4 224G11 humanized VL domain with the triple mutation L4M/M39L/R84G.

Given the experimental data obtained regarding the anti-cMet binding properties of the fully humanized 224G11 antibody the bioinformatic analysis of both heavy and light chain variable domains sequences was then performed to evaluate the <<humaness>> level of the VH0/VL4-2× and VH0/VL4-3× best humanized versions. It has been previously demonstrated the "full-IMGT" humanization of the VH0 224G11 VH domain. Regarding the humaness level of the VL4-2× and -3× 224G11 humanized VL domain versions, they only contain murine residues M39 and/or H40. These two potential key residues are located at the end of the CDR1, M39 being the N-terminal CDR anchor. Given the CDR length problem that we faced during the 224G11 VL domain humanization, and considering those positions as part of the Kabat definition of the VL CDR1, the humaness level of the fully humanized 224G11 antibody should display a strongly reduced immunogenicity due to the minimal conserved murine residues.

The invention claimed is:

1. A method of treating a c-Met expressing cancer, the method comprising administering to a subject in need of treatment for a c-Met expressing cancer a therapeutically effective amount of a recombinant anti-cMet antibody comprising:

a heavy chain comprising complementarity-determining region (CDR) CDR-H1, CDR-H2, and CDR-H3 comprising, respectively, SEQ ID NOs: 1, 2, and 3; and a light chain comprising CDR-L1, CDR-L2, and CDR-L3 comprising, respectively, SEQ ID NOs: 10, 11, and 12.

2. The method of claim 1, wherein the recombinant anti-cMet antibody comprises a heavy chain variable region comprising SEQ ID NO: 18 and a light chain variable region comprising SEQ ID NO: 21.

3. The method of claim 1, wherein the recombinant anti-cMet antibody is a monoclonal antibody.

4. The method of claim 3, wherein the recombinant anti-cMet antibody is a chimeric antibody comprising light chain and heavy chain constant regions derived from an antibody of a species heterologous to mouse.

5. The method of claim 4, wherein the species heterologous to mouse is human.

6. The method of claim 5, wherein the light chain constant region derived from the antibody of human species is a kappa region and the heavy chain constant region derived from the antibody of human species is chosen from the gamma-1, gamma-2, and gamma-4 regions.

7. The method of claim 1, wherein the antibody is capable of inhibiting both ligand-dependent and ligand-independent activation of c-Met.

8. The method of claim 7, wherein the antibody is capable of inhibiting c-Met dimerization.

9. The method of claim 8, wherein the antibody is capable of inhibiting at least 50% of tumoral cell proliferation for at least one c-Met expressing tumor type.

10. The method of claim 1, wherein the antibody is capable of inhibiting c-Met dimerization.

11. The method according to any one of claims 7-10, wherein the antibody does not bind to the semaphorin (SEMA) domain of cMet.

12. The method of claim 2, wherein the recombinant anti-cMet antibody is capable of inhibiting both ligand-dependent and ligand-independent activation of cMet.

13. The method of claim 12, wherein the antibody is capable of inhibiting cMet dimerization.

14. The method of claim 13, wherein the antibody is capable of inhibiting at least 50% of tumoral cell proliferation for at least one c-Met expressing tumor type.

15. The method of claim 2, wherein the antibody is capable of inhibiting c-Met dimerization.

16. The method according claim 12, wherein the antibody does not bind to the semaphorin (SEMA) domain of c-Met.

17. The method of claim 1, wherein the antibody is capable of one or more of the following:
   inhibiting both ligand-dependent and ligand-independent activation of c-Met;
   inhibiting at least 50% of tumoral cell proliferation for at least one c-Met expressing tumor type; and
   inhibiting c-Met dimerization.

18. The method of claim 2, wherein the antibody is capable of one or more of the following:
   inhibiting both ligand-dependent and ligand-independent activation of c-Met;
   inhibiting at least 50% of tumoral cell proliferation for at least one c-Met expressing tumor type; and
   inhibiting c-Met dimerization.

19. The method according to claim 1, wherein the cMet-binding fragment is a divalent fragment.

20. The method according to claim 1, wherein the cMet-binding fragment is a F(ab')$_2$ fragment.

21. The method according to claim 1, wherein the cMet-binding fragment is a scFv fragment.

22. The method according to claim 1, wherein the antibody is conjugated to a cytotoxic agent, a cell toxin, a radioelement, or a combination thereof.

23. The method according to claim 11, wherein the antibody is conjugated to a cytotoxic agent, a cell toxin, a radioelement, or a combination thereof.

24. The method according to claim 16, wherein the antibody is conjugated to a cytotoxic agent, a cell toxin, a radioelement, or a combination thereof.

25. The method according to claim 22, wherein the antibody is chemically coupled to a cytotoxic agent chosen from alkylating agents, anti-metabolites, anti-tumor antibiotics, mitotic inhibitors, chromatin function inhibitors, anti-angiogenesis agents, anti-estrogenic agents, anti-androgenic agents, immunomodulators.

26. The method according to claim 23, wherein the antibody is chemically coupled to a cytotoxic agent chosen from alkylating agents, anti-metabolites, anti-tumor antibiotics, mitotic inhibitors, chromatin function inhibitors, anti-angiogenesis agents, anti-estrogenic agents, anti-androgenic agents, immunomodulators.

27. The method according to claim 24, wherein the antibody is chemically coupled to a cytotoxic agent chosen from alkylating agents, anti-metabolites, anti-tumor antibiotics, mitotic inhibitors, chromatin function inhibitors, anti-angiogenesis agents, anti-estrogenic agents, anti-androgenic agents, immunomodulators.

28. The method according to claim 1, wherein the antibody is conjugated to a mitotic inhibitor.

29. The method according to claim 1, wherein the cMet-binding fragment is conjugated to a mitotic inhibitor.

30. The method according to claim 2, wherein the antibody is conjugated to a mitotic inhibitor.

\* \* \* \* \*

```
                         SEQUENCE LISTING

<160> NUMBER OF SEQ ID NOS: 71

<210> SEQ ID NO 1
<211> LENGTH: 8
<212> TYPE: PRT
<213> ORGANISM: mus musculus

<400> SEQUENCE: 1

Gly Tyr Ile Phe Thr Ala Tyr Thr
1               5

<210> SEQ ID NO 2
<211> LENGTH: 8
<212> TYPE: PRT
<213> ORGANISM: mus musculus

<400> SEQUENCE: 2

Ile Lys Pro Asn Asn Gly Leu Ala
1               5

<210> SEQ ID NO 3
<211> LENGTH: 11
<212> TYPE: PRT
<213> ORGANISM: mus musculus

<400> SEQUENCE: 3

Ala Arg Ser Glu Ile Thr Thr Glu Phe Asp Tyr
1               5                   10

<210> SEQ ID NO 4
<211> LENGTH: 8
<212> TYPE: PRT
<213> ORGANISM: mus musculus

<400> SEQUENCE: 4

Gly Tyr Ser Phe Thr Asp Tyr Thr
1               5

<210> SEQ ID NO 5
<211> LENGTH: 8
<212> TYPE: PRT
<213> ORGANISM: mus musculus

<400> SEQUENCE: 5

Ile Asn Pro Tyr Asn Gly Gly Thr
1               5

<210> SEQ ID NO 6
<211> LENGTH: 11
<212> TYPE: PRT
```

<210> SEQ ID NO 6
<211> LENGTH: (not shown)
<212> TYPE: PRT
<213> ORGANISM: mus musculus

<400> SEQUENCE: 6

Ala Arg Glu Glu Ile Thr Lys Asp Phe Asp Phe
1               5                   10

<210> SEQ ID NO 7
<211> LENGTH: 8
<212> TYPE: PRT
<213> ORGANISM: mus musculus

<400> SEQUENCE: 7

Gly Tyr Thr Phe Thr Asp Tyr Asn
1               5

<210> SEQ ID NO 8
<211> LENGTH: 8
<212> TYPE: PRT
<213> ORGANISM: mus musculus

<400> SEQUENCE: 8

Ile Asn Pro Asn Asn Gly Gly Thr
1               5

<210> SEQ ID NO 9
<211> LENGTH: 14
<212> TYPE: PRT
<213> ORGANISM: mus musculus

<400> SEQUENCE: 9

Ala Arg Gly Arg Tyr Val Gly Tyr Tyr Ala Met Asp Tyr
1               5                   10

<210> SEQ ID NO 10
<211> LENGTH: 10
<212> TYPE: PRT
<213> ORGANISM: mus musculus

<400> SEQUENCE: 10

Glu Ser Val Asp Ser Tyr Ala Asn Ser Phe
1               5                   10

<210> SEQ ID NO 11
<211> LENGTH: 3
<212> TYPE: PRT
<213> ORGANISM: mus musculus

<400> SEQUENCE: 11

Arg Ala Ser
1

<210> SEQ ID NO 12
<211> LENGTH: 9
<212> TYPE: PRT
<213> ORGANISM: mus musculus

<400> SEQUENCE: 12

Gln Gln Ser Lys Glu Asp Pro Leu Thr
1               5

<210> SEQ ID NO 13
<211> LENGTH: 10
<212> TYPE: PRT
<213> ORGANISM: mus musculus

```
<400> SEQUENCE: 13

Glu Ser Ile Asp Thr Tyr Gly Asn Ser Phe
1               5                   10

<210> SEQ ID NO 14
<211> LENGTH: 9
<212> TYPE: PRT
<213> ORGANISM: mus musculus

<400> SEQUENCE: 14

Gln Gln Ser Asn Glu Asp Pro Phe Thr
1               5

<210> SEQ ID NO 15
<211> LENGTH: 6
<212> TYPE: PRT
<213> ORGANISM: mus musculus

<400> SEQUENCE: 15

Glu Asn Ile Tyr Ser Asn
1               5

<210> SEQ ID NO 16
<211> LENGTH: 3
<212> TYPE: PRT
<213> ORGANISM: mus musculus

<400> SEQUENCE: 16

Ala Ala Thr
1

<210> SEQ ID NO 17
<211> LENGTH: 9
<212> TYPE: PRT
<213> ORGANISM: mus musculus

<400> SEQUENCE: 17

Gln His Phe Trp Gly Pro Pro Tyr Thr
1               5

<210> SEQ ID NO 18
<211> LENGTH: 118
<212> TYPE: PRT
<213> ORGANISM: mus musculus

<400> SEQUENCE: 18

Glu Val Gln Leu Gln Gln Ser Gly Pro Glu Leu Val Lys Pro Gly Ala
1               5                   10                  15

Ser Val Lys Ile Ser Cys Lys Thr Ser Gly Tyr Ile Phe Thr Ala Tyr
            20                  25                  30

Thr Met His Trp Val Arg Gln Ser Leu Gly Glu Ser Leu Asp Trp Ile
        35                  40                  45

Gly Gly Ile Lys Pro Asn Asn Gly Leu Ala Asn Tyr Asn Gln Lys Phe
    50                  55                  60

Lys Gly Lys Ala Thr Leu Thr Val Asp Lys Ser Ser Ser Thr Ala Tyr
65                  70                  75                  80

Met Asp Leu Arg Ser Leu Thr Ser Glu Asp Ser Ala Val Tyr Tyr Cys
                85                  90                  95

Ala Arg Ser Glu Ile Thr Thr Glu Phe Asp Tyr Trp Gly Gln Gly Thr
            100                 105                 110

Ala Leu Thr Val Ser Ser
```

```
<210> SEQ ID NO 19
<211> LENGTH: 118
<212> TYPE: PRT
<213> ORGANISM: mus musculus

<400> SEQUENCE: 19

Glu Val Gln Leu Gln Gln Ser Gly Pro Glu Leu Val Lys Pro Gly Ala
1               5                   10                  15

Ser Met Lys Ile Ser Cys Lys Ala Ser Gly Tyr Ser Phe Thr Asp Tyr
            20                  25                  30

Thr Leu Asn Trp Val Lys Gln Ser His Gly Lys Thr Leu Glu Trp Ile
        35                  40                  45

Gly Leu Ile Asn Pro Tyr Asn Gly Gly Thr Thr Tyr Asn Gln Lys Phe
    50                  55                  60

Lys Gly Lys Ala Thr Leu Thr Val Asp Lys Ser Ser Ser Thr Ala Tyr
65                  70                  75                  80

Met Glu Leu Leu Ser Leu Thr Ser Glu Asp Ser Ala Val Tyr Tyr Cys
                85                  90                  95

Ala Arg Glu Glu Ile Thr Lys Asp Phe Asp Phe Trp Gly Gln Gly Thr
            100                 105                 110

Thr Leu Thr Val Ser Ser
        115

<210> SEQ ID NO 20
<211> LENGTH: 121
<212> TYPE: PRT
<213> ORGANISM: mus musculus

<400> SEQUENCE: 20

Glu Val Leu Leu Gln Gln Ser Gly Pro Glu Leu Val Lys Pro Gly Ala
1               5                   10                  15

Ser Val Lys Ile Pro Cys Lys Ala Ser Gly Tyr Thr Phe Thr Asp Tyr
            20                  25                  30

Asn Met Asp Trp Val Lys Gln Ser His Gly Met Ser Leu Glu Trp Ile
        35                  40                  45

Gly Asp Ile Asn Pro Asn Asn Gly Gly Thr Ile Phe Asn Gln Lys Phe
    50                  55                  60

Lys Gly Lys Ala Thr Leu Thr Val Asp Lys Ser Ser Ser Thr Ala Tyr
65                  70                  75                  80

Met Glu Leu Arg Ser Leu Thr Ser Glu Asp Thr Ala Val Tyr Tyr Cys
                85                  90                  95

Ala Arg Gly Arg Tyr Val Gly Tyr Tyr Tyr Ala Met Asp Tyr Trp Gly
            100                 105                 110

Gln Gly Thr Ser Val Thr Val Ser Ser
        115                 120

<210> SEQ ID NO 21
<211> LENGTH: 111
<212> TYPE: PRT
<213> ORGANISM: mus musculus

<400> SEQUENCE: 21

Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Ser Tyr
            20                  25                  30
```

```
Ala Asn Ser Phe Met His Trp Tyr Gln Gln Lys Pro Gly Gln Pro Pro
            35                  40                  45

Lys Leu Leu Ile Tyr Arg Ala Ser Asn Leu Glu Ser Gly Ile Pro Ala
        50                  55                  60

Arg Phe Ser Gly Ser Gly Ser Arg Thr Asp Phe Thr Leu Thr Ile Asn
65                  70                  75                  80

Pro Val Glu Ala Asp Val Ala Thr Tyr Tyr Cys Gln Gln Ser Lys
                85                  90                  95

Glu Asp Pro Leu Thr Phe Gly Ser Gly Thr Lys Leu Glu Met Lys
            100                 105                 110

<210> SEQ ID NO 22
<211> LENGTH: 111
<212> TYPE: PRT
<213> ORGANISM: mus musculus

<400> SEQUENCE: 22

Gly Ile Val Leu Thr Gln Ser Pro Ala Ser Leu Ala Val Ser Leu Gly
1               5                   10                  15

Gln Arg Ala Thr Ile Ser Cys Arg Val Ser Glu Ser Ile Asp Thr Tyr
            20                  25                  30

Gly Asn Ser Phe Ile His Trp Tyr Gln Gln Lys Pro Gly Gln Pro Pro
        35                  40                  45

Lys Leu Leu Ile Tyr Arg Ala Ser Asn Leu Glu Ser Gly Ile Pro Ala
    50                  55                  60

Arg Phe Ser Gly Ser Gly Ser Arg Thr Asp Phe Thr Leu Thr Ile Asn
65                  70                  75                  80

Pro Val Glu Ala Asp Ser Ala Thr Tyr Tyr Cys Gln Gln Ser Asn
                85                  90                  95

Glu Asp Pro Phe Thr Phe Gly Ser Gly Thr Lys Leu Glu Met Lys
            100                 105                 110

<210> SEQ ID NO 23
<211> LENGTH: 107
<212> TYPE: PRT
<213> ORGANISM: mus musculus

<400> SEQUENCE: 23

Asp Ile Gln Met Thr Gln Ser Pro Ala Ser Leu Ser Val Ser Val Gly
1               5                   10                  15

Glu Thr Val Thr Ile Thr Cys Arg Ala Ser Glu Asn Ile Tyr Ser Asn
            20                  25                  30

Leu Ala Trp Tyr Gln Gln Lys Gln Gly Lys Ser Pro Gln Leu Leu Val
        35                  40                  45

Tyr Ala Ala Thr Asn Leu Val Asp Gly Val Pro Ser Arg Phe Ser Gly
    50                  55                  60

Ser Gly Ser Gly Thr Gln Tyr Ser Leu Lys Ile Asn Ser Leu Gln Ser
65                  70                  75                  80

Glu Asp Phe Gly Ser Tyr Tyr Cys Gln His Phe Trp Gly Pro Pro Tyr
                85                  90                  95

Thr Phe Gly Gly Gly Thr Lys Leu Glu Ile Lys
            100                 105

<210> SEQ ID NO 24
<211> LENGTH: 24
<212> TYPE: DNA
<213> ORGANISM: mus musculus
```

```
<400> SEQUENCE: 24
ggatacatat tcactgcata cacc                                              24

<210> SEQ ID NO 25
<211> LENGTH: 24
<212> TYPE: DNA
<213> ORGANISM: mus musculus

<400> SEQUENCE: 25
attaaaccaa acaatggtct tgct                                              24

<210> SEQ ID NO 26
<211> LENGTH: 33
<212> TYPE: DNA
<213> ORGANISM: mus musculus

<400> SEQUENCE: 26
gcaagatctg agattacgac ggaatttgac tac                                    33

<210> SEQ ID NO 27
<211> LENGTH: 24
<212> TYPE: DNA
<213> ORGANISM: mus musculus

<400> SEQUENCE: 27
ggttattcat tcactgacta cacc                                              24

<210> SEQ ID NO 28
<211> LENGTH: 24
<212> TYPE: DNA
<213> ORGANISM: mus musculus

<400> SEQUENCE: 28
attaatcctt acaatggtgg tact                                              24

<210> SEQ ID NO 29
<211> LENGTH: 33
<212> TYPE: DNA
<213> ORGANISM: mus musculus

<400> SEQUENCE: 29
gcaagagagg aaattacgaa ggactttgat ttc                                    33

<210> SEQ ID NO 30
<211> LENGTH: 24
<212> TYPE: DNA
<213> ORGANISM: mus musculus

<400> SEQUENCE: 30
ggatacacat tcactgacta caac                                              24

<210> SEQ ID NO 31
<211> LENGTH: 24
<212> TYPE: DNA
<213> ORGANISM: mus musculus

<400> SEQUENCE: 31
attaatccta acaatggtgg tact                                              24

<210> SEQ ID NO 32
<211> LENGTH: 42
<212> TYPE: DNA
```

<213> ORGANISM: mus musculus

<400> SEQUENCE: 32
gcaagaggga ggtatgttgg ttactactat gctatggact ac                42

<210> SEQ ID NO 33
<211> LENGTH: 30
<212> TYPE: DNA
<213> ORGANISM: mus musculus

<400> SEQUENCE: 33
gaaagtgttg atagttatgc caatagtttt                              30

<210> SEQ ID NO 34
<211> LENGTH: 9
<212> TYPE: DNA
<213> ORGANISM: mus musculus

<400> SEQUENCE: 34 cgtgcatcc                                                      9

<210> SEQ ID NO 35
<211> LENGTH: 27
<212> TYPE: DNA
<213> ORGANISM: mus musculus

<400> SEQUENCE: 35
cagcaaagta aggaggatcc tctcacg                                 27

<210> SEQ ID NO 36
<211> LENGTH: 30
<212> TYPE: DNA
<213> ORGANISM: mus musculus

<400> SEQUENCE: 36
gaaagtattg atacttatgg caatagtttt                              30

<210> SEQ ID NO 37
<211> LENGTH: 27
<212> TYPE: DNA
<213> ORGANISM: mus musculus

<400> SEQUENCE: 37
cagcaaagta atgaggatcc attcacg                                 27

<210> SEQ ID NO 38
<211> LENGTH: 18
<212> TYPE: DNA
<213> ORGANISM: mus musculus

<400> SEQUENCE: 38
gagaatattt acagtaat                                           18

<210> SEQ ID NO 39
<211> LENGTH: 9
<212> TYPE: DNA
<213> ORGANISM: mus musculus

<400> SEQUENCE: 39 gctgcaaca                                                      9

<210> SEQ ID NO 40
<211> LENGTH: 27

<212> TYPE: DNA
<213> ORGANISM: mus musculus

<400> SEQUENCE: 40 caacatttttt ggggtcctcc gtacacg                                  27

<210> SEQ ID NO 41
<211> LENGTH: 354
<212> TYPE: DNA
<213> ORGANISM: mus musculus

<400> SEQUENCE: 41
gaggtccagc tgcaacagtc tggacctgag ctggtgaagc ctggggcttc agtgaagata      60
tcctgcaaga cttctggata catattcact gcatacacca tgcactgggt gaggcagagc     120
cttggagaga gccttgactg gattggaggt attaaaccaa acaatggtct tgctaactac     180
aaccagaagt tcaagggcaa ggccacattg actgtagaca agtcctccag cacagcctac     240
atggaccTcc gcagcctgac atctgaggat tctgcagtct attactgtgc aagatctgag     300
attacgacgg aatttgacta ctggggccaa ggcaccgctc tcacagtctc ctca           354

<210> SEQ ID NO 42
<211> LENGTH: 354
<212> TYPE: DNA
<213> ORGANISM: mus musculus

<400> SEQUENCE: 42
gaggtccagc tgcaacagtc tggacctgaa ctggtgaagc ctggagcttc aatgaagatt      60
tcctgcaagg cttctggtta ttcattcact gactacaccc tgaactgggt gaagcagagc     120
catggaaaga cccttgagtg gattggactt attaatcctt acaatggtgg tactacctac     180
aaccagaagt tcaagggcaa ggccacatta actgtagaca agtcatccag cacagcctac     240
atggagctcc tcagtctgac atctgaggac tctgcagtct attactgtgc aagagaggaa     300
attacgaagg actttgattt ctggggccaa ggcaccactc tcacagtctc ctca           354

<210> SEQ ID NO 43
<211> LENGTH: 363
<212> TYPE: DNA
<213> ORGANISM: mus musculus

<400> SEQUENCE: 43
gaggtcctgc tgcaacagtc tggacctgag ctggtgaagc ctggggcttc agtgaagata      60
ccctgcaagg cttctggata cacattcact gactacaaca tggactgggt gaagcagagc     120
catggaatga gccttgagtg gattggagat attaatccta acaatggtgg tactatcttc     180
aaccagaagt tcaagggcaa ggccacattg actgtagaca agtcctccag cacagcctac     240
atggagctcc gcagcctgac atctgaggac actgcagtct attactgtgc aagagggagg     300
tatgttggtt actactatgc tatggactac tggggtcaag gaacctcagt caccgtctcc     360
tca                                                                    363

<210> SEQ ID NO 44
<211> LENGTH: 333
<212> TYPE: DNA
<213> ORGANISM: mus musculus

<400> SEQUENCE: 44
gacattgtgc tgacccaatc tccagcttct ttggctgtgt ctctagggca gagggccacc      60

```
atatcctgca gagccagtga aagtgttgat agttatgcca atagttttat gcactggtac    120
cagcagaaac caggacagcc acccaaactc ctcatctatc gtgcatccaa cctagaatct    180
gggatccctg ccaggttcag tggcagtggg tctaggacag acttcaccct caccattaat    240
cctgtggagg ctgatgatgt tgcaacctat tactgtcagc aaagtaagga ggatcctctc    300
acgttcggct cggggacaaa attggaaatg aaa                                 333
```

<210> SEQ ID NO 45
<211> LENGTH: 333
<212> TYPE: DNA
<213> ORGANISM: mus musculus

<400> SEQUENCE: 45

```
ggcattgtgt tgacccaatc tccagcttct ttggctgtgt ctctaggaca gagggccacc     60
atatcctgca gagtcagtga aagtattgat acttatggca atagttttat acactggtac    120
cagcagaaac caggacagcc acccaaactc ctcatctatc gtgcatccaa cctagaatct    180
gggatccctg ccaggttcag tggcagtggg tctaggacag acttcaccct caccattaat    240
cctgtggagg ctgatgattc tgcaacctat tactgtcagc aaagtaatga ggatccattc    300
acgttcggct cggggacaaa gttggaaatg aaa                                 333
```

<210> SEQ ID NO 46
<211> LENGTH: 321
<212> TYPE: DNA
<213> ORGANISM: mus musculus

<400> SEQUENCE: 46

```
gacatccaga tgactcagtc tccagcctcc ctatctgtat ctgtgggaga aactgtcacc     60
atcacatgtc gagcaagtga gaatatttac agtaatttag catggtatca gcagaaacag    120
ggaaaatctc ctcagctcct ggtctatgct gcaacaaact tagtagatgg tgtgccatca    180
aggttcagtg gcagtggatc aggcacacag tattccctca agatcaacag cctgcagtct    240
gaagattttg ggagttatta ctgtcaacat ttttggggtc ctccgtacac gttcggaggg    300
gggaccaagc tggagataaa g                                              321
```

<210> SEQ ID NO 47
<211> LENGTH: 24
<212> TYPE: DNA
<213> ORGANISM: artificial sequence
<220> FEATURE:
<223> OTHER INFORMATION: Primer for housekeeping gene Ribosomal protein, large, P0 (RPL0)

<400> SEQUENCE: 47

```
gaaactctgc attctcgctt cctg                                            24
```

<210> SEQ ID NO 48
<211> LENGTH: 22
<212> TYPE: DNA
<213> ORGANISM: artificial sequence
<220> FEATURE:
<223> OTHER INFORMATION: Primer for housekeeping gene Ribosomal protein, large, P0 (RPL0)

<400> SEQUENCE: 48

```
aggactcgtt tgtacccgtt ga                                              22
```

<210> SEQ ID NO 49
<211> LENGTH: 26

<210> SEQ ID NO 49
<211> LENGTH: 26
<212> TYPE: DNA
<213> ORGANISM: artificial sequence
<220> FEATURE:
<223> OTHER INFORMATION: Primer for housekeeping gene Ribosomal protein, large, P0 (RPL0)

<400> SEQUENCE: 49
tgcagattgg ctacccaact gttgca         26

<210> SEQ ID NO 50
<211> LENGTH: 18
<212> TYPE: DNA
<213> ORGANISM: artificial sequence
<220> FEATURE:
<223> OTHER INFORMATION: Primer for HGF

<400> SEQUENCE: 50
aacaatgcct ctggttcc         18

<210> SEQ ID NO 51
<211> LENGTH: 20
<212> TYPE: DNA
<213> ORGANISM: artificial sequence
<220> FEATURE:
<223> OTHER INFORMATION: Primer for HGF

<400> SEQUENCE: 51
cttgtagctg cgtcctttac         20

<210> SEQ ID NO 52
<211> LENGTH: 27
<212> TYPE: DNA
<213> ORGANISM: artificial sequence
<220> FEATURE:
<223> OTHER INFORMATION: Probe for HGF

<400> SEQUENCE: 52
ccttcaatag catgtcaagt ggagtga         27

<210> SEQ ID NO 53
<211> LENGTH: 28
<212> TYPE: DNA
<213> ORGANISM: artificial sequence
<220> FEATURE:
<223> OTHER INFORMATION: Primer for c-Met

<400> SEQUENCE: 53
cattaaagga gacctcacca tagctaat         28

<210> SEQ ID NO 54
<211> LENGTH: 22
<212> TYPE: DNA
<213> ORGANISM: artificial sequence
<220> FEATURE:
<223> OTHER INFORMATION: Primer for c-Met

<400> SEQUENCE: 54
cctgatcgag aaaccacaac ct         22

<210> SEQ ID NO 55
<211> LENGTH: 25
<212> TYPE: DNA
<213> ORGANISM: artificial sequence
<220> FEATURE:
<223> OTHER INFORMATION: Probe for c-Met

<400> SEQUENCE: 55
catgaagcga ccctctgatg tccca                                                    25

<210> SEQ ID NO 56
<211> LENGTH: 8
<212> TYPE: PRT
<213> ORGANISM: mus musculus

<400> SEQUENCE: 56

Gly Tyr Thr Phe Thr Ser Tyr Trp
1               5

<210> SEQ ID NO 57
<211> LENGTH: 8
<212> TYPE: PRT
<213> ORGANISM: mus musculus

<400> SEQUENCE: 57

Ile Asn Pro Thr Thr Gly Ser Thr
1               5

<210> SEQ ID NO 58
<211> LENGTH: 11
<212> TYPE: PRT
<213> ORGANISM: mus musculus

<400> SEQUENCE: 58

Ala Ile Gly Gly Tyr Gly Ser Trp Phe Ala Tyr
1               5                   10

<210> SEQ ID NO 59
<211> LENGTH: 7
<212> TYPE: PRT
<213> ORGANISM: mus musculus

<400> SEQUENCE: 59

Ser Ser Val Ser Ser Thr Tyr
1               5

<210> SEQ ID NO 60
<211> LENGTH: 3
<212> TYPE: PRT
<213> ORGANISM: mus musculus

<400> SEQUENCE: 60

Thr Thr Ser
1

<210> SEQ ID NO 61
<211> LENGTH: 9
<212> TYPE: PRT
<213> ORGANISM: mus musculus

<400> SEQUENCE: 61

His Gln Trp Ser Ser Tyr Pro Phe Thr
1               5

<210> SEQ ID NO 62
<211> LENGTH: 118
<212> TYPE: PRT
<213> ORGANISM: mus musculus

<400> SEQUENCE: 62

Gln Val Gln Leu Gln Gln Ser Gly Ala Glu Leu Ala Lys Pro Gly Ala
1               5                   10                  15

-continued

Ser Val Lys Met Ser Cys Lys Ala Ser Gly Tyr Thr Phe Thr Ser Tyr
            20                  25                  30

Trp Met Asn Trp Val Lys Gln Arg Pro Gly Gln Gly Leu Glu Trp Ile
                35                  40                  45

Gly Tyr Ile Asn Pro Thr Thr Gly Ser Thr Asp Tyr Asn Gln Lys Leu
 50                  55                  60

Lys Asp Lys Ala Thr Leu Thr Ala Asp Lys Ser Ser Asn Thr Ala Tyr
 65                  70                  75                  80

Met Gln Leu Ser Ser Leu Thr Ser Glu Asp Ser Ala Val Tyr Tyr Cys
                85                  90                  95

Ala Ile Gly Gly Tyr Gly Ser Trp Phe Ala Tyr Trp Gly Gln Gly Thr
            100                 105                 110

Leu Val Thr Val Ser Ala
            115

<210> SEQ ID NO 63
<211> LENGTH: 108
<212> TYPE: PRT
<213> ORGANISM: mus musculus

<400> SEQUENCE: 63

Gln Ile Val Leu Thr Gln Ser Pro Ala Ile Met Ser Ala Ser Pro Gly
 1               5                  10                  15

Glu Lys Val Thr Leu Thr Cys Ser Ala Ser Ser Ser Val Ser Ser Thr
                20                  25                  30

Tyr Leu Tyr Trp Tyr Gln Gln Lys Pro Gly Ser Ser Pro Lys Leu Trp
            35                  40                  45

Ile Tyr Thr Thr Ser Ile Leu Ala Ser Gly Val Pro Ala Arg Phe Ser
 50                  55                  60

Gly Ser Gly Ser Gly Thr Ser Tyr Ser Leu Thr Ile Ser Ser Met Glu
 65                  70                  75                  80

Thr Glu Asp Ala Ala Ser Tyr Phe Cys His Gln Trp Ser Ser Tyr Pro
                85                  90                  95

Phe Thr Phe Gly Ser Gly Thr Lys Leu Asp Ile Lys
            100                 105

<210> SEQ ID NO 64
<211> LENGTH: 24
<212> TYPE: DNA
<213> ORGANISM: mus musculus

<400> SEQUENCE: 64
ggctacactt ttacttccta ctgg                                          24

<210> SEQ ID NO 65
<211> LENGTH: 24
<212> TYPE: DNA
<213> ORGANISM: mus musculus

<400> SEQUENCE: 65 attaaccccta ccactggttc tact                                         24

<210> SEQ ID NO 66
<211> LENGTH: 33
<212> TYPE: DNA
<213> ORGANISM: mus musculus

<400> SEQUENCE: 66

```
gcaataggag gatatgggtc ctggtttgct tac                                    33

<210> SEQ ID NO 67
<211> LENGTH: 21
<212> TYPE: DNA
<213> ORGANISM: mus musculus

<400> SEQUENCE: 67
tcaagtgtaa gttccaccta c                                                 21

<210> SEQ ID NO 68
<211> LENGTH: 9
<212> TYPE: DNA
<213> ORGANISM: mus musculus

<400> SEQUENCE: 68 accacatcc                                                                9

<210> SEQ ID NO 69
<211> LENGTH: 27
<212> TYPE: DNA
<213> ORGANISM: mus musculus

<400> SEQUENCE: 69
catcagtgga gtagttaccc attcacg                                           27

<210> SEQ ID NO 70
<211> LENGTH: 354
<212> TYPE: DNA
<213> ORGANISM: mus musculus

<400> SEQUENCE: 70
caggtccagc ttcagcagtc tggggctgaa ctggcaaaac ctggggcctc agtgaagatg       60
tcctgcaagg cttctggcta cactttact  tcctactgga tgaactgggt gaaacagagg      120
cctggacagg gtctggaatg gattggatac attaaccta ccactggttc tactgactac       180
aatcagaagt taaggacaa ggccacattg actgcagaca atcctccaa cacagcctac        240 atgcaactga gcagcctgac atctgaggac tctgcagtct attactgtgc aataggaga       300 tatgggtcct ggtttgctta ctggggccaa gggactctgg tcactgtctc tgca            354

<210> SEQ ID NO 71
<211> LENGTH: 324
<212> TYPE: DNA
<213> ORGANISM: mus musculus

<400> SEQUENCE: 71
caaattgttc tcacccagtc tccagcaatc atgtctgcat ctcctgggga gaaggtcacc       60
ttgacctgca gtgccagctc aagtgtaagt tccacctact tgtactggta ccagcagaag      120
ccaggatcct cccccaaact ctggatttat accacatcca tcctggcttc tggagtccct      180
gctcgcttca gtggcagtgg gtctgggacc tcttactctc tcacaatcag cagcatggag      240
actgaagatg ctgcctctta tttctgccat cagtggagta gttacccatt cacgttcggc      300
tcggggacaa agttggacat aaaa                                             324
```